(12) United States Patent
Bate et al.

(10) Patent No.: US 12,365,911 B2
(45) Date of Patent: Jul. 22, 2025

(54) MODIFICATION OF BRASSINOSTEROID RECEPTOR GENES TO IMPROVE YIELD TRAITS

(71) Applicant: Pairwise Plants Services, Inc., Durham, NC (US)

(72) Inventors: Nicholas Bate, Raleigh, NC (US); Lolita George Mathew, Cary, NC (US); Devin O'Connor, Hillsborough, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 124 days.

(21) Appl. No.: 17/819,023

(22) Filed: Aug. 11, 2022

(65) Prior Publication Data

US 2023/0078990 A1 Mar. 16, 2023

Related U.S. Application Data

(60) Provisional application No. 63/232,297, filed on Aug. 12, 2021.

(51) Int. Cl.
*C12N 15/82* (2006.01)
*C07K 14/415* (2006.01)
*C12N 15/11* (2006.01)

(52) U.S. Cl.
CPC ........ *C12N 15/8261* (2013.01); *C07K 14/415* (2013.01); *C12N 15/11* (2013.01); *C12N 15/8213* (2013.01); *C12N 2310/20* (2017.05)

(58) Field of Classification Search
None
See application file for complete search history.

(56) References Cited

FOREIGN PATENT DOCUMENTS

| WO | WO-2014150879 A1 * | 9/2014 | ......... C12N 15/8261 |
|---|---|---|---|
| WO | WO-2019076355 A1 * | 4/2019 | ........... C07K 14/415 |

OTHER PUBLICATIONS

Kinoshita, Toshinori, et al. "Binding of brassinosteroids to the extracellular domain of plant receptor kinase BRI1." Nature 433. 7022 ( 005): 167-171. (Year: 2005).*
Jaiswal, Sarita, Monica Bâga, and Ravindra N. Chibbar. "Brassinosteroid receptor mutation influences starch granule size distribution in barley grains." Plant Physiology and Biochemistry 154 (2020): 369-378. (Year: 2020).*
Fang, Jingjing, Weiqi Zhu, and Yiping Tong. "Knock-down the expression of brassinosteroid receptor TaBRI1 reduces photosynthesis, tolerance to high light and high temperature stresses and grain yield in wheat." Plants 9.7 (2020): 840. (Year: 2020).*
Van Esse, G. Wilma, et al. "A mathematical model for Brassinosteroid Insensitive1-mediated signaling in root growth and hypocotyl elongation." Plant physiology 160.1 (2012): 523-532. (Year: 2012).*
SlBRI1 (Solanum lycopersicum, NP_001296180.1) as denoted in Wang et al. (2021) (Year: 2021).*
SlBRI1 (Solanum lycopersicum, NM_001309251.1) as denoted in Wang et al. (2021) (Year: 2021).*
GenBank Accession NM_001250482.2 "Glycine max brassinosteroid receptor (BRI1B), mRNA" dated Dec. 16, 2017 https://www.ncbi.nlm.nih.gov/nucleotide/NM_001250482.2?report=genbank&logS=nuclalign&blast_rank=4&RID=NKS274HM016 (Year: 2017).*
"The Biology of *Glycine max* (L.) Merr. (Soybean)" https://inspection.canada.ca/en/plant-varieties/plants-novel-traits/applicants/directive-94-08/biology-documents/glycine-max-merr (Year: 2024).*
Noguchi, Takahiro, et al. "Brassinosteroid-insensitive dwarf mutants of Arabidopsis accumulate brassinosteroids." Plant physiology 121.3 (1999): 743-752. (Year: 1999).*
Wang, Shufen, et al. "Modification of threonine-825 of SlBRI1 enlarges cell size to enhance fruit yield by regulating the cooperation of BR-GA signaling in tomato." International Journal of Molecular Sciences 22.14 (2021): 7673. (Year: 2021).*
International Search Report and the Written Opinion of the International Searching Authority corresponding to International Patent Application No. PCT/US2022/074790 mailed Nov. 23, 2022 (14 pages).
Belkhadir, Youssef, et al., "Intragenic Suppression of a Trafficking-Defective brassinosteroid Receptor Mutant in *Arabidopsis*", Genetics. 185(4): 1283-1296 (2010).
Belkhadir, Youssef, et al., "The molecular circuitry of brassinosteroid signaling", New Phytologist. 206(2): 522-540 (2015).
Clouse, Steven D., et al., "A Brassinosteroid-Insensitive Mutant in *Arabidopsis thaliana* Exhibits Multiple Defects in Growth and Development", Plant Physiology. 111(3): 671-678 (1996).
Divi, Uday K., et al., "Brassinosteroid: a biotechnological target for enhancing crop yield and stress tolerance", New Biotechnology. 26(3/4): 131-136 (2009).
Gendron, Joshua M., et al., "Multiple mechanisms modulate brassinosteroid signaling", Current Opinion in Plant Biology, 10(5): 436-441 (2007).
Gruszka, Damian, "Exploring the Brassinosteroid Signaling in Monocots Reveals Novel Components of the Pathway and Implications for Plant Breeding", International Journal of Molecular Sciences. 21(1): 354, doi: 10.3390/ijms21010354 (2020).
Li, Jianming, et al., "Regulation of brassinosteroid signaling", Trends in Plant Science. 12(1): 37-41 (2007).
Wang, Xuelu, et al., "Autoregulation and Homodimerization Are Involved in the Activation of the Plant Steroid Receptor BRI1", Developmental Cell. 8(6): 855-865 (2005).
Wang, Zhi-Yong, et al., "BRI1 is a critical component of a plasma-membrane receptor for plant steroids", Nature. 410(6826): 380-383 (2001).

(Continued)

*Primary Examiner* — Charles Logsdon
*Assistant Examiner* — Kelsey L McWilliams
(74) *Attorney, Agent, or Firm* — Myers Bigel, P.A.

(57) ABSTRACT

This invention relates to compositions and methods for modifying Brassinosteroid Insensitive-1 (BRI1) genes in plants by introducing at least one mutation in a region of the BRI1 gene encoding the kinase domain, optionally to improve yield traits. The invention further relates to a mutated BRI1 gene, a modified BRI1 polypeptide, and plants having increased improved yield traits produced using the methods and compositions of the invention.

13 Claims, No Drawings
Specification includes a Sequence Listing.

(56) References Cited

OTHER PUBLICATIONS

Wang, Shufen, et al., "Modification of Threonine-1050 of SlBRI1 regulates BR Signalling and increases fruit yield of tomato", BMC Plant Biology. 19(1): 256 (2019).

Wang, Qiannan, et al., "Role of Specific Phosphorylation Sites of *Arabidopsis* Brassinosteroid-Insensitive 1 Receptor Kinase in Plant Growth and Development", Journal of Plant Growth Regulation. 35(3): 755-769 (2016).

Yan, Liuhua, et al., "High-Efficiency Genome Editing in *Arabidopsis* using YAO Promoter-Driven CRISPR/Cas9 System", Molecular Plant. 8(12): 1820-1823 (2015).

* cited by examiner

MODIFICATION OF BRASSINOSTEROID RECEPTOR GENES TO IMPROVE YIELD TRAITS

STATEMENT OF PRIORITY

This application claims the benefit, under 35 U.S.C. § 119 (e), of U.S. Provisional Application No. 63/232,297 filed on Aug. 12, 2021, the entire contents of which is incorporated by reference herein.

STATEMENT REGARDING ELECTRONIC FILING OF A SEQUENCE LISTING

A Sequence Listing in XML text format, submitted under 37 C.F.R. § 1.831-1.834, entitled 1499.69_ST26. xml, 294, 430 bytes in size, generated on Jul. 28, 2022 and filed electronically, is provided in lieu of a paper copy. This Sequence Listing is hereby incorporated herein by reference into the specification for its disclosures.

FIELD OF THE INVENTION

This invention relates to compositions and methods for modifying Brassinosteroid Insensitive-1 (BRI1) genes in plants, optionally to improve yield traits. The invention further relates to plants having increased improved yield traits produced using the methods and compositions of the invention.

BACKGROUND OF THE INVENTION

Intensive breeding across row crops has led to incremental increases in plant yield. However, genetic gain from breeding has started to plateau and assembling multiple small-effect genes in a breeding program has substantially increased research and development costs. Single gene solutions have been challenging for a complex trait such as yield, where background genetics and environment combine to reduce the impact of individual genes. Breeding has been successful by combining many individual genes with small contributing effects but is requiring greater resources to find unique combinations with improved effects. To increase the rate of yield gain, novel variation needs to be introduced in important genes and pathways that contribute to yield.

Transgenic approaches involving stable transformation to increase yield have largely been unsuccessful and there are no commercially relevant single gene approaches that have successfully created a step change in yield. Modifying hormone related pathways through GM approaches has not been fruitful because the simple over- or under-expression through transgene technology is not consistent with the fine-tuning effect required for improving plant yield.

The present invention addresses these shortcomings in the art by providing new compositions and methods for improving/enhancing yield traits in plants, including soybean, corn and other plant species.

SUMMARY OF THE INVENTION

One aspect of the invention provides a plant or plant part thereof comprising at least one mutation in an endogenous Brassinosteroid Insensitive-1 (BRI1) gene encoding a BRI1 polypeptide (brassinosteroid receptor polypeptide), optionally wherein the mutation may be a non-natural mutation.

A second aspect of the invention provides a plant cell, comprising an editing system comprising: (a) a CRISPR-Cas effector protein; and (b) a guide nucleic acid (e.g., gRNA, gDNA, crRNA, crDNA, sgRNA, sgDNA) comprising a spacer sequence with complementarity to an endogenous target gene encoding a Brassinosteroid Insensitive-1 (BRI1) polypeptide (a brassinosteroid receptor polypeptide).

A third aspect of the invention provides a plant cell comprising at least one mutation within an endogenous Brassinosteroid Insensitive-1 (BRI1) gene, wherein the mutation is a substitution, insertion, or deletion that is introduced using an editing system that comprises a nucleic acid binding domain that binds to a target site in the endogenous BRI1 gene, optionally wherein the mutation may be a non-natural mutation.

A fourth aspect of the invention provides a method of producing/breeding a transgene-free edited plant, comprising: crossing the plant of the invention with a transgene free plant, thereby introducing the at least one mutation into the plant that is transgene-free; and selecting a progeny plant that comprises the at least one mutation and is transgene-free, thereby producing a transgene free edited plant, optionally wherein the mutation may be a non-natural mutation.

A fifth aspect of the invention provides a method of providing a plurality of plants having one or more improved yield traits, optionally increased seed size (e.g., seed area and/or seed weight) and/or seed oil content, the method comprising planting two or more plants of the invention in a growing area, thereby providing a plurality of plants having one or more improved yield traits as compared to a plurality of control plants not comprising the at least one mutation.

A sixth aspect of the invention provides a method of generating variation in a region of a Brassinosteroid Insensitive-1 (BRI1) polypeptide, comprising: introducing an editing system into a plant cell, wherein the editing system is targeted to a region of a Brassinosteroid Insensitive-1 (BRI1) gene that encodes the region of the BRI1 polypeptide, and contacting the region of the BRI1 gene with the editing system, thereby introducing a mutation into the BRI1 gene and generating variation in the BRI1 polypeptide of the plant cell.

A seventh aspect provides a method for editing a specific site in the genome of a plant cell, the method comprising: cleaving, in a site-specific manner, a target site within an endogenous Brassinosteroid Insensitive-1 (BRI1) gene in the plant cell, the endogenous BRI1 gene: (a) comprising a sequence having at least 80% sequence identity to any one of the nucleotide sequences of SEQ ID NOs:69, 70, 85, 86, 99, 100, 112, 113, 123, or 124; (b) comprising a region having at least 80% sequence identity to any one of the nucleotide sequences of SEQ ID NOs:72-76, 89-94, 102-106, 115-118, or 126-130; (c) encoding an amino acid sequence having at least 80% sequence identity to any one of SEQ ID NOs:71, 87, 88, 101, 114, or 125; and/or (d) encoding a region having at least 80% sequence identity to an amino acid sequence of any one of SEQ ID NOs:77-81, 95-98, 107-111, 119-122 or 131-135, thereby generating an edit in the endogenous BRI1 gene of the plant cell and producing a plant cell comprising the edit in the endogenous BRI1 gene.

An eighth aspect provides a method for making a plant, comprising: ((a) contacting a population of plant cells comprising an endogenous Brassinosteroid Insensitive-1 (BRI1) gene with a nuclease linked to a nucleic acid binding domain (e.g., editing system) that binds to a sequence (a) having at least 80% sequence identity to the nucleotide sequence of any one of SEQ ID NOs:69, 70, 85, 86, 99, 100, 112, 113, 123, or 124, (b) encoding an amino acid sequence having at least 80% sequence identity to any one of SEQ ID NOs:71, 87, 88, 101, 114, or 125, (c) encoding an amino acid sequence comprising a region having at least 80% sequence identity to any one of SEQ ID NOs:77-81, 95-98, 107-111, 119-122 or 131-135, and/or (d) comprising a region having at least 80% identity to any one of SEQ ID NOs:72-76, 89-94, 102-106, 115-118, or 126-130; (b) selecting a plant cell from the population in which an endogenous BRI1 gene has been mutated, thereby producing a plant cell comprising a mutation in the endogenous BRI1 gene; and (c) growing the selected plant cell into a plant.

A ninth aspect provides a method for improving one or more yield traits in a plant, comprising (a) contacting a plant cell comprising an endogenous Brassinosteroid Insensitive-1 (BRI1) gene with a nuclease targeting the endogenous BRI1 gene, wherein the nuclease is linked to a nucleic acid binding domain (e.g., editing system) that binds to a target site in the endogenous BRI1 gene, wherein the endogenous BRI1 gene: (i) comprises a sequence having at least 80% sequence identity to the nucleotide sequence of any one of SEQ ID NOs:69, 70, 85, 86, 99, 100, 112, 113, 123, or 124; (ii) comprises a region having at least 80% identity to any one of SEQ ID NOs:72-76, 89-94, 102-106, 115-118, or 126-130; (iii) encodes an amino acid sequence having at least 80% sequence identity to any one of SEQ ID NOs:71, 87, 88, 101, 114, or 125; and/or (iv) encodes an amino acid sequence comprising a region having at least 80% identity to any one of SEQ ID NOs:77-81, 95-98, 107-111, 119-122 or 131-135 to produce a plant cell comprising a mutation in the endogenous BRI1 gene; and (b) growing the plant cell into a plant comprising the mutation in the endogenous BRI1 gene, thereby producing a plant have a mutated endogenous BRI1 gene and one or more improved yield traits.

A tenth aspect provides producing a plant or part thereof comprising at least one cell having a mutated endogenous Brassinosteroid Insensitive-1 (BRI1) gene, the method comprising contacting a target site in an endogenous BRI1 gene in the plant or plant part with a nuclease comprising a cleavage domain and a nucleic acid binding domain, wherein the nucleic acid binding domain binds to a target site in the endogenous BRI1 gene, wherein the endogenous BRI1 gene (a) comprises a sequence having at least 80% sequence identity to the nucleotide sequence of any one of SEQ ID NOs:69, 70, 85, 86, 99, 100, 112, 113, 123, or 124; (b) comprises a region having at least 80% identity to any one of SEQ ID NOs:72-76, 89-94, 102-106, 115-118, or 126-130; (c) encodes an amino acid sequence having at least 80% sequence identity to any one of SEQ ID NOs:71, 87, 88, 101, 114, or 125; and/or (d) encodes an amino acid sequence comprising a region having at least 80% identity to any one of SEQ ID NOs:77-81, 95-98, 107-111, 119-122 or 131-135, thereby producing the plant or part thereof comprising at least one cell having a mutation in the endogenous BRI1 gene.

An eleventh aspect of the invention provides a method for producing a plant or part thereof comprising a mutated endogenous Brassinosteroid Insensitive-1 (BRI1) gene and exhibiting one or more improved yield traits, the method comprising contacting a target site in an endogenous BRI1 gene in the plant or plant part with a nuclease comprising a cleavage domain and a nucleic acid binding domain, wherein the nucleic acid binding domain binds to a target site in the endogenous BRI1 gene, wherein the endogenous BRI1 gene: (a) comprises a sequence having at least 80% sequence identity to the nucleotide sequence of any one of SEQ ID NOs:69, 70, 85, 86, 99, 100, 112, 113, 123, or 124; (b) comprises a region having at least 80% identity to any one of SEQ ID NOs:72-76, 89-94, 102-106, 115-118, or 126-130; (c) encodes an amino acid sequence having at least 80% sequence identity to any one of SEQ ID NOs:71, 87, 88, 101, 114, or 125; and/or (d) encodes an amino acid sequence comprising a region having at least 80% identity to any one of SEQ ID NOs:77-81, 95-98, 107-111, 119-122 or 131-135, thereby producing the plant or part thereof comprising an endogenous BRI1 gene having a mutation and exhibiting one or more improved yield traits.

A twelfth aspect provides a method of creating a mutation in an endogenous Brassinosteroid Insensitive-1 (BRI1) gene in a plant, the method comprising: (a) targeting a gene editing system to a portion of the BRI1 gene that (i) comprises a sequence having at least 80% sequence identity to any one of SEQ ID NOs:72-76, 89-94, 102-106, 115-118, or 126-130; and/or (ii) encodes a sequence having at least 80% identity to any one of SEQ ID NOs:77-81, 95-98, 107-111, 119-122 or 131-135, and (b) selecting a plant that comprises a modified amino acid residue located: from about position 955-975 with reference to amino acid position numbering of SEQ ID NO:71, from about position 1023-1043 with reference to amino acid position numbering of SEQ ID NO:87 or SEQ ID NO:88, from about position 1081-1101 with reference to amino acid position numbering of SEQ ID NO:101, from about position 1065-1085 with reference to amino acid position numbering of SEQ ID NO:114, and/or from about position 1026-1046 with reference to amino acid position numbering of SEQ ID NO:125, optionally, located: at position 965 with reference to amino acid position numbering of SEQ ID NO:71, at position 1033 with reference to amino acid position numbering of SEQ ID NO:87 or SEQ ID NO:88, at position 1091 with reference to amino acid position numbering of SEQ ID NO:101, at position 1075 with reference to amino acid position numbering of SEQ ID NO:114, or at position 1036 with reference to amino acid position numbering of SEQ ID NO:125.

A thirteenth aspect provides a method of detecting a mutant BRI1 gene, the method comprising detecting in the genome of a plant an endogenous BRI1 gene encoding a BRI1 polypeptide comprising a mutation in a kinase domain, optionally wherein the kinase domain is located in a region of the BRI1 polypeptide located: (a) from about position 929-1002, 942-994, 949-987, 956-975 and/or 960-970 with reference to amino acid position numbering of SEQ ID NO:74 (e.g., SEQ ID NOs:80-84), (b) from about position 997-1070, 1008-1059, 1018-1048, and/or 1028-1039 with reference to amino acid position numbering of SEQ ID NO:90 or SEQ ID NO:91 (e.g., SEQ ID NOs:98-101), (c) from about position 1048-1122, 1068-1102, 1075-1095, 1085-1096 with reference to amino acid position numbering of SEQ ID NO:104 (e.g., SEQ ID NOs:110-114), (d) from about position 1051-1097, 1057-1090, 1064-1082, and/or 1069-1080 with reference to amino acid position numbering of SEQ ID NO:117 (e.g., SEQ ID NOs:122-125), and/or (e) from about position 1000-1073, 1013-1059, 1020-1053, 1027-1046 and/or 1031-1042 with reference to amino acid position numbering of SEQ ID NO:128 (e.g., SEQ ID NOs:101, 134-137).

A fourteenth aspect provides a guide nucleic acid that binds to a target site in a Brassinosteroid Insensitive-1 (BRI1) gene, wherein the target site is in a region of the BRI1 gene located (a) from about nucleotide 3096-3235, 3136-3295, 3156-3275, 3176-3255, and/or 3176-3237 with reference to nucleotide position numbering of SEQ ID NO:69 (e.g., SEQ ID NOs:72-76), (b) from about nucleotide 2784-3023, 2824-2983, 2844-2963, 2864-2943 and/or 2864-2924 with reference to nucleotide position numbering of SEQ ID NO:70 (e.g., SEQ ID NOs:72-76), (c) from about nucleotide 3198-3420, 3238-3380, 3258-3360, 3278-3340 and/or 3291-3327 with reference to nucleotide position numbering of SEQ ID NO:85 (e.g., SEQ ID NOs:89-94), (d) from about nucleotide 1944-2166, 1984-2126, 2004-2106, 2024-2085 and/or 2036-2073 with reference to nucleotide position numbering of SEQ ID NO:86 (e.g., SEQ ID NOs: 89-94), (e) from about nucleotide 3070-3292, 3110-3252, 3130-3232, 3150-3212 and/or 3180-3228 with reference to nucleotide position numbering of SEQ ID NO:99 or SEQ ID NO:100 (e.g., SEQ ID NOs:102-106), (f) from about nucleotide 3109-3331, 3149-3291, 3169-3271, 3189-3251 and/or 3204-3244 with reference to nucleotide position numbering of SEQ ID NO:113 or SEQ ID NO:114 (e.g., SEQ ID NOs:115-118), (g) from about nucleotide 3289-3511, 3329-3471, 3349-3451, 3369-3431 and/or 3381-3419 with reference to nucleotide position numbering of SEQ ID NO:123 (e.g., SEQ ID NOs:126-130) and/or (h) from about nucleotide 2997-3219, 3037-3179, 3057-3159, 3077-3139 and/or 3089-3126 with reference to nucleotide position numbering of SEQ ID NO:124 (e.g., SEQ ID NOs:126-130).

In a fifteenth aspect, a system is provided comprising a guide nucleic acid of the invention and a CRISPR-Cas effector protein that associates with the guide nucleic acid.

In a sixteenth aspect, a gene editing system is provided comprising a CRISPR-Cas effector protein in association with a guide nucleic acid, wherein the guide nucleic acid comprises a spacer sequence that binds to an endogenous Brassinosteroid Insensitive-1 (BRI1) gene.

In a seventeenth aspect, a complex comprising a guide nucleic acid and a CRISPR-Cas effector protein comprising a cleavage domain is provided, wherein the guide nucleic acid binds to a target site in an endogenous Brassinosteroid Insensitive-1 (BRI1) gene, wherein the endogenous BM gene: (a) comprises a sequence having at least 80% sequence identity to the nucleotide sequence of any one of SEQ ID NOs:69, 70, 85, 86, 99, 100, 112, 113, 123, or 124; (b) comprises a region having at least 80% identity to any one of SEQ ID NOs:72-76, 89-94, 102-106, 115-118, or 126-130; (c) encodes an amino acid sequence having at least 80% sequence identity to any one of SEQ ID NOs:71, 87, 88, 101, 114, or 125; and/or (d) encodes an amino acid sequence comprising a region having at least 80% identity to any one of SEQ ID NOs:77-81, 95-98, 107-111, 119-122 or 131-135, wherein the cleavage domain cleaves a target strand in the BRI1 gene.

In an eighteenth aspect, an expression cassette is provided, the expression cassette comprising (a) a polynucleotide encoding CRISPR-Cas effector protein comprising a cleavage domain and (b) a guide nucleic acid that binds to a target site in an endogenous Brassinosteroid Insensitive-1 (BRI1) gene, wherein the guide nucleic acid comprises a spacer sequence that is complementary to and binds to (i) a portion of a nucleic acid having at least 80% sequence identity to any one of the nucleotide sequences of SEQ ID NOs:69, 70, 85, 86, 99, 100, 112, 113, 123, or 124; (ii) a portion of a nucleic acid having at least 80% sequence identity to any one of SEQ ID NOs:72-76, 89-94, 102-106, 115-118, or 126-130; (iii) a portion of a nucleic acid encoding an amino acid sequence having at least 80% sequence identity to any one of SEQ ID NOs:71, 87, 88, 101, 114, or 125; and/or (iv) a portion of a nucleic acid encoding an amino acid sequence having at least 80% identity to any one of SEQ ID NOs:77-81, 95-98, 107-111, 119-122 or 131-135.

In a nineteenth aspect, a nucleic acid encoding a dominant negative mutation or a null mutation of a Brassinosteroid Insensitive-1 (BRI1) polypeptide.

In a twentieth aspect, a modified Brassinosteroid Insensitive-1 (BRI1) polypeptide is provided, the modified BRI1 polypeptide comprising a mutation in an amino acid residue located: from about position 955-975 with reference to amino acid position numbering of SEQ ID NO:71, from about position 1023-1043 with reference to amino acid position numbering of SEQ ID NO:87 or SEQ ID NO:88, from about position 1081-1101 with reference to amino acid position numbering of SEQ ID NO:101, from about position 1065-1085 with reference to amino acid position numbering of SEQ ID NO:114, and/or from about position 1026-1046 with reference to amino acid position numbering of SEQ ID NO:125, optionally, located: at position 965 with reference to amino acid position numbering of SEQ ID NO:71, at position 1033 with reference to amino acid position numbering of SEQ ID NO:87 or SEQ ID NO:88, at position 1091 with reference to amino acid position numbering of SEQ ID NO:101, at position 1075 with reference to amino acid position numbering of SEQ ID NO:114, or at position 1036 with reference to amino acid position numbering of SEQ ID NO:125.

In another aspect, plants are provided that comprise in their genome one or more mutated Brassinosteroid Insensitive-1 (BRI1) genes produced by the methods of the invention.

A further aspect of the invention provides a corn plant or plant part thereof comprising at least one mutation in at least one endogenous Brassinosteroid Insensitive-1 (BRI1) gene having the gene identification number (gene ID) of GRMZM6G437417 (Locus370), optionally wherein the mutation may be a non-natural mutation.

In an additional aspect, a soybean plant or plant part thereof is provided the soybean plant comprising at least one mutation in at least one endogenous Brassinosteroid Insensitive-1 (BRI1) gene having the gene identification number (gene ID) of Glyma.06g147600 (Locus325), Glyma.04g115700 (Locus326), Glyma.06g320600 (Locus327) and/or Glyma.04g218300 (Locus328), optionally wherein the mutation may be a non-natural mutation.

In a further aspect, a guide nucleic acid is provided that binds to a target nucleic acid within a Brassinosteroid Insensitive-1 (BRI1) gene having the gene identification number (gene ID) of GRMZM6G437417 (Locus370), Glyma.06g147600 (Locus325), Glyma.04g115700 (Locus326), Glyma.06g320600 (Locus327) and/or Glyma.04g218300 (Locus328). Further provided are polypeptides, polynucleotides, nucleic acid constructs, expression cassettes and vectors for making a plant of this invention.

These and other aspects of the invention are set forth in more detail in the description of the invention below.

BRIEF DESCRIPTION OF THE SEQUENCES

SEQ ID NOs:1-17 are exemplary Cas12a amino acid sequences useful with this invention.

SEQ ID NOs:18-20 are exemplary Cas12a nucleotide sequences useful with this invention.

SEQ ID NO:21-22 are exemplary regulatory sequences encoding a promoter and intron.

SEQ ID NOs:23-29 are exemplary cytosine deaminase sequences useful with this invention.

SEQ ID NOs:30-40 are exemplary adenine deaminase amino acid sequences useful with this invention.

SEQ ID NO:41 is an exemplary uracil-DNA glycosylase inhibitor (UGI) sequences useful with this invention.

SEQ ID NOs:42-44 provide example peptide tags and affinity polypeptides useful with this invention.

SEQ ID NOs:45-55 provide example RNA recruiting motifs and corresponding affinity polypeptides useful with this invention.

SEQ ID NOs:56-57 are exemplary Cas9 polypeptide sequences useful with this invention.

SEQ ID NOs:58-68 are exemplary Cas9 polynucleotide sequences useful with this invention.

SEQ ID NO:69 is an example BRI1 genomic sequence from corn.

SEQ ID NO:70 is an example BRI1 cDNA sequence from corn.

SEQ ID NO:71 is an example BRI1 polypeptide sequence from corn.

SEQ ID NOs:72-76 are example portions or regions of corn BRI1 genomic and coding sequences.

SEQ ID NOs:77-81 are example portions or regions of a corn BRI1 polypeptide sequence.

SEQ ID NOs:85, 99, 112, and 123 are example BRI1 genomic sequences from soybean.

SEQ ID NO:86 and SEQ ID NO:100 are example BRI1 cDNA sequences from soybean and SEQ ID NO:113 and 1 SEQ ID NO:124, are example BRI1 coding sequences from soybean.

SEQ ID NOs:87, 88, 101, 114, and 125 are example BRI1 polypeptide sequences from soybean.

SEQ ID NOs:89-94, 102-106, 115-118, and 126-130 are example portions or regions of soybean BRI1 genomic and coding sequences.

SEQ ID NOs:95-98, 107-111, 119-122, and 131-135 are example portions or regions of soybean BRI1 polypeptide sequences.

SEQ ID NOs:82-84 and 136-139 are example spacer sequences for nucleic acid guides useful with this invention.

SEQ ID NOs:140-142 are examples of BRI1 genomic sequences that have been edited in soybean as described herein.

SEQ ID NOs:143-145 are examples of BRI1 genomic sequences that have been edited in corn as described herein.

DETAILED DESCRIPTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention.

For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention.

Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 5%, 10%, 15%, 20%, 25%, 50%, 75%, 100%, 150%, 200%, 300%, 400%, 500% or more as compared to a control. For example, a plant comprising a mutation in a Brassinosteroid Insensitive-1 (BRI1) gene as described herein can exhibit an improved yield trait (e.g., one or more improved yield traits; e.g., optionally increased seed size (e.g., seed area and/or seed weight) and/or increased seed oil content and) that is at least about 5% or greater than that of a control plant not comprising the same mutation. A control plant is typically the same plant as the edited plant, but the control plant has not been similarly edited and therefore is devoid of the mutation. A control plant maybe an isogenic plant and/or a wild type plant. Thus, a control plant can be the same breeding line, variety, or cultivar as the subject plant into which a mutation as described herein is introgressed, but the control breeding line, variety, or cultivar is free of the mutation. In some embodiments, a comparison between a plant of the invention and a control plant is made under the same growth conditions, e.g., the same environmental conditions (soil, hydration, light, heat, nutrients, and the like).

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In some embodiments, a mutation may result in a reduction in the amount of a BRI1 polypeptide or BRI1 enzyme activity, e.g., can result in no or essentially no (i.e., an insignificant amount, e.g., less than about 10% or even 5%) detectable activity or amount.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

A "heterologous" or a "recombinant" nucleotide sequence is a nucleotide sequence not naturally associated with a host cell into which it is introduced, including non-naturally occurring multiple copies of a naturally occurring nucleotide sequence. A "heterologous" nucleotide/polypeptide may originate from a foreign species, or, if from the same species, is substantially modified from its native form in composition and/or genomic locus by deliberate human intervention.

A "native" or "wild type" nucleic acid, nucleotide sequence, polypeptide or amino acid sequence refers to a naturally occurring or endogenous nucleic acid, nucleotide sequence, polypeptide or amino acid sequence. In some contexts, a "wild type" nucleic acid is a nucleic acid that is not edited as described herein and can differ from an "endogenous" gene that may be edited as described herein (e.g., a mutated endogenous gene). In some contexts, a "wild type" nucleic acid (e.g., unedited) may be heterologous to the organism in which the wild type nucleic acid is found (e.g., a transgenic organism). As an example, a "wild type endogenous Brassinosteroid Insensitive-1 (BRI1) gene" is a BRI1 gene that is naturally occurring in or endogenous to the reference organism, e.g., a plant, e.g., a soybean plant, a maize plant, and may be subject to modification as described herein, after which, such a modified endogenous gene is no longer wild type.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "null allele" is a nonfunctional allele caused by a genetic mutation that results in a complete lack of production of the corresponding protein or produces a protein that is non-functional.

A "recessive mutation" is a mutation in a gene that produces a phenotype when homozygous but the phenotype is not observable when the locus is heterozygous.

A "dominant mutation" is a mutation in a gene that produces a mutant phenotype in the presence of a non-mutated copy of the gene. A dominant mutation may be a loss or a gain of function mutation, a hypomorphic mutation, a hypermorphic mutation or a weak loss of function or a weak gain of function.

A "dominant negative mutation" is a mutation that produces an altered gene product (e.g., having an aberrant function relative to wild type), which gene product adversely affects the function of the wild-type allele or gene product. For example, a "dominant negative mutation" may block a function of the wild type gene product. A dominant negative mutation may also be referred to as an "antimorphic mutation."

A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wildtype gene product.

A "hypomorphic mutation" is a mutation that results in a partial loss of gene function, which may occur through reduced expression (e.g., reduced protein and/or reduced RNA) or reduced functional performance (e.g., reduced activity), hut not a complete loss of function/activity. A "hypomorphic" allele is a semi-functional allele caused by a genetic mutation that results in production of the corresponding protein that functions at anywhere between 1% and 99% of normal efficiency.

A "hypermorphic mutation" is a mutation that results in increased expression of the gene product and/or increased activity of the gene product.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one (e.g., one or more) progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms "cultivar" and "variety" refer to a group of similar plants that by structural or genetic features and/or performance can be distinguished from other varieties within the same species.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterologous" refers to a nucleotide/polypeptide that originates from a foreign species, or, if from the same species, is substantially modified from its native form in composition and/or genomic locus by deliberate human intervention.

A plant in which at least one (e.g., one or more, e.g., 1, 2, 3, or 4, or more) endogenous BRI1 gene is modified as described herein (e.g., comprises a modification as described herein) may have improved yield traits as compared to a plant that does not comprise the modification in the at least one BRI1 gene. As used herein, "improved yield traits" refers to any plant trait associated with growth, for example, biomass, yield, nitrogen use efficiency (NUE), inflorescence size/weight, fruit yield, fruit quality, fruit size, seed size (e.g., seed area, seed size), seed number, foliar tissue weight, nodulation number, nodulation mass, nodulation activity, number of seed heads, number of tillers, number of branches, number of flowers, number of tubers, tuber mass, bulb mass, number of seeds, total seed mass, rate of leaf emergence, rate of tiller/branch emergence, rate of seedling emergence, length of roots, number of roots, size and/or weight of root mass, or any combination thereof. Thus, in some aspects, "improved yield traits" may include, but is not limited to, increased inflorescence production, increased fruit production (e.g., increased number, weight and/or size of fruit; e.g., increase number, weight, and/or length of ears for, e.g., maize), increased fruit quality, increased number, size and/or weight of roots, increased meristem size, increased seed size (e.g., seed area and/or seed weight), increased biomass, increased leaf size, increased nitrogen use efficiency, increased height, increased internode number and/or increased internode length as compared to a control plant or part thereof (e.g., a plant that does not comprise a mutated endogenous BRI1 nucleic acid (e.g., a mutated BRI1 gene)). In some embodiments, improved yield traits can be expressed as quantity of grain produced per area of land (e.g., bushels per acre of land). In some embodiments, one or more improved yield traits can refer to an increase in seed number.

As used herein, an "increased seed size" can mean a seed that is increased in area. In some embodiments, an seed may be increased in area by up to about 70% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, 50, 51, 52, 53, 54, 55, 56, 57, 58, 59, 60, 61, 62, 63, 64, 65, 66, 67, 68, 69, 70%) as compared to a seed from a control plant (e.g., a plant not comprising the mutation in an endogenous BRI1 gene as described herein). In some embodiments, an seed may be increased in weight by up to about 50% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, or 50%) as compared to a seed from a control plant (e.g., a plant not comprising the mutation in an endogenous BRI1 gene as described herein). In some embodiments, an increase in seed size can include an increase in both seed area and seed size.

As used herein a "control plant" means a plant that does not contain an edited BRI1 gene or genes as described herein that imparts an enhanced/improved trait (e.g., yield trait) or altered phenotype. A control plant is used to identify and select a plant edited as described herein and that has an enhanced trait or altered phenotype as compared to the control plant. A suitable control plant can be a plant of the parental line used to generate a plant comprising a mutated BRI1 gene(s), for example, a wild type plant devoid of an edit in an endogenous BRI1 gene as described herein. A suitable control plant can also be a plant that contains recombinant nucleic acids that impart other traits, for example, a transgenic plant having enhanced herbicide tolerance. A suitable control plant can in some cases be a progeny of a heterozygous or hemizygous transgenic plant line that is devoid of the mutated BRI1 gene as described herein, known as a negative segregant, or a negative isogenic line.

An enhanced trait (e.g., improved yield trait) may include, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, increased yield, increased nitrogen use efficiency, and increased water use efficiency as compared to a control plant. An altered phenotype may be, for example, plant height, biomass, canopy area, anthocyanin content, chlorophyll content, water applied, water content, and water use efficiency.

In some embodiments, a plant of this invention may comprise one or more improved yield traits including, but not limited to, higher yield (bu/acre), increased biomass, increased plant height, increased stem diameter, increased leaf area, increased number of flowers, increased kernel row number, optionally wherein ear length is not substantially reduced, increased kernel number, increased kernel size, increased ear length, decreased tiller number, decreased tassel branch number, increased number of pods, including an increased number of pods per node and/or an increased number of pods per plant, increased number of seeds per pod, increase number of seeds, increased seed size, and/or increased seed weight (e.g., increase in 100-seed weight) as compared to a control plant devoid of the mutation. In some embodiments, a plant of this invention may comprise one or more improved yield traits including, but not limited to, increased kernel row number (wherein ear length is not substantially reduced), increased ear length, increased number of pods and/or an increased number of seeds.

As used herein a "trait" is a physiological, morphological, biochemical, or physical characteristic of a plant or particular plant material or cell. In some instances, this characteristic is visible to the human eye and can be measured mechanically, such as seed or plant size, weight, shape, form, length, height, growth rate and development stage, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. However, any technique can be used to measure the amount of, the comparative level of, or the difference in any selected chemical compound or macromolecule in the transgenic plants.

As used herein an "enhanced trait" means a characteristic of a plant resulting from mutations in a BRI1 gene(s) as described herein. Such traits include, but are not limited to, an enhanced agronomic trait characterized by enhanced plant morphology, physiology, growth and development, yield, nutritional enhancement, disease or pest resistance, or environmental or chemical tolerance. In some embodiments, an enhanced trait/altered phenotype may be, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, drought tolerance, increased water use efficiency, cold tolerance, increased nitrogen use efficiency, and increased yield. In some embodiments, a trait is increased yield under nonstress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, ear size, ear tip filling, kernel abortion, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), flowering time and duration, ear number, ear size, ear weight, seed number per ear or pod, seed size, composition of seed (starch, oil, protein) and characteristics of seed fill.

Also used herein, the term "trait modification" encompasses altering the naturally occurring trait by producing a detectable difference in a characteristic in a plant comprising a mutation in an endogenous BRI1 gene as described herein relative to a plant not comprising the mutation, such as a wild-type plant, or a negative segregant. In some cases, the trait modification can be evaluated quantitatively. For example, the trait modification can entail an increase or decrease in an observed trait characteristics or phenotype as compared to a control plant. It is known that there can be natural variations in a modified trait. Therefore, the trait modification observed entails a change of the normal distribution and magnitude of the trait characteristics or phenotype in the plants as compared to a control plant.

The present disclosure relates to a plant with improved economically relevant characteristics, more specifically increased yield. More specifically the present disclosure relates to a plant comprising a mutation(s) in a BRI1 gene(s) as described herein, wherein the plant has increased yield as compared to a control plant devoid of said mutation(s). In some embodiments, plants produced as described herein exhibit increased yield or improved yield trait components as compared to a control plant. In some embodiments, a plant of the present disclosure exhibits an improved trait that is related to yield, including but not limited to increased nitrogen use efficiency, increased nitrogen stress tolerance, increased water use efficiency and increased drought tolerance, as defined and discussed infra.

Yield can be defined as the measurable produce of economic value from a crop. Yield can be defined in the scope of quantity and/or quality. Yield can be directly dependent on several factors, for example, the number and size of organs, plant architecture (such as the number of branches, plant biomass, e.g., increased root biomass, steeper root angle and/or longer roots, and the like), flowering time and duration, grain fill period. Root architecture and development, photosynthetic efficiency, nutrient uptake, stress tolerance, early vigor, delayed senescence and functional stay green phenotypes may be factors in determining yield. Optimizing the above-mentioned factors can therefore contribute to increasing crop yield.

Reference herein to an increase/improvement in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens.

"Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination.

"Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor, for example, can be a combination of the ability of seeds to germinate and emerge after planting and the ability of the young plants to grow and develop after emergence. Plants having early vigor also show increased seedling survival and better establishment of the crop, which often results in highly uniform fields with the majority of the plants reaching the various stages of development at substantially the same time, which often results in increased yield. Therefore, early vigor can be determined by measuring various factors, such as kernel weight, percentage germination, percentage emergence, seedling growth, seedling height, root length, root and shoot biomass, canopy size and color and others.

Further, increased yield can also manifest as increased total seed yield, which may result from one or more of an increase in seed biomass (seed weight) due to an increase in the seed weight on a per plant and/or on an individual seed basis an increased number of, for example, flowers/panicles per plant; an increased number of pods; an increased number of nodes; an increased number of flowers ("florets") per panicle/plant; increased seed fill rate; an increased number of filled seeds; increased seed size (length, width, area, perimeter, and/or weight), which can also influence the composition of seeds; and/or increased seed volume, which can also influence the composition of seeds. In one embodiment, increased yield can be increased seed yield, for example, increased seed weight; increased number of filled seeds; and increased harvest index.

Increased yield can also result in modified architecture, or can occur because of modified plant architecture.

Increased yield can also manifest as increased harvest index, which is expressed as a ratio of the yield of harvestable parts, such as seeds, over the total biomass The disclosure also extends to harvestable parts of a plant such as, but not limited to, seeds, leaves, fruits, flowers, bolls, pods, siliques, nuts, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Typically, plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein, "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein, "water deficit" refers to the conditions or environments that provide less than optimal amounts of water needed for adequate/successful growth and development of plants.

As used herein, "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein with respect to nucleic acids, the term "fragment" or "portion" refers to a nucleic acid that is reduced in length relative (e.g., reduced by 1, 2, 3, 4, 5, 6, 7, 8, 9, 10, 11, 12, 13, 14, 15, 16, 17, 18, 19, 20, 20, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, or 900 or more nucleotides or any range or value therein) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a "portion" of a wild type CRISPR-Cas repeat sequence (e.g., a wild type CRISPR-Cas repeat; e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like).

In some embodiments, a nucleic acid fragment or portion may comprise, consist essentially of or consist of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 285, 290, 300, 310, 320, 330, 340, 350, 360, 370, 380, 390, 395, 396, 397, 398, 399, 400, 410, 411, 412, 413, 414, 415, 420, 425, 430, 435, 440, 445, 450 or 500 or more consecutive nucleotides, or any range or value therein, of a nucleic acid encoding a BRI1 polypeptide, optionally a fragment of a BRI1 gene may be about 5, 6, 7, 8, 9, or 10 consecutive nucleotides to about 300, 320, 350, 375, 400 or more consecutive nucleotides in length, may be about 5, 6, 7, 8, 9, 10, 11, 12, 13, 14, 15, 16, 17, 18, 19, or 20 consecutive nucleotides to about 30, 35, 40, 45, 50, 55, 60, 65, 70, 75, 80, 85, 90, 95, or 100 consecutive nucleotides, or about 80, 85, 90, 95, or 100 consecutive nucleotides to about 150, 155, 160, 165, 170, 175, 180, 185, 190, 195, 200, 205, 210, 215, 220, 225, 230 or more consecutive nucleotides in length, or any range or value therein (e.g., a fragment or portion of any one of SEQ ID NOs:69, 70, 85, 86, 99, 100, 112, 113, 123, or 124 (e.g., SEQ ID NOs:72-76, 89-94, 102-106, 115-118, or 126-130).

In some embodiments, a "sequence-specific nucleic acid binding domain" may bind to one or more fragments or portions of nucleotide sequences (e.g., DNA, RNA) encoding, for example, BRI1 polypeptides as described herein.

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, a polypeptide fragment may comprise, consist essentially of or consist of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 260, 270, 280, or 290 or more consecutive amino acids of a reference polypeptide. In some embodiments, a polypeptide fragment may comprise, consist essentially of or consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 or more consecutive amino acid residues, or any range or value therein, of a BRI1 polypeptide (e.g., a fragment or a portion of SEQ ID NOs:71, 87, 88, 101, 114, or 125 (e.g., SEQ ID NOs:77-81, 95-98, 107-111, 119-122 or 131-135).

In some embodiments, a "portion" in reference to a nucleic acid means at least 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 141, 142, 143, 144, 145, 150, 160, 170, 180, 190, 200, 210, 220, 221, 222, 223, 224, 225, 230, 240, 250, 260, 270, 280, 285, 290, 300, 310, 320, 330, 340, 350, 360, 370, 380, 390, 395, 396, 397, 398, 399, 400, 401, 402, 403, 404, 405, 406, 407, 408, 409, 410, 411, 412, 413, 414, 415, 416. 417, 418, 419, 420, 425, 430, 435, 440, 445, 450 or 500 or more consecutive nucleotides from a gene (e.g., consecutive nucleotides from a BRI1 gene) (e.g., a fragment or portion of any one of SEQ ID NOs:69, 70, 85, 86, 99, 100, 112, 113, 123, or 124 (e.g., SEQ ID NOs:72-76, 89-94, 102-106, 115-118, or 126-130).

In some embodiments, a portion or fragment of a BRI1 polypeptide sequence may be about 10 to about 100 or more consecutive amino acid residues in length (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 or more consecutive amino acid residues in length (e.g., a portion of any one of SEQ ID NOs:71, 87, 88, 101, 114, or 125 (e.g., SEQ ID NOs:77-81, 95-98, 107-111, 119-122 or 131-135)).

As used herein with respect to nucleic acids, the term "functional fragment" refers to nucleic acid that encodes a functional fragment of a polypeptide. A "functional fragment" with respect to a polypeptide is a fragment of a polypeptide that retains one or more of the activities of the native reference polypeptide.

The term "gene," as used herein, refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, inversions and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue. A truncation can include a truncation at the C-terminal end of a polypeptide or at the N-terminal end of a polypeptide. A truncation of a polypeptide can be the result of a deletion of the corresponding 5' end or 3' end of the gene encoding the polypeptide. A frameshift mutation can occur when deletions or insertions of one or more base pairs are introduced into a gene, optionally resulting in an out-of-frame mutation or an in-frame mutation. Frameshift mutations in a gene can result in the production of a polypeptide that is longer, shorter or the same length as the wild type polypeptide depending on when the first stop codon occurs following the mutated region of the gene. As an example, an out-of-frame mutation that produces a premature stop codon can produce a polypeptide that is shorter that the wild type polypeptide, or, in some embodiments, the polypeptide may be absent/undetectable. In some embodiments, a mutation may be a DNA inversion, optionally a DNA inversion having a length of about 10 to about 2000 consecutive base pairs.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity) to the comparator nucleotide sequence.

Different nucleic acids or proteins having homology are referred to herein as "homologues." The term homologue includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data*, Part I (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent sequence identity" can refer to the percentage of identical amino acids in an amino acid sequence as compared to a reference polypeptide.

As used herein, the phrase "substantially identical," or "substantial identity" in the context of two nucleic acid molecules, nucleotide sequences, or polypeptide sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, about 100 nucleotides to about 200 nucleotides, about 100 nucleotides to about 300 nucleotides, about 100 nucleotides to about 400 nucleotides, about 100 nucleotides to about 500 nucleotides, about 100 nucleotides to about 600 nucleotides, about 100 nucleotides to about 800 nucleotides, about 100 nucleotides to about 900 nucleotides, or more in length, or any range therein, up to the full length of the sequence. In some embodiments, nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40, 50, 60, 70, or 80 nucleotides or more).

In some embodiments of the invention, the substantial identity exists over a region of consecutive amino acid residues of a polypeptide of the invention that is about 3 amino acid residues to about 20 amino acid residues, about 5 amino acid residues to about 25 amino acid residues, about 7 amino acid residues to about 30 amino acid residues, about 10 amino acid residues to about 25 amino acid residues, about 15 amino acid residues to about 30 amino acid residues, about 20 amino acid residues to about 40 amino acid residues, about 25 amino acid residues to about 40 amino acid residues, about 25 amino acid residues to about 50 amino acid residues, about 30 amino acid residues to about 50 amino acid residues, about 40 amino acid residues to about 50 amino acid residues, about 40 amino acid residues to about 70 amino acid residues, about 50 amino acid residues to about 70 amino acid residues, about 60 amino acid residues to about 80 amino acid residues, about 70 amino acid residues to about 80 amino acid residues, about 90 amino acid residues to about 100 amino acid residues, or more amino acid residues in length, and any range therein, up to the full length of the sequence. In some embodiments, polypeptide sequences can be substantially identical to one another over at least about 8 consecutive amino acid residues (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, 300, 350 or more amino acids in length or more consecutive amino acid residues). In some embodiments, two or more BRI1 polypeptides may be identical or substantially identical (e.g., at least 70% to 99.9% identical; e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% identical or any range or value therein) over at least 10 amino acids to about 350 amino acids or more.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the sequence analysis software distributed under the trade name GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2x SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1x SSC at 45° C. for 15 minutes. An example of a low stringency wash for a duplex of, e.g., more than 100 nucleotides, is 4-6x SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2x (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention (e.g., expression cassettes and/or vectors) may be codon optimized for expression. In some embodiments, the polynucleotides, nucleic acid constructs, expression cassettes, and/or vectors of the editing systems of the invention (e.g., comprising/encoding a sequence-specific nucleic acid binding domain (e.g., a sequence-specific nucleic acid binding domain (e.g., DNA binding domain) from a polynucleotide-guided endonuclease, a zinc finger nuclease, a transcription activator-like effector nuclease (TALEN), an Argonaute protein, and/or a CRISPIR-Cas endonuclease (e.g., CMSPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, the codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acids, polynucleotides, expression cassettes, and/or vectors that have not been codon optimized.

In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a nucleic acid binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

As used herein, the term "linked," or "fused" in reference to polynucleotides, refers to the attachment of one polynucleotide to another. In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g., extension of the hairpin structure in the guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in *Genetic Engineering of Plants*, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. Gene 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. Gene 403:132-142 (2007)) and Pdca1 is induced by salt (Li et al. *Mol Biol. Rep.* 37:1143-1154 (2010)). In some embodiments, a promoter useful with this invention is RNA polymerase II (Pol II) promoter. In some embodiments, a U6 promoter or a 7SL promoter from Zea mays may be useful with constructs of this invention. In some embodiments, the U6c promoter and/or 7SL promoter from Zea mays may be useful for driving expression of a guide nucleic acid. In some embodiments, a U6c promoter, U6i promoter and/or 7SL promoter from Glycine max may be useful with constructs of this invention. In some embodiments, the U6c promoter, U6i promoter and/or 7SL promoter from Glycine max may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) Nature 313:810-812), CaMV 19S promoter (Lawton et al. (1987) *Plant Mol. Biol.* 9:315-324), nos promoter (Ebert et al. (1987) Proc. Natl. Acad. Sci USA 84:5745-5749), Adh promoter (Walker et al. (1987) *Proc. Natl. Acad. Sci. USA* 84:6624-6629), sucrose synthase promoter (Yang & Russell (1990) Proc. Natl. Acad. Sci. USA 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and arabidopsis (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2_USP from maize (Wang et al. *Genome* 60(6):485-495 (2017)), LAT52 and LAT59 from tomato (Twell et al. *Development* 109(3):705-713 (1990)), Zm13 (U.S. Pat. No. 10,421,972), PLA$_2$-δ promoter from arabidopsis (U.S. Pat. No. 7,141,424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology*, 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO* 1 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from Arabidopsis (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron (see, e.g., SEQ ID NO:21 and SEQ ID NO:22).

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a one or more polynucleotides of the invention (e.g., a polynucleotide encoding a sequence-specific nucleic acid binding domain, a polynucleotide encoding a deaminase protein or domain, a polynucleotide encoding a reverse transcriptase protein or domain, a polynucleotide encoding a 5'-3' exonuclease polypeptide or domain, a guide nucleic acid and/or reverse transcriptase (RT) template), wherein polynucleotide(s) is/are operably associated with one or more control sequences (e.g., a promoter, terminator and the like). Thus, in some embodiments, one or more expression cassettes may be provided, which are designed to express, for example, a nucleic acid construct of the invention (e.g., a polynucleotide encoding a sequence-specific nucleic acid binding domain, a polynucleotide encoding a nuclease polypeptide/domain, a polynucleotide encoding a deaminase protein/domain, a polynucleotide encoding a reverse transcriptase protein/domain, a polynucleotide encoding a 5'-3' exonuclease polypeptide/domain, a polynucleotide encoding a peptide tag, and/or a polynucleotide encoding an affinity polypeptide, and the like, or comprising a guide nucleic acid, an extended guide nucleic acid, and/or RT template, and the like). When an expression cassette of the present invention comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter, or they may be different promoters. Thus, a polynucleotide encoding a sequence specific nucleic acid binding domain, a polynucleotide encoding a nuclease protein/domain, a polynucleotide encoding a CRISPR-Cas effector protein/domain, a polynucleotide encoding an deaminase protein/domain, a polynucleotide encoding a reverse transcriptase polypeptide/domain (e.g., RNA-dependent DNA polymerase), and/or a polynucleotide encoding a 5'-3' exonuclease polypeptide/domain, a guide nucleic acid, an extended guide nucleic acid and/or RT template when comprised in a single expression cassette may each be operably linked to a single promoter, or separate promoters in any combination.

An expression cassette comprising a nucleic acid construct of the invention may be chimeric, meaning that at least one (e.g., one or more) of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to, for example, a gene encoding a sequence-specific nucleic acid binding protein, a gene encoding a nuclease, a gene encoding a reverse transcriptase, a gene encoding a deaminase, and the like, or may be native to a host cell, or may be native to another source (e.g., foreign or heterologous to, for example, to a promoter, to a gene encoding a sequence-specific nucleic acid binding protein, a gene encoding a nuclease, a gene encoding a reverse transcriptase, a gene encoding a deaminase, and the like, or to the host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct (e.g., expression cassette(s)) comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or Agrobacterium binary vectors in double or single stranded linear or circular form which may or may not be self-transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g., autonomous replicating plasmid with an origin of replication). Additionally, included are shuttle vectors by which is meant a DNA vehicle capable, naturally or by design, of replication in two different host organisms, which may be selected from actinomycetes and related species, bacteria and eukaryotic (e.g., higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid or polynucleotide of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific nucleic acid binding protein (e.g., polynucleotide-guided endonuclease, a CMSPR-Cas endonuclease (e.g., CMSPR-Cas effector protein), a zinc finger nuclease, a transcription activator-like effector nuclease (TALEN) and/or an Argonaute protein)) and a deaminase or a nucleic acid construct encoding the same, under conditions whereby the sequence-specific nucleic acid binding protein, the reverse transcriptase and/or the deaminase are expressed and the sequence-specific nucleic acid binding protein binds to the target nucleic acid, and the reverse transcriptase and/or deaminase may be fused to either the sequence-specific nucleic acid binding protein or recruited to the sequence-specific nucleic acid binding protein (via, for example, a peptide tag fused to the sequence-specific nucleic acid binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions, and also RNA-protein interactions and chemical interactions may be used for protein-protein and protein-nucleic acid recruitment.

As used herein, "modifying" or "modification" in reference to a target nucleic acid includes editing (e.g., mutating), covalent modification, exchanging/substituting nucleic acids/nucleotide bases, deleting, cleaving, nicking, and/or altering transcriptional control of a target nucleic acid. In some embodiments, a modification may include one or more single base changes (SNPs) of any type.

"Introducing," "introduce," "introduced" (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention. In some embodiments, a host cell or host organism may be transiently transformed with a polynucleotide/nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)). General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via Agrobacterium transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

Phytohormones regulate plant growth and development as well as responses to the changes in the growing environment (for example in response to drought or other abiotic stresses). Phytohormone signals can be modulated through biosynthesis or breakdown of the phytohormone at a metabolic level, or through control of phytohormone signaling. Brassinosteroids are a class of polyhydroxylated steroidal phytohormones that are growth promoting phytohormones in plants. Brassinolide was the first brassinosteroid isolated, and since then, over 70 additional brassinosteroid compounds have been isolated from plants. Brassinosteroid phytohormones have been associated with yield and abiotic stress in plants (Divi and Krishna 2009 *New Biotechnology* 26(3-4), 131-136; Gruszka 2020 *Intl. J. Molecular Sci.* 21(1), 354. Brassinosteroid signaling in plants is tightly controlled by multiple layers of transcriptional and post-transcriptional regulation (Li and Jin 2007 *Trends Plant Sci.* 12(1): 37-41; Gendron and Wang 2007 *Curr. Opin. Plant Biol.* 10(5), 436-441).

The present invention is directed to modification of a brassinosteroid gene, Brassinosteroid Insensitive-1 (BRI1), in plants through editing technology to provide plants that exhibit one or more improved yield traits. Mutations that may be useful for producing plants with one or more improved yield traits include, for example, substitutions, deletions, and/or insertions. In some aspects, a mutation generated by the editing technology can be a point mutation.

In some embodiments, the invention provides a plant or plant part thereof comprising at least one mutation in an endogenous Brassinosteroid Insensitive-1 (BRI1) gene encoding a BRI1 polypeptide (brassinosteroid receptor polypeptide). In some embodiments, the at least one mutation may be a non-natural mutation. In some embodiments, the BRI1 polypeptide comprises a kinase domain, optionally wherein the mutation decreases phosphorylation of the BRI1 kinase domain. In some embodiments, the mutation increases autophosphorylation of the BRI1 polypeptide, optionally increasing brassinosteroid receptor signaling of the encoded BRI1 polypeptide in the presence of a brassinosteroid plant hormone.

As used herein, a "non-natural mutation" refers to a mutation that is generated though human intervention and differs from mutations found in the same gene that have occurred in nature (e.g., occurred naturally)).

In some embodiments, a plant cell is provided, the plant cell comprising an editing system, the editing system comprising: (a) a CRISPR-Cas effector protein; and (b) a guide nucleic acid (e.g., gRNA, gDNA, crRNA, crDNA, sgRNA, sgDNA) comprising a spacer sequence with complementarity to an endogenous target gene encoding a BRI1 protein. The editing system may be used to generate a mutation in the endogenous target gene encoding a BRI1 polypeptide. In some embodiments, the mutation is a non-natural mutation. In some embodiments, a guide nucleic acid of an editing system may comprise the nucleotide sequence (a spacer sequence, e.g., one or more spacers) of any of SEQ ID NOs:82-84 and/or SEQ ID NOs:136-139 (e.g., SEQ ID NO:82 (PWsp1405), SEQ ID NO:83, SEQ ID NO:84 (PWsp3877), SEQ ID NO:136, SEQ ID NO:137 (PWsp1504), SEQ ID NO:138 (PWsp1568), and/or SEQ ID NO:139 (PWsp1569)).

A mutation in a BRI1 gene of the plant, plant part thereof or the plant cell useful for this invention may be any type of mutation, including a base substitution, a base deletion, and/or a base insertion. In some embodiments, a mutation may be a non-natural mutation. In some embodiments, a mutation may comprise a base substitution to an A, a T, a G, or a C, optionally the base substitution may be from an A to a G. In some embodiments, a mutation may be a deletion of at least one base pair (e.g., 1 base pair to about 15 base pairs; e.g., 1, 2, 3, 4, 5, 6, 7, 8, 9, 10, 11, 12, 13, 14, or 15 consecutive base pairs) or an insertion of at least one base pair (e.g., 1 base pair to about 15 base pairs; e.g., 1, 2, 3, 4, 5, 6, 7, 8, 9, 10, 11, 12, 13, 14, or 15 consecutive base pairs), optionally an in-frame deletion or insertion. In some embodiments, a mutation may be a deletion of 3, 6, 9, 12, or 15 consecutive base pairs, optionally resulting in a deletion of one amino acid residue to about 5 consecutive amino acid residues. In some embodiments, a plant, plant part or plant cell comprising a mutation in a BRI1 gene as described herein comprises a nucleic acid sequence having at least 90% sequence identity to any one of SEQ ID NOs:140-145. In some embodiments, the plant, plant part or plant cell comprising a mutation in a BRI1 gene is soybean and mutated BRI1 gene comprises a nucleic acid sequence having at least 90% sequence identity to any one of SEQ ID NOs:140-142. In some embodiments, the plant, plant part or plant cell comprising a mutation in a BRI1 gene is corn and mutated BRI1 gene comprises a nucleic acid sequence having at least 90% sequence identity to any one of SEQ ID NOs:143-145.

In some embodiments, such a deletion or insertion when comprised in a plant can result in the plant exhibiting one or more improved yield traits, as compared to a plant not comprising said deletion. A BRI1 gene may be edited in one or more than one location (and using one or more different editing tools), thereby providing a BRI1 gene comprising one or more than one mutation. In some embodiments, a BRI1 polypeptide mutated as described herein may comprise one or more than one edit that may result in a polypeptide having one or more than one amino acid deletion, optionally wherein the polypeptide comprises 1, 2, 3, 4 or 5 amino acid deletions.

The types of editing tools that may be used to generate these and other mutations in BRI1 genes include any base editors or cutters, which are guided to a target site using spacers having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) complementarity to a portion of a BRI1 gene as described herein.

In some embodiments, a mutation of a BRI1 gene may be within a portion of the endogenous BRI1 gene that encodes the BRI1 polypeptide (e.g., the coding regions (exons)). As an example, the mutation may be in the region of the BRI1 gene that encodes the kinase domain of the BRI1 polypeptide, optionally wherein the mutation results in the BRI1 polypeptide having an amino acid substitution as compared to a wild type mature BRI1 polypeptide.

In some embodiments, a mutation of a BRI1 gene is within a portion or region of the endogenous BRI1 gene located (a) from about position 929-1002, 942-994, 949-987, 956-975 and/or 960-970 with reference to amino acid position numbering of SEQ ID NO:71 (e.g., SEQ ID NOs: 77-81), (b) from about position 997-1070, 1008-1059, 1018-1048, and/or 1028-1039 with reference to amino acid position numbering of SEQ ID NO:87 or SEQ ID NO:88 (e.g., SEQ ID NOs:95-98), (c) from about position 1048-1122, 1068-1102, 1075-1095, 1085-1096 with reference to amino acid position numbering of SEQ ID NO:101 (e.g., SEQ ID NOs:107-111), (d) from about position 1051-1097, 1057-1090, 1064-1082, and/or 1069-1080 with reference to amino acid position numbering of SEQ ID NO:114 (e.g., SEQ ID NOs:119-122), and/or (e) from about position 1000-1073, 1013-1059, 1020-1053, 1027-1046 and/or 1031-1042 with reference to amino acid position numbering of SEQ ID NO:125 (e.g., SEQ ID NOs:98, 131-135).

In some embodiments, the at least one mutation in an endogenous BRI1 gene results in a mutation of one or more amino acid residue(s) located in a region: (a) from about position 929-1002, 942-994, 949-987, 956-975 and/or 960-970 with reference to amino acid position numbering of SEQ ID NO:71 (e.g., SEQ ID NOs:77-81), (b) from about position 997-1070, 1008-1059, 1018-1048, and/or 1028-1039 with reference to amino acid position numbering of SEQ ID NO:87 or SEQ ID NO:88 (e.g., SEQ ID NOs:95-98), (c) from about position 1048-1122, 1068-1102, 1075-1095, 1085-1096 with reference to amino acid position numbering of SEQ ID NO:101 (e.g., SEQ ID NOs:107-111), (d) from about position 1051-1097, 1057-1090, 1064-1082, and/or 1069-1080 with reference to amino acid position numbering of SEQ ID NO:114 (e.g., SEQ ID NOs:119-122), and/or (e) from about position 1000-1073, 1013-1059, 1020-1053, 1027-1046 and/or 1031-1042 with reference to amino acid position numbering of SEQ ID NO:125 (e.g., SEQ ID NOs:98, 131-135). In some embodiments, the at least one mutation may be a non-natural mutation.

In some embodiments, the at least one mutation may result in a substitution of any one or more of the amino acid residues located: from about position 955-975 with reference to amino acid position numbering of SEQ ID NO:71, from about position 1023-1043 with reference to amino acid position numbering of SEQ ID NO:87 or SEQ ID NO:88, from about position 1081-1101 with reference to amino acid position numbering of SEQ ID NO:101, from about position 1065-1085 with reference to amino acid position numbering of SEQ ID NO:114, and/or from about position 1026-1046 with reference to amino acid position numbering of SEQ ID NO:125. In some embodiments, the at least one mutation may result in a substitution of an amino acid residue located: at position 965 with reference to amino acid position numbering of SEQ ID NO:71, at position 1033 with reference to amino acid position numbering of SEQ ID NO:87 or SEQ ID NO:88, at position 1091 with reference to amino acid position numbering of SEQ ID NO:101, at position 1075 with reference to amino acid position numbering of SEQ ID NO:114, or at position 1036 with reference to amino acid position numbering of SEQ ID NO:125, optionally wherein the substitution is a threonine to an alanine (T>A). In some embodiments, the at least one mutation may be a non-natural mutation.

An endogenous BRI1 gene useful with this invention (e.g., an endogenous target gene) encodes a Brassinosteroid Insensitive-1 (BRI1) polypeptide. In some embodiments, an endogenous BRI1 gene (e.g., endogenous target gene) may comprise a nucleic acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) sequence identity to any one SEQ ID NOs:69, 70, 85, 86, 99, 100, 112, 113, 123, or 124, may comprise a region having at least 80% sequence identity to any one of SEQ ID NOs:72-76, 89-94, 102-106, 115-118, or 126-130, may encode a BRI1 polypeptide having at least 80% sequence identity to any one of SEQ ID NOs:71, 87, 88, 101, 114, or 125, and/or may encode a region having at least 80% sequence identity to any one of SEQ ID NOs:77-81, 95-98, 107-111, 119-122 or 131-135.

In some embodiments, a plant (e.g., a corn plant, a soybean plant) comprising at least one (e.g., one or more) mutation as described herein in an endogenous BRI1 exhibits one or more improved yield traits as compared to a plant devoid of the at least one mutation (e.g., an isogenic plant (e.g., wild type unedited plant or a null segregant), optionally wherein the mutation may be a non-natural mutation. In some embodiments, the one or more improved yield traits can include, but is not limited to, higher yield (bu/acre), increased biomass, increased plant height, increased stem diameter, increased leaf area, increased number of flowers, increased kernel row number, optionally wherein ear length is not substantially reduced, increased kernel number, increased kernel size, increased ear length, decreased tiller number, decreased tassel branch number, increased number of pods per node, increased number of pods per plant, increase number of seeds, increased number of seeds per pod, increased seed size, and/or increased seed weight (e.g., increase in 100-seed weight) as compared to a control plant devoid of the at least one mutation. In some embodiments, the one or more improved yield traits may include, but is not limited to, increased kernel row number (wherein ear length is not substantially reduced), increased ear length, increased number of pods and/or an increased number of seeds. In some embodiments, a plant, comprising at least one mutation in a BRI1 gene as described herein and having one or more improved yield traits may comprise a nucleic acid sequence having at least 90% sequence identity to any one of SEQ ID NOs:140-145. In some embodiments, the plant comprising a mutation in a BRI1 gene is soybean and mutated BM gene comprises a nucleic acid sequence having at least 90% sequence identity to any one of SEQ ID NOs:140-142. In some embodiments, the plant comprising a mutation in a BM/gene is corn and mutated BRI1 gene comprises a nucleic acid sequence having at least 90% sequence identity to any one of SEQ ID NOs:143-145.

In some embodiments, a plant may be regenerated from a plant part and/or plant cell of the invention comprising a mutation in a BRI1 gene as described herein, wherein the regenerated plant comprises the mutation in the endogenous BRI1 gene and a phenotype of improvement in one or more yield traits, as compared to a plant devoid of the same mutation in the BRI1 gene.

As used herein, the term "without substantially decreasing the length of the ears" refers to the length of an ear having increased kernel row number as a result of one or more mutations in one or more BRI1 genes as described herein, wherein the length of the ear is not decreased by more than about 5, 6, 7, 8, 9, 10, 11, 12, 13, 14, 15, 16, 17, 18, 19, 20, 21, 22, 23, 24, 25, 26, 27, 28, 29, or 30% as compared to an ear of a plant devoid of the same mutation(s) in the same BRI1 gene(s).

In some embodiments, a plant cell is provided, the plant cell comprising at least one (e.g., one or more) mutation within an endogenous Brassinosteroid Insensitive-1 (BRI1) gene, wherein the mutation is a substitution, insertion, or deletion that is introduced using an editing system that comprises a nucleic acid binding domain that binds to a target site in the endogenous BRI1 gene. In some embodiments, the at least one mutation may be a non-natural mutation. In some embodiments, the substitution, insertion, or deletion results in, for example, an amino acid substitution. In some embodiments, the at least one mutation is a point mutation. In some embodiments, the at least one mutation within the BRI1 gene is an insertion and/or a deletion, optionally the at least one mutation is an in-frame insertion or deletion. In some embodiments, the plant cell comprising at least one mutation in a BRI1 gene as described herein may comprise a nucleic acid sequence having at least 90% (e.g., 90%, 91%, 92%, 93%, 94%, 95%, 96%, 97%, 98%, 99%, 99.5%. 99.9% or 100%) sequence identity to any one of SEQ ID NOs:140-145. In some embodiments, the plant cell comprising a mutation in a BRI1 gene is from soybean and mutated BRI1 gene comprises a nucleic acid sequence having at least 90% sequence identity to any one of SEQ ID NOs:140-142. In some embodiments, the plant cell comprising a mutation in a BRI1 gene is from corn and mutated BRI1 gene comprises a nucleic acid sequence having at least 90% sequence identity to any one of SEQ ID NOs:143-145.

In some embodiments, the target site in the BRI1 gene of the plant cell is within a region of the BRI1 gene located: (a) from about nucleotide 3096-3235, 3136-3295, 3156-3275, 3176-3255, and/or 3176-3237 with reference to nucleotide position numbering of SEQ ID NO:69 (e.g., SEQ ID NOs: 72-76), (b) from about nucleotide 2784-3023, 2824-2983, 2844-2963, 2864-2943 and/or 2864-2924 with reference to nucleotide position numbering of SEQ ID NO:70 (e.g., SEQ ID NOs:72-76), (c) from about nucleotide 3198-3420, 3238-3380, 3258-3360, 3278-3340 and/or 3291-3327 with reference to nucleotide position numbering of SEQ ID NO:85 (e.g., SEQ ID NOs:89-94), (d) from about nucleotide 1944-2166, 1984-2126, 2004-2106, 2024-2085 and/or 2036-2073 with reference to nucleotide position numbering of SEQ ID NO:86 (e.g., SEQ ID NOs:89-94), (e) from about nucleotide 3070-3292, 3110-3252, 3130-3232, 3150-3212 and/or 3180-3228 with reference to nucleotide position numbering of SEQ ID NO:99 or SEQ ID NO:100 (e.g., SEQ ID NOs:102-106), (f) from about nucleotide 3109-3331, 3149-3291, 3169-3271, 3189-3251 and/or 3204-3244 with reference to nucleotide position numbering of SEQ ID NO:113 or SEQ ID NO:114 (e.g., SEQ ID NOs:115-118), (g) from about nucleotide 3289-3511, 3329-3471, 3349-3451, 3369-3431 and/or 3381-3419 with reference to nucleotide position numbering of SEQ ID NO:123 (e.g., SEQ ID NOs:126-130) and/or (h) from about nucleotide 2997-3219, 3037-3179, 3057-3159, 3077-3139 and/or 3089-3126 with reference to nucleotide position numbering of SEQ ID NO:124 (e.g., SEQ ID NOs:126-130). In some embodiments, the target site in the BRI1 gene is within a region of the BRI1 gene that encodes an amino acid sequence comprising the consecutive amino acid residues located: (a) from about position 929-1002, 942-994, 949-987, 956-975 and/or 960-970 with reference to amino acid position numbering of SEQ ID NO:71 (e.g., SEQ ID NOs:77-81), (b) from about position 997-1070, 1008-1059, 1018-1048, and/or 1028-1039 with reference to amino acid position numbering of SEQ ID NO:87 or SEQ ID NO:88 (e.g., SEQ ID NOs:95-98), (c) from about position 1048-1122, 1068-1102, 1075-1095, 1085-1096 with reference to amino acid position numbering of SEQ ID NO:101 (e.g., SEQ ID NOs:107-111), (d) from about position 1051-1097, 1057-1090, 1064-1082, and/or 1069-1080 with reference to amino acid position numbering of SEQ ID NO:114 (e.g., SEQ ID NOs:119-122), and/or (e) from about position 1000-1073, 1013-1059, 1020-1053, 1027-1046 and/or 1031-1042 with reference to amino acid position numbering of SEQ ID NO:125 (e.g., SEQ ID NOs:98, 131-135).

In some embodiments, the mutation is made following cleavage by an editing system that comprises a nuclease and a nucleic acid binding domain that binds to a target site within a sequence having least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) sequence identity to a sequence encoding of any one of SEQ ID NOs:69, 70, 85, 86, 99, 100, 112, 113, 123, or 124, or having at least 80% sequence identity to a sequence encoding any one of SEQ ID NOs:72-76, 89-94, 102-106, 115-118, or 126-130, and the at least one mutation within a BRI1 gene is made following cleavage by the nuclease. In some embodiments, the at least one mutation results in a modified amino acid residue located: at position 965 with reference to amino acid position numbering of SEQ ID NO:71, at position 1033 with reference to amino acid position numbering of SEQ ID NO:87 or SEQ ID NO:88, at position 1091 with reference to amino acid position numbering of SEQ ID NO:101, at position 1075 with reference to amino acid position numbering of SEQ ID NO:114, or at position 1036 with reference to amino acid position numbering of SEQ ID NO:125. In some embodiments, the at least one mutation may be a non-natural mutation.

In some embodiments, the plant cell is regenerated into a plant that comprises the at least one mutation, optionally wherein the plant regenerated from the plant cell exhibits a phenotype of at least one (one or more) improved yield trait when compared to a wild-type plant not comprising/devoid of the allele (e.g., an isogenic wild type plant), optionally wherein the one or more improved yield traits includes, but is not limited to, higher yield (bu/acre), increased biomass, increased plant height, increased stem diameter, increased leaf area, increased number of flowers, increased kernel row number, optionally wherein ear length is not substantially reduced, increased kernel number, increased kernel size, increased ear length, decreased tiller number, decreased tassel branch number, increased number of pods per node, increased number of pods per plant, increase number of seeds, increased number of seeds per pod, increased seed size, and/or increased seed weight (e.g., increase in 100-seed weight) as compared to a control plant devoid of the at least one mutation. In some embodiments, the one or more improved yield traits resulting from a mutation as described herein includes, but is not limited to, increased kernel row number (wherein ear length is not substantially reduced), increased ear length, increased number of pods and/or an increased number of seeds. In some embodiments, a regenerated plant as described herein may comprise a mutated BRI1 gene as described herein optionally wherein the mutated BRI gene comprises a nucleic acid sequence having at least 90% sequence identity to any one of SEQ ID NOs:140-145. In some embodiments, the regenerated plant comprising a mutation in a BRI1 gene is a soybean plant and mutated BRI1 gene comprises a nucleic acid sequence having at least 90% sequence identity to any one of SEQ ID NOs:140-142. In some embodiments, the regenerated plant comprising a mutation in a BRI1 gene is a corn plant and mutated BRI1 gene comprises a nucleic acid sequence having at least 90% sequence identity to any one of SEQ ID NOs:143-145. In some embodiments, the at least one mutation may be a non-natural mutation.

In some embodiments, a method of producing/breeding a transgene-free edited plant (e.g., a corn plant, a soybean plant) is provided, the method comprising: crossing a plant of the present invention (e.g., a plant comprising one or more mutations (e.g., non-natural mutations) in one or more BRI1 genes and having one or more improved yield traits) with a transgene free plant, thereby introducing the mutation into the plant that is transgene-free; and selecting a progeny plant that comprises the mutation and is transgene-free, thereby producing a transgene free edited plant.

Also provided herein is a method of providing a plurality of plants (e.g., corn plants, soybean plants) having one or more improved yield traits, the method comprising planting two or more plants of the invention (e.g., 2, 3, 4, 5, 6, 7, 8, 9, 10, 20, 30, 40, 50, 100, 200, 300, 400, 500, 1000, 2000, 3000, 400, 5000, or 10,000 or more plants comprising one or more mutations (e.g., non-natural mutations) in one or more BRI1 genes and having one or more improved yield traits in a growing area (e.g., a field (e.g., a cultivated field, an agricultural field), a growth chamber, a greenhouse, a recreational area, a lawn, and/or a roadside and the like), thereby providing a plurality of plants having one or more improved yield traits as compared to a plurality of control plants devoid of the mutation.

The invention further provides a method of generating variation in a region of a Brassinosteroid Insensitive-1 (BRI1) polypeptide, comprising: introducing an editing system into a plant cell, wherein the editing system is targeted to a region of a Brassinosteroid Insensitive-1 (BRI1) gene that encodes the region of the BRI1 polypeptide, and contacting the region of the BRI1 gene with the editing system, thereby introducing a mutation into the BRI1 gene and generating variation in the BRI1 polypeptide of the plant cell. In some embodiments, the BRI1 gene comprises a nucleotide sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) sequence identity to any one of SEQ ID NOs:69, 70, 85, 86, 99, 100, 112, 113, 123, or 124 and/or encodes an amino acid sequence having at least 80% sequence identity to any one of SEQ ID NOs:71, 87, 88, 101, 114, or 125, and the mutation is made following cleavage by the editing system that comprises a nuclease and a nucleic acid binding domain that binds to a target site within a sequence having at least 80% sequence identity to any one of the nucleotide sequences of SEQ ID NOs:69, 70, 85, 86, 99, 100, 112, 113, 123, or 124. In some embodiments, the variation that is generated in a BM gene as described herein results in a nucleic acid sequence having at least 90% (90%, 91%, 92%, 93%, 94%, 95%, 96%, 97%, 98%, 99%, 99.5%. 99.9% or 100%) sequence identity to any one of SEQ ID NOs:140-145.

In some embodiments, the region of the BRI1 gene that is targeted for generating variation in a BRI1 polypeptide comprises at least 80% sequence identity to any one of SEQ ID NOs:72-76, 89-94, 102-106, 115-118, or 126-130 and/or is located (a) from about nucleotide 3096-3235, 3136-3295, 3156-3275, 3176-3255, and/or 3176-3237 with reference to nucleotide position numbering of SEQ ID NO:69 (e.g., SEQ ID NOs:72-76), (b) from about nucleotide 2784-3023, 2824-2983, 2844-2963, 2864-2943 and/or 2864-2924 with reference to nucleotide position numbering of SEQ ID NO:70 (e.g., SEQ ID NOs:72-76), (c) from about nucleotide 3198-3420, 3238-3380, 3258-3360, 3278-3340 and/or 3291-3327 with reference to nucleotide position numbering of SEQ ID NO:85 (e.g., SEQ ID NOs:89-94), (d) from about nucleotide 1944-2166, 1984-2126, 2004-2106, 2024-2085 and/or 2036-2073 with reference to nucleotide position numbering of SEQ ID NO:86 (e.g., SEQ ID NOs:89-94), (e) from about nucleotide 3070-3292, 3110-3252, 3130-3232, 3150-3212 and/or 3180-3228 with reference to nucleotide position numbering of SEQ ID NO:99 or SEQ ID NO:100 (e.g., SEQ ID NOs:102-106), (f) from about nucleotide 3109-3331, 3149-3291, 3169-3271, 3189-3251 and/or 3204-3244 with reference to nucleotide position numbering of SEQ ID NO:113 or SEQ ID NO:114 (e.g., SEQ ID NOs:115-118), (g) from about nucleotide 3289-3511, 3329-3471, 3349-3451, 3369-3431 and/or 3381-3419 with reference to nucleotide position numbering of SEQ ID NO:123 (e.g., SEQ ID NOs:126-130) and/or (h) from about nucleotide 2997-3219, 3037-3179, 3057-3159, 3077-3139 and/or 3089-3126 with reference to nucleotide position numbering of SEQ ID NO:124 (e.g., SEQ ID NOs:126-130).

In some embodiments, the region of the BRI1 polypeptide in which variation is generated encodes an amino acid sequence having at least 80% sequence identity to any one of SEQ ID NOs:77-81, 95-98, 107-111, 119-122 or 131-135, and/or encodes a sequence of consecutive amino acid residues located: (a) from about position 929-1002, 942-994, 949-987, 956-975 and/or 960-970 with reference to amino acid position numbering of SEQ ID NO:71 (e.g., SEQ ID NOs:77-81), (b) from about position 997-1070, 1008-1059, 1018-1048, and/or 1028-1039 with reference to amino acid position numbering of SEQ ID NO:87 or SEQ ID NO:88 (e.g., SEQ ID NOs:95-98), (c) from about position 1048-1122, 1068-1102, 1075-1095, 1085-1096 with reference to amino acid position numbering of SEQ ID NO:101 (e.g., SEQ ID NOs:107-111), (d) from about position 1051-1097, 1057-1090, 1064-1082, and/or 1069-1080 with reference to amino acid position numbering of SEQ ID NO:114 (e.g., SEQ ID NOs:119-122), and/or (e) from about position 1000-1073, 1013-1059, 1020-1053, 1027-1046 and/or 1031-1042 with reference to amino acid position numbering of SEQ ID NO:125 (e.g., SEQ ID NOs:98, 131-135).

In some embodiments, a method for editing a specific site in the genome of a plant cell is provided, the method comprising: cleaving, in a site-specific manner, a target site within an endogenous Brassinosteroid Insensitive-1 (BRI1) gene in the plant cell, the endogenous BRI1 gene: (a) comprising a sequence having at least 80% sequence identity to any one of the nucleotide sequences of SEQ ID NOs:69, 70, 85, 86, 99, 100, 112, 113, 123, or 124, (b) comprising a region having at least 80% sequence identity to any one of the nucleotide sequences of SEQ ID NOs:72-76, 89-94, 102-106, 115-118, or 126-130, (c) encoding an amino acid sequence having at least 80% sequence identity to any one of SEQ ID NOs:71, 87, 88, 101, 114, or 125, and/or (d) encoding a region having at least 80% sequence identity to an amino acid sequence of any one of SEQ ID NOs:77-81, 95-98, 107-111, 119-122 or 131-135, thereby generating an edit in the endogenous BRI1 gene of the plant cell and producing a plant cell comprising the edit in the endogenous BRI1 gene.

In some embodiments, the edit results in a mutation, optionally a non-natural mutation, wherein the mutation includes but is not limited to a deletion, substitution, or insertion. In some embodiments, the edit may be a nucleotide substitution of an A to a G (A>G). In some embodiments, an edit results in variation of amino acids in the coding region of the BRI1 polypeptide, optionally in the kinase domain of the BRI1 polypeptide. As an example, an edit may result in variation in a sequence having at least 80% identity to any one of SEQ ID NOs:77-81, 95-98, 107-111, 119-122 or 131-135 and/or in amino acid residues located: (i) from about position 929-1002, 942-994, 949-987, 956-975 and/or 960-970 with reference to amino acid position numbering of SEQ ID NO:71 (e.g., SEQ ID NOs:77-81), (b) from about position 997-1070, 1008-1059, 1018-1048, and/or 1028-1039 with reference to amino acid position numbering of SEQ ID NO:87 or SEQ ID NO:88 (e.g., SEQ ID NOs:95-98), (c) from about position 1048-1122, 1068-1102, 1075-1095, 1085-1096 with reference to amino acid position numbering of SEQ ID NO:101 (e.g., SEQ ID NOs:107-111), (d) from about position 1051-1097, 1057-1090, 1064-1082, and/or 1069-1080 with reference to amino acid position numbering of SEQ ID NO:114 (e.g., SEQ ID NOs:119-122), and/or (e) from about position 1000-1073, 1013-1059, 1020-1053, 1027-1046 and/or 1031-1042 with reference to amino acid position numbering of SEQ ID NO:125 (e.g., SEQ ID NOs:98, 131-135). In some embodiments, the edit produces an amino acid substitution in a BRI1 polypeptide of a Threonine (T) to an Alanine (A). In some embodiments, an edit as described herein results in a mutated BRI1 gene comprising a nucleic acid sequence having at least 90% sequence identity to any one of SEQ ID NOs:140-145.

In some embodiments, a method of editing may further comprise regenerating a plant from the plant cell comprising the edit in the endogenous BRI1 gene, thereby producing a plant comprising the edit in its endogenous BRI1 gene and having a phenotype of one or more improved yield traits when compared to a control plant that is devoid of the edit. In some embodiments, a regenerated plant may comprise a mutated BRI1 gene as described herein, optionally wherein the mutated BRI1 gene comprises a nucleic acid sequence having at least 90% (e.g., 90%, 91%, 92%, 93%, 94%, 95%, 96%, 97%, 98%, 99%, 99.5%. 99.9% or 100%) sequence identity to any one of SEQ ID NOs:140-145. In some embodiments, the regenerated plant comprising a mutation in a BRI1 gene is a soybean plant and mutated BRI1 gene comprises a nucleic acid sequence having at least 90% sequence identity to any one of SEQ ID NOs:140-142. In some embodiments, the regenerated plant comprising a mutation in a BRI1 gene is a corn plant and mutated BRI1 gene comprises a nucleic acid sequence having at least 90% sequence identity to any one of SEQ ID NOs:143-145.

In some embodiments, a method for making a plant is provided, (a) contacting a population of plant cells comprising an endogenous Brassinosteroid Insensitive-1 (BRI1) gene with a nuclease linked to a nucleic acid binding domain (e.g., editing system) that binds to a sequence (i) having at least 80% sequence identity to the nucleotide sequence of any one of SEQ ID NOs:69, 70, 85, 86, 99, 100, 112, 113, 123, or 124, (ii) encoding an amino acid sequence having at least 80% sequence identity to any one of SEQ ID NOs:71, 87, 88, 101, 114, or 125, (iii) encoding an amino acid sequence comprising a region having at least 80% sequence identity to any one of SEQ ID NOs:77-81, 95-98, 107-111, 119-122 or 131-135, and/or (iv) comprising a region having at least 80% identity to any one of SEQ ID NOs:72-76, 89-94, 102-106, 115-118, or 126-130; (b) selecting a plant cell from the population in which an endogenous BRI1 gene has been mutated, thereby producing a plant cell comprising a mutation in the endogenous BRI1 gene; and (c) growing the selected plant cell into a plant. In some embodiments, the plant that is produced comprises a mutated BRI1 gene comprising a nucleic acid sequence having at least 90% sequence identity to any one of SEQ ID NOs:140-145. In some embodiments, the plant comprising a mutation in a BRI1 gene is a soybean plant and mutated BRI1 gene comprises a nucleic acid sequence having at least 90% sequence identity to any one of SEQ ID NOs:140-142. In some embodiments, the plant comprising a mutation in a BRI1 gene is a corn plant and mutated BRI1 gene comprises a nucleic acid sequence having at least 90% sequence identity to any one of SEQ ID NOs:143-145.

In some embodiments, a method of improving one or more yield traits in a plant is provided, the method comprising (a) contacting a plant cell comprising an endogenous Brassinosteroid Insensitive-1 (BRI1) gene with a nuclease targeting the endogenous BRI1 gene, wherein the nuclease is linked to a nucleic acid binding domain (e.g., editing system) that binds to a target site in the endogenous BRI1 gene, wherein the endogenous BRI1 gene:(i) comprises a sequence having at least 80% sequence identity to the nucleotide sequence of any one of SEQ ID NOs:69, 70, 85, 86, 99, 100, 112, 113, 123, or 124; (ii) comprises a region having at least 80% identity to any one of SEQ ID NOs: 72-76, 89-94, 102-106, 115-118, or 126-130; (iii) encodes an amino acid sequence having at least 80% sequence identity to any one of SEQ ID NOs:71, 87, 88, 101, 114, or 125; and/or (iv) encodes an amino acid sequence comprising a region having at least 80% identity to any one of SEQ ID NOs:77-81, 95-98, 107-111, 119-122 or 131-135 to produce a plant cell comprising a mutation in the endogenous BRI1 gene; and (b) growing the plant cell into a plant comprising the mutation in the endogenous BRI1 gene, thereby producing a plant have a mutated endogenous BRI1 gene and one or more improved yield traits. In some embodiments, the plant having one or more improved yield traits comprises a mutated endogenous BRI1 gene having at least 90% sequence identity to any one of SEQ ID NOs:140-145. In some embodiments, the plant having one or more improved yield traits and comprising a mutated BRI1 gene is a soybean plant and the BRI1 gene comprises a nucleic acid sequence having at least 90% sequence identity to any one of SEQ ID NOs:140-142. In some embodiments, the plant having one or more improved yield traits and comprising a mutated BRI1 gene is a corn plant and the BRI1 gene comprises a nucleic acid sequence having at least 90% sequence identity to any one of SEQ ID NOs:143-145.

In some embodiments, a method for producing a plant or part thereof comprising at least one cell having a mutated endogenous BRI1 gene is provided, the method comprising contacting a target site in an endogenous BRI1 gene in the plant or plant part with a nuclease comprising a cleavage domain and a nucleic acid binding domain, wherein the nucleic acid binding domain binds to a target site in the endogenous BRI1 gene, wherein the endogenous BRI1 gene (a) comprises a sequence having at least 80% sequence identity to the nucleotide sequence of any one of SEQ ID NOs:69, 70, 85, 86, 99, 100, 112, 113, 123, or 124; (b) comprises a region having at least 80% identity to any one of SEQ ID NOs:72-76, 89-94, 102-106, 115-118, or 126-130; (c) encodes an amino acid sequence having at least 80% sequence identity to any one of SEQ ID NOs:71, 87, 88, 101, 114, or 125; and/or (d) encodes an amino acid sequence comprising a region having at least 80% identity to any one of SEQ ID NOs:77-81, 95-98, 107-111, 119-122 or 131-135, thereby producing the plant or part thereof comprising at least one cell having a mutation in the endogenous BRI1 gene. In some embodiments, the plant or part thereof comprising at least one cell and having a mutation in the endogenous BRI1 gene comprises a mutated BRI1 gene having at least 90% sequence identity to any one of SEQ ID NOs:140-145. In some embodiments, the plant or part thereof comprising at least one cell with a mutated BRI1 gene is a soybean plant and the mutated BRI1 gene comprises a nucleic acid sequence having at least 90% sequence identity to any one of SEQ ID NOs:140-142. In some embodiments, the plant or part thereof comprising at least one cell with a mutated BRI1 gene is a corn plant and the mutated BRI1 gene comprises a nucleic acid sequence having at least 90% sequence identity to any one of SEQ ID NOs:143-145.

Also provided herein is a method for producing a plant or part thereof comprising a mutated endogenous Brassinosteroid Insensitive-1 (BRI1) gene and exhibiting one or more improved yield traits, the method comprising contacting a target site in an endogenous BRI1 gene in the plant or plant part with a nuclease comprising a cleavage domain and a nucleic acid binding domain, wherein the nucleic acid binding domain binds to a target site in the endogenous BRI1 gene, wherein the endogenous BRI1 gene: (a) comprises a sequence having at least 80% sequence identity to the nucleotide sequence of any one of SEQ ID NOs:69, 70, 85, 86, 99, 100, 112, 113, 123, or 124; (b) comprises a region having at least 80% identity to any one of SEQ ID NOs: 72-76, 89-94, 102-106, 115-118, or 126-130; (c) encodes an amino acid sequence having at least 80% sequence identity to any one of SEQ ID NOs:71, 87, 88, 101, 114, or 125; and/or (d) encodes an amino acid sequence comprising a region having at least 80% identity to any one of SEQ ID NOs:77-81, 95-98, 107-111, 119-122 or 131-135, thereby producing the plant or part thereof comprising an endogenous BRI1 gene having a mutation and exhibiting one or more improved yield traits, optionally wherein the one or more improved yield traits includes, but is not limited to, higher yield (bu/acre), increased biomass, increased plant height, increased stem diameter, increased leaf area, increased number of flowers, increased kernel row number, optionally wherein ear length is not substantially reduced, increased kernel number, increased kernel size, increased ear length, decreased tiller number, decreased tassel branch number, increased number of pods per node, increased number of pods per plant, increase number of seeds, increased number of seeds per pod, increased seed size, and/or increased seed weight (e.g., increase in 100-seed weight) as compared to a control plant devoid of the at least one mutation. In some embodiments, the one or more improved yield traits includes, but not limited to, increased kernel row number (wherein ear length is not substantially reduced), increased ear length, increased number of pods and/or an increased number of seeds. In some embodiments, the plant or part thereof comprising a mutated endogenous BRI1 gene as described herein comprises a nucleic acid sequence having at least 90% sequence identity to any one of SEQ ID NOs:140-145. In some embodiments, the plant or part thereof comprising a mutated endogenous BRI1 gene as described herein is a soybean plant and mutated BRI1 gene comprises a nucleic acid sequence having at least 90% sequence identity to any one of SEQ ID NOs:140-142. In some embodiments, the plant or part thereof comprising a mutated endogenous BRI1 gene as described herein is a corn plant and mutated BRI1 gene comprises a nucleic acid sequence having at least 90% sequence identity to any one of SEQ ID NOs:143-145.

In some embodiments, a nuclease may cleave an endogenous BRI1 gene, thereby introducing the mutation into the endogenous BRI1 gene. A nuclease useful with the invention may be any nuclease that can be utilized to edit/modify a target nucleic acid. Such nucleases include, but are not limited to a zinc finger nuclease, transcription activator-like effector nucleases (TALEN), endonuclease (e.g., Fok1) and/or a CRISPR-Cas effector protein. Likewise, any nucleic acid binding domain useful with the invention may be any DNA binding domain or RNA binding domain that can be utilized to edit/modify a target nucleic acid. Such nucleic acid binding domains include, but are not limited to, a zinc finger, transcription activator-like DNA binding domain (TAL), an argonaute and/or a CRISPR-Cas effector DNA binding domain.

In some embodiments, a nucleic acid binding domain (e.g., DNA binding domain) is comprised in a nucleic acid binding polypeptide. A "nucleic acid binding protein" or "nucleic acid binding polypeptide" as used herein refers to a polypeptide that binds and/or is capable of binding a nucleic acid in a site- and/or sequence-specific manner. In some embodiments, a nucleic acid binding polypeptide may be a sequence-specific nucleic acid binding polypeptide (e.g., a sequence-specific DNA binding domain) such as, but not limited to, a sequence-specific binding polypeptide and/or domain from, for example, a polynucleotide-guided endonuclease, a CRISPR-Cas effector protein (e.g., a CRISPR-Cas endonuclease), a zinc finger nuclease, a transcription activator-like effector nuclease (TALEN) and/or an Argonaute protein. In some embodiments, a nucleic acid binding polypeptide comprises a cleavage polypeptide (e.g., a nuclease polypeptide and/or domain) such as, but not limited to, an endonuclease (e.g., Fok1), a polynucleotide-guided endonuclease, a CRISPR-Cas endonuclease, a zinc finger nuclease, and/or a transcription activator-like effector nuclease (TALEN). In some embodiments, the nucleic acid binding polypeptide associates with and/or is capable of associating with (e.g., forms a complex with) one or more nucleic acid molecule(s) (e.g., forms a complex with a guide nucleic acid as described herein) that can direct or guide the nucleic acid binding polypeptide to a specific target nucleotide sequence (e.g., a gene locus of a genome) that is complementary to the one or more nucleic acid molecule(s) (or a portion or region thereof), thereby causing the nucleic acid binding polypeptide to bind to the nucleotide sequence at the specific target site. In some embodiments, the nucleic acid binding polypeptide is a CRISPR-Cas effector protein as described herein. In some embodiments, reference is made to specifically to a CRISPR-Cas effector protein for simplicity, but a nucleic acid binding polypeptide as described herein may be used. In some embodiments, a polynucleotide and/or a nucleic acid construct of the invention can be an "expression cassette" or can be comprised within an expression cassette. In some embodiments, a method of editing an endogenous BRI1 gene in a plant or plant part is provided, the method comprising contacting a target site in an endogenous BRI1 gene in the plant or plant part with a cytosine base editing system comprising a cytosine deaminase and a nucleic acid binding domain that binds to a target site in the endogenous BRI1 gene, wherein the endogenous BRI1 gene: (a) comprises a sequence having at least 80% sequence identity to the nucleotide sequence of any one of SEQ ID NOs:69, 70, 85, 86, 99, 100, 112, 113, 123, or 124; (b) comprises a region having at least 80% identity to any one of SEQ ID NOs:72-76, 89-94, 102-106, 115-118, or 126-130; (c) encodes an amino acid sequence having at least 80% sequence identity to any one of SEQ ID NOs:71, 87, 88, 101, 114, or 125; and/or (d) encodes an amino acid sequence comprising a region having at least 80% identity to any one of SEQ ID NOs:77-81, 95-98, 107-111, 119-122 or 131-135, thereby editing the endogenous BRI1 gene in the plant or part thereof and producing a plant or part thereof comprising at least one cell having a mutation in the endogenous BRI1 gene.

In some embodiments, a method of editing an endogenous BRI1 gene in a plant or plant part is provided, the method comprising contacting a target site in an BRI1 gene in the plant or plant part with an adenosine base editing system comprising an adenosine deaminase and a nucleic acid binding domain that binds to a target site in the BRI1 gene, the BRI1 gene (a) comprises a sequence having at least 80% sequence identity to the nucleotide sequence of any one of SEQ ID NOs:69, 70, 85, 86, 99, 100, 112, 113, 123, or 124; (b) comprises a region having at least 80% identity to any one of SEQ ID NOs:72-76, 89-94, 102-106, 115-118, or 126-130; (c) encodes an amino acid sequence having at least 80% sequence identity to any one of SEQ ID NOs:71, 87, 88, 101, 114, or 125; and/or (d) encodes an amino acid sequence comprising a region having at least 80% identity to any one of SEQ ID NOs:77-81, 95-98, 107-111, 119-122 or 131-135, thereby editing the endogenous BRI1 gene in the plant or part thereof and producing a plant or part thereof comprising at least one cell having a mutation in the endogenous BRI1 gene.

In some embodiments, a method of creating a mutation in an Brassinosteroid Insensitive-1 (BRI1) gene in a plant is provided, comprising: (a) targeting a gene editing system to a portion of the BRI1 gene that (i) comprises a sequence having at least 80% sequence identity to any one of SEQ ID NOs:72-76, 89-94, 102-106, 115-118, or 126-130; and/or (ii) encodes a sequence having at least 80% identity to any one of SEQ ID NOs:77-81, 95-98, 107-111, 119-122 or 131-135, and (b) selecting a plant that comprises a modified amino acid residue located: from about position 955-975 with reference to amino acid position numbering of SEQ ID NO:71, from about position 1023-1043 with reference to amino acid position numbering of SEQ ID NO:87 or SEQ ID NO:88, from about position 1081-1101 with reference to amino acid position numbering of SEQ ID NO:101, from about position 1065-1085 with reference to amino acid position numbering of SEQ ID NO:114, and/or from about position 1026-1046 with reference to amino acid position numbering of SEQ ID NO:125, optionally, located: at position 965 with reference to amino acid position numbering of SEQ ID NO:71, at position 1033 with reference to amino acid position numbering of SEQ ID NO:87 or SEQ ID NO:88, at position 1091 with reference to amino acid position numbering of SEQ ID NO:101, at position 1075 with reference to amino acid position numbering of SEQ ID NO:114, or at position 1036 with reference to amino acid position numbering of SEQ ID NO:125. In some embodiments, the mutation in a BRI1 gene may comprise a nucleic acid sequence having at least 90% sequence identity to any one of SEQ ID NOs:140-145.

A mutation provided by methods of the invention may be, for example, a non-natural mutation. In some embodiments, the mutation may be a substitution, an insertion and/or a deletion, optionally wherein the insertion or deletion is an in-frame insertion or in-frame deletion. In some embodiments, the mutation may be a deletion of about 1 base pair to about 15 consecutive base pairs, optionally a deletion of a 3, 6, 9, 12, or 15 consecutive base pairs. In some embodiments, a deletion of a 3, 6, 9, 12, or 15 consecutive base pairs results in a deletion of one to about 5 consecutive amino acid residues from a BRI1 polypeptide. In some embodiments, the mutation is in a BRI1 kinase domain encoded by the endogenous BRI1 gene. In some embodiments, BRI1 kinase domain encoded by the BRI1 gene is located (a) from about nucleotide 3156-3275, 3176-3255, and/or 3176-3237 with reference to nucleotide position numbering of SEQ ID NO:69 (e.g., SEQ ID NOs:72-76), (b) from about nucleotide 2844-2963, 2864-2943 and/or 2864-2924 with reference to nucleotide position numbering of SEQ ID NO:70 (e.g., SEQ ID NOs:72-76), (c) from about nucleotide 3258-3360, 3278-3340 and/or 3291-3327 with reference to nucleotide position numbering of SEQ ID NO:85 (e.g., SEQ ID NOs:89-94), (d) from about nucleotide 2004-2106, 2024-2085 and/or 2036-2073 with reference to nucleotide position numbering of SEQ ID NO:86 (e.g., SEQ ID NOs:89-94), (e) from about nucleotide 3130-3232, 3150-3212 and/or 3180-3228 with reference to nucleotide position numbering of SEQ ID NO:99 or SEQ ID NO:100 (e.g., SEQ ID NOs:102-106), (f) from about nucleotide 3169-3271, 3189-3251 and/or 3204-3244 with reference to nucleotide position numbering of SEQ ID NO:113 or SEQ ID NO:114 (e.g., SEQ ID NOs: 115-118), (g) from about nucleotide 3349-3451, 3369-3431 and/or 3381-3419 with reference to nucleotide position numbering of SEQ ID NO:123 (e.g., SEQ ID NOs:126-130) and/or (h) from about nucleotide 3057-3159, 3077-3139 and/or 3089-3126 with reference to nucleotide position numbering of SEQ ID NO:124 (e.g., SEQ ID NOs:126-130).

In some embodiments, the mutation results in a modified amino acid residue located: from about position 955-975 with reference to amino acid position numbering of SEQ ID NO:74, from about position 1023-1043 with reference to amino acid position numbering of SEQ ID NO:90 or SEQ ID NO:91, from about position 1081-1101 with reference to amino acid position numbering of SEQ ID NO:104, from about position 1065-1085 with reference to amino acid position numbering of SEQ ID NO:117, and/or from about position 1026-1046 with reference to amino acid position numbering of SEQ ID NO:128, optionally, located: at position 965 with reference to amino acid position numbering of SEQ ID NO:74, at position 1033 with reference to amino acid position numbering of SEQ ID NO:90 or SEQ ID NO:91, at position 1091 with reference to amino acid position numbering of SEQ ID NO:104, at position 1075 with reference to amino acid position numbering of SEQ ID NO:117, or at position 1036 with reference to amino acid position numbering of SEQ ID NO:128.

In some embodiments, a method of detecting a mutant BRI1 gene is provide, the method comprising detecting in the genome of a plant an endogenous BRI1 gene encoding a BRI1 polypeptide comprising a mutation in a kinase domain, optionally wherein the kinase domain is located in a region of the BRI1 polypeptide located: (a) from about position 929-1002, 942-994, 949-987, 956-975 and/or 960-970 with reference to amino acid position numbering of SEQ ID NO:74 (e.g., SEQ ID NOs:80-84), (b) from about position 997-1070, 1008-1059, 1018-1048, and/or 1028-1039 with reference to amino acid position numbering of SEQ ID NO:90 or SEQ ID NO:91 (e.g., SEQ ID NOs:98-101), (c) from about position 1048-1122, 1068-1102, 1075-1095, 1085-1096 with reference to amino acid position numbering of SEQ ID NO:104 (e.g., SEQ ID NOs:110-114), (d) from about position 1051-1097, 1057-1090, 1064-1082, and/or 1069-1080 with reference to amino acid position numbering of SEQ ID NO:117 (e.g., SEQ ID NOs:122-125), and/or (e) from about position 1000-1073, 1013-1059, 1020-1053, 1027-1046 and/or 1031-1042 with reference to amino acid position numbering of SEQ ID NO:128 (e.g., SEQ ID NOs:101, 134-137). In some embodiments, a method of detecting a mutant BRI1 gene is provide, the method comprising detecting in the genome of a plant a nucleic acid encoding the amino acid sequence of any one of SEQ ID NOs:71, 87, 88, 101, 114, or 125, wherein the amino acid sequence of any one of SEQ ID NOs:71, 87, 88, 101, 114, or 125 comprises a mutation in one or more of the amino acid residues located: from about position 955-975 with reference to amino acid position numbering of SEQ ID NO:74, from about position 1023-1043 with reference to amino acid position numbering of SEQ ID NO:90 or SEQ ID NO:91, from about position 1081-1101 with reference to amino acid position numbering of SEQ ID NO:104, from about position 1065-1085 with reference to amino acid position numbering of SEQ ID NO:117, and/or from about position 1026-1046 with reference to amino acid position numbering of SEQ ID NO:128, optionally, located: at position 965 with reference to amino acid position numbering of SEQ ID NO:74, at position 1033 with reference to amino acid position numbering of SEQ ID NO:90 or SEQ ID NO:91, at position 1091 with reference to amino acid position numbering of SEQ ID NO:104, at position 1075 with reference to amino acid position numbering of SEQ ID NO:117, or at position 1036 with reference to amino acid position numbering of SEQ ID NO:128. In some embodiments, the mutation is the result of a nucleotide substitution of an A to a G (A>G). In some embodiments, a mutated BRI1 polypeptide comprises at least one mutation comprising a substitution of Threonine for an Alanine. In some embodiments, the mutation that is detected may be a non-natural mutation.

In some embodiments, the present invention provides a method of producing a plant comprising a mutation in an endogenous Brassinosteroid Insensitive-1 (BRI1) gene and at least one polynucleotide of interest, the method comprising crossing a plant of the invention comprising at least one mutation in an endogenous BRI1 gene (a first plant) with a second plant that comprises the at least one polynucleotide of interest to produce progeny plants; and selecting progeny plants comprising at least one mutation in the BRI1 gene and the at least one polynucleotide of interest, thereby producing the plant comprising a mutation in an endogenous BRI1 gene and at least one polynucleotide of interest.

The present invention further provides a method of producing a plant comprising a mutation in an endogenous BRI1 gene and at least one polynucleotide of interest, the method comprising introducing at least one polynucleotide of interest into a plant of the present invention comprising at least one mutation in a BRI1 gene, thereby producing a plant comprising at least one mutation in a BRI1 gene and at least one polynucleotide of interest. In some embodiments, the plant is a corn plant. In some embodiments, the plant is a soybean plant.

In some embodiments, also provided is a method of producing a plant comprising a mutation in an endogenous BRI1 gene and exhibiting a phenotype of improved yield traits, improved plant architecture and/or improved defense traits, the method comprising crossing a first plant, which is a plant of the present invention comprising at least one mutation in a BRI1 gene, with a second plant that exhibits a phenotype of improved yield traits, improved plant architecture and/or improved defense traits; and selecting progeny plants comprising the mutation in the BRI1 gene and a phenotype of improved yield traits, improved plant architecture and/or improved defense traits, thereby producing the plant comprising a mutation in an endogenous BRI1 gene and exhibiting a phenotype of improved yield traits, improved plant architecture and/or improved defense traits as compared to a control plant.

Further provided is a method of controlling weeds in a container (e.g., pot, or seed tray and the like), a growth chamber, a greenhouse, a field, a recreational area, a lawn, or on a roadside, the method comprising applying an herbicide to one or more (a plurality) plants of the invention growing in a container, a growth chamber, a greenhouse, a field, a recreational area, a lawn, or on a roadside, thereby controlling the weeds in the container, the growth chamber, the greenhouse, the field, the recreational area, the lawn, or on the roadside in which the one or more plants are growing.

In some embodiments, a method of reducing insect predation on a plant is provided, the method comprising applying an insecticide to one or more plants of the invention, optionally, wherein the one or more plants are growing in a container, a growth chamber, a greenhouse, a field, a recreational area, a lawn, or on a roadside, thereby reducing insect predation on the one or more plants.

In some embodiments, a method of reducing fungal disease on a plant is provided, the method comprising applying a fungicide to one or more plants of the invention, optionally, wherein the one or more plants are growing in a container, a growth chamber, a greenhouse, a field, a recreational area, a lawn, or on a roadside, thereby reducing fungal disease on the one or more plants.

A polynucleotide of interest may be any polynucleotide that can confer a desirable phenotype or otherwise modify the phenotype or genotype of a plant. In some embodiments, a polynucleotide of interest may be polynucleotide that confers herbicide tolerance, insect resistance, nematode resistance, disease resistance, increased yield, increased nutrient use efficiency or abiotic stress resistance.

Thus, plants or plant cultivars which are to be treated with preference in accordance with the invention include all plants which, through genetic modification, received genetic material which imparts particular advantageous useful properties ("traits") to these plants. Examples of such properties are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products.

Further examples of such properties are an increased resistance against animal and microbial pests, such as against insects, arachnids, nematodes, mites, slugs and snails owing, for example, to toxins formed in the plants. Among DNA sequences encoding proteins which confer properties of tolerance to such animal and microbial pests, in particular insects, mention will particularly be made of the genetic material from Bacillus thuringiensis encoding the Bt proteins widely described in the literature and well known to those skilled in the art. Mention will also be made of proteins extracted from bacteria such as Photorhabdus (WO97/17432 and WO98/08932). In particular, mention will be made of the Bt Cry or VIP proteins which include the Cry1A, CryIAb, CryIAc, CryIIA, CryIIIA, CryIIIB2, Cry9c Cry2Ab, Cry3Bb and CryIF proteins or toxic fragments thereof and also hybrids or combinations thereof, especially the Cry1F protein or hybrids derived from a Cry1F protein (e.g. hybrid Cry1A-Cry1F proteins or toxic fragments thereof), the CryIA-type proteins or toxic fragments thereof, preferably the Cry1Ac protein or hybrids derived from the Cry1Ac protein (e.g. hybrid Cry1Ab-Cry1Ac proteins) or the Cry1Ab or Bt2 protein or toxic fragments thereof, the Cry2Ae, Cry2Af or Cry2Ag proteins or toxic fragments thereof, the CryIA.105 protein or a toxic fragment thereof, the VIP3Aa19 protein, the VIP3Aa20 protein, the VIP3A proteins produced in the COT202 or COT203 cotton events, the VIP3Aa protein or a toxic fragment thereof as described in Estruch et al. (1996), Proc Natl Acad Sci USA. 28; 93(11):5389-94, the Cry proteins as described in WO2001/47952, the insecticidal proteins from *Xenorhabdus* (as described in WO98/50427), Serratia (particularly from *S. entomophila*) or *Photorhabdus* species strains, such as Tc-proteins from *Photorhabdus* as described in WO98/08932. Also any variants or mutants of any one of these proteins differing in some amino acids (1-10, preferably 1-5) from any of the above named sequences, particularly the sequence of their toxic fragment, or which are fused to a transit peptide, such as a plastid transit peptide, or another protein or peptide, is included herein.

Another and particularly emphasized example of such properties is conferred tolerance to one or more herbicides, for example imidazolinones, sulphonylureas, glyphosate or phosphinothricin. Among DNA sequences encoding proteins (i.e., polynucleotides of interest) which confer properties of tolerance to certain herbicides on the transformed plant cells and plants, mention will be particularly be made to the bar or PAT gene or the *Streptomyces coelicolor* gene described in WO2009/152359 which confers tolerance to glufosinate herbicides, a gene encoding a suitable EPSPS (5-Enolpyruvylshikimat-3-phosphat-Synthase) which confers tolerance to herbicides having EPSPS as a target, especially herbicides such as glyphosate and its salts, a gene encoding glyphosate-n-acetyltransferase, or a gene encoding glyphosate oxidoreductase. Further suitable herbicide tolerance traits include at least one ALS (acetolactate synthase) inhibitor (e.g., WO2007/024782), a mutated Arabidopsis ALS/AHAS gene (e.g., U.S. Pat. No. 6,855,533), genes encoding 2,4-D-monooxygenases conferring tolerance to 2,4-D (2,4-dichlorophenoxyacetic acid) and genes encoding Dicamba monooxygenases conferring tolerance to dicamba (3,6-dichloro-2-methoxybenzoic acid).

Further examples of such properties are increased resistance against phytopathogenic fungi, bacteria and/or viruses owing, for example, to systemic acquired resistance (SAR), systemin, phytoalexins, elicitors and also resistance genes and correspondingly expressed proteins and toxins.

Particularly useful transgenic events in transgenic plants or plant cultivars which can be treated with preference in accordance with the invention include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946);

Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US-A 2005-216969); Event 3006-210-23 (cotton, insect control—herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control—herbicide tolerance, deposited as ATCC PTA-11508, described in WO 11/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLR1 (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480);); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control—herbicide tolerance, deposited as ATCC PTA 11384, described in US-A 2006-070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-I (brinjal, insect control, not deposited, described in WO 07/091277); Event Fil 17 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO98/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLINI (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait—herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control—herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MS1 1 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control—herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control—herbicide tolerance, not deposited, described in US-A 2005-039226 or WO2004/099447); Event VIP1034 (corn, insect control—herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession N° PTA-11041) optionally stacked with event EE-GM1/LL27 or event EE-GM2/LL55 (WO2011/063413A2), event DAS-68416-4 (soybean, herbicide tolerance, ATCC Accession N° PTA-10442, WO2011/066360A1), event DAS-68416-4 (soybean, herbicide tolerance, ATCC Accession N° PTA-10442, WO2011/066384A1), event DP-040416-8 (corn, insect control, ATCC Accession N° PTA-11508, WO2011/075593A1), event DP-043A47-3 (corn, insect control, ATCC Accession N° PTA-11509, WO2011/075595A1), event DP-004114-3 (corn, insect control, ATCC Accession N° PTA-11506, WO2011/084621A1), event DP-032316-8 (corn, insect control, ATCC Accession N° PTA-11507, WO2011/084632A1), event MON-88302-9 (oilseed rape, herbicide tolerance, ATCC Accession N° PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession N°. PTA-10296, WO2012/051199A2), event DAS-44406-6 (soybean, stacked herbicide tolerance, ATCC Accession N°. PTA-11336, WO2012/075426A1), event DAS-14536-7 (soybean, stacked herbicide tolerance, ATCC Accession N°. PTA-11335, WO2012/075429A1), event SYN-000H2-5 (soybean, herbicide tolerance, ATCC Accession N°. PTA-11226, WO2012/082548A2), event DP-061061-7 (oilseed rape, herbicide tolerance, no deposit N° available, WO2012071039A1), event DP-073496-4 (oilseed rape, herbicide tolerance, no deposit N° available, US2012131692), event 8264.44.06.1 (soybean, stacked herbicide tolerance, Accession N° PTA-11336, WO2012075426A2), event 8291.45.36.2 (soybean, stacked herbicide tolerance, Accession N°. PTA-11335, WO2012075429A2), event SYHT0H2 (soybean, ATCC Accession N°. PTA-11226, WO2012/082548A2), event MON88701 (cotton, ATCC Accession N° PTA-11754, WO2012/134808A1), event KK179-2 (alfalfa, ATCC Accession N° PTA-11833, WO2013/003558A1), event pDAB8264.42.32.1 (soybean, stacked herbicide tolerance, ATCC Accession N° PTA-11993, WO2013/010094A1), event MZDTO9Y (corn, ATCC Accession N° PTA-13025, WO2013/012775A1).

The genes/events (e.g., polynucleotides of interest), which impart the desired traits in question, may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails, as well as the increased resistance of the plants to one or more herbicides.

Commercially available examples of such plants, plant parts or plant seeds that may be treated with preference in accordance with the invention include commercial products, such as plant seeds, sold or distributed under the GENUITY®, DROUGHTGARD®, SMARTSTAX®, RIB COMPLETE®, ROUNDUP READY®, VT DOUBLE PRO®, VT TRIPLE PRO®, BOLLGARD II®, ROUNDUP READY 2 YIELD®, YIELDGARD®, ROUNDUP READY® 2 XTEND™, INTACTA RR2 PRO®, VISTIVE GOLD®, and/or XTENDFLEX™ trade names.

A BRI1 gene useful with this invention includes any BRI1 gene in which a mutation as described herein can confer improvement in one or more yield traits in a plant or part thereof comprising the mutation. In some embodiments, an endogenous BRI1 gene (a) comprises a sequence having at least 80% sequence identity to the nucleotide sequence of any one of SEQ ID NOs:69, 70, 85, 86, 99, 100, 112, 113, 123, or 124; (b) comprises a region having at least 80% identity to any one of SEQ ID NOs:72-76, 89-94, 102-106, 115-118, or 126-130; (c) encodes an amino acid sequence having at least 80% sequence identity to any one of SEQ ID NOs:71, 87, 88, 101, 114, or 125; and/or (d) encodes an amino acid sequence comprising a region having at least 80% identity to any one of SEQ ID NOs:77-81, 95-98, 107-111, 119-122 or 131-135.

In some embodiments, the at least one mutation in an endogenous BRI1 gene in a plant may be a base substitution, a base deletion and/or a base insertion, optionally wherein the mutation may be a non-natural mutation. In some embodiments, the at least one mutation in an endogenous BRI1 gene in a plant may result in a plant having the phenotype of one or more improved yield traits as compared to a control plant devoid of the edit/mutation, optionally wherein the improved yield trait can include but is not limited to, higher yield (bu/acre), increased biomass, increased plant height, increased stem diameter, increased leaf area, increased number of flowers, increased kernel row number, optionally wherein ear length is not substantially reduced, increased kernel number, increased kernel size, increased ear length, decreased tiller number, decreased tassel branch number, increased number of pods per node, increased number of pods per plant, increase number of seeds, increased number of seeds per pod, increased seed size, and/or increased seed weight (e.g., increase in 100-seed weight). In some embodiments, the one or more improved yield traits includes, but not limited to, increased kernel row number (wherein ear length is not substantially reduced), increased ear length, increased number of pods and/or an increased number of seeds. In some embodiments, a mutation in an endogenous BRI1 gene may be a base substitution, a base deletion and/or a base insertion of at least 1 nucleotide to about 15 nucleotides (e.g., about 1, 2, 3, 4, 5, 6, 7, 8, 9, 10, 11, 12, 13, 14, or 15 nucleotides, or any range or value therein), optionally where the mutation may result in a substitution, a deletion and/or an insertion of one or more amino acid residues (e.g., 1, 2, 3, 4, or 5 amino acids) of the BRI1 polypeptide. In some embodiments, the at least one mutation may be a base substitution to an A, a T, a G, or a C. In some embodiments, the at least one mutation may be, for example, a base substitution to from an A to a G (A>G). A mutation may be a point mutation. In some embodiments, the mutation may result in a substituted amino acid residue located from about position 955-975 with reference to amino acid position numbering of SEQ ID NO:71, from about position 1023-1043 with reference to amino acid position numbering of SEQ ID NO:87 or SEQ ID NO:88, from about position 1081-1101 with reference to amino acid position numbering of SEQ ID NO:103, from about position 1065-1085 with reference to amino acid position numbering of SEQ ID NO:114, and/or from about position 1026-1046 with reference to amino acid position numbering of SEQ ID NO:125, optionally, located: at position 965 with reference to amino acid position numbering of SEQ ID NO:71, at position 1033 with reference to amino acid position numbering of SEQ ID NO:87 or SEQ ID NO:88, at position 1091 with reference to amino acid position numbering of SEQ ID NO:103, at position 1075 with reference to amino acid position numbering of SEQ ID NO:114, or at position 1036 with reference to amino acid position numbering of SEQ ID NO:125.

In some embodiments, a mutation in an endogenous BRI1 gene may be made following cleavage by an editing system that comprises a nuclease and a nucleic acid binding domain that binds to a target site within a target nucleic acid (e.g., a BRI1 gene), the target nucleic acid comprising a sequence having at least 80% sequence identity to any one of the nucleotide sequences of SEQ ID NOs:69, 70, 85, 86, 99, 100, 112, 113, 123, or 124, and/or encoding an amino acid sequence having at least 80% sequence identity to any one of SEQ ID NOs:71, 87, 88, 101, 114, or 125, optionally wherein the target site is located in a region of the BRI1 gene: the region comprising a sequence having at least 80% identity to any one of SEQ ID NOs:72-76, 89-94, 102-106, 115-118, or 126-130 and/or encoding a sequence having at least 80% sequence identity to an amino acid sequence of any one of SEQ ID NOs:77-81, 95-98, 107-111, 119-122 or 131-135.

Further provided are guide nucleic acids (e.g., gRNA, gDNA, crRNA, crDNA) that bind to a target site in a Brassinosteroid Insensitive-1 (BRI1) gene, wherein the target site is in a region of the BRI1 gene located (a) from about 3096-3235, 3136-3295, 3156-3275, 3176-3255, and/or 3176-3237 with reference to nucleotide position numbering of SEQ ID NO:69 (e.g., SEQ ID NOs:72-76), (b) from about nucleotide 2784-3023, 2824-2983, 2844-2963, 2864-2943 and/or 2864-2924 with reference to nucleotide position numbering of SEQ ID NO:70 (e.g., SEQ ID NOs:72-76), (c) from about nucleotide 3198-3420, 3238-3380, 3258-3360, 3278-3340 and/or 3291-3327 with reference to nucleotide position numbering of SEQ ID NO:85 (e.g., SEQ ID NOs:89-94), (d) from about nucleotide 1944-2166, 1984-2126, 2004-2106, 2024-2085 and/or 2036-2073 with reference to nucleotide position numbering of SEQ ID NO:86 (e.g., SEQ ID NOs:89-94), (e) from about nucleotide 3070-3292, 3110-3252, 3130-3232, 3150-3212 and/or 3180-3228 with reference to nucleotide position numbering of SEQ ID NO:99 or SEQ ID NO:100 (e.g., SEQ ID NOs:102-106), (0 from about nucleotide 3109-3331, 3149-3291, 3169-3271, 3189-3251 and/or 3204-3244 with reference to nucleotide position numbering of SEQ ID NO:113 or SEQ ID NO:114 (e.g., SEQ ID NOs:115-118), (g) from about nucleotide 3289-3511, 3329-3471, 3349-3451, 3369-3431 and/or 3381-3419 with reference to nucleotide position numbering of SEQ ID NO:123 (e.g., SEQ ID NOs:126-130) and/or (h) from about nucleotide 2997-3219, 3037-3179, 3057-3159, 3077-3139 and/or 3089-3126 with reference to nucleotide position numbering of SEQ ID NO:124 (e.g., SEQ ID NOs:126-130). In some embodiments, the guide nucleic acid comprises a spacer comprising any one of the nucleotide sequences of SEQ ID NOs:82-84 and/or SEQ ID NOs:136-139.

In some embodiments, a corn plant or plant part thereof is provided comprising at least one mutation in at least one endogenous Brassinosteroid Insensitive-1 (BRI1) gene having the gene identification number (gene ID) of GRMZM6G437417 (Locus370), optionally wherein the mutation may be a non-natural mutation.

In some embodiments, a soybean plant or plant part thereof is provided comprising at least one mutation in at least one endogenous Brassinosteroid Insensitive-1 (BRI1) gene having the gene identification number (gene ID) of Glyma.06g147600 (Locus325), Glyma.04g115700 (Locus326), Glyma.06g320600 (Locus327) and/or Glyma.04g218300 (Locus328), optionally wherein the mutation may be a non-natural mutation.

In some embodiments, a guide nucleic acid is provided that binds to a target nucleic acid in a Brassinosteroid Insensitive-1 (BRI1) gene having the gene identification number (gene ID) of GRMZM6G437417 (Locus370), Glyma.06g147600 (Locus325), Glyma.04g115700 (Locus326), Glyma.06g320600 (Locus327) and/or Glyma.04g218300 (Locus328).

In some embodiments, a system is provided comprising a guide nucleic acid comprising a spacer (e.g., one or more spacers) having the nucleotide sequence of any one of SEQ ID NOs:82-84 and/or SEQ ID NOs:136-139, and a CRISPR-Cas effector protein that associates with the guide nucleic acid. In some embodiments, the system may further comprise a tracr nucleic acid that associates with the guide nucleic acid and a CRISPR-Cas effector protein, optionally wherein the tracr nucleic acid and the guide nucleic acid are covalently linked.

As used herein, "a CRISPR-Cas effector protein in association with a guide nucleic acid" refers to the complex that is formed between a CRISPR-Cas effector protein and a guide nucleic acid in order to direct the CRISPR-Cas effector protein to a target site in a gene.

The invention further provides a gene editing system comprising a CRISPR-Cas effector protein in association with a guide nucleic acid and the guide nucleic acid comprises a spacer sequence that binds to a Brassinosteroid Insensitive-1 (BRI1) gene, optionally wherein the BRI1 gene (a) comprises a sequence having at least 80% sequence identity to the nucleotide sequence of any one of SEQ ID NOs:69, 70, 85, 86, 99, 100, 112, 113, 123, or 124; (b) comprises a region having at least 80% identity to any one of SEQ ID NOs:72-76, 89-94, 102-106, 115-118, or 126-130; (c) encodes an amino acid sequence having at least 80% sequence identity to any one of SEQ ID NOs:71, 87, 88, 101, 114, or 125; and/or (d) encodes an amino acid sequence comprising a region having at least 80% identity to any one of SEQ ID NOs:77-81, 95-98, 107-111, 119-122 or 131-135. In some embodiments, a spacer sequence of the guide nucleic acid may comprise the nucleotide sequence of any of SEQ ID NOs:82-84 and/or SEQ ID NOs:136-139. In some embodiments, the gene editing system may further comprise a tracr nucleic acid that associates with the guide nucleic acid and a CRISPR-Cas effector protein, optionally wherein the tracr nucleic acid and the guide nucleic acid are covalently linked.

The present invention further provides a complex comprising a CRISPR-Cas effector protein comprising a cleavage domain and a guide nucleic acid, wherein the guide nucleic acid binds to a target site in an endogenous Brassinosteroid Insensitive-1 (BRI1) gene, wherein the endogenous BRI1 gene(a) comprises a sequence having at least 80% sequence identity to the nucleotide sequence of any one of SEQ ID NOs:69, 70, 85, 86, 99, 100, 112, 113, 123, or 124; (b) comprises a region having at least 80% identity to any one of SEQ ID NOs:72-76, 89-94, 102-106, 115-118, or 126-130; (c) encodes an amino acid sequence having at least 80% sequence identity to any one of SEQ ID NOs:71, 87, 88, 101, 114, or 125; and/or (d) encodes an amino acid sequence comprising a region having at least 80% identity to any one of SEQ ID NOs:77-81, 95-98, 107-111, 119-122 or 131-135, wherein the cleavage domain cleaves a target strand in the BRI1 gene.

In some embodiments, an expression cassette(s) is/are provided that comprise (a) a polynucleotide encoding CRISPR-Cas effector protein comprising a cleavage domain and (b) a guide nucleic acid that binds to a target site in an endogenous Brassinosteroid Insensitive-1 (BRI1) gene, wherein the guide nucleic acid comprises a spacer sequence that is complementary to and binds to (i) a portion of a nucleic acid having at least 80% sequence identity to any one of the nucleotide sequences of SEQ ID NOs:69, 70, 85, 86, 99, 100, 112, 113, 123, or 124; (ii) a portion of a nucleic acid having at least 80% sequence identity to any one of SEQ ID NOs:72-76, 89-94, 102-106, 115-118, or 126-130; (iii) a portion of a nucleic acid encoding an amino acid sequence having at least 80% sequence identity to any one of SEQ ID NOs:71, 87, 88, 101, 114, or 125; and/or (iv) a portion of a nucleic acid encoding an amino acid sequence having at least 80% identity to any one of SEQ ID NOs: 77-81, 95-98, 107-111, 119-122 or 131-135.

In some embodiments a modified Brassinosteroid Insensitive-1 (BRI1) polypeptide is provided comprising a mutation in an amino acid residue located: from about position 955-975 with reference to amino acid position numbering of SEQ ID NO:71, from about position 1023-1043 with reference to amino acid position numbering of SEQ ID NO:87 or SEQ ID NO:88, from about position 1081-1101 with reference to amino acid position numbering of SEQ ID NO:101, from about position 1065-1085 with reference to amino acid position numbering of SEQ ID NO:114, and/or from about position 1026-1046 with reference to amino acid position numbering of SEQ ID NO:125, optionally, located: at position 965 with reference to amino acid position numbering of SEQ ID NO:71, at position 1033 with reference to amino acid position numbering of SEQ ID NO:87 or SEQ ID NO:88, at position 1091 with reference to amino acid position numbering of SEQ ID NO:101, at position 1075 with reference to amino acid position numbering of SEQ ID NO:114, or at position 1036 with reference to amino acid position numbering of SEQ ID NO:125. Also provided are nucleic acids encoding mutated BRI1 polypeptides, optionally wherein when present in a plant or plant part the mutated BRI1 polypeptide/BRI1 gene results in the plant comprising a phenotype of one or more improved yield traits as compared to a plant or plant part not devoid of the mutation.

Nucleic acid constructs of the invention (e.g., a construct comprising a sequence specific nucleic acid binding domain (e.g., sequence specific DNA binding domain), a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids (e.g., endogenous BRI1 genes) and/or their expression.

Any plant comprising an endogenous BRI1 gene that is capable of conferring at least one improved yield trait when modified as described herein may be modified (e.g., mutated, e.g., base edited, cleaved, nicked, etc.) as described herein (e.g., using the polypeptides, polynucleotides, RNPs, nucleic acid constructs, expression cassettes, and/or vectors of the invention) to improve one or more yield traits in the plant. A plant exhibiting an improved yield trait may show an improvement of about 5% to about 100% (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% or more or any range or value therein; e.g., about 5% to about 10%, about 5% to about 15%, about 5% to about 20%, about 10% to about 50%, about 10% to about 80%, about 10% to about 90%, about 10% to about 100%, about 20% to about 50%, about 20% to about 80%, about 20% to about 90%, about 20% to about 100%, about 30% to about 50%, about 30% to about 80%, about 30% to about 90%, about 30% to about 100%, about 50% to about 100%, about 75% to about 100% or more, and any range or value therein) in the yield trait as compared to a plant or part thereof that is devoid of the mutated endogenous BRI1 gene.

An editing system useful with this invention can be any site-specific (sequence-specific) genome editing system now known or later developed, which system can introduce mutations in a target specific manner. For example, an editing system (e.g., site- or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or more polypeptides and/or one or more polynucleotides that when expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (DNA binding domain), a nuclease, and/or other polypeptide, and/or a polynucleotide.

In some embodiments, an editing system can comprise one or more sequence-specific nucleic acid binding domains (DNA binding domains) that can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRiSPR-Cas endonuclease (e.g., CRISPR-Cas effector protein), a zinc finger nuclease, and/or a transcription activator-like effector nuclease (TALEN). In some embodiments, an editing system can comprise one or more polypeptides that include, but are not limited to, a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but is not limited to, a CRISPR array (CRISPR guide) nucleic acid, extended guide nucleic acid, and/or a reverse transcriptase template.

In some embodiments, a method of modifying or editing a Brassinosteroid Insensitive-1 (BRI1) gene may comprise contacting a target nucleic acid (e.g., a nucleic acid encoding a BRI1 polypeptide) with a base-editing fusion protein (e.g., a sequence specific DNA binding protein (e.g., a CRISPR-Cas effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing a locus within the target nucleic acid. In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific nucleic acid binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, a method of modifying or editing a Brassinosteroid Insensitive-1 (BRI1) gene may comprise contacting a target nucleic acid (e.g., a nucleic acid encoding a BRI1 polypeptide) with a sequence-specific nucleic acid binding fusion protein (e.g., a sequence-specific DNA binding protein (e.g., a CRISPR-Cas effector protein or domain) fused to a peptide tag, a deaminase fusion protein comprising a deaminase domain (e.g., an adenine deaminase and/or a cytosine deaminase) fused to an affinity polypeptide that is capable of binding to the peptide tag, and a guide nucleic acid, wherein the guide nucleic acid is capable of guiding/targeting the sequence-specific nucleic acid binding fusion protein to the target nucleic acid and the sequence-specific nucleic acid binding fusion protein is capable of recruiting the deaminase fusion protein to the target nucleic acid via the peptide tag-affinity polypeptide interaction, thereby editing a locus within the target nucleic acid. In some embodiments, the sequence-specific nucleic acid binding fusion protein may be fused to the affinity polypeptide that binds the peptide tag and the deaminase may be fused to the peptide tag, thereby recruiting the deaminase to the sequence-specific nucleic acid binding fusion protein and to the target nucleic acid. In some embodiments, the sequence-specific binding fusion protein, deaminase fusion protein, and guide nucleic acid may be comprised in one or more expression cassettes. In some embodiments, the target nucleic acid may be contacted with a sequence-specific binding fusion protein, deaminase fusion protein, and an expression cassette comprising a guide nucleic acid. In some embodiments, the sequence-specific nucleic acid binding fusion proteins, deaminase fusion proteins and guides may be provided as ribonucleoproteins (RNPs).

In some embodiments, methods such as prime editing may be used to generate a mutation in an endogenous BRI1 gene. In prime editing, RNA-dependent DNA polymerase (reverse transcriptase, RT) and reverse transcriptase templates (RT template) are used in combination with sequence specific nucleic acid binding domains that confer the ability to recognize and bind the target in a sequence-specific manner, and which can also cause a nick of the PAM-containing strand within the target. The nucleic acid binding domain may be a CRISPR-Cas effector protein and in this case, the CRISPR array or guide RNA may be an extended guide that comprises an extended portion comprising a primer binding site (PSB) and the edit to be incorporated into the genome (the template). Similar to base editing, prime editing can take advantages of the various methods of recruiting proteins for use in the editing to the target site, such methods including both non-covalent and covalent interactions between the proteins and nucleic acids used in the selected process of genome editing.

As used herein, a "CRISPR-Cas effector protein" is a protein or polypeptide or domain thereof that cleaves or cuts a nucleic acid, binds a nucleic acid (e.g., a target nucleic acid and/or a guide nucleic acid), and/or that identifies, recognizes, or binds a guide nucleic acid as defined herein. In some embodiments, a CRISPR-Cas effector protein may be an enzyme (e.g., a nuclease, endonuclease, nickase, etc.) or portion thereof and/or may function as an enzyme. In some embodiments, a CRISPR-Cas effector protein refers to a CRISPR-Cas nuclease polypeptide or domain thereof that comprises nuclease activity or in which the nuclease activity has been reduced or eliminated, and/or comprises nickase activity or in which the nickase has been reduced or eliminated, and/or comprises single stranded DNA cleavage activity (ss DNAse activity) or in which the ss DNAse activity has been reduced or eliminated, and/or comprises self-processing RNAse activity or in which the self-processing RNAse activity has been reduced or eliminated. A CRISPR-Cas effector protein may bind to a target nucleic acid.

In some embodiments, a sequence-specific nucleic acid binding domain may be a CRISPR-Cas effector protein. In some embodiments, a CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g., Cas9 nickase, Cas12a nickase.

A CRISPR Cas9 effector protein or CRISPR Cas9 effector domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes, S. thermophilus*), *Lactobacillus* spp., *Bifidobacterium* spp., *Kandleria* spp., *Leuconostoc* spp., *Oenococcus* spp., *Pediococcus* spp., *Weissella* spp., and/or *Olsenella* spp. Example Cas9 sequences include, but are not limited to, the amino acid sequences of SEQ ID NO:56 and SEQ ID NO:57 or the nucleotide sequences of SEQ ID NOs:58-68.

In some embodiments, the CRISPR-Cas effector protein may be a Cas9 polypeptide derived from *Streptococcus pyogenes* and recognizes the PAM sequence motif NGG, NAG, NGA (Mali et al, Science 2013; 339(6121): 823-826). In some embodiments, the CRISPR-Cas effector protein may be a Cas9 polypeptide derived from *Streptococcus thermophiles* and recognizes the PAM sequence motif NGGNG and/or NNAGAAW (W=A or T) (See, e.g., Horvath et al, Science, 2010; 327(5962): 167-170, and Deveau et al, J Bacteriol 2008; 190(4): 1390-1400). In some embodiments, the CRISPR-Cas effector protein may be a Cas9 polypeptide derived from *Streptococcus mutans* and recognizes the PAM sequence motif NGG and/or NAAR (R=A or G) (See, e.g., Deveau et al, J BACTERIOL 2008; 190(4): 1390-1400). In some embodiments, the CRISPR-Cas effector protein may be a Cas9 polypeptide derived from *Streptococcus aureus* and recognizes the PAM sequence motif NNGRR (R=A or G). In some embodiments, the CRISPR-Cas effector protein may be a Cas9 protein derived from *S. aureus*, which recognizes the PAM sequence motif N GRRT (R=A or G). In some embodiments, the CRISPR-Cas effector protein may be a Cas9 polypeptide derived from *S. aureus*, which recognizes the PAM sequence motif N GRRV (R=A or G). In some embodiments, the CRISPR-Cas effector protein may be a Cas9 polypeptide that is derived from *Neisseria meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the CRISPR-Cas effector protein may be a Cas13a protein derived from *Leptotrichia shahii*, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease see, e.g., amino acid sequences of SEQ ID NOs:1-17, nucleic acid sequences of SEQ ID NOs:18-20. Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cast2a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. *Nat. Biotechnol.* 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally occurring cytosine deaminase, including but not limited to a primate (e.g., a human, monkey, chimpanzee, gorilla), a dog, a cow, a rat or a mouse. Thus, in some embodiments, a cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same (e.g., SEQ ID NO:27, SEQ ID NO:28 or SEQ ID NO:29). In some embodiments, the cytosine deaminase may be an APOBEC1 deaminase having the amino acid sequence of SEQ ID NO:23. In some embodiments, the cytosine deaminase may be an APOBEC3A deaminase having the amino acid sequence of SEQ ID NO:24. In some embodiments, the cytosine deaminase may be an CDA1 deaminase, optionally a CDA1 having the amino acid sequence of SEQ ID NO:25. In some embodiments, the cytosine deaminase may be a FERNY deaminase, optionally a FERNY having the amino acid sequence of SEQ ID NO:26. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NO:23, SEQ ID NO:24, SEQ ID NO:25 or SEQ ID NO:26 (e.g., at least 80%, at least 85%, at least 90%, at least 92%, at least 95%, at least 96%, at least 97%, at least 98%, at least 99%, or at least 99.5% identical to the amino acid sequence of SEQ ID NO:23, SEQ ID NO:24, SEQ ID NO:25, SEQ ID NO:26, SEQ ID NO:27, SEQ ID NO:28 or SEQ ID NO:29). In some embodiments, a polynucleotide encoding a cytosine deaminase may be codon optimized for expression in a plant and the codon optimized polypeptide may be about 70% to 99.5% identical to the reference polynucleotide.

In some embodiments, a nucleic acid construct of this invention may further encode a uracil glycosylase inhibitor (UGI) (e.g., uracil-DNA glycosylase inhibitor) polypeptide/domain. Thus, in some embodiments, a nucleic acid construct encoding a CRISPR-Cas effector protein and a cytosine deaminase domain (e.g., encoding a fusion protein comprising a CRISPR-Cas effector protein domain fused to a cytosine deaminase domain, and/or a CRISPR-Cas effector protein domain fused to a peptide tag or to an affinity polypeptide capable of binding a peptide tag and/or a deaminase protein domain fused to a peptide tag or to an affinity polypeptide capable of binding a peptide tag) may further encode a uracil-DNA glycosylase inhibitor (UGI), optionally wherein the UGI may be codon optimized for expression in a plant. In some embodiments, the invention provides fusion proteins comprising a CRISPR-Cas effector polypeptide, a deaminase domain, and a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and a UGI may be fused to any combination of peptide tags and affinity polypeptides as described herein, thereby recruiting the deaminase domain and UGI to the CRISPR-Cas effector polypeptide and a target nucleic acid. In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:41 or a polypeptide having about 70% to about 99.5% sequence identity to the amino acid sequence of SEQ ID NO:41 (e.g., at least 80%, at least 85%, at least 90%, at least 92%, at least 95%, at least 96%, at least 97%, at least 98%, at least 99%, or at least 99.5% identical to the amino acid sequence of SEQ ID NO:41). For example, in some embodiments, a UGI domain may comprise a fragment of the amino acid sequence of SEQ ID NO:41 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:41. In some embodiments, a UGI domain may be a variant of a known UGI (e.g., SEQ ID NO:41) having about 70% to about 99.5% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% sequence identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:30. In some embodiments, a mutated/evolved *E. coli* TadA* comprises the amino acid sequence of SEQ ID NOs:31-40 (e.g., SEQ ID NOs: 31, 32, 33, 34, 35, 36, 37, 38, 39 or 40). In some embodiments, a polynucleotide encoding a TadA/TadA* may be codon optimized for expression in a plant.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a sequence-specific nucleic acid binding protein and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt function; and/or generation of point mutations in genomic DNA to disrupt splice junctions.

The nucleic acid constructs of the invention encoding a base editor comprising a sequence-specific nucleic acid binding protein and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt function; and/or generation of point mutations in genomic DNA to disrupt splice junctions.

The nucleic acid constructs of the invention comprising a CRISPR-Cas effector protein or a fusion protein thereof may be used in combination with a guide RNA (gRNA, CRISPR array, CRISPR RNA, crRNA), designed to function with the encoded CRISPR-Cas effector protein or domain, to modify a target nucleic acid. A guide nucleic acid useful with this invention comprises at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex (e.g., a CRISPR-Cas effector fusion protein (e.g., CRISPR-Cas effector domain fused to a deaminase domain and/or a CRISPR-Cas effector domain fused to a peptide tag or an affinity polypeptide to recruit a deaminase domain and optionally, a UGI) to the target nucleic acid, wherein the target nucleic acid may be modified (e.g., cleaved or edited) or modulated (e.g., modulating transcription) by the deaminase domain.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made, and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. Nucleic Acids Res. 35(Web Server issue):W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is substantially complementary to a target nucleic acid (e.g., target DNA) (e.g., protospacer) (e.g., substantially complementary to consecutive nucleotides of a portion/region of a BRI1 nucleotide sequence that (a) comprises a sequence having at least 80% sequence identity to the nucleotide sequence of any one of SEQ ID NOs:69, 70, 85, 86, 99, 100, 112, 113, 123, or 124; (b) comprises a region having at least 80% identity to any one of SEQ ID NOs: 72-76, 89-94, 102-106, 115-118, or 126-130; (c) encodes an amino acid sequence having at least 80% sequence identity to any one of SEQ ID NOs:71, 87, 88, 101, 114, or 125; and/or (d) encodes an amino acid sequence comprising a region having at least 80% identity to any one of SEQ ID NOs:77-81, 95-98, 107-111, 119-122 or 131-135. In some embodiments, a spacer sequence (e.g., one or more spacers) may include, but is not limited to, the nucleotide sequences of any one of SEQ ID NOs:82-84 and/or 136-139. The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to a target nucleic acid. Thus, in some embodiments, the spacer sequence can have one, two, three, four, or five mismatches as compared to the target nucleic acid, which mismatches can be contiguous or non-contiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length.

In some embodiments, the 5' region of a spacer sequence of a guide nucleic acid may be identical to a target DNA, while the 3' region of the spacer may be substantially complementary to the target DNA (e.g., Type V CRISPR-Cas), or the 3' region of a spacer sequence of a guide nucleic acid may be identical to a target DNA, while the 5' region of the spacer may be substantially complementary to the target DNA (e.g., Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length. As used herein, a "target nucleic acid", "target DNA," "target nucleotide sequence," "target region," or a "target region in the genome" refers to a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (such as for a Type V CRISPR-Cas system) or immediately 5' (such as for a Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

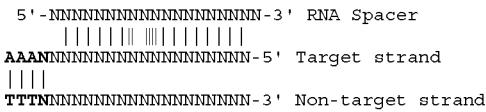

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention (e.g., one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct comprising a CRISPR-Cas effector protein and a deaminase domain (e.g., a fusion protein)) or the components for base editing (e.g., a CRISPR-Cas effector protein fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

Fusion proteins of the invention may comprise sequence-specific nucleic acid binding domains (e.g., sequence-specific DNA binding domains), CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26(5): 910-924 (2017)); Gilbreth (*Curr Opin Struc Biol* 22(4):413-420 (2013)), U.S. Pat. No. 9,982,053, each of which are incorporated by reference in their entireties for the teachings relevant to affibodies, anticalins, monobodies and/or DARPins. Example peptide tag sequences and their affinity polypeptides include, but are not limited to, the amino acid sequences of SEQ ID NOs:42-44.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases). Example RNA recruiting motifs and their affinity polypeptides include, but are not limited to, the sequences of SEQ ID NOs:45-55.

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat—spacer-extended portion (RT template-primer binding site)-RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited to, a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide Pumilio/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide Pumilio/fem-3 mRNA binding factor (PUF).

In some embodiments, the components for recruiting polypeptides and nucleic acids may those that function through chemical interactions that may include, but are not limited to, rapamycin-inducible dimerization of FRB—FKBP; Biotin-streptavidin; SNAP tag; Halo tag; CLIP tag; DmrA-DmrC heterodimer induced by a compound; bifunctional ligand (e.g., fusion of two protein-binding chemicals together, e.g., dihyrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

Further provided herein are cells comprising one or more polynucleotides, guide nucleic acids, nucleic acid constructs, expression cassettes or vectors of the invention.

The nucleic acid constructs of the invention (e.g., a construct comprising a sequence specific DNA binding domain, a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids and/or their expression.

A target nucleic acid of any plant or plant part (or groupings of plants, for example, into a genus or higher order classification) may be modified (e.g., mutated, e.g., base edited, cleaved, nicked, etc.) using the polypeptides, polynucleotides, ribonucleoproteins (RNPs), nucleic acid constructs, expression cassettes, and/or vectors of the invention including an angiosperm, a gymnosperm, a monocot, a dicot, a C3, C4, CAM plant, a bryophyte, a fern and/or fern ally, a microalgae, and/or a macroalgae. A plant and/or plant part that may be modified as described herein may be a plant and/or plant part of any plant species/variety/cultivar. In some embodiments, a plant that may be modified as described herein is a monocot. In some embodiments, a plant that may be modified as described herein is a dicot.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

Any plant comprising an endogenous Brassinosteroid Insensitive-1 (BRI1) gene may be modified as described herein to improve one or more yield traits. Non-limiting examples of plants that may be modified as described herein may include, but are not limited to, turf grasses (e.g., bluegrass, bentgrass, ryegrass, fescue), feather reed grass, tufted hair grass, miscanthus, arundo, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, papaya, and lychee, a field crop plant such as clover, alfalfa, timothy, evening primrose, meadow foam, corn/maize (field, sweet, popcorn), hops, jojoba, buckwheat, safflower, quinoa, wheat, rice, barley, rye, millet, sorghum, oats, triticale, sorghum, tobacco, kapok, a leguminous plant (beans (e.g., green and dried), lentils, peas, soybeans), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), Cannabis (e.g., *Cannabis sativa*, *Cannabis indica*, and *Cannabis ruderalis*), lauraceae (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, or sunflower.

In some embodiments, a plant that may be modified as described herein may include, but is not limited to, corn, soybean, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, or a *Brassica* spp (e.g., *B. napus, B. oleracea, B. rapa, B. juncea,* and/or *B. nigra*). In some embodiments, a plant that may be modified as described herein is a dicot. In some embodiments, a plant that may be modified as described herein is a monocot. In some embodiments, a plant that may be modified as described herein is corn (i.e., *Zea mays*). In some embodiments, a plant that may be modified as described herein is soybean (i.e., *Glycine max*).

The invention will now be described with reference to the following examples. It should be appreciated that these examples are not intended to limit the scope of the claims to the invention but are rather intended to be exemplary of certain embodiments. Any variations in the exemplified methods that occur to the skilled artisan are intended to fall within the scope of the invention.

EXAMPLES

Example 1. Editing Strategy

A strategy to generate edits in the kinase domain of the soybean Brassinosteroid Insensitive-1 (BRI1) gene genes of Glyma.06g147600(Locus325) (SEQ ID NO:88) and Glyma.04g218300(Locus328) (SEQ ID NO:126) to decrease the kinase activity and subsequently increase the autophosphorylation of the BRI1 gene product leading to increased Brassinosteroid Insensitive-1 (BRI1) based signaling with the ultimate intent of generating more vigorous growing soybean plants. To generate a range of alleles, Cas12a guide nucleic acids comprising spacers (e.g., SEQ ID NOs:136-139) having complementarity to targets within each of the BRI1 soybean genes were designed and placed into a vector construct.

Regenerated lines carrying edits in the BRI1 genes were screened and those that showed edits in the targeted gene were transferred to the greenhouse to set E1 seed.

Additional guide constructs comprising different spacers are designed to engineer targeted edits to the kinase domain of the BRI1 genes (including additional BRI1 soybean genes).

Example 2. Edited Alleles in Soybean

Three E1 plants generated-as described in Example 1 and comprising in-frame deletions were selected for further analysis. Soybean line CE94379 contains an edited allele of the BRI1a gene Glyma06g147600 (SEQ ID NO:85) which was found to be a 6 bp deletion of the sequence (TGAGCA), at position 3302 of SEQ ID NO:85 giving rise to the edited allele of Glyma06g147600 of SEQ ID NO:140 Soybean line CE94453 contains an edited allele of the BRI1a gene Glyma06g147600 (SEQ ID NO:85) which was found to be a 9 bp deletion of the sequence (GTGAGCACA) at position 3301 of SEQ ID NO:85 giving rise to the edited allele of Glyma06g147600 of SEQ ID NO:141. Soybean line CE94394 contains an edited allele of the BRI1d gene Glyma04g218300 (SEQ ID NO:123) which was found to be a 6 bp deletion of the sequence (AGCACA) at position 3395 of SEQ ID NO:123 giving rise to the edited allele of Glyma04g218300 of SEQ ID NO:142.

Example 3. Soybean Yield Phenotypes in the E1 Generation

The E1 plants described in Example 2 were evaluated at the R6 growth stage for plant architectural features that may be indicative of an increase in yield, as well as seed counts which are a direct indication of plant yield. The plant phenotypes measured included plant height, number of nodes on the mainstem, number of branches, pods on branches, pods on mainstem, pod per node on the mainstem, pods per plant, seeds per pod and seeds per plant. Results are summarized in Table 1. The values marked with an asterisk (*) note phenotypic traits that were different than the unedited/wild type plants. These observations suggest the edited alleles of the soybean BRI1 genes affect yield traits.

TABLE 1

| Phenotype analysis | | | | | |
| --- | --- | --- | --- | --- | --- |
| Edit/Genotype | N | Plant height cm) | Nodes on Mainstem | Number of branches | Pods on branches | Pods on Mainstem |
| BRI1a (CE94379) | 2 | 107.5 | 21.5 | 14.5 | 132.5 | 28* |
| BRI1a (CE94453) | 2 | 104.5 | 27* | 17.5 | 110 | 63* |
| BRI1d (CE94394) | 1 | 107 | 26 | 15 | 103 | 62 |
| unedited | 14 | 107.43 | 24 | 17.64 | 129.79 | 45.57 |

| Edit/Genotype | N | Pods per node on mainstem | Pods per plant | Seeds per plant | Seeds per pod |
| --- | --- | --- | --- | --- | --- |
| BRI1a (CE94379) | 2 | 1.27* | 160.5 | 242.5* | 1.51* |
| BRI1a (CE94453) | 2 | 2.33 | 173 | 296.67 | 1.67* |
| BRI1d (CE94394) | 1 | 2.38 | 165 | 186 | 1.13 |
| unedited | 14 | 1.9 | 175.36 | 397.86 | 2.24 |

Example 4. Soybean Yield Phenotypes in the E2 Generation

The E1 plants described in Example 2 were allowed to set E2 seed. The E2 seed was collected and planted and the resulting E2 plants were evaluated at the R6 growth stage for plant architectural features that may be indicative of an increase in yield, as well as seed counts which are a direct indication of plant yield. The plant phenotypes measured included plant height, number of nodes on the mainstem, number of branches, pods on branches, pods on mainstem, pod per node on the mainstem, pods per plant, seeds per pod and seeds per plant. Results are summarized in Table 2 and demonstrate that the edits obtained in the BRI1 genes are altering plant architecture and may affect plant yield.

TABLE 2

Soybean phenotypic analysis

| E2 progeny from | Nodes on mainstem (standard deviation) | Branches per plant (standard deviation) | Pods on branches (standard deviation) | Pods on mainstem (standard deviation) | Pods per node mainstem (standard deviation) | Pods per plant (standard deviation) |
|---|---|---|---|---|---|---|
| CE94379 | 20.9 (0.8) * | 5.7 (1.2) | 67.8 (9.1) * | 44.1 (6.6) | 2.1 (0.3) * | 113.6 (6.8) * |
| CE94453 | 21.9 (1.3) * | 5.4 (0.9) | 63.3 (10.9) | 44.3 (7.5) | 2.1 (0.3) * | 107.6 (7.3) |
| CE94394 | 21.3 (0.8) * | 5.4 (0.9) | 56.1 (9.9) * | 44.7 (7.0) | 2.0 (0.3) * | 99.6 (12.4) |
| Unedited/WT control | 18.8 (0.7) | 7.4 (0.5) | 52.3 (10.3) | 52.6 (1.3) | 2.8 (0.2) | 102.0 (7.7) |
| Null segregant | 20.0 (1.4) | 5.5 (0.9) | 48.6 (7.3) | 50.9 (8.1) | 2.5 (0.3) | 101.1 (5.7) |

* indicates an observation that was statistically validated at a probability of <0.05 when compared to the unedited/wild type control Example 5. Corn Edited Alleles An editing strategy was developed to generate edits in the kinase domain of the corn BRI1 gene (GRMZM6G437417, SEQ ID NO:69). To generate edited alleles, the CRISPR guide nucleic acids comprising spacer PWsp1407 (GTGGCACGTAACCTGGAGTGCCG, SEQ ID NO:84) having complementarity (reverse) to targets within the BRI1 gene was designed and placed into a construct. Lines carrying edits in the BRI1 gene were screened and those that showed about 10% of the sequencing reads having edits in the targeted gene were advanced to the next generation. The edited alleles of the corn BRI1 gene recovered are further described in the Table 3 below.

ears were permitted to mature and dry down on the plant. The mature ears were harvested and directly measured for ear length starting from the base (top of the shank) to the tip, including any tip void. The ear width of the harvested ear was measured directly at the widest part of the ear. In addition to direct measurement, ear length and ear width was calculated based upon image analysis of the harvested ears. As outlined in Table 4 below, all of the edited allele combinations demonstrated an increase in ear length as compared to a wild type plant and those entries identified with an asterisk (*) identify statistically significant differences. These observations suggest the edited alleles of the BRI1 gene in corn are affecting ear architecture.

TABLE 4

Phenotype analysis of corn with edited BRI1 genes

| Edited allele | # of plants | Ear length (cm) | Ear width (cm) |
|---|---|---|---|
| Heterozygous Allele A | 10 | 16.41 | 4.42 |
| Homozygous Allele A | 5 | 17.19 | 4.09 |
| Homozygous Allele B | 3 | 17.51 | 4.46 |
| Homozygous Allele C | 7 | 18.15* | 4.32 |
| Compound heterozygous with one Allele C and one Allele B | 15 | 18.48* | 4.36 |
| Unedited | 10 | 14.97 | 4.15 |

TABLE 3

Edited corn alleles

| Edited Allele | | Notes |
|---|---|---|
| Allele A (SEQ ID NO: 143) CE78038 | 7 bp (GGCACTC) deletion at position 3214 of SEQ ID NO: 72 | Out-of-frame mutation leading to an early stop codon |
| Allele B (SEQ ID NO: 144) | 6 bp (GGCACT) deletion at position 3214 of SEQ ID NO: 72 | In-frame mutation |
| Allele C (SEQ ID NO: 145) CE78042 7D | 7 bp (CACTCCA) deletion at position 3216 of SEQ ID NO: 72 | Out-of-frame mutation leading to an early stop codon |

Example 6. Corn Phenotype Analysis

Corn plants were grown to flowering under greenhouse conditions. At flowering, the plants were self-pollinated. The The foregoing is illustrative of the present invention and is not to be construed as limiting thereof. The invention is defined by the following claims, with equivalents of the claims to be included therein.

That which is claimed is:

1. A plant or part thereof comprising at least one mutation in an endogenous Brassinosteroid Insensitive-1 (BRI1) gene encoding a BRI1 polypeptide (brassinosteroid receptor polypeptide) comprising a kinase domain, wherein the at least one mutation is in a region of the endogenous BRI1 gene that encodes the kinase domain, and
   wherein the plant or part thereof is a corn plant or part thereof.

2. The plant or part thereof of claim 1, wherein the at least one mutation decreases phosphorylation of the kinase domain.

3. The plant or part thereof of claim 1, wherein the at least one mutation is a deletion or an insertion of at least one base.

4. The plant or part thereof of claim 1, wherein the endogenous BRI1 gene comprises a nucleotide sequence having at least 80% sequence identity to any one of SEQ ID NOs: 69, 70, 85, 86, 99, 100, 112, 113, 123, or 124 or comprises a region having at least 80% sequence identity to any one of SEQ ID NOs: 72-76, 89-94, 102-106, 115-118, or 126-130.

5. The plant or part thereof of claim 1, wherein the endogenous BRI1 gene encodes a BRI1 polypeptide having at least 80% sequence identity to any one of SEQ ID NOs: 71, 87, 88, 101, 114, or 125 or encodes a region having at least 80% sequence identity to any one of SEQ ID NOs: 77-81, 95-98, 107-111, 119-122 or 131-135.

6. The plant or part thereof of claim 1, wherein the at least one mutation in the endogenous BRI1gene results in a mutation of one or more amino acid residue(s) located in a region: (a) from position 929-1002, 942-994, 949-987, 956-975 and/or 960-970 with reference to amino acid position numbering of SEQ ID NO:71, (b) from position 997-1070, 1008-1059, 1018-1048, and/or 1028-1039 with reference to amino acid position numbering of SEQ ID NO:87 or SEQ ID NO:88, (c) from position 1048-1122, 1068-1102, 1075-1095, 1085-1096 with reference to amino acid position numbering of SEQ ID NO:101, (d) from position 1051-1097, 1057-1090, 1064-1082, and/or 1069-1080 with reference to amino acid position numbering of SEQ ID NO:114, and/or (e) from position 1000-1073, 1013-1059, 1020-1053, 1027-1046 and/or 1031-1042 with reference to amino acid position numbering of SEQ ID NO: 125.

7. The plant or part thereof of claim 1, wherein the at least one mutation is in a region of the endogenous BRI1gene located (a) from nucleotide 3096-3235, 3136-3295, 3156-3275, 3176-3255, and/or 3176-3237 with reference to nucleotide position numbering of SEQ ID NO:69, (b) from nucleotide 2784-3023, 2824-2983, 2844-2963, 2864-2943 and/or 2864-2924 with reference to nucleotide position numbering of SEQ ID NO:70, (c) from nucleotide 3198-3420, 3238-3380, 3258-3360, 3278-3340 and/or 3291-3327 with reference to nucleotide position numbering of SEQ ID NO:85, (d) from nucleotide 1944-2166, 1984-2126, 2004-2106, 2024-2085 and/or 2036-2073 with reference to nucleotide position numbering of SEQ ID NO:86, (e) from nucleotide 3070-3292, 3110-3252, 3130-3232, 3150-3212 and/or 3180-3228 with reference to nucleotide position numbering of SEQ ID NO:99 or SEQ ID NO: 100, (f) from nucleotide 3109-3331, 3149-3291, 3169-3271, 3189-3251 and/or 3204-3244 with reference to nucleotide position numbering of SEQ ID NO:112 or SEQ ID NO:113, (g) from nucleotide 3289-3511, 3329-3471, 3349-3451, 3369-3431 and/or 3381-3419 with reference to nucleotide position numbering of SEQ ID NO:123 and/or (h) from nucleotide 2997-3219, 3037-3179, 3057-3159, 3077-3139 and/or 3089-3126 with reference to nucleotide position numbering of SEQ ID NO:124.

8. The plant or part thereof of claim 1, wherein the at least one mutation results in a substitution of any one or more of the amino acid residues located: from position 955-975 with reference to amino acid position numbering of SEQ ID NO:71, from position 1023-1043 with reference to amino acid position numbering of SEQ ID NO:87 or SEQ ID NO: 88, from position 1081-1101 with reference to amino acid position numbering of SEQ ID NO: 101, from position 1065-1085 with reference to amino acid position numbering of SEQ ID NO: 114, and/or from position 1026-1046 with reference to amino acid position numbering of SEQ ID NO:125.

9. The plant or part thereof of claim 1, wherein the at least one mutation results in a substitution of an amino acid residue located: at position 965 with reference to amino acid position numbering of SEQ ID NO:71, at position 1033 with reference to amino acid position numbering of SEQ ID NO:87 or SEQ ID NO:88, at position 1091 with reference to amino acid position numbering of SEQ ID NO:101, at position 1075 with reference to amino acid position numbering of SEQ ID NO:114, or at position 1036 with reference to amino acid position numbering of SEQ ID NO:125.

10. The plant or part thereof of claim 9, wherein the substitution is a threonine to an alanine (T>A).

11. The plant or part thereof of claim 1, wherein the plant comprising the at least one mutation has a phenotype of one or more improved yield traits as compared to a plant devoid of the at least one mutation.

12. The plant or part thereof of claim 1, wherein the at least one mutation results in a mutated BRI1gene comprising a nucleotide sequence having at least 90% sequence identity to any one of SEQ ID NOs: 140-145.

13. A modified Brassinosteroid Insensitive-1 (BRI1) polypeptide having at least 80% sequence identity to any one of SEQ ID NOs: 71, 87, 88, 101, the modified BRI1 polypeptide comprising a mutation in an amino acid residue located: from position 955-975 with reference to amino acid position numbering of SEQ ID NO:71, from position 1023-1043 with reference to amino acid position numbering of SEQ ID NO:87 or SEQ ID NO:88, from position 1081-1101 with reference to amino acid position numbering of SEQ ID NO:101, from position 1065-1085 with reference to amino acid position numbering of SEQ ID NO:114, and/or from position 1026-1046 with reference to amino acid position numbering of SEQ ID NO: 125.

\* \* \* \* \*

SEQUENCE LISTING

```
Sequence total quantity: 145
SEQ ID NO: 1             moltype = AA  length = 1228
FEATURE                  Location/Qualifiers
REGION                   1..1228
                         note = Lachnospiraceae bacterium
source                   1..1228
                         mol_type = protein
                         organism = unidentified
SEQUENCE: 1
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQKL PKFKPLYKQV LSDRESLSFY GEGYTSDEEV   300
LEVFRNTLNK NSEIFSSIKK LEKLFKNFDE YSSAGIFVKN GPAISTISKD IFGEWNVIRD   360
KWNAEYDDIH LKKKAVVTEK YEDDRRKSFK KIGSFSLEQL QEYADADLSV VEKLKEIIIQ   420
KVDEIYKVYG SSEKLFDADF VLEKSLKKND AVVAIMKDLL DSVKSFENYI KAFFGEGKET   480
NRDESFYGDF VLAYDILLKV DHIYDAIRNY VTQKPYSKDK FKLYFQNPQF MGGWDKDKET   540
DYRATILRYG SKYYLAIMDK KYAKCLQKID KDDVNGNYEL INYKLLPGPN KMLPKVFFSK   600
KWMAYYNPSE DIQKIYKNGT FKKGDMFNLN DCHKLIDFFK DSISRYPKWS NAYDFNFSET   660
EKYKDIAGFY REVEEQGYKV SFESASKKEV DKLVEEGKLY MFQIYNKDFS DKSHGTPNLH   720
TMYFKLLFDE NNHGQIRLSG GAELFMRRAS LKKEELVVHP ANSPIANKNP DNPKKTTTLS   780
YDVYKDKRFS EDQYELHIPI AINKCPKNIF KINTEVRVLL KHDDNPYVIG IDRGERNLLY   840
IVVVDGKGNI VEQYSLNEII NNFNGIRIKT DYHSLLDKKE KERFEARQNW TSIENIKELK   900
AGYISQVVHK ICELVEKYDA VIALEDLNSG FKNSRVKVEK QVYQKFEKML IDKLNYMVDK   960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                    1228

SEQ ID NO: 2             moltype = AA  length = 1307
FEATURE                  Location/Qualifiers
source                   1..1307
                         mol_type = protein
                         organism = Acidaminococcus sp.
SEQUENCE: 2
MTQFEGFTNL YQVSKTLRFE LIPQGKTLKH IQEQGFIEED KARNDHYKEL KPIIDRIYKT    60
YADQCLQLVQ LDWENLSAAI DSYRKEKTEE TRNALIEEQA TYRNAIHDYF IGRTDNLTDA   120
INKRHAEIYK GLFKAELFNG KVLKQLGTVT TTEHENALLR GKFKTTYFS GFYENRKNVF    180
SAEDISTAIP HRIVQDNFPK FKENCHIFTR LITAVPSLRE HFENVKKAIG IFVSTSIEEV   240
FSFPFYNQLL TQTQIDLYNQ LLGGISREAG TEKIKGLNEV LNLAIQKNDE TAHIIASLPH   300
RFIPLFKQIL SDRNTLSFIL EEFKSDEEVI QSFCKYKTLL RNENVLETAE ALFNELNSID   360
LTHIFISHKK LETISSALCD HWDTLRNALY ERRISELSAI ITKSAKEKVQ RSLKHEDINL   420
QEIISAAGKE LSEAFKQKTS EILSHAHAAL DQPLPTTLKK QEEKEILKSQ LDSLLGLYHL   480
LDWFAVDESN EVDPEFSARL TGIKLEMEPS LSFYNKARNY ATKKPYSVEK FKLNFQMPTL   540
ASGWDVNKEK NNGAILFVKN GLYYLGIMPK QKGRYKALSF EPTEKTSEGF DKMYYDYFPD   600
AAKMKCST QLKAVTAHFQ THTTPILLSN NFIEPLEITK EIYDLNNPEK EPKKFQTAYA    660
KKTGDQKGYR EALCKWIDFT RDFLSKYTKT TSIDLSSLRP SSQYKDLGEY YAELNPLLYH   720
ISFQRIAEKE IMDAVETGKL YLFQIYNKDF AKGHHGKPNL HTLYWTGLFS PENLAKTSIK   780
LNGQAELFYR PKSRMKRMAH RLGEKMLNKK LKDQKTPIPD TLYQELYDYV NHRLSHDLSD   840
EARALLPNVI TKEVSHEIIK DRRFTSDKFF FHVPITLNYQ AANSPSKFNQ RVNAYLKEHP   900
ETPIIGIDRG ERNLIYITVI DSTGKILEQR SLNTIQQFDY QKKLDNREKE RVAARQAWSV   960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN              1307

SEQ ID NO: 3             moltype = AA  length = 1241
FEATURE                  Location/Qualifiers
source                   1..1241
                         mol_type = protein
                         organism = Butyrivibrio proteoclasticus
SEQUENCE: 3
MLLYENYTKR NQITKSLRLE LRPQGKTLRN IKELNLLEQD KAIYALLEREL KPVIDEGIKD   60
IARDTLKNCE LSFEKLYEHF LSGDKKAYAK ESERLKKEIV KTLIKNLPEG IKISEINSA   120
KYLNGVLYDF IDKTHKDSEE KQNILSDILE TKGYLALFSK FLTSRITTLE QSMPKRVIEN   180
FEIYAANIPK MQDALERGAV SFAIEYESIC SVDYYNQILS QEDIDSYNRL ISGIMDEDGA   240
KEKGINQTIS EKNIKIKSEH LEEKPFRILK QLHKQILEER EKAFTIDHID SDEEVVQVTK   300
EAFEQTKEQW ENIKKINGFY AKDPGDITLF IVVGPNQTHV LSQLIYGEHD RIRLLLEEYE   360
KNTLEVLPRR TKSEDARYDK FVNAVPKKVA KESHTFDGLG KMTGDDRLFI LYRDELARNY   420
MRIKEAYGTF ERDILKSRRG IKGNRDVQES LVSFYDELTK FRSALRIINS GNDEKADPIF   480
YNTFDGIFEK ANRTYKAENL CRNYVTKSPA DDARIMASCL GTPARLRTHW WNGEENFAIN   540
DVAMIRRGDE YYYFVLTPDV KPVDLKTKDE TDAQIFVQRK GAKSFLGLPK ALFKCILEPY   600
FESPEHKNDK NCVIEEYVSK PLTIDRRAYD IFKNGTFKKT NIGIDGLTEE KFKDDCRYLI   660
DVYKEFIAVY TRYSCFNMSG LKRADEYNDI GEFFSDVDTR LCTMEWIPVS FERINDMVDK   720
```

```
KEGLLFLVRS MFLYNRPRKP YERTFIQLFS DSNMEHTSML LNSRAMIQYR AASLPRRVTH   780
KKGSILVALR DSNGEHIPMH IREAIYKMKN NFDISSEDFI MAKAYLAEHD VAIKKANEDI   840
IRNRRYTEDK FFLSLSYTKN ADISARTLDY INDKVEEDTQ DSRMAVIVTR NLKDLTYVAV   900
VDEKNNVLEE KSLNEIDGVN YRELLKERTK IKYHDKTRLW QYDVSSKGLK EAYVELAVTQ   960
ISKLATKYNA VVVVESMSST FKDKFSFLDE QIFKAFEARL CARMSDLSFN TIKEGEAGSI  1020
SNPIQVSNNN GNSYQDGVIY FLNNAYTRTL CPDTGFVDVF DKTRLITMQS KRQFFAKMKD  1080
IRIDDGEMLF TFNLEEYPTK RLLDRKEWTV KIAGDSYFD KDKGEYVYVN DIVREQIIPA   1140
LLEDKAVFDG NMAEKFLDKT AISGKSVELI YKWFANALYG IITKKDGEKI YRSPITGTEI  1200
DVSKNTTYNF GKKFMKQEY RGDGDFLDAF LNYMQAQDIA V                      1241

SEQ ID NO: 4            moltype = AA  length = 1238
FEATURE                 Location/Qualifiers
source                  1..1238
                        mol_type = protein
                        organism = Candidatus Methanoplasma termitum
SEQUENCE: 4
MNNYDEFTKL YPIQKTIRFE LKPQGRTMEH LETFNFFEED RDRAEKYKIL KEAIDEYHKK    60
FIDEHLTNMS LDWNSLKQIS EKYYKSREEK DKKVFLSEQK RMRQEIVSEF KKDDRFKDLF   120
SKKLFSELLK EEIYKKGNHQ EIDALKSFDK FSGYFIGLHE NRKNMYSDGD EITAISNRIV   180
NENFPKFLDN LQKYQEARKK YPEWIIKAES ALVAHNIKMD IVFSLEYFNK VLNQEGIQRY   240
NLALGGYVTK SGEKMMGLND ALNLAHQSEK SSKGRIHMTP LFKQILSEKE SFSYIPDVFT   300
EDSQLLPSIG GFFAQIENDK DGNIFDRALE LISSYAEYDT ERIYIRQADI NRVSNVIFGE   360
WGTLGGLMRE YKADSINDIN LERTCKKVDK WLDSKEFALS DVLEAIDRTG NNDAFNEYIS   420
KMRTAREKID AARKEMKFIS EKISGDEESI HIIKTLLDSV QQFLHFFNLF KARQDIPLDG   480
AFYAEFDEVH SKLFAIVPLY NKVRNYLTKN NLNTKKIKLN FKNPTLANGW DQNKVYDYAS   540
LIFLRDGNYY LGIINPKRKK NIKFEQGSGN GPFYRKMVYK QIPGPNKNLR PVFLTSTKGK   600
KEYKPSKEII EGYEADKHIR GDKFDLDFCH KLIDFFKESI EKHKDWSKFN FYFSPTESYG   660
DISEFYLDVE KQGYRMHFEN ISAETIDEYV EKGDLFLFQI YNKDFVKAAT GKKDMHTIYW   720
NAAFSPENLQ DVVVKLNGEA ELFYRDKSDI KEIVHREGEI LVNRTYNGRT PVPDKIHKKL   780
TDYHNGRTKD LGEAKEYLDK VRYFKAHYDI TKDRRYLNDK IYPHVPLTLN FKANGKKNLN   840
KMVIEKFLSD EKAHIIGIDR GERNLLYYSI IDRSGKIIDQ QSLNVIDGFD YREKLNQREI   900
EMKDARQSWN AIGKIKDLKE GYLSKAVHEI TKMAIQYNAI VVMEELNYGF KRGRFKVEKQ   960
IYQKFENMLI DKMNYLVFKD APDESPGGVL NAYQLTNPLE SFAKLGKQTG ILFYVPAAYT  1020
SKIDPTTGFV NLFNTSSKTN AQERKEFLQK FESISYSAKD GGIFAFAFDY RKFGTSKTDH  1080
KNVWTAYTNG ERMRYIKEKK RNELFDPSKE IKEALTSSGI KYDGGQNILP DILRSNNNGL  1140
IYTMYSSFIA AIQMRVYDGK EDYIISPIKN SKGEFFRTDP KRRELPIDAD ANGAYNIALR  1200
GELTMRAIAE KFDPDSEKMA KLELKHKDWF EFMQTRGD                         1238

SEQ ID NO: 5            moltype = AA  length = 1281
FEATURE                 Location/Qualifiers
source                  1..1281
                        mol_type = protein
                        organism = Eubacterium eligens
SEQUENCE: 5
MNGNRSIVYR EFVGVIPVAK TLRNELRPVG HTQEHIIQNG LIQEDELRQE KSTELKNIMD    60
DYYREYIDKS LSGVTDLDFT LLFELMNLVQ SSPSKDNKKA LEKEQSKMRE QICTHLQSDS   120
NYKNIFNAKL LKEILPDFIK NYNQYDVKDK AGKLETLALF NGFSTYFTDF FEKRKNVFTK   180
EAVSTSIAYR IVHENSLIFL ANMTSYKKIS EKALDEIEVI EKNNQDKMGD WELNQIFNPD   240
FYNMVLIQSG IDFYNEICGV VNAHMNLYCQ QTKNNYNLFK MRKLHKQILA YTSTSFEVPK   300
MFEDDMSVYN AVNAFIDETE KGNIIGKLKD IVNKYDELDE KRIYISKDFY ETLSCFMSGN   360
WNLITGCVEN FYDENIHAKG KSKEEKVKKA VKEDKYKSIN DVNDLVEKYI DEKERNEFKN   420
SNAKQYIREI SNIITDTETA HLEYDDHISL IESEEKADEM KKRLDMYMNM YHWAKAFIVD   480
EVLDRDEMFY SDIDDIYNIL ENIVPLYNRV RNYVTQKPYN SKKIKLNFQS PTLANGWSQS   540
KEFDNNAIIL IRDNKYYLAI FNAKNKPDKK IIQGNSDKKN DNDYKKMVYN LLPGANKMLP   600
KVFLSKKGIE TFKPSDYIIS GYNAHKHIKT SENFDISFCR DLIDYFKNSI EKHAEWRKYE   660
FKFSATDSYS DISEFYREVE MQGYRIDWTY ISEADINKLD EEGKIYLFQI YNKDFAENST   720
GKENLHTMYF KNIFSEENLD KIIKLNGQAE LFYRRASVKN PVKHKKDSVL VNKTYKNQLD   780
NGDVVRIPIP DDIYNEIYKM YNGYIKESDL SEAAKEYLDK VEVRTAQKDI VKDYRYTVDK   840
YFIHTPITIN YKVTARNNVN DMVVKYIAQN DDIHVIGIDR GERNLIYISV IDSHGNIVKQ   900
KSYNILNNYD YKKKLVEKEK TREYARKNWK SIGNIKELKE GYISGVVHEI AMLIVEYNAI   960
IAMEDLNYGF KRGRFKVERQ VYQKFESMLI NKLNYFASKE KSVDEPGGLL KGYQLTYVPD  1020
NIKNLGKQCG VIFYVPAAFT SKIDPSTGFI SAFNFKSIST NASRKQFFMQ FDEIRYCAEK  1080
DMFSFGFDYN NFDTYNITMG KTQWTVYTNG ERLQSEFNNA RRTGKTKSIN LTEIKILLLE  1140
DNEINYADGH DIRIDMEKMD EDKKSEFFAQ LLSLYKLTVQ MRNSYTEAEE QENGISYDKI  1200
ISPVINDEGE FFDSDNYKES DDKECKMPKD ADANGAYCIA LKGLYEVLKI KSEWTEDGFD  1260
RNCLKLPHAE WLDFIQNKRY E                                           1281

SEQ ID NO: 6            moltype = AA  length = 1300
FEATURE                 Location/Qualifiers
source                  1..1300
                        mol_type = protein
                        organism = Francisella novicida
SEQUENCE: 6
MSIYQEFVNK YSLSKTLRFE LIPQGKTLEN IKARGLILDD EKRAKDYKKA KQIIDKYHQF    60
FIEEILSSVC ISEDLLQNYS DVYFKLKKSD DDNLQKDFKS AKDTIKKQIS EYIKDSEKFK   120
NLFNQNLIDA KKGQESDLIL WLKQSKDNGI ELFKANSDIT DIDEALEIIK SPKGWTTYFK   180
GFHENRKVNY SSNDIPTSII YRIVDDNLPK FLENKAKYES LKDKAPEAIN YEQIKKDLAE   240
ELTFDIDYKT SEVNQRVFSL DEVFEIANFN NYLNQSGITK FNTIIGGKFV NGENTKRKGI   300
NEYINLYSQQ INDKTLKKYK MSVLFKQILS DTESKSFVID KLEDDSDVVT TMQSFYEQIA   360
```

```
APKTVEEKSI KETLSLLFDD LKAQKLDLSK IYFKNDKSLT DLSQQVFDDY SVIGTAVLEY    420
ITQQIAPKNL DNPSKKEQEL IAKKTEKAKY LSLETIKLAL EEFNKHRDID KQCRFEEILA    480
NPAAIPMIFD EIAQNKDNLA QISIKYQNQG KKDLLQASAE DDVKAIKDLL DQTNNLLHKL    540
KIFHISQSED KANILDKDEH FYLVFEECYF ELANIVPLYN KIRNYITQKP YSDEKFKLNF    600
ENSTLANGWD KNKEPDNTAI LFIKDDKYYL GVMNKKNNKI FDDKAIKENK GEGYKKIVYK    660
LLPGANKMLP KVFFSAKSIK FYNPSEDILR IRNHSTHTKN GSPQKGYEKF EFNIEDCRKF    720
IDFYKQSISK HPEWKDFGFR FSDTQRYNSI DEFYREVENQ GYKLTFENIS ESYIDSVVNQ    780
GKLYLFQIYN KDFSAYSKGR PNLHTLYWKA LFDERNLQDV VYKLNGEAEL FYRKQSIPKK    840
ITHPAKEAIA NKNKDNPKKE SVFEYDLIKD KRFTEDKFFF HCPITINFKS SGANKFNDEI    900
NLLLKEKAND VHILSIDRGE RHLAYYTLVD GKGNIIKQDT FNIIGNDRMK TNYHDKLAAI    960
EKDRDSARKD WKKINNIKEM KEGYLSQVVH EIAKLVIEYN AIVVFEDLNF GPKRGRFKVE   1020
KQVYQKLEKM LIEKLNYLVF KDNEFDKTGG VLRAYQLTAP FETFKKMGKQ TGIIYYVPAG   1080
FTSKICPVTG FVNQLYPKYE SVSKSQEFFS KFDKICYNLD KGYFEFSPDY KNFGDKAAKG   1140
KWTIASFGSR LINFRNSDKN HNWDTREVYP TKELEKLLKD YSIEYGHGEC IKAAICGESD   1200
KKFFAKLTSV LNTILQMRNS KTGTELDYLI SPVADVNGNF FDSRQAPKNM PQDADANGAY   1260
HIGLKGLMLL GRIKNNQEGK KLNLVIKNEE YFEFVQNRNN                         1300

SEQ ID NO: 7            moltype = AA  length = 1206
FEATURE                 Location/Qualifiers
source                  1..1206
                        mol_type = protein
                        note = Lachnospiraceae sp.
                        organism = unidentified
SEQUENCE: 7
MYYESLTKQY PVSKTIRNEL IPIGKTLDNI RQNNILESDV KRKQNYEHVK GILDEYHKQL     60
INEALDNCTL PSLKIAAEIY LKNQKEVSDR EDFNKTQDLL RKEVVEKLKA HENFTKIGKK    120
DILDLLEKLP SISEDDYNAL ESFRNFYTYF TSYNKVRENL YSDKEKSSTV AYRLINENFP    180
KFLDNVKSYR FVKTAGILAD GLGEEEQDSL FIVETFNKTL TQDGIDTYNS QVGKINSSIN    240
LYNQKNQKAN GFRKIPKMKM LYKQILSDRE ESFIDEFQSD EVLIDNVESY GSVLIESLKS    300
SKVSAFFDAL RESKGKNVYV KNDLAKTAMS VIVFENWRTF DDLLNQEYDL ANENKKKDDK    360
YFEKRQKELK KNKSYSLEHL CNLSEDSCNL IENYIHQISD DIENIIINNE TFLRIVINEH    420
DRSRKLAKNR KAVKAIKDFL DSIKVLEREL KLINSSGQEL EKDLIVYSAH EELLVELKQV    480
DSLYNMTRNY LTKKPFSTEK VKLNFNRSTL LNGWDRNKET DNLGVLLLKD GKYYLGIMNT    540
SANKAFVNPP VAKTEKVFKK VDYKLLPVPN QMLPKVFFAK SNIDFYNPSS EIYSNYKKGT    600
HKKGNMFSLE DCHNLIDFFK ESISKHEDWS KFGFKFDTQA SYNDISEFYR EVEKQGYKLT    660
YTDIDETYIN DLIERNELYL FQIYNKDFSM YSKGKLNLHT LYFMMLFDQR NIDDVVYKLN    720
GEAEVFYRPA SISEDELIIH KAGEEIKNKN PNRARTKETS TFSYDIVKDK RYSKDKFTLH    780
IPITMNFGVD EVKRFNDAVN SAIRIDENVN VIGIDRGERN LLYVVVIDSK GNILEQISLN    840
SIINKEYDIE TDYHALLDER EGGRDKARKD WNTVENIRDL KAGLYLQVVN VVAKLVLKYN    900
AIICLEDLNF GFKRGRQKVE KQVYQKFEKM LIDKLNYLVI DKSREQTSPK ELGGALNALQ    960
LTSKFKSFKE LGKQSGVIYY VPAYLTSKID PTTGFANLFY MKCENVEKSK RFFDGFDFIR   1020
FNALENVFEF GFDYRSFTQR ACGINSKWTV CTNGERIIKY RNPDKNNMFD EKVVVVTDEM   1080
KNLFEQYKIP YEDGRNVKDM IISNEEAEFY RRLYRLLQQT LQMRNSTSDG TRDYIISPVK   1140
NKREAYFNSE LSDGSVPKDA DANGAYNIAR KGLWVLEQIR QKSEGEKINL AMTNAEWLEY   1200
AQTHLL                                                              1206

SEQ ID NO: 8            moltype = AA  length = 1233
FEATURE                 Location/Qualifiers
source                  1..1233
                        mol_type = protein
                        note = Lachnospiraceae sp.
                        organism = unidentified
SEQUENCE: 8
MDYGNGQFER RAPLTKTITL RLKPIGETRE TIREQKLLEQ DAAFRKLVET VTPIVDDCIR     60
KIADNALCHF GTEYDFSCLG NAISKNDSKA IKKETEKVEL LLAKVLTENL PDGLRKVNDI    120
NSAAFIQDTL TSFVQDDADK RVLIQELKGK TVLMQRFLTT RITALTVWLP DRVFENFNIF    180
IENAEKMRIL LDSPLNEKIM KFDPDAEQYA SLEFYGQCLS QKDIDSYNLI ISGIYADDEV    240
KNPGINEIVK EYNQQIRGDK DESPLPKLKK LHQILMPVE KAFFVRVLSN DSDARSILEK    300
ILKDTEMLPS KIIEAMKEAD AGDIAVYGSR LHELSHVIYG DHGKLSQIIY DKESKRISEL    360
METLSPKERK ESKKRLEGLE EHIRKSTYTF DELNRYAEKN VMAAYIAAVE ESCAEIMRKE    420
KDLRTLLSKE DVKIRGNRHN TLIVKNYFNA WTVFRNLIRI LRRKSEAEID SDFYDVLDDS    480
VEVLSLTYKG ENLCRSYITK KIGSDLKPEI ATYGSALRPN SRWWSPGEKF NVKFHTIVRR    540
DGRLYYFILP KGAKPVELED MDGDIECLQM RKIPNPTIPL FLVFKDPEA FFRDNPEADE    600
FVFLSGMKAP VTITRETYEA YRYKLYTVGK LRDGEVSEEE YKRALLQVLT AYKEFLENRM    660
IYADLNFGFK DLEEYKDSSE FIKQVETHNT FMCWAKVSSS QLDDLVKSGN GLLFEIWSER    720
LESYYKYGNE KVLRGYEGVL LSILKDENLV SMRTLLNSRP MLVYRPKESS KPMVHRDGS    780
RVVDRFDKDG KYIPPEVHDE LYRFFNNLLI KEKLGEKARK ILDNKKVKVK VLESERVKWS    840
KFYDEQFAVT FSVKKNADCL DTTKDLNAEV MEQYSESNRL ILIRNTTDIL YYLVLDKNGK    900
VLKQRSLNII NDGARDVDWK ERFRQVTKDR NEGYNEWDYS RTSNDLKEVY LNYALKEIAE    960
AVIEYNAILI IEKMSNAFKD KYSFLDDVTF KGFETKKLAK LSDLHFRGIK DGEPCSFTNP   1020
LQLCQNDSNK ILQDGVIFMV PNSMTRSLDP DTGFIFAIND HNIRTKKAKL NFLSKFDQLK   1080
VSSEGCLIMK YSGDSLPTHN TDNRVWNCCC NHPITNYDRE TKKVEFIEEP VEELSRVLEE   1140
NGIETDTELN KLNERENVPG KVVDAIYSLV LNYLRGTVSG VAGQRAVYYS PVTGKKYDIS   1200
FIQAMNLNRK CDYYRIGSKE RGEWTDFVAQ LIN                                1233

SEQ ID NO: 9            moltype = AA  length = 1227
FEATURE                 Location/Qualifiers
source                  1..1227
                        mol_type = protein
```

```
                    note                 = Lachnospiraceae sp.
                    organism             = unidentified
SEQUENCE: 9
MSKLEKFTNC  YSLSKTLRFK  AIPVGKTQEN  IDNKRLLVED  EKRAEDYKGV  KKLLDRYYLS    60
FINDVLHSIK  LKNLNNYISL  FRKKTRTEKE  NKELENLEIN  LRKEIAKAFK  GNEGYKSLFK   120
KDIIETILPE  FLDDKDEIAL  VNSFNGFTTA  FTGFFDNREN  MFSEEAKSTS  IAFRCINENL   180
TRYISNMDIF  EKVDAIFDKH  EVQEIKEKIL  NSDYDVEDFF  EGEFFNFVLT  QEGIDVYNAI   240
IGGFVTESGE  KIKGLNEYIN  LYNQKTKQKL  PKFKPLYKQV  LSDRESLSFY  GEGYTSDEEV   300
LEVFRNTLNK  NSEIFSSIKK  LEKLFKNFDE  YSSAGIFVKN  GPAISTISKD  IPGEWNVIRD   360
KWNAEYDDIH  LKKKAVVTEK  YEDDRRKSFK  KIGSFSLEQL  QEYADADLSV  VEKLKEIIIQ   420
KVDEIYKVYG  SSEKLFDADF  VLEKSLKKND  AVVAIMKDLL  DSVKSFENYI  KAFFGEGKET   480
NRDESFYGDF  VLAYDILLKV  DHIYDAIRNY  VTQKPYSKDK  FKLYFQNPQF  MGGWDKDKET   540
DYRATILRYG  SKYYLAIMDK  KYAKCLQKID  KDDVNGNYEK  INYKLLPGPN  KMLPKVFFSK   600
KWMAYYNPSE  DIQKIYKNGT  FKKGDMFNLN  DCHKLIDFFK  DSISRYPKWS  NAYDFNFSET   660
EKYKDIAGFY  REVEEQGYKV  SFESASKKEV  DKLVEEGKLY  MFQIYNKDFS  DKSHGTPNLH   720
TMYFKLLFDE  NNHGQIRLSG  GAELFMRRAS  LKKEELVVHP  ANSPIANKNP  DNPKKTTTLS   780
YDVYKDKRFS  EDQYELHIPI  ANINKCPKNI  FKINTEVRVL  LKHDDNPYVI  GIDRGERNLL   840
YIVVVDGKGN  IVEQYSLNEI  INNFNGIRIK  TDYHSLLDKK  EKERFEARQN  WTSIENIKEL   900
KAGYISQVVH  KICELVEKYD  AVIALEDLNS  GFKNSRVKVE  KQVYQKFEKM  LIDKLNYMVD   960
KKSNPCATGG  ALKGYQITNK  FESFKSMSTQ  NGFIFYIPAW  LTSKIDPSTG  FVNLLKTKYT  1020
SIADKKFISS  FDRIMYVPEE  DLFEFALDYK  NFSRTDADYI  KKWKLYSYGN  RIRIFRNPKK  1080
NNVFDWEEVC  LTSAYKELFN  KYGINYQQGD  IRALLCEQSD  KAFYSSFMAL  MSLMLQMRNS  1140
ITGRTDVDFL  ISPVKNSDGI  FYDSRNYEAQ  ENAILPKNAD  ANGAYNIARK  VLWAIGQFKK  1200
AEDEKLDKVK  IASNKEWLEY  AQTSVKH                                         1227

SEQ ID NO: 10           moltype = AA   length = 1264
FEATURE                 Location/Qualifiers
source                  1..1264
                        mol_type = protein
                        organism = Leptospira inadai
SEQUENCE: 10
MEDYSGFVNI  YSIQKTLRFE  LKPVGKTLEH  IEKKGFLKKD  KIRAEDYKAV  KKIIDKYHRA    60
YIEEVFDSVL  HQKKKKDKTR  FSTQFIKEIK  EFSELYYKTE  KNIPDKERLE  ALSEKLRKML   120
VGAFKGEFSE  EVAEKYNKNL  FSKELIRNEI  EKFCETDEER  KQVSNFKSFT  TYFTGPHSNR   180
QNIYSDEKKS  TAIGYRIIHQ  NLPKFLDNLK  IIESIQRRFK  DFPWSDLKKN  LKKIDKNIKL   240
TEYFSIDGFV  NVLNQKGIDA  YNTILGGKSE  ESGEKIQGLN  EYINLYRQKN  NIDRKNPLNV   300
KILFKQILGD  RETKSFIPEA  FPDDQSVLNS  ITEFAKYLKL  DKKKKSIIAE  LKKFLSSFNR   360
YELDGIYLAN  DNSLASISTF  LFDDWSFIKK  SVSFKYDESV  GDPKKKIKSP  LKYEKEKEKW   420
LKQKYYTISF  LNDAIESYSK  SQDEKRVKIR  LEAYFAEFKS  KDDAKKQFDL  LERIEEAYAI   480
VEPLLGAEYP  RDRNLKADKK  EVGKIKDFLD  SIKSLQFFLK  PLLSAEIFDE  KDLGFYNQLE   540
GYYEEIDISG  HLYNKVRNYL  TGKIYSKEKF  KLNFENSTLL  KGWDENREVA  NLCVIFREDQ   600
KYYLGVMDKE  NNTILSDIPK  VKPNELFYEK  MVYKLIPTPH  MQLPRIIFSS  DNLSIYNPSK   660
SILKIREAKS  FKEGKNFKLK  DCHKFIDFYK  ESISKNEDWS  RFDFKFSKTS  SYENISEFYR   720
EVERQGYNLD  FKKVSKFYID  SLVEDGKLYL  FQIYNKDFSI  FSKGKPNLHT  IYFRSLFSKE   780
NLKDVCLKLN  GEAEMFFRKK  SINYDEKKKR  EGHHPELFEK  LKYPILKDKR  YSEDKFQFHL   840
PISLNFKSKE  RLNFNLKVNE  FLKRNDINI   IGIDRGERNL  LYLVMINQKG  EILKQTLLDS   900
MQSGKGRPEI  NYKEKLQEKE  IERDKARKSW  GTVENIKELK  EGYLSIVIHQ  ISKLMVENNA   960
IVVLEDLNIG  FKRGRQKVER  QVYQKFEKML  IDKLNFLVFK  ENKPTEPGGV  LKAYQLTDEF  1020
QSFEKLSKQT  GFLFYVPSWN  TSKIDPRTGF  IDFLHPAYEN  IEKAKQWINK  FDSIRFNSKM  1080
DWFEFTADTR  KFSENLMLGK  NRVWVICTTN  VERYFTSKTA  NSSIQYNSIQ  ITEKLKELFV  1140
DIPFSNGQDL  KPEILRKNDA  VFFKSLLFYI  KTTLSLRQNN  GKKGEEEKDF  ILSPVVDSKG  1200
RFFNSLEASD  DEPKDADANG  AYHIALKGLM  NLLVLNETKE  ENLSRPKWKI  KNDWLEFVW   1260
ERNR                                                                    1264

SEQ ID NO: 11           moltype = AA   length = 1373
FEATURE                 Location/Qualifiers
source                  1..1373
                        mol_type = protein
                        organism = Moraxella bovoculi
SEQUENCE: 11
MLFQDFTHLY  PLSKTVRFEL  FIDRTLEHIH  AKNFLSQDET  MADMHQKVKV  ILDDYHRDFI    60
ADMMGEVKLT  KLAEFYDVYL  KFRKNPKDDE  LQKAQLKDLQ  AVLRKEIVKP  IGNGGKYKAG   120
YDRLFGAKLF  KDGDLGDLA   KFVIAQEGES  SPKLAHLAHF  EKFSTYFTGF  HDNRKNMYSD   180
EDKHTAIAYR  LIHENLPRFI  DNLQILTTIK  QKHSALYDQI  INELTASGLD  VSLASHLDGY   240
HKLLTQEGIT  AYNTLLGGIS  GEAGSPKIQG  INELINSHHN  QHCHKSERIA  KLRPLHKQIL   300
SDGMSVSFLP  SKFADDSEMC  QAVNEFYRHY  ADVFAKVQSL  FDGFDDHQKD  GIYVEHKNLN   360
ELSKQAFGDF  ALLGRVLDGY  YVDVVNPEFN  ERFAKAKTDN  AKAKLTKEKD  KFIKGVHSLA   420
SLEQAIEHYT  ARHDDESVQA  GKLGQYFKHG  LAGVDNPIQK  IHNHSTIKG   FLERERPAGE   480
RALPKIKSGK  NPEMTQLRQL  KELLDNALNV  AHFAKLLTTK  TTLDNQDGNF  YGEFGVLYDE   540
LAKIPTLYNK  VRDYLSQKPF  STEKYKLNFG  NPTLLNGWDL  NKEKDNFGVI  LQKDGCYYLA   600
LLDKAHKKVF  DNAPNTGKSI  YQKMIYKYLE  VRKQFPKVFF  SKEAIAINYH  PSKELVEIKD   660
KGRQRSDDER  LKLYRFILEC  LKIHPKYDKK  FEGAIGDIQL  FKKDKKGREV  PISEKDLFKD   720
INGIFSSKPK  LEMEDFFIGE  FKRYNPSQDL  VDQYNIYKKI  DSNDNRRKEN  FYNNHPKFKS   780
DLVRYYYESM  CKHEEWEESF  EFSKKLQDIG  CYVDVNELFT  EIETRRLNYK  ISFCNINADY   840
IDELVEQGQL  YLFQIYNKDF  SPKAHGKPNL  HTLYFKALFS  EDNLADPIYK  LNGEAQIFYR   900
KASLDMNETT  IHRAGEVLEN  KNPDNPKRRQ  FVYDIIKDKR  YTQDKFMLHV  PITMNFGVQG   960
MTIKEFNKKV  NQSIQQYDEV  NVIGIDRGER  HLLYLTVINS  KGEILEQCSL  NDITTASANG  1020
TQMTTPYHKI  LDKREIERLN  ARVGWGEIET  IKELKSGYLS  HVVHQISQLM  LKYNAIVLE   1080
DLNFGFKRGR  FKVEKQIYQN  FENALIKKLN  HLVLKDKADD  EIGSYKNALQ  LTNNFTDLKS  1140
```

```
IGKQTGFLFY VPAWNTSKID PETGFVDLLK PRYENIQASQ AFFGKFDKIC YNADKDYFEF  1200
HIDYAKFTDK AKNSRQIWTI CSHGDKRYVY DKTANQNKGA AKGINVNDIL KSLFARHHIN  1260
EKQPNLVMDI CQNNDKEFHK SLMYLLKTLL ALRYSNASSD EDFILSPVAN DEGVFFNSAL  1320
ADDTQPQNAD ANGAYHIALK GLWLLNELKN SDDLNKVKLA IDNQTWLNFA QNR         1373

SEQ ID NO: 12              moltype = AA  length = 1352
FEATURE                    Location/Qualifiers
source                     1..1352
                           mol_type = protein
                           note = Parcubacteria bacterium
                           organism = unidentified
SEQUENCE: 12
MENIFDQFIG KYSLSKTLRF ELKPVGKTED FLKINKVFEK DQTIDDSYNQ AKFYFDSLHQ   60
KFIDAALASD KTSELSFQNF ADVLEKQNKI ILDKKREMGA LRKRDKNAVG IDRLQKEIND  120
AEDIIQKEKE KIYKDVRTLF DNEAESWKTY YQEREVDGKK ITESKADLKQ KGADFLTAAG  180
ILKVLKYEFP EEKEKEFQAK NQPSLFVEEK ENPGQKRYIF DSFDKFAGYL TKFQQTKKNL  240
YAADGTSTAV ATRIADNFII FHQNTKVFRD KYKNNHTDLG FDEENIFEIE RYKNCLLQRE  300
IEHIKNENSY NKIIGRINKK IKEYRDQKAR DTKLTKSDFP FFKNLDKQIL GEVEKEKQLI  360
EKTREKTEED VLIERFKEFI ENNEERFTAA KKLMNAFCNG EFESEYEGIY LKNKAINTIS  420
RRWFVSDRDF ELKLPQQKSK NKSEKNEPKV KKFISIAEIK NAVEELDGDI FKAVFYDKKI  480
IAQGGSKLEQ FLVIWKYEFE YLFRDIEREN GEKLLGYDSC LKIAKQLGIF PQEKEAREKA  540
TAVIKNYADA GLGIFQMMKY FSLDDKDRKN TPGQLSTNFY AEYDGYYKDF EFIKYYNEFR  600
NFITKKPFDE DKIKLNFENG ALLKGWDENK EYDFMGVILK KEGRLYLGIM HKNHRKLFQS  660
MGNAKGDNAN RYQKMIYKQI ADASKDVPRL LLTSKKAMEK FKPSQEILRI KKEKTFKRES  720
KNFSLRDLHA LIEYYRNCIP QYSNWSFYDF QFQDTGKYQN IKEFTDDVQK YGYKISFRDI  780
DDEYINQALN EGKMYLFEVV NKDIYNTKNG SKNLHTLYFE HILSAENLND PVFKLSGMAE  840
IFQRQPSVNE REKITTQKNQ CILDKGDRAY KYRRYTEKKI MFHMSLVLNT GKGEIKQVQF  900
NKIINQRISS SDNEMRVNVI GIDRGEKNLL YYSVVKQNGE IIEQASLNEI NGVNYRDKLI  960
EREKERLKNR QSWKPVVKIK DLKKGYISHV IHKICQLIEK YSAIVVLEDL NMRFKQIRGG 1020
IERSVYQQFE KALIDKLGYL VFKDNRDLRA PGGVLNGYQL SAPFVSFEKM RKQTGILFYT 1080
QAEYTSKTDP ITGFRKNVYI SNSASLDKIK EAVKKFDAIG WDGKEQSYFF KYNPYNLADE 1140
KYKNSTVSKE WAIFASAPRI RRQKGEDGYW KYDRVKVNEE FEKLLKVWNF VNPKATDIKQ 1200
EIIKKIKAGD LQGEKELDGR LRNFWHSFIY LFNLVLELRN SFSLQIKIKA GEVIAVDEGV 1260
DFIASPVKPF FTTPNPYIPS NLCWLAVENA DANGAYNIAR KGVMILKKIR EHAKKDPEFK 1320
KLPNLFISNA EWDEAARDWG KYAGTTALNL DH                               1352

SEQ ID NO: 13              moltype = AA  length = 1260
FEATURE                    Location/Qualifiers
source                     1..1260
                           mol_type = protein
                           organism = Porphyromonas crevioricanis
SEQUENCE: 13
MDSLKDFTNL YPVSKTLRFE LKPVGKTLEN IEKAGILKED EHRAESYRRV KKIIDTYHKV   60
FIDSSLENMA KMGIENEIKA MLQSFCELYK KDHRTEGEDK ALDKIRAVLR GLIVGAFTGV  120
CGRRENTVQN EKYESLFKEK LIKEILPDFV LSTEAESLPF SVEEATRSLK EFDSFTSYFA  180
GFYENRKNIY STKPQSTAIA YRLIHENLPK FIDNILVFQK IKEPIAKELE HIRADFSAGG  240
YIKKDERLED IFSLNYYIHV LSQAGIEKYN ALIGKIVTEG DGEMKGLNEH INLYNQQRGR  300
EDRLPLFRPL YKQILSDREQ LSYLPESFEK DEELLRALKE FYDHIAEDIL GRTQQLMTSI  360
SEYDLSRIYV RNDSQLTDIS KKMLGDWNAI YMARERAYDH EQAPKRITAK YERDRIKALK  420
GEESISLANL NSCIAFLDNV RDCRVDTYLS TLGQKEGPHG LSNLVENVFA SYHEAEQLLS  480
FPYPEENNLI QDKDNVVLIK NLLDNISDLQ RFLKPLWGME RPEDIGGLLR AYQFTAPFKS  540
DQVIPLYNKV RNYLTRKPYS TRKVKLNFGN SQLLSGWDRN KEKDNSCVIL RKGQNFYLAI  600
MNNRHKRSFE NKMLPEYKEG EPYFEKMDYK FLPDPNKMLP KVFLSKKGIE IYKPSPKLLE  660
QYGHGTHKKG DTFSMDDLHE LIDFFKHSIE AHEDWKQFGF KFSDTATYEN VSSFYREVED  720
QGYKLSFRKV SESYVYSLID QGKLYLFQIY NKDFSPCSLG TPNLHTLYWR MLFDERNLAD  780
VIYKLDGKAE IFFREKSLKN DHPTHPAGKP IKKKSRQKKG EESLFEYDLV KDRRYTMDKF  840
QFHVPITMNF KCSAGSKVND MVNAHIREAK DMHVIGIDRG ERNLLYICVI DSRGTILDQI  900
SLNTINDIDY HDLLESRDKD RQQEHRNWQT IEGIKELKQG YLSQAVHRIA ELMVAYKAVV  960
ALEDLNMGFK RGRQKVESSV YQQFEKQLID KLNYLVDKKK RPEDIGGLLR AYQFTAPFKS 1020
FKEMGKQNGF LFYIPAWNTS NIDPTTGFVN LFHVQYENVD KAKSFFQKFD SISYNPKKDW 1080
FEFAFDYKNF TKKAEGSRSM WILCTHGSRI KNFRNSQKNG QWDSEEFALT EAFKSLFVRY 1140
EIDYTADLKT AIVDEKQKDF FVDLLKLFKL TVQMRNSWKE KDLDYLISPV AGADGRFFDT 1200
REGNKSLPKD ADANGAYNIA LKGLWALRQI RQTSEGGKLK LAISNKEWLQ FVQERSYEKD 1260

SEQ ID NO: 14              moltype = AA  length = 664
FEATURE                    Location/Qualifiers
source                     1..664
                           mol_type = protein
                           organism = Prevotella disiens
SEQUENCE: 14
NSYKEDKKRL NKVIIAYIEQ IKQTNIKKSI IESISKYPNI SDDDKVTPSS LLEKIKKVSI   60
DSYNGILSFK SFQSVNKEVI DNLLKTISPL KNKAEFLDLI NKDYQIFTEV QAVIDEICKQ  120
KTFIYFPISN VELEKEMGDK DKPLCLFQIS NKDLSFAKTF SANLRKKRGA ENLHTMLFKA  180
LMEGNQDNLD LGSGAIFYRA KSLDGNKPTH PANEAIKCRN VANKDKVSLF TYDIYKNRRY  240
MENKFLFHLS IVQNYKAAND SAQLNSSATE YIRKADDLHI IGIDRGERNL LYYSVIDMKG  300
NIVEQDSLNI IRNNDLETDY HDLLDKREKE RKANRQNWEA VEGIKDLKKG YLSQAVHQIA  360
QLMLKYNAII ALEDLGQMFV TRGQKIEKAV YQQFEKSLVD KLSYLVDKKR PYNELGGILK  420
AYQLASSITK NNSDKQNGFL FYVPAWNTSK IDPVTGFTDL LRPKAMTIKE AQDFFGAFDN  480
ISYNDKGYFE FETNYDKFKI RMKSAQTRWT ICTFGNRIKR KKDKNYWNYE EVELTEEFKK  540
```

-continued

```
LFKDSNIDYE NCNLKEEIQN KDNRKFFDDL IKLLQLTLQM RNSDDKGNDY IISPVANAEG    600
QFFDSRNGDK KLPLDADANG AYNIARKGLW NIRQIKQTKN KDDLNLSISS TEWLDFVREK    660
PYLK                                                                664

SEQ ID NO: 15           moltype = AA  length = 1484
FEATURE                 Location/Qualifiers
SITE                    1073
                        note = misc_feature - Xaa can be any naturally occurring
                         amino acid
source                  1..1484
                        mol_type = protein
                        note = Peregrinibacteria bacterium
                        organism = unidentified
SEQUENCE: 15
MSNFFKNFTN LYELSKTLRF ELKPVGDTLT NMKDHLEYDE KLQTFLKDQN IDDAYQALKP     60
QFDEIHEEFI TDSLESKKAK EIDFSEYLDL FQEKKELNDS EKKLRNKIGE TFNKAGEKWK    120
KEKYPQYEWK KGSKIANGAD ILSCQDMLQF IKYKNPEDEK IKNYIDDTLK GFFTYFGGFN    180
QNRANYYETK KEASTAVATR IVHENLPKFC DNVIQFKHII KRKKDGTVEK TERKTEYLNA    240
YQYLKNNNKI TQIKDAETEK MIESTPIAEK IFDVYYFSSC LSQKQIEEYN RIIGHYNLLI    300
NLYNQAKRSE GKHLSANEKK YKDLPKFKTL YKQIGCGKKK DLFYTIKCDT EEEANKSRNE    360
GKESHSVEEI INKAQEAINK YFKSNNDCEN INTVPDFINY ILTKENYEGV YWSKAAMNTI    420
SDKYFANYHD LQDRLKEAKV FQKADKKSED DIKIPEAIEL SGLFGVLDSL ADWQTTLFKS    480
SILSNEKLKI ITDSQTPSEA LLKMIFNDIE KNMESFLKET NDIITLKKYK GNKEGTEKIK    540
QWFDYTLAIN RMLKYFLVKE NKIKGNSLDT NISEALKTLI YSDDAEWFKW YDALRNYLTQ    600
KPQDEAKENK LKLNFDNPSL AGGWDVNKEC SNFCVILKDK NEKKYLAMIK KGENTLFQKE    660
WTEGRGKNLT KKSNPLFEIN NCEILSKMEY DFWADVSKMI PKCSTQLKAV VNHFKQSDNE    720
FIFPIGYKVT SGEKFREECK ISKQDFELNN KVFNKNELSV TAMRYDLSST QEKQYIKAFQ    780
KEYWELLFKQ EKRDTKLTNN EIFNEWINFC NKKYSELLSW ERKYKDALTN WINFCKYFLS    840
KYPKTTLFNY SFKESENYNS LDEFYRDVDI CSYKLNINTT INKSILDRLV EEGKLYLFEI    900
KNQDSNDGKS IGHKNNLHTI YWNAIFENFD NRPKLNGEAE IFYRKAISKD KLGIVKGKKT    960
KNGTWIIKNY RFSKEKFILH VPITLNFCSN NEYVNDIVNT KFYNFSNLHF LGIDRGEKHL   1020
AYYSLVNKNG EIVDQGTLNL PFTDKDGNQR SIKKEKYFYN KQEDKWEAKE VDXWNYNDLL   1080
DAMASNRDMA RKNWQRIGTI KEAKNGYVSL VIRKIADLAV NNERPAFIVL EDLNTGFKRS   1140
RQKIDKSVYQ KFELALAKKL NFLVDKNAKR DEIGSPTKAL QLTPPVNNYG DIENKQAGI    1200
MLYTRANYTS QTDPATGWRK TIYLKAGPEE TTYKKDGKIK NKSVKDQIIE TFTDIGFDGK   1260
DYYFEYDKGE FVDEKTGEIK PKKWRLYSGE NGKSLDRFRG EREKDKYEWK IDKIDIVKIL   1320
DDLFVNFDKN ISLLKQLKEG VELTRNNEHG TGESLRFAIN LIQQIRNTGN NERDNDFILS   1380
PVRDENGKHF DSREYWDKET KGEKISMPSS GDANGAFNIA RKGIIMNAHI LANSDSKDLS   1440
LFVSDEEWDL HLNNKTEWKK QLNIFSSRKA MAKRKKKRPA ATKK                    1484

SEQ ID NO: 16           moltype = AA  length = 1245
FEATURE                 Location/Qualifiers
source                  1..1245
                        mol_type = protein
                        organism = Porphyromonas macacae
SEQUENCE: 16
MKTQHFFEDF TSLYSLSKTI RFELKPIGKT LENIKKNGLI RRDEQRLDDY ELKKKVIDEY     60
HEDFIANILS SFSFSEEILQ SYIQNLSISE ARAKIEKTMR DTLAKAFSED ERYKSIFKKE    120
LVKKDIPVWC PAYKSLCKKF DNFTTSLVPF HENRKNLYTS NEITASIPYR IVHVNLPKFI    180
QNIEALCELQ KKMGADLYLE MMENLRNVWP SFVKTPDDLC NLKTYNHLMV QSSISEYNRF    240
VGGYSTEDGT KHQGINEWIN IYRQRNKEMR LPGLVFLHKQ ILAKVDSSSF ISDTLENDDQ    300
VFCVLRQFRK LFWNTVSSKE DDAASLKDLF CGLSGYDPEA IYVSDAHLAT ISKNIFDRWN    360
YISDAIRRKT EVLMPRKKES VERYAEKISK QIKKRQSYSL AELDDLLAHY SEESLPAGFS    420
LLSYFTSLGG QKYLVSDGEV ILYEEGSNIW DEVLIAFRDL QVILDKDFTE KKLGKDEEAV    480
SVIKKALDSA LRLRKFFDLL SGTGAEIRRD SSFYALYTDR MDKLKGLLKM YDKVRNYLTK    540
KPYSIEKFKL HFDNPSLLSG WDKNKELNNL SVIFRQNGYY YLGIMTPKGK NLFKTLPKLG    600
AEEMFYEKME YKQIAEPMLM LPKVFFPKKT KPAFAPDQSV VDIYNKKTFK TGQKGFNKKD    660
LYRLIDFYKE ALTVHEWKLF NFSFSPTEQY RNIGEFFDEV REQAYKVSMV NVPASYIDEA    720
VENGKLYLFQ IYNKDFSPYS KGIPNLHTLY WKALFSEQNQ SRVYKLCGGG ELFYRKASLH    780
MQDTTVHPKG ISIHKKNLNK KGETSLFNYD LVKDKRFTED KFFFHVPISI NYKNKKITNV    840
NQMVRDYIAQ NDDLQHGIDR GERNLLYISR IDTRGNLLEQ FSLNVIESDK GDLRTDYQKI    900
LGDREQERLR RRQEWKSIES IKDLKDGYMS QVVHKICNMV VEHKAIVVLE NLNLSFMKGR    960
KKVEKSVYEK FERMLVDKLN YLVVDKKNLS NEPGGLYAAY QLTNPLFSFE ELHRYPQSGI   1020
LFFVDPWNTS LTDPSTGFVN LLGRINYTNV GDARKFFDRF NAIRYDGKGN ILFDLDLSRF   1080
DVRVETQRKL WTLTTFGSRI AKSKKSGKWM VERIENLSLC FLELFEQFNI GYRVEKDLKK   1140
AILSQDRKEF YVRLIYLFNL MMQIRNSDGE EDYILSPALN EKNLQFDSRL IEAKDLPVDA   1200
DANGAYNVAR KGLMVVQRIK RGDHESIHRI GRAQWLRYVQ EGIVE                   1245

SEQ ID NO: 17           moltype = AA  length = 1250
FEATURE                 Location/Qualifiers
source                  1..1250
                        mol_type = protein
                        organism = Smithella sp.
SEQUENCE: 17
MQTLFENFTN QYPVSKTLRF ELIPQGKTKD FIEQKGLLKK DEDRAEKYKK VKNIIDEYHK     60
DPIEKSLNGL KLDGLEKYKT LYLKQEKDDK DKKAFDKEKE NLRKQIANAF RNNEKFKTLF   120
AKELIKNDLM SFACEEDKKN VKEFEAFTTY FTGFHQNRAN MYVADEKRTA IASRLIHENL   180
PKFIDNIKIF EKMKKEAPEL LSPFNQTLKD MKDVIKGTTL EEIFSLDYFN KTLTQSGIDI   240
YNSVIGGRTP EEGKTKIKGL NEYINTDFNQ KQTDKKKRQP KFKQLYKQIL SDRQSLSFIA   300
```

```
EAFKNDTEIL EAIEKFYVNE LLHFSNEGKS TNVLDAIKNA VSNLESFNLT KMYFRSGASL    360
TDVSRKVFGE WSIINRALDN YYATTYPIKP REKSEKYEER KEKWLKQDFN VSLIQTAIDE    420
YDNETVKGKN SGKVIADYFA KFCDDKETDL IQKVNEGYIA VKDLLNTPCP ENEKLGSNKD    480
QVKQIKAFMD SIMDIMHFVR PLSLKDTDKE KDETFYSLFT PLYDHLTQTI ALYNKVRNYL    540
TQKPYSTEKI KLNFENSTLL GGWDLNKETD NTAIILRKDN LYYLGIMDKR HNRIFRNVPK    600
ADKKDFCYEK MVYKLLPGAN KMLPKVFFSQ SRIQEFTPSA KLLENYANET HKKGDNFNLN    660
HCHKLIDFFK DSINKHEDWK NFDFRFSATS TYADLSGFYH EVEHQGYKIS FQSVADSFID    720
DLVNEGKLYL FQIYNKDFSP FSKGKPNLHT LYWKMLFDEN NLKDVVYKLN GEAEVFYRKK    780
SIAEKNTTIH KANESIINKN PDNPKATSTF NYDIVKDKRY TIDKFQPHIP ITMNFKAEGI    840
FNMNQRVNQF LKANPDINII GIDRGERHLL YYALINQKGK ILKQDTLNVI ANEKQKVDYH    900
NLLDKKEGDR ATARQEWGVI ETIKELKEGY LSQVIHKLTD LMIENNAIIV MEDLNFGFKR    960
GRQKVEKQVY QKFEKMLIDK LNYLVDKNKK ANELGGLLNA FQLANKFESF QKMGKQNGFI   1020
FYVPAWNTSK TDPATGFIDF LKPRYENLNQ AKDFFEKFDS IRLNSKADYF EFAFDFKNFT   1080
EKADGGRTKW TVCTTNEDRY QWNRALNNNR GSQEKYDITA ELKSLFDGKV DYKSGKDLKQ   1140
QIASQESADF FKALMKNLSI TLSLRHNNGE KGDNEQDYIL SPVADSKGRF FDSRKADDDM   1200
PKNADANGAY HIALKGLWCL EQISKTDDLK KVKLAISNKE WLEFVQTLKG              1250

SEQ ID NO: 18           moltype = DNA   length = 3987
FEATURE                 Location/Qualifiers
source                  1..3987
                        mol_type = other DNA
                        organism = synthetic construct
SEQUENCE: 18
atggccggga gcaagaagcg ccggataaag caggacacgc agttcgaggg cttcaccaac     60
ctgtaccaag tctccaagac gctccggttc gagcttatcc cgcaagggaa gaccctgaaa    120
cacatccagg aacaaggttt catcgaggag gacaaggccg gcaacgacca ctacaaggag    180
ctcaagccca taatcgatcg gatctacaag acgtacgccg accagtgcct ccaactggtg    240
cagctcgact gggagaacct gagcgccgcc attgacagct accgcaagga aaagacggag    300
gagacgcgca acgcccttat tgaggagcaa gccacctacc gcaacgccat ccacgactac    360
ttcatcgggc gcaccgacaa cctgacggac gcgatcaaca agcgccacgc ggaaatctac    420
aagggccttt tcaaggccga gctcttcaac ggggaaggtcc taaaacagct cgggactgtc    480
acgacaaccg agcatgagaa cgccctcctt cgcagcttcg acaagttcac cacatacttc    540
tcgggcttct accggaaccg caagaacgtt ttcagcgccg aggacatctc caccgccatc    600
ccgcacagga tcgtccagga caacttcccc aagttcaagg agaactgcca catcttccgg    660
cgcctgatta cagccgtacc ttcacttcgt gagcacttcg agaacgtcaa aaaggccatc    720
gggatcttcg tctccacgtc catcgaggag gtattctctt tccgttccta taaccagctc    780
ctgacccaga cgcagatcga cctctacaac agctactggg cggcatcag ccgggaggcc    840
gggaccgaga aaataaaggg cctcaacgaa gttctcaacc tggccatcca gaagaacgac    900
gagaccgcgc atatcatcgc atccctgccg catcgcttca ttccttttgtt caagcagata    960
ttgagcgacc ggaacaccct ctcgttcatc ctcgaagaat tcaagagcga cgaggggtc   1020
attcagtctt tctgcaagta caagacgctc tacggaatgg agaatgtgct ggagaccgcg   1080
gaggcactct tcaatgagct gaactccatt gacctgaccc acatcttcat tagccacaag   1140
aaactggaga cgatctccag cgccctgtgc gaccactggg acactctccg caacgccctc   1200
tacgaacgcc ggatctccga acttaccggc aagataacta agtcggctaa ggagaaggtg   1260
caacggagcc tcaagcacga ggacatcaac cttcaggaaa tcatctcagc cgcgggcaag   1320
gagctgagcg aaggcgtttaa gcagaaaaca tcggagatac tgaccacgc gcacgcggcc   1380
ctggatcaac cgctgccgac gactctcaag aagcaagagg aagagaaat ccttaagtcc   1440
cagctcgact cgctgctcgg cctctatcac ttgctcgact ggttcgcggt tgatgagtcc   1500
aacgaggtgg acccggagtt ctccgcgcgc ctcacgggta ttaagctgga gatgagcca   1560
agcttaagct tctacaacaa ggcccgcaac tacgcgacca aaaaaccgta ctcagtcgag   1620
aaattcaagc tgaatttcca gatgcctaca ttggcgcgag ggtgggacgt gaaccggcag   1680
aagaacaatg gagccatcct gttcgtcaaa aatgggttgt actacctggg catcatgccc   1740
aagcagaagg gccgttacaa ggcctgtca ttcgagccta ccgagaagac ctcggagggc   1800
ttcgacaaga tgtactacga ctatttcccg gacgccgcca agatgatcc gaagtgctcc   1860
acgcagctca aagccgtcac ggcccacttc cagacgcata ccacgccgat acttctgagc   1920
aacaacttca ttgagccgct agagatcacg aaggagatat acgacctaaa caaccccgaa   1980
aaggagccca agaagttcca gacagcctac gctaagaaga caggtgatca aagggatat   2040
agggaggcac tctgcaagtg gatcgacttc acgcgcgact tcctgtcgaa atatacaaag   2100
acgaccagca ttgacctaag ttctctccgc ccatcctccc agtacaagga tctgggcgag   2160
tattatgcgg agctgaaccc attgctgtac cacatcagct tccagaagat cgccgagaag   2220
gagattatgg acgcggtgga cacggggaaa ctataccgtgt tccaaatata taacaaggac   2280
ttcgctaaag gcaccacgg aagcccaac ctgcacacac tctactggac gggcttgttt   2340
tcgccagaaa atttggccaa gacttcgatc aagctcaacg gccaggcgga gttgttttac   2400
cgtcccaagt ctcgcatgaa gcgcatggcg catcgcctcg gagagaaaat gcttaacaag   2460
aagctcaagg atcagaagac gcccatacct gatacgttgt accaggaatt gtacgactac   2520
gtgaaccacc gcctatcgca cgacctctca gacgaggccc gcgcctcct cccaaacgtg   2580
attactaagg aggtttccca tgaaataatc aaggaccgac ggttcaccag cgacaaattt   2640
tttttccacg tgcctatcac gctcaattac caggcggcca actccccatc gaagttcaac   2700
cagcgcgtga acgcctacct taaggagcac ccggagaccc caatcatcgg gatcgaccgt   2760
ggcgagcgga acctgatcta tattacggtg atcgatagca ccggaagat cctggagcag   2820
cgctccctga acacaatcca gcagtttgac taccagaaga aactcgacaa ccgggagaag   2880
gagcgcgtcg cagcccggca agcatggagt gtggtcggca ccataaagga cctgaaacag   2940
ggttacctaa gtcaagttat ccacgagatc gttgacctga tgatacacta tcaagccgta   3000
gtcgtgctga agaacctcaa ctcgggttt aagtccaagc tgggcgagaa   3060
gcggtgtacc agcagttcga gaagatgctg atcgacaagc tgaactgcct ggtgctcaag   3120
gactaccctg cggagaaggt cggcgggtc ttgaacccgt accagctaac gaccagttc   3180
acgagcttcg ccaaaatggg cacgcagtcc ggattcttgt tttatgtccc ggctccatat   3240
acaagtaaga tcgaccgct gacagggttt gttgacccat cgtgtggaa gaccatcaag   3300
aaccacgaga gcaggaaaca cttcctagag ggcttcgact cctgcatta cgacgttaag   3360
```

```
acaggcgact tcatcctgca cttcaagatg aaccgcaacc tgtcgttcca gaggggcctg   3420
cccggcttca tgcccgcctg ggatatcgtc tttgagaaga atgagacgca gttcgacgcg   3480
aaggggacgc cgttcatcgc tggaaagcgg atcgtgccgg tcatcgagaa ccaccgcttc   3540
acgggtcgct accgagattt ataccccgcc aacgaactaa ttgcgctgct ggaggagaag   3600
gggatcgtgt tccgagatgg cagcaacatt ctcccgaagc tgctggagaa cgacgactcg   3660
cacgctattg acacgatggt cgccctcata cggagcgtgc ttcagatgcg gaacagtaac   3720
gctgccacgg gcgaggacta cattaactcc ccgtccgcg  acctcaacgg ggtctgcttc   3780
gatagccgct tccagaaccc ggagtggcct atggatgcgg acgcgaacgg ggcctaccac   3840
atcgccctca agggccaact cctgctcaac cacttgaagg aaagcaaaga cctcaaattg   3900
cagaatggca tcagtaacca ggactggctc gcgtacatcc aggaactgag aaacgggtcc   3960
aagaagcggc gtatcaagca agattga                                       3987

SEQ ID NO: 19        moltype = DNA  length = 3987
FEATURE              Location/Qualifiers
source               1..3987
                     mol_type = other DNA
                     organism = synthetic construct
SEQUENCE: 19
atggcgggaa gcaaaaagcg ccggattaag caagacacgc agttcgaggg cttcacgaac   60
ctctaccaag tcagcaagac cctccggttc gagctgatac cacagggaaa gacgctcaag   120
cacatccagg aacagggctt catcgaggag acaaggcgc  gcaacgacca ctacaaggag   180
ttgaaaccga tcatcgaccg catctacaag acgtacgccg accagtgcct ccagctcgtg   240
cagctcgact gggagaacct ctccgccgcc attgactcgt accggaagga gaagactgag   300
gagacccgca acgccctgat cgaggagcaa gcaacctacc ggaacgccat ccacgactac   360
ttcatcggcc gcaccgacaa cctcaccgac gcgatcaaca agcggcacgc ggagatatac   420
aaagggctgt tcaaggcgga gctgttcaac ggcaaggtgc tcaagcagct agggacggtg   480
accacgaccg agcacgagaa cgcgctcctc cgcagcttcg acaagttcac cacctacttc   540
agcggcttct accggaaccg caagaatgtt ttcagcgcgg aggacatcag cacggccatc   600
ccgcaccgca tcgtccagga caacttcccg aagttcaagg agaactgcca catcttcacc   660
cgcctgataa ccgccgtccc ctccctgcgg gagcaattttg agaacgtcaa aaaggcaatt   720
gggatcttcg tctcgaccag cattgaggag gtgttcagct tccccttcta caaccagctc   780
ctcacccaga cgcagatcga cctgtacaat cagttgctcg gcgggataag ccgcgaggcg   840
ggaaccgaaa aaatcaaggg gctgaacgaa gtgttgaacc tcgccatcca agaacgac    900
gagaccgcgc acatcatcgc ctccctgccc caccggttca tccccgctgtt caagcagatc   960
ctctctgacc ggaacaccct gtccttcatt cttggaggagt tcaagtcgga cggaggtc    1020
atccagagct tctgcaagta caagacgctg ctacggaacg agaacgtgct ggagacggcg   1080
gaggcactgt tcaacgagct aaacagcatc gacctcacgc acatcttcat cagtcacaag   1140
aaaactggaga ccatctcctc cgcgctgtgc gaccactggg acacgctcag gaacgcgctc   1200
tacgagcgcc gaatcagtga gctgacgggc aagatcacga agtccgcgaa ggagaaggtg   1260
cagcggtccc tcaagcacga ggacatcaac ctccaggaga tcatctcagc ggctgggaaa   1320
gagctgtccg aggcgttcaa gcagaaaacg agcgaaatcc tgtcccacgc gcacgcggcc   1380
ctggatcagc tctgccgac  gaccctcaag aaacaagaag aaaaggaaat cctcaagtcg   1440
cagctcgact cgctgctggg cctgtaccat ctcctcgact ggttcgccgt ggacgagagc   1500
aacgaggtgg accccgagtt ctccgcgcgg cttacgggga tcaagctgga gatggagccc   1560
agcctgtcct tctacaacaa ggcgcgcaac tacgccacca gaagcccta  cagcgtggag   1620
aagttcaagc tcaacttcca gatgcccact ctcgcacgtg ggtgggacgt caaccgcgaa   1680
aaaaataatg gggcgatcct gttcgtcaag aacggccgtgt actacttggg catcatgccg   1740
aaacagaagg gccgctacaa ggccctgagc ttcaaccgga ccgagaaaac gagcgagggg   1800
ttcgacaaga tgtactacga ctacttcccc gacgccgcga agatgattcc aaaagtgctcc   1860
acgcagctta aggccgtgac ggcccacttc cagacgcaca cgaccccgat cctcctcagc   1920
aacaacttca tcgagcccct ggagatcacg aaggagatat acgacctgaa caacccggag   1980
aaggagccca gaaattcca  gaccgcctac gccaagaaga caggcgacca aaagggttac   2040
aggagggccc tctgcaagtg gatcgacttc actagggact tcctgtccaa gtacaccaag   2100
actacctcta tcgacctgtc cagcctccgc ccgtcgtccc agtacaaaga tttgggcgag   2160
tattacgag  agctgaaccc actgctctac cacatcagct tccagcgcat cgcggagaag   2220
gagatcatgg acgcagtgga cacgggcaag ctataccctat ttcagatata caacaaagac   2280
ttcgctaagg acaccacgg  caagcctaac ctgcacaccc tctactggac ggggctcttc   2340
agcccggaga acctcgccaa gacctcgatc aagctcaacg gccaggccga gctgttctac   2400
cggcccaagt ccgcgcatgaa gcggatgcc  caccggctcg ggggagaaaat gctcaacaag   2460
aaattgaagg accaaaaaac gccgataccc gacaccctat accaggagct gtacgactat   2520
gtgaaccacc gcctgagcca cgacctcagc gacgaggcgc gggccctcct gccgaacgtc   2580
atcacaaagg aggtcagcca cgagatcatc aaggaccggc gcttcacctc cgacaagttt   2640
ttcttttcacg tgcccatcac gctcaactac caggccgcca actcgccgtc caagttcaac   2700
cagcgcgtga acgcctacct caaggagcac cccgagaccc cgatcatcgg gattgaccga   2760
gggagcggaa acctcatcta catcaccgtc atcgacagca ccggaagat  ccttgaacag   2820
cggtcgctca acaccatcca gcagttcgac taccagaaga aactcgacaa ccgggagaag   2880
gagagagtgg cggcccgcca ggcttggtcc gtcgtcggga cgattaagga cttgaaacaa   2940
ggttacctgt cgcaagtgat ccacgagatc gttgacctga tgatccacta ccaagccgtc   3000
gtggtcctgg agaaccttcaa cttcggcttc aagagcaaac gaaccggcat cgccggagaa   3060
gccgtgtacc agcagttcga aaaaatgctg atcgacaagc tgaactgcct cgtgctcaag   3120
gactaccccg ctgagaaggt cggcggggtg ctgaacccgt accagctcac tgaccagttc   3180
accagcttcg caaagatggg caccagtcc ggcttcctgt tctacgtgcc tgcgcctac   3240
acctcgaaga tcgacccgct caccgggttc gtggaccct  tcgtctggaa gaccatcaag   3300
aaccacgaga gccgcaagca cttcctggag ggcttcgact tcctccacta cgacgtcaag   3360
acggggact  tcatcctgca cttcaagatg aaccgcaacc tcagtttcca gcgcggcctg   3420
ccgggggttca tgcccgcttg ggatatagtc ttcgagaaga atgagacgca gttcgacgcg   3480
aagggcaccc cgttcatcgc cgggaagcgc atcgtgccgg tcatcgagaa ccaccggttc   3540
accggggcgct accgcgacct ataccccgcg aacgagttga tcgccctcct ggaggagaag   3600
ggcatcgtgt tccgcgacgg ctccaacatc ctcccgaagc tgctcgaaaa cgacgactcc   3660
```

```
cacgccatcg acacgatggt cgcgctgatc cggtcggtgc tccagatgcg gaactccaac 3720
gccgcgacgg gcgaggacta catcaacagt ccggtccgcg atctgaacgg cgtctgcttc 3780
gactccggt tccagaaccc cgagtggccg atggacgcgg acgcgaacgg cgcataccac 3840
atcgccctaa aagggcaatt gctgctcaac caccctcaagg aatccaaaga cctaaagctc 3900
cagaacggca tctccaacca ggactggctg gcgtacatcc aggaactgcg gaacgggagc 3960
aaaaaacgtc ggatcaagca agattga                                    3987
```

SEQ ID NO: 20    moltype = DNA   length = 3987
FEATURE          Location/Qualifiers
source           1..3987
                 mol_type = other DNA
                 organism = synthetic construct
SEQUENCE: 20

```
atggcgggct ccaagaaacg ccggattaag caagataccc agttcgaggg gttcacgaac 60
ctctaccaag tgagcaagac cctccgattc gaactgattc ctcaggggaa gaccctcaag 120
cacatccagg agcaagggtt catcgaggag gacaaggcgc ggaacgacca ctacaaggaa 180
ctcaaaccca tcatcgaccg catctacaag acctacgccg atcagtgcct ccagctcgtg 240
cagttggact gggagaacct cagcgcggcc attgactcct accggaagga gaaaacggag 300
gagacgcgca acgcgctcat cgaggaacag gcaacctatc gcaacgccat ccacgactac 360
ttcatcggga ggactgacaa cctcactgac gcgattaaca agcgcacgc ggagatatac 420
aagggactct tcaaagcgga gctgtttaac ggcaaggttc tcaagcaact cggcactgtg 480
accacgaccg agcatgagaa cgccctgctc cgctcctttc acaagttcac cacctacttc 540
tccgggttct accgcaaccg caagaatgtc ttcagcgcgg aggacatcag cacgccatt 600
ccacatcgaa tcgtccaaga taacttcccg aagttcaagg agaactgcca catcttcacc 660
cgactcatta ctgctgtacc gtcgttacgc gaacacttcg agaacgtcaa gaaggcaatt 720
ggaatcttcg tctctacgtc aatagaggag tgttcagtc tccctttcta caaccagctc 780
cttacgcaga cccagataga cctgtacaat cagctcctcg gtgggatcag ccggaggcg 840
gggactgaga agattaaagg gctcaacgag gtcttgaacc tggccatcca aaaaaacgat 900
gagacggcgc acatcatcgc ctcgctgccc caccggttca tcccgctgtt caagcagatc 960
ctcagtgaca ggaacacctt gagctttatc ctagaggagt tcaagagcga cgaggaggtg 1020
atccagagct tctgcaagta caaaaccctg ctgaggaacg agaacgtcct ggagacggcg 1080
gaggcgctgt tcaacgagct gaactctatc gacttaactc acatattcat ctcgcacaag 1140
aagctggaga ctattagctc tgcactctgc gaccactggg acaccctccg caacgcgctc 1200
tacgagcgcc gcatctcgga gctgaccggg aagatcacca aatccgcgaa ggaaaaggtc 1260
cagcgttccc tcaaacacga ggatattaac ttacaggaga ttatctcagc ggctgggaag 1320
gagttgtcag aggcgttcaa gcagaaaact tccgagatcc tgagccacgc gcacgcagcg 1380
ctcgaccagc tctgcccac caccctcaaa agcaggaag aaaaagagat cctcaagagc 1440
cagttggact ccctgctggg gctctatcac cttctcgact ggtcgccgt cgatgagtcg 1500
aacgaggtgg accccgagtt ctccgcccgg ctgaccggca tcaagctaga gatggagccg 1560
tccctcagct tctacaataa ggccgcaac tacgcgacca aaaaacccta cagcgtggag 1620
aagttcaagc tgaacttcca gatgccgacc ttagcacgcg gttgggacgt aaacaggag 1680
aagaacaatg gagccatcct gttcgtcaag aacgggcttt actacctcgg gataatgccc 1740
aagcagagga gccgctacaa ggccctttcc ttcgagccga cggagaaaac ctccgagggg 1800
ttcgacaaga tgtactacga ctacttcccc gacgccgcca agatgatccc gaagtgctca 1860
acgcagctaa agccgtgac cgcccacttc cagacccaca cgacgccgat cctgctgagc 1920
aacaacttca tcgagcccct tgagatcact aaggagatat acgacctgaa caaccccgag 1980
aaggagccca agaagttca aaccgcctac gccaaaaaaa ctggccacca aaagggctac 2040
agggaggcgc tgtgtaagtg gatcgacttc acacgcgact tccttcgaa gtatacgaag 2100
acaacctcta ttgacctgag cagcctgcgt cctagctccc agtacaaaga tttgggcgag 2160
tactacgcgg agcttaatcc actactctac cacatctcat tccagcgcat cgctgagaag 2220
gaaatcatgg acgcggtgga gacaggcaaa ctgtacctct tccagatata caacaaagac 2280
ttcgctaagg ggcaccacgg gaagcccaac cttcatacgc tctactggac gggcctattc 2340
agccccgaaa atctgccaa gacctccatc aagctgaacg gccaagcgga gctgttctac 2400
agacccaaga gccggatgaa gcggatggcc cacaggctcg gcgagaaaat gcttaacaaa 2460
aagttgaagg accagaaaac ccctatcccc gacaccctct accaggaact gtacgactac 2520
gtgaaccaca ggctctcgca cgacctttc gacgaggccc gtgccctact cccgaacgtc 2580
attaccaaag aggtttcgca cgagatcatc aaggaccggc ggttcacgag cgacaagttt 2640
ttctttcacg tccccatcac ccttaactac caggcggcca actccccatc caagttcaac 2700
cagcgtgtga atgcctacct caaggagcac ccagagaccc cgatcattgg gatcgaccgg 2760
ggcgagcgga acctgatcta catcaccgtc atcgactcga cgggcaagat tcttgagcag 2820
agatcgttga ataccataca gcagttcgac taccagaaga aactcgacaa ccgcgagaag 2880
gagcgcgtgg cggcccgcca ggcgtggcc gtcgttggga cgattaagga cttgaaacaa 2940
ggttatctgt cccaagtcat ccacgagatc gttgatctga tgatccacta tcaggcagtg 3000
gtggtgctgg agaatctcaa cttcggcttc aagagtaagc ggactggacg aaagggcatg 3060
gccgtgtacc agcagttcga gaagatgctg atcgacaagc tcaactgcct tgtgctgaaa 3120
gactaccgg ccgagaaggt cggcggcgtc tcaacccgt accaacttac cgaccagttc 3180
acctccttcg ccaagatggg cactcagtcc gggttcttgt tctacgtccc cgcacccttac 3240
acctctaaga tcgatcctct gactggcttc gtagatccat tcgtgtggaa gaccattaag 3300
aaccacgaga gccgcaagca cttcctggag gcttcgact tcctgcacta cgacgtgaag 3360
accgggaact tcatccttca cttcaagatg aaccggaacc tcagcttcca gcggggcctg 3420
ccgggggttca tgcccgcctg ggacatcgtg ttcgagaaga acgagaccca gttcgacgcg 3480
aagggcacgc ccttcatcgc cgggaagcgt atcgtgccgg tgatcgagaa ccatcgtttc 3540
acgggtcgct accgtgacct ctaccgcgcg aacgagctta tcgcactcct ggaggagaag 3600
ggcatcgtct tcccgggacg ctccaacatc ctcccgaaac tctgtgaaaa tgctgagactc 3660
cacgccatcg acacgatggt ggccctcatc cggtccgtgc tccaaatgcg gaacagcaac 3720
gccgccaccg gtgaggacta catcaacagc ccggtccggg atctgaacgg ggtgtgcttc 3780
gattcgcggt tccagaatcc tgagtggccg atggacgcgg atgcaaacgg ggcgtaccac 3840
atcgcgctca agggccagtt acttctgaac caccttaagg agtctaaaga tttgaaactc 3900
cagaacggga tctcgaacca ggactggctg gcctacatcc aagagttgcg gaacggcagc 3960
```

```
aagaagcggc ggattaagca agattag                                        3987

SEQ ID NO: 21         moltype = DNA   length = 1592
FEATURE               Location/Qualifiers
source                1..1592
                      mol_type = other DNA
                      organism = Medicago truncatula
SEQUENCE: 21
actgttaata atttttaaac gtcagcgcac taaaaaaacg aaaagacgga cacgtgaaaa    60
taaaaaacac acactagttt atgacgcaat actattttac ttatgatttg ggtacattag   120
acaaaaccgt gaaagagatg tatcagctat gaaacctgta tacttcaata cagagactta   180
ctcatatcgg atacgtacgc acgaagtatc atattaatta ttttaatttt taataaatat   240
tttatcggat acttatgtga tactctacat atacacaagg atatttctaa gatactttat   300
agatacgtat cctagaaaaa catgaagagt aaaaagtga gacaatgttg taaaaattca    360
ttataaatgt atatgattca attttagata tgcatcagta taattgattc tcgatgaaac   420
acttaaaatt atatttcttg tggaagaacg tagcgagaga ggtgattcag ttagacaaca   480
ttaaataaaa ttaatgttaa gttcttttaa tgatgtttct ctcaatatca catcatatga   540
aaatgtaata tgatttataa gaaaatttt aaaaaattta tttaataat cacatgtact    600
attttttaaa aattgtatct tttataataa tacaataata aagagtaatc agtgttaatt   660
tttcttcaaa tataagttttt attataaatc attgttaacg tatcataagt cattaccgta   720
tcgtatctta attttttttt aaaaccgct aattcacgta cccgtattgt attgtacccg    780
cacctgtatc acaatcgatc ttagttagaa gaattgtctc gaggcggtgc aagacagcat   840
ataatagacg tggactctct tataccaaac gttgtcgtat cacaaagggt taggtaacaa   900
gtcacagttt gtccacgtgt cacgttttaa ttggaagagg tgccgttggc gtaatataac   960
agccaatcga ttttgctat aaaagcaaat caggtaaact aaacttcttc attctttct    1020
tcccatcgc tacaaaaccg gttccttgg aaaagagatt cattcaaacc tagcacccaa    1080
ttccgtttca aggtataatc tactttctat tcttcgatta tttattatt attagctact   1140
atcgtttaat cgatctttc ttttgatccg tcaaatttaa attcaattag ggttttgttc    1200
ttttctttca tctgattgaa atccttctga attgaaccgt ttacttgatt ttactgttta   1260
ttgtatgatt taatcctttg tttttcaaag acagtcttta gattgtgatt aggggttcat   1320
ataaatttt agatttggat ttttgtattg tatgattcaa aaaatacgtc ctttaattag    1380
attagtacat ggatatttt tacccgattt attgattgtc agggagaatt tgatgagcaa    1440
gttttttga tgtctgttgt aaattgaatt gattataatt gctgatctgc tgcttccagt    1500
tttcataacc catattcttt taaccttgtt gtacacacaa tgaaaattg gtgattgatt    1560
catttgtttt tctttgtttt ggattataca gg                                 1592

SEQ ID NO: 22         moltype = DNA   length = 2000
FEATURE               Location/Qualifiers
source                1..2000
                      mol_type = other DNA
                      organism = Zea mays
SEQUENCE: 22
gtcgtgcccc tctctagaga taaagagcat tgcatgtcta aagtataaaa aattaccaca    60
tatttttttg tcacacttat ttgaagtgta gtttatctat ctctatacat atatttaaac   120
ttcactctac aaataatata gtctataata ctaaaataat attagtgttt tagaggatca   180
tataaataaa ctgctagaca tggtctaaag gataattgaa tattttgaca atctacagtt   240
ttatctttt agtgtgcatg tgatctctct gtttttttg caaatagctt gacctatata    300
atacttcatc cattttatta gtacatccat ttaggattta gggttgatgg tttctataga   360
ctaatttta gtacatccat tttattcttt ttagtctcta aattttttaa aactaaaact   420
ctatttagt tttttattta ataatttaga tataaaatga aataaaataa attgactaca    480
aataaacaa atacccttta agaaataaaa aaactaagca aacatttttc ttgtttcgag   540
tagataatga caggctgttc aacgccgtcg acgagtctaa cggacaccaa ccagcgaacc   600
agcagcgtcg cgtcgggcca agcgaagcag acggcacggc atctctgtag ctgcctctgg   660
acccctctcg agagttccgc tccacgttg gacttgctcc gctgtcggca tccagaaatt    720
gcgtggcgga gcggcagacg tgaggcggca cggcaggcgg cctcttcctc ctctcacgcg   780
accggcagct acgggggatt cctttccac cgctccttcg ctttcccttc ctcgcccgcc    840
gtaataaata gacacccct ccacaccctc tttcccaac ctcgtgttcg ttcggagcgc    900
acacacacgc aaccagatct cccccaaatc cagccgtcgg cacctccgct tcaaggtacg    960
ccgctcatcc tcccccccc cctctctcta ccttctctag atcggcgatc cggtccatgg   1020
ttagggcccg gtagttctac ttctgttcat gtttgtgtta gagcaaacat gttcatgttc   1080
atgtttgtga tgatgtggtc tggttgggcg gtcgttctag atcggagtag gatactgttt   1140
caagctacct ggtggattta ttaattttgt atctgtatgt gtgtgccata catcttcata   1200
gttacgagtt aagatgatg gatggaaata tcgatctagg ataggtatac atgttgatgc   1260
gggttttact gatgcatata cagagatgct tttttctcg cttggttgtg atgatatggt   1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
atttattaaa ggatctgtat gtatgtgcct acatcttcat agttacgagt taagatgat    1500
ggatggaaat atcgatctag gataggtata catgttgatg cgggttttac tgatgcatat   1560
acagagatgc tttttttcgc ttggttgtga tgatggtg gtcgttctag                1620
atcggagtag aatactgttt caaactacct ggtggattta ttaattttgt atctttatgt   1680
gtgtgccata catcttcata gttacgagtt aagatgatg gatggaaata ttgatctagg   1740
ataggtatac atgttgatgt gggttttact gatgcatata catgatggca tatgcggcat   1800
ctattcatat gctctaacct tgagtaccta tctattataa taaacaagta tgttttataa   1860
ttattttgat cttgatatac ttggatgatg gcatatgcag cagctatatg tggatttttt   1920
agccctgcct tcatacgcta ttatttgct tggtactgtt tcttttgtcc gatgctcacc    1980
ctgttgtttg gtgatacttc                                               2000

SEQ ID NO: 23         moltype = AA   length = 228
FEATURE               Location/Qualifiers
```

```
source                  1..228
                        mol_type = protein
                        organism = Rattus norvegicus
SEQUENCE: 23
SSETGPVAVD PTLRRRIEPH EFEVFFDPRE LRKETCLLYE INWGGRHSIW RHTSQNTNKH    60
VEVNFIEKFT TERYFCPNTR CSITWFLSWS PCGECSRAIT EFLSRYPHVT LFIYIARLYH   120
HADPRNQGL RDLISSGVTI QIMTEQESGY CWRNFVNYSP SNEAHWPRYP HLWVRLYVLE   180
LYCIILGLPP CLNILRRKQP QLTFFTIALQ SCHYQRLPPH ILWATGLK               228

SEQ ID NO: 24           moltype = AA  length = 199
FEATURE                 Location/Qualifiers
source                  1..199
                        mol_type = protein
                        organism = Homo sapiens
SEQUENCE: 24
MEASPASGPR HLMDPHIFTS NFNNGIGRHK TYLCYEVERL DNGTSVKMDQ HRGFLHNQAK    60
NLLCGFYGRH AELRFLDLVP SLQLDPAQIY RVTWFISWSP CFSWGCAGEV RAFLQENTHV   120
RLRIFAARIY DYDPLYKEAL QMLRDAGAQV SIMTYDEFKH CWDTFVDHQG CPFQPWDGLD   180
EHSQALSGRL RAILQNQGN                                               199

SEQ ID NO: 25           moltype = DNA  length = 621
FEATURE                 Location/Qualifiers
source                  1..621
                        mol_type = other DNA
                        organism = Petromyzon marinus
SEQUENCE: 25
acagatgcag agtatgtgag aattcacgaa aagctggaca tctatacctt caagaagcag    60
ttctttaaca ataagaagtc tgtgagccat aggtgctacg tgctgttcga gctgaagaga   120
aggggtgaaa gaagggcatg ttttgggggg tatgctgtga acaagcccca gtctggaact   180
gagagggca ttcacgccga aattttcagc atcagaaagg tggaggaata cctgagggat   240
aaccctggac agtttacaat taattggtat tctagctggt ctccatgcgc tgactgtgcc   300
gagaagatcc tggaatggta caaccaggag ctgagaggaa atggccatac cctgaagatt   360
tgggcctgca agctgtacta tgaaaagaac gcaagaaatc agatcggact gtggaacctg   420
agggataatg gtgtggggct gaacgtgatg gtgtccgagc actatcagtg ctgtagaaag   480
attttcattc agtcctcaca taatcagctg aacgagaata gatggctgga aaagactctg   540
aagagggctg agaagagaag gtccgaactg tcaattatga tccaggtgaa gatcctgcac   600
accactaagt cacctgccgt g                                            621

SEQ ID NO: 26           moltype = AA  length = 160
FEATURE                 Location/Qualifiers
source                  1..160
                        mol_type = protein
                        organism = synthetic construct
SEQUENCE: 26
FERNYDPREL RKETYLLYEI KWGKSGKLWR HWCQNNRTQH AEVYFLENIF NARRFNPSTH    60
CSITWYLSWS PCAECSQKIV DFLKEHPNVL EIYVARLYYH EDERNRQGLR DLVNSGVTIR   120
IMDLPDYNYC WKTFVSDQGG DEDYWPGHFA PWIKQYSLKL                        160

SEQ ID NO: 27           moltype = AA  length = 207
FEATURE                 Location/Qualifiers
source                  1..207
                        mol_type = protein
                        organism = synthetic construct
SEQUENCE: 27
TDAEYVRIHE KLDIYTFKKQ FSNNKKSVSH RCYVLFELKR RGERRACFWG YAVNKPQSGT    60
ERGIHAEIFS IRKVEEYLRD NPGQFTINWY SSWSPCADCA EKILEWYNQE LRGNGHTLKI   120
WVCKLYYEKN ARNQIGLWNL RDNGVGLNVM VSEHYQCCRK IFIQSSHNQL NENRWLEKTL   180
KRAEKRRSEL SIMFQVKILH TTKSPAV                                      207

SEQ ID NO: 28           moltype = AA  length = 228
FEATURE                 Location/Qualifiers
source                  1..228
                        mol_type = protein
                        organism = synthetic construct
SEQUENCE: 28
SSKTGPVAVD PTLRRRIEPH EFEVFFDPRE LRKETCLLYE INWGGRHSIW RHTSQNTNKH    60
VEVNFIEKFT TERYFCPNTR CSITWFLSWS PCGECSRAIT EFLSRYPNVT LFIYIARLYH   120
LANPRNQGL RDLISSGVTI QIMTEQESGY CWHNFVNYSP SNESHWPRYP HLWVRLYVLE   180
LYCIILGLPP CLNILRRKQS QLTSFTIALQ SCHYQRLPPH ILWATGLK               228

SEQ ID NO: 29           moltype = AA  length = 162
FEATURE                 Location/Qualifiers
source                  1..162
                        mol_type = protein
                        organism = synthetic construct
SEQUENCE: 29
SFERNYDPRE LRKETYLLYE IKWGKSGKLW RHWCQNNRTQ HAEVYFLENI FNARRFNPST    60
HCSITWYLSW SPCAECSQKI VDFLKEHPNV NLEIYVARLY YPENERNRQG LRDLVNSGVT   120
IRIMDLPDYN YCWKTFVSDQ GGDEDYWPGH FAPWIKQYSL KL                     162
```

```
SEQ ID NO: 30            moltype = AA  length = 166
FEATURE                  Location/Qualifiers
source                   1..166
                         mol_type = protein
                         organism = Escherichia coli
SEQUENCE: 30
SEVEFSHEYW MRHALTLAKR AWDEREVPVG AVLVHNNRVI GEGWNRPIGR HDPTAHAEIM    60
ALRQGGLVMQ NYRLIDATLY VTLEPCVMCA GAMIHSRIGR VVFGARDAKT GAAGSLMDVL   120
HHPGMNHRVE ITEGILADEC AALLSDFFRM RRQEIKAQKK AQSSTD                  166

SEQ ID NO: 31            moltype = AA  length = 166
FEATURE                  Location/Qualifiers
source                   1..166
                         mol_type = protein
                         organism = synthetic construct
SEQUENCE: 31
SEVEFSHEYW MRHALTLAKR ARDEREVPVG AVLVLNNRVI GEGWNRAIGL HDPTAHAEIM    60
ALRQGGLVMQ NYRLIDATLY VTFEPCVMCA GAMIHSRIGR VVFGVRNAKT GAAGSLMDVL   120
HYPGMNHRVE ITEGILADEC AALLCYFFRM PRQVFNAQKK AQSSTD                  166

SEQ ID NO: 32            moltype = AA  length = 166
FEATURE                  Location/Qualifiers
source                   1..166
                         mol_type = protein
                         organism = synthetic construct
SEQUENCE: 32
SEVEFSHEYW MRHALTLAKR AWDEREVPVG AVLVLNNRVI GEGWNRSIGL HDPTAHAEIM    60
ALRQGGLVMQ NYRLIDATLY VTFEPCVMCA GAMIHSRIGR VVFGVRNAKT GAAGSLMDVL   120
HYPGMNHRVE ITEGILADEC AALLCYFFRM RRQVFNAQKK AQSSTD                  166

SEQ ID NO: 33            moltype = AA  length = 166
FEATURE                  Location/Qualifiers
source                   1..166
                         mol_type = protein
                         organism = synthetic construct
SEQUENCE: 33
SEVEFSHEYW MRHALTLAKR ALDEREVPVG AVLVLNNRVI GEGWNRAIGL HDPTAHAEIM    60
ALRQGGLVMQ NYRLIDATLY VTFEPCVMCA GAMIHSRIGR VVFGVRNAKT GAAGSLMDVL   120
HYPGMNHRVE ITEGILADEC NALLCYFFRM RRQVFNAQKK AQSSTD                  166

SEQ ID NO: 34            moltype = AA  length = 166
FEATURE                  Location/Qualifiers
source                   1..166
                         mol_type = protein
                         organism = synthetic construct
SEQUENCE: 34
SEVEFSHEYW MRHALTLAKR ALDEREVPVG AVLVLNNRVI GEGWNRAIGL HDPTAHAEIM    60
ALRQGGLVMQ NYRLIDATLY VTFEPCVMCA GAMIHSRIGR VVFGVRNAKT GAAGSLMDVL   120
HYPGMNHRVE ITEGILADEC NALLCYFFRM PRQVFNAQKK AQSSTD                  166

SEQ ID NO: 35            moltype = AA  length = 1763
FEATURE                  Location/Qualifiers
source                   1..1763
                         mol_type = protein
                         organism = synthetic construct
SEQUENCE: 35
SEVEFSHEYW MRHALTLAKR AWDEREVPVG AVLVHNNRVI GEGWNRPIGR HDPTAHAEIM    60
ALRQGGLVMQ NYRLIDATLY VTLEPCVMCA GAMIHSRIGR VVFGARDAKT GAAGSLMDVL   120
HHPGMNHRVE ITEGILADEC AALLSDFFRM RRQEIKAQKK AQSSTDSGGS SGGSSGGSETP  180
GTSESATPES SGGSSGGSSE VEFSHEYWMR HALTLAKRAR DEREVPVGAV LVLNNRVIGE   240
GWNRAIGLHD PTAHAEIMAL RQGGLVMQNY RLIDATLYVT FEPCVMCAGA MIHSRIGRVV   300
FGVRNAKTGA AGSLMDVLHY PGMNHRVEIT EGILADECAA LLCYFFRMPR QVFNAQKKAQ   360
SSTDSGGSSG GSSSGETPGT SESATPESSG GSSGGSDKKY SIGLAIGTNS VGWAVITDEY   420
KVPSKKFKVL GNTDRHSIKK NLIGALLFDS GETAEATRLK RTARRRYTRR KNRICYLQEI   480
FSNEMAKVDD SFFHRLEESF LVEEDKKHER HPIFGNIVDE VAYHEKYPTI YHLRKKLVDS   540
TDKADLRLIY LALAHMIKFR GHFLIEGDLN PDNSDVDKLF IQLVQTYNQL FEENPINASG   600
VDAKAILSAR LSKSRRLENL IAQLPGEKKN GLFGNLIALS LGLTPNFKSN FDLAEDAKLQ   660
LSKDTYDDDL DNLLAQIGDQ YADLFLAAKN LSDAILLSDI LRVNTEITKA PLSASMIKRY   720
DEHHQDLTLL KALVRQQLPE KYKEIFFDQS KNGYAGYIDG GASQEEFYKF IKPILEKMDG   780
TEELLVKLNR EDLLRKQRTF DNGSIPHQIH LGELHAILRR QEDFYPFLKD NREKIEKILT   840
FRIPYYVGPL ARGNSRFAWM TRKSEETITP WNFEEVVDKG ASAQSFIERM TNFDKNLPNE   900
KVLPKHSLLY EYFTVYNELT KVKYVTEGMR KPAFLSGEQK KAIVDLLFKT NRKVTVKQLK   960
EDYFKKIECF DSVEISGVED RFNASLGTYH DLLKIIKDKD FLDNEENEDI LEDIVLTLTL  1020
FEDREMIEER LKTYAHLFDD KVMKQLKRRR YTGWGRLSRK LINGIRDKQS GKTILDFLKS  1080
DGFANRNFMQ LIHDDSLTFK EDIQKAQVSG QGDSLHEHIA NLAGSPAIKK GILQTVKVVD  1140
ELVKVMGRHK PENIVIEMAR ENQTTQKGQK NSRERMKRIE EGIKELGSQI LKEHPVENTQ  1200
LQNEKLYLYY LQNGRDMYVD QELDINRLSD YDVDHIVPQS FLKDDSIDNK VLTRSDKNRG  1260
KSDNVPSEEV VKKMKNYWRQ LLNAKLITQR KFDNLTKAER GGLSELDKAG FIKRQLVETR  1320
```

-continued

```
QITKHVAQIL DSRMNTKYDE NDKLIREVKV ITLKSKLVSD FRKDFQFYKV REINNYHHAH  1380
DAYLNAVVGT ALIKKYPKLE SEFVYGDYKV YDVRKMIAKS EQEIGKATAK YFFYSNIMNF  1440
FKTEITLANG EIRKRPLIET NGETGEIVWD KGRDFATVRK VLSMPQVNIV KKTEVQTGGF  1500
SKESILPKRN SDKLIARKKD WDPKKYGGFD SPTVAYSVLV VAKVEKGKSK KLKSVKELLG  1560
ITIMERSSFE KNPIDFLEAK GYKEVKKDLI IKLPKYSLFE LENGRKRMLA SAGELQKGNE  1620
LALPSKYVNF LYLASHYEKL KGSPEDNEQK QLFVEQHKHY LDEIIEQISE FSKRVILADA  1680
NLDKVLSAYN KHRDKPIREQ AENIIHLFTL TNLGAPAAFK YFDTTIDRKR YTSTKEVLDA  1740
TLIHQSITGL YETRIDLSQL GGD                                         1763

SEQ ID NO: 36          moltype = AA  length = 1565
FEATURE                Location/Qualifiers
source                 1..1565
                       mol_type = protein
                       organism = synthetic construct
SEQUENCE: 36
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNSKR GAAGSLMNVL  120
NYPGMNHRVE ITEGILADEC AALLCDFYRM PRQVFNAQKK AQSSINSGGS SGGSSGSETP  180
GTSESATPES SGGSSGGSDK KYSIGLAIGT NSVGWAVITD EYKVPSKKFK VLGNTDRHSI  240
KKNLIGALLF DSGETAEATR LKRTARRRYT RRKNRICYLQ EIFSNEMAKV DDSFFHRLEE  300
SFLVEEDKKH ERHPIFGNIV DEVAYHEKYP TIYHLRKKLV DSTDKADLRL IYLALAHMIK  360
FRGHFLIEGD LNPDNSDVDK LFIQLVQTYN QLFEENPINA SGVDAKAILS ARLSKSRRLE  420
NLIAQLPGEK KNGLFGNLIA LSLGLTPNFK SNFDLAEDAK LQLSKDTYDD DLDNLLAQIG  480
DQYADLFLAA KNLSDAILLS DILRVNTEIT KAPLSASMIK RYDEHHQDLT LLKALVRQQL  540
PEKYKEIFFD QSKNGYAGYI DGGASQEEFY KFIKPILEKM DGTEELLVKL NREDLLRKQR  600
TFDNGSIPHQ IHLGELHAIL RRQEDFYPFL KDNREKIEKI LTFRIPYYVG PLARGNSRFA  660
WMTRKSEETI TPWNFEEVVD KGASAQSFIE RMTNFDKNLP NEKVLPKHSL LYEYFTVYNE  720
LTKVKYVTEG MRKPAFLSGE QKKAIVDLLF KTNRKVTVKQ LKEDYFKKIE CFDSVEISGV  780
EDRFNASLGT YHDLLKIIKD KDFLDNEENE DILEDIVLTL TLFEDREMIE ERLKTYAHLF  840
DDKVMKQLKR RRYTGWGRLS RKLINGIRDK QSGKTILDFL KSDGFANRNF MQLIHDDSLT  900
FKEDIQKAQV SGQGDSLHEH IANLAGSPAI KKGILQTVKV VDELVKVMGR HKPENIVIEM  960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                             1565

SEQ ID NO: 37          moltype = AA  length = 1565
FEATURE                Location/Qualifiers
source                 1..1565
                       mol_type = protein
                       organism = synthetic construct
SEQUENCE: 37
SEVEFSHEYW MRHALTLAKR ARDEREVPVG AVLVLNNRVI GEGWNRAIGL HDPTAHAEIM  60
ALRQGGLVMQ NYRLYDATLY STFEPCVMCA GAMIHSRIGR VVFGVRNAKT GAAGSLMNVL  120
HHPGMNHRVE ITEGILADEC AALLCRFFRM PRRVFNAQKK AQSSTDSGGS SGGSSGSETP  180
GTSESATPES SGGSSGGSDK KYSIGLAIGT NSVGWAVITD EYKVPSKKFK VLGNTDRHSI  240
KKNLIGALLF DSGETAEATR LKRTARRRYT RRKNRICYLQ EIFSNEMAKV DDSFFHRLEE  300
SFLVEEDKKH ERHPIFGNIV DEVAYHEKYP TIYHLRKKLV DSTDKADLRL IYLALAHMIK  360
FRGHFLIEGD LNPDNSDVDK LFIQLVQTYN QLFEENPINA SGVDAKAILS ARLSKSRRLE  420
NLIAQLPGEK KNGLFGNLIA LSLGLTPNFK SNFDLAEDAK LQLSKDTYDD DLDNLLAQIG  480
DQYADLFLAA KNLSDAILLS DILRVNTEIT KAPLSASMIK RYDEHHQDLT LLKALVRQQL  540
PEKYKEIFFD QSKNGYAGYI DGGASQEEFY KFIKPILEKM DGTEELLVKL NREDLLRKQR  600
TFDNGSIPHQ IHLGELHAIL RRQEDFYPFL KDNREKIEKI LTFRIPYYVG PLARGNSRFA  660
WMTRKSEETI TPWNFEEVVD KGASAQSFIE RMTNFDKNLP NEKVLPKHSL LYEYFTVYNE  720
LTKVKYVTEG MRKPAFLSGE QKKAIVDLLF KTNRKVTVKQ LKEDYFKKIE CFDSVEISGV  780
EDRFNASLGT YHDLLKIIKD KDFLDNEENE DILEDIVLTL TLFEDREMIE ERLKTYAHLF  840
DDKVMKQLKR RRYTGWGRLS RKLINGIRDK QSGKTILDFL KSDGFANRNF MQLIHDDSLT  900
FKEDIQKAQV SGQGDSLHEH IANLAGSPAI KKGILQTVKV VDELVKVMGR HKPENIVIEM  960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                             1565

SEQ ID NO: 38          moltype = AA  length = 364
FEATURE                Location/Qualifiers
```

```
source                  1..364
                        mol_type = protein
                        organism = synthetic construct
SEQUENCE: 38
SEVEFSHEYW MRHALTLAKR AWDEREVPVG AVLVHNNRVI GEGWNRPIGR HDPTAHAEIM    60
ALRQGGLVMQ NYRLIDATLY VTLEPCVMCA GAMIHSRIGR VVFGARDAKT GAAGSLMDVL   120
HHPGMNHRVE ITEGILADEC AALLSDFFRM RRQEIKAQKK AQSSTDSGGS SGGSSGSETP   180
GTSESATPES SGGSSGGSSE VEFSHEYWMR HALTLAKRAR DEREVPVGAV LVLNNRVIGE   240
GWNRAIGLHD PTAHAEIMAL RQGGLVMQNY RLIDATLYVT FEPCVMCAGA MIHSRIGRVV   300
FGVRNAKTGA AGSLMDVLHY PGMNHRVEIT EGILADECAA LLCYFFRMPR QVFNAQKKAQ   360
SSTD                                                                364

SEQ ID NO: 39           moltype = AA  length = 167
FEATURE                 Location/Qualifiers
source                  1..167
                        mol_type = protein
                        organism = synthetic construct
SEQUENCE: 39
MSEVEFSHEY WMRHALTLAK RARDEREVPV GAVLVLNNRV IGEGWNRAIG LHDPTAHAEI    60
MALRQGGLVM QNYRLYDATL YSTFEPCVMC AGAMIHSRIG RVVFGVRNAK TGAAGSLMDV   120
LHHPGMNHRV EITEGILADE CAALLCRFFR MPRRVFNAQK KAQSSTD                 167

SEQ ID NO: 40           moltype = AA  length = 167
FEATURE                 Location/Qualifiers
source                  1..167
                        mol_type = protein
                        organism = synthetic construct
SEQUENCE: 40
MSEVEFSHEY WMRHALTLAK RARDEREVPV GAVLVLNNRV IGEGWNRAIG LHDPTAHAEI    60
MALRQGGLVM QNYRLIDATL YVTFEPCVMC AGAMIHSRIG RVVFGVRNSK RGAAGSLMNV   120
LNYPGMNHRV EITEGILADE CAALLCDFYR MPRQVFNAQK KAQSSIN                 167

SEQ ID NO: 41           moltype = AA  length = 83
FEATURE                 Location/Qualifiers
source                  1..83
                        mol_type = protein
                        organism = Bacillus phage AR9
SEQUENCE: 41
TNLSDIIEKE TGKQLVIQES ILMLPEEVEE VIGNKPESDI LVHTAYDEST DENVMLLTSD    60
APEYKPWALV IQDSNGENKI KML                                           83

SEQ ID NO: 42           moltype = AA  length = 24
FEATURE                 Location/Qualifiers
source                  1..24
                        mol_type = protein
                        organism = synthetic construct
SEQUENCE: 42
EELLSKNYHL ENEVARLKKG SGSG                                          24

SEQ ID NO: 43           moltype = AA  length = 241
FEATURE                 Location/Qualifiers
source                  1..241
                        mol_type = protein
                        organism = synthetic construct
SEQUENCE: 43
EEELLSKNYH LENEVARLKK GSGSGEELLS KNYHLENEVA RLKKGSGSGE ELLSKNYHLE    60
NEVARLKKGS GSGEELLSKN YHLENEVARL KKGSGSGEEL LSKNYHLENE VARLKKGSGS   120
GEELLSKNYH LENEVARLKK GSGSGEELLS KNYHLENEVA RLKKGSGSGE ELLSKNYHLE   180
NEVARLKKGS GSGEELLSKN YHLENEVARL KKGSGSGEEL LSKNYHLENE VARLKKGSGS   240
G                                                                   241

SEQ ID NO: 44           moltype = AA  length = 277
FEATURE                 Location/Qualifiers
source                  1..277
                        mol_type = protein
                        organism = synthetic construct
SEQUENCE: 44
MGPDIVMTQS PSSLSASVGD RVTITCRSST GAVTTSNYAS WVQEKPGKLF KGLIGGTNNR    60
APGVPSRFSG SLIGDKATLT ISSLQPEDFA TYFCALWYSN HWVFGQGTKV ELKRGGGGSG   120
GGGSGGGGSS GGGSEVKLLE SGGGLVQPGG SLKLSCAVSG FSLTDYGVNW VRQAPGRGLE   180
WIGVIWGDGI TDYNSALKDR FIISKDNGKN TVYLQMSKVR SDDTALYYCV TGLFDYWGQG   240
TLVTVSSYPY DVPDYAGGGG GSGGGGSGGG GSGGGGS                            277

SEQ ID NO: 45           moltype = DNA  length = 66
FEATURE                 Location/Qualifiers
source                  1..66
                        mol_type = other DNA
                        organism = Saccharomyces bayanus
SEQUENCE: 45
```

-continued

```
ttcttgtcgt acttatagat cgctacgtta tttcaatttt gaaaatctga gtcctgggag    60
tgcgga                                                                66

SEQ ID NO: 46           moltype = AA  length = 605
FEATURE                 Location/Qualifiers
source                  1..605
                        mol_type = protein
                        organism = Homo sapiens
SEQUENCE: 46
MSGWESYYKT EGDEEAEEEQ EENLEASGDY KYSGRDSLIF LVDASKAMFE SQSEDELTPF     60
DMSIQCIQSV YISKIISSDR DLLAWFYGTE KDKNSVNFKI YVLQELDNPG AKRILELDQF    120
KGQQGQKRFQ DMMGHGSDYS LSEVLWVCAN LFSDVQFKMS HKRIMLFTNE DNPHGNDSAK    180
ASRARTKAGD LRDTGIFLDL HLKKPGGFDI SLFYRDIISI AEDEDLRVHF EESSKLEDLL    240
RKVRAKETRK RALSRLKLKL NKDIVISVGI YNLVQKALKP PPIKLYRETN EPVKTKTRTF    300
NTSTGGLLLP SDTKRSQIYG SRQIILEKEE TEELKRFDDP GLMLMGFKPL VLLKKHHYLR    360
PSLFVYPEES LVIGSSTLFS ALLIKCLEKE VAALCRYTPR RNIPPYFVAL VPQEEELDDQ    420
KIQVTPPGFQ LVFLPFADDK RKMPFTEKIM ATPEQVGKMK AIVEKLRFTY RSDSFENPVL    480
QQHFRNLEAL ALDLMEPEQA VDLTLPKVEA MNKRLGSLVD EFKELVYPPD YNPEGKVTLR    540
KHDNEGSGSK RPKVEYSEEE LKTHISKGTL GKFTVPLKEA CRAYGLKSGL KKQELLEALT    600
KHFQD                                                               605

SEQ ID NO: 47           moltype = AA  length = 482
FEATURE                 Location/Qualifiers
source                  1..482
                        mol_type = protein
                        organism = synthetic construct
SEQUENCE: 47
MVRSGNKAAW LCMDVGFTMS NSIPGIESPF EQAKKVITMF VQRQVFAENK DEIALVLFGT     60
DGTDNPLSGG DQYQNITVHR HLMLPDFDLL EDIESKIQPG SQQADFLDAL IVSMDVIQHE    120
TIGKKFEKRH IEIFTDLSSR FSKSQLDIII HSLKKCDISE RHSIHWPCRL TIGSNLSIRI    180
AAYKSILQER VKKTTWDAKT LKKEDIQKET VYCLNDDDET EVLKEDIIQG FRYGSDIVPF    240
SKVDEEQMKY KSEGKCFSVL GFCKSSQVQR RFFMGNQVLK VFAARDDEAA AVALSSLIHA    300
LDDLDIWAIV RYAYDKRANP QVGVAFPHIK HNYECLVYVQ LPFMEDLRQY MFSSLKNSKK    360
YAPTEAQLNA VDALIDSMSL AKKDEKTDTL EDLFPTTKIP NPRFQRLFQC LLHRALHPRE    420
PLPPIQQHIW NMLNPPAEVT TKSQIPLSKI KTLFPLIEAK KKDQVTAQEI FQDNHEDGPT    480
AK                                                                  482

SEQ ID NO: 48           moltype = DNA  length = 10
FEATURE                 Location/Qualifiers
source                  1..10
                        mol_type = other DNA
                        organism = Methanobacterium thermoautotrophicum
SEQUENCE: 48
aattttttgga                                                           10

SEQ ID NO: 49           moltype = AA  length = 83
FEATURE                 Location/Qualifiers
source                  1..83
                        mol_type = protein
                        organism = Methanobacterium thermoautotrophicum
SEQUENCE: 49
GSVIDVSSQR VNVQRPLDAL GNSLNSPVII KLKGDREFRG VLKSFDLHMN LVLNDAEELE     60
DGEVTRRLGT VLIRGDNIVY ISP                                             83

SEQ ID NO: 50           moltype = DNA  length = 25
FEATURE                 Location/Qualifiers
source                  1..25
                        mol_type = other DNA
                        organism = Bacteriophage MS2
SEQUENCE: 50
gcgcacatga ggatcaccca tgtgc                                           25

SEQ ID NO: 51           moltype = AA  length = 116
FEATURE                 Location/Qualifiers
source                  1..116
                        mol_type = protein
                        organism = Bacteriophage MS2
SEQUENCE: 51
MASNFTQFVL VDNGGTGDVT VAPSNFANGI AEISSNSRSQ AYKVTCSVRQ SSAQNRKYTI     60
KVEVPKGAWR SYLNMELTIP IFATNSDCEL IVKAMQGLLK DGNPIPSAIA ANSGIY        116

SEQ ID NO: 52           moltype = DNA  length = 26
FEATURE                 Location/Qualifiers
source                  1..26
                        mol_type = other DNA
                        organism = Bacteriophage PP7
SEQUENCE: 52
ataaggagtt tatatggaaa cccctta                                         26
```

```
SEQ ID NO: 53                moltype = AA  length = 127
FEATURE                      Location/Qualifiers
source                       1..127
                             mol_type = protein
                             organism = Bacteriophage PP7
SEQUENCE: 53
MSKTIVLSVG EATRTLTEIQ STADRQIFEE KVGPLVGRLR LTASLRQNGA KTAYRVNLKL   60
DQADWDCSTS VCGELPKVRY TQVWSHDVTI VANSTEASRK SLYDLTKSLV ATSQVEDLVV   120
NLVPLGR                                                            127

SEQ ID NO: 54                moltype = DNA  length = 19
FEATURE                      Location/Qualifiers
source                       1..19
                             mol_type = other DNA
                             organism = Shigella phage
SEQUENCE: 54
ctgaatgcct gcgagcatc                                                19

SEQ ID NO: 55                moltype = AA  length = 62
FEATURE                      Location/Qualifiers
source                       1..62
                             mol_type = protein
                             organism = Shigella phage
SEQUENCE: 55
MKSIRCKNCN KLLFKADSFD HIEIRCPRCK RHIIMLNACE HPTEKHCGKR EKITHSDETV   60
RY                                                                 62

SEQ ID NO: 56                moltype = AA  length = 1367
FEATURE                      Location/Qualifiers
source                       1..1367
                             mol_type = protein
                             organism = synthetic construct
SEQUENCE: 56
DKKYSIGLAI GTNSVGWAVI TDEYKVPSKK FKVLGNTDRH SIKKNLIGAL LFDSGETAEA   60
TRLKRTARRR YTRRKNRICY LQEIFSNEMA KVDDSFFHRL EESFLVEEDK KHERHPIFGN   120
IVDEVAYHEK YPTIYHLRKK LVDSTDKADL RLIYLALAHM IKFRGHFLIE GDLNPDNSDV   180
DKLFIQLVQT YNQLFEENPI NASGVDAKAI LSARLSKSRR LENLIAQLPG EKKNGLFGNL   240
IALSLGLTPN FKSNFDLAED AKLQLSKDTY DDDLDNLLAQ IGDQYADLFL AAKNLSDAIL   300
LSDILRVNTE ITKAPLSASM IKRYDEHHQD LTLLKALVRQ QLPEKYKEIF FDQSKNGYAG   360
YIDGGASQEE FYKFIKPILE KMDGTEELLV KLNREDLLRK QRTFDNGSIP HQIHLGELHA   420
ILRRQEDFYP FLKDNREKIE KILTFRIPYY VGPLARGNSR FAWMTRKSEE TITPWNFEEV   480
VDKGASAQSF IERMTNFDKN LPNEKVLPKH SLLYEYFTVY NELTKVKYVT EGMRKPAFLS   540
GEQKKAIVDL LFKTNRKVTV KQLKEDYFKK IECFDSVEIS GVEDRFNASL GTYHDLLKII   600
KDKDFLDNEE NEDILEDIVL TLTLFEDREM IEERLKTYAH LFDDKVMKQL KRRRYTGWGR   660
LSRKLINGIR DKQSGKTILD FLKSDGFANR NFMQLIHDDS LTFKEDIQKA QVSGQGDSLH   720
EHIANLAGSP AIKKGILQTV KVVDELVKVM GRHKPENIVI EMARENQTTQ KGQKNSRERM   780
KRIEEGIKEL GSQILKEHPV ENTQLQNEKL YLYYLQNGRD MYVDQELDIN RLSDYDVDHI   840
VPQSFLKDDS IDNKVLTRSD KNRGKSDNVP SEEVVKKMKN YWRQLLNAKL ITQRKFDNLT   900
KAERGGLSEL DKAGFIKRQL VETRQITKHV AQILDSRMNT KYDENDKLIR EVKVITLKSK   960
LVSDFRKDFQ FYKVREINNY HHAHDAYLNA VVGTALIKKY PKLESEFVYG DYKVYDVRKM   1020
IAKSEQEIGK ATAKYFFYSN IMNFFKTEIT LANGEIRKRP LIETNGETGE IVWDKGRDFA   1080
TVRKVLSMPQ VNIVKKTEVQ TGGFSKESIL PKRNSDKLIA RKKDWDPKKY GGFDSPTVAY   1140
SVLVVAKVEK GKSKKLKSVK ELLGITIMER SSFEKNPIDF LEAKGYKEVK KDLIIKLPKY   1200
SLFELENGRK RMLASAGELQ KGNELALPSK YVNFLYLASH YEKLKGSPED NEQKQLFVEQ   1260
HKHYLDEIIE QISEFSKRVI LADANLDKVL SAYNKHRDKP IREQAENIIH LFTLTNLGAP   1320
AAFKYFDTTI DRKRYTSTKE VLDATLIHQS ITGLYETRID LSQLGGD                1367

SEQ ID NO: 57                moltype = AA  length = 1367
FEATURE                      Location/Qualifiers
source                       1..1367
                             mol_type = protein
                             organism = synthetic construct
SEQUENCE: 57
DKKYSIGLAI GTNSVGWAVI TDEYKVPSKK FKVLGNTDRH SIKKNLIGAL LFDSGETAEA   60
TRLKRTARRR YTRRKNRICY LQEIFSNEMA KVDDSFFHRL EESFLVEEDK KHERHPIFGN   120
IVDEVAYHEK YPTIYHLRKK LVDSTDKADL RLIYLALAHM IKFRGHFLIE GDLNPDNSDV   180
DKLFIQLVQT YNQLFEENPI NASGVDAKAI LSARLSKSRR LENLIAQLPG EKKNGLFGNL   240
IALSLGLTPN FKSNFDLAED AKLQLSKDTY DDDLDNLLAQ IGDQYADLFL AAKNLSDAIL   300
LSDILRVNTE ITKAPLSASM IKRYDEHHQD LTLLKALVRQ QLPEKYKEIF FDQSKNGYAG   360
YIDGGASQEE FYKFIKPILE KMDGTEELLV KLNREDLLRK QRTFDNGSIP HQIHLGELHA   420
ILRRQEDFYP FLKDNREKIE KILTFRIPYY VGPLARGNSR FAWMTRKSEE TITPWNFEEV   480
VDKGASAQSF IERMTNFDKN LPNEKVLPKH SLLYEYFTVY NELTKVKYVT EGMRKPAFLS   540
GEQKKAIVDL LFKTNRKVTV KQLKEDYFKK IECFDSVEIS GVEDRFNASL GTYHDLLKII   600
KDKDFLDNEE NEDILEDIVL TLTLFEDREM IEERLKTYAH LFDDKVMKQL KRRRYTGWGR   660
LSRKLINGIR DKQSGKTILD FLKSDGFANR NFMQLIHDDS LTFKEDIQKA QVSGQGDSLH   720
EHIANLAGSP AIKKGILQTV KVVDELVKVM GRHKPENIVI EMARENQTTQ KGQKNSRERM   780
KRIEEGIKEL GSQILKEHPV ENTQLQNEKL YLYYLQNGRD MYVDQELDIN RLSDYDVDHI   840
VPQSFLADDS IDNKVLTRSD KNRGKSDNVP SEEVVKKMKN YWRQLLNAKL ITQRKFDNLT   900
KAERGGLSEL DKAGFIKRQL VETRQITKHV AQILDSRMNT KYDENDKLIR EVKVITLKSK   960
```

```
LVSDFRKDFQ FYKVREINNY HHAHDAYLNA VVGTALIKKY PALESEFVYG DYKVYDVRKM   1020
IAKSEQEIGK ATAKYFFYSN IMNFFKTEIT LANGEIRKAP LIETNGETGE IVWDKGRDFA   1080
TVRKVLSMPQ VNIVKKTEVQ TGGFSKESIL PKRNSDKLIA RKKDWDPKKY GGFDSPTVAY   1140
SVLVVAKVEK GKSKKLKSVK ELLGITIMER SSFEKNPIDF LEAKGYKEVK KDLIIKLPKY   1200
SLFELENGRK RMLASAGELQ KGNELALPSK YVNFLYLASH YEKLKGSPED NEQKQLFVEQ   1260
HKHYLDEIIE QISEFSKRVI LADANLDKVL SAYNKHRDKP IREQAENIIH LFTLTNLGAP   1320
AAFKYFDTTI DRKRYTSTKE VLDATLIHQS ITGLYETRID LSQLGGD              1367

SEQ ID NO: 58           moltype = DNA  length = 4101
FEATURE                 Location/Qualifiers
source                  1..4101
                        mol_type = other DNA
                        organism = synthetic construct
SEQUENCE: 58
gacaagaagt acagcatcgg gctggcgatc gggaccaact ccgtcggctg ggctgtgatt    60
accgacgagt acaaggtgcc atccaagaag ttcaaggtcc tcggcaacac tgaccggcac   120
agcattaaga agaacctgat tggggcgctg ctgttcgatt cgggggagac tgcggaggcg   180
accaggctga agcggactgc gcgccggagg tacaccagga ggaagaatcg gatctgctac   240
ctccaggaga tttttctcgaa tgagatggcc aaggtggacg attccttctt ccatcgcctg   300
gaggagtcgt tcctccgttga ggaggacaag aagcatgaga ggcatcccat tttcgggaat   360
atcgttgacg aggtggctta ccatgagaag tacccgacca tctaccatct gcggaagaag   420
ctcgtcgatt cgaccgataa ggccgacctg cggctgatct acctggcccc cggcacatg    480
attaagttcc ggggccattt cctcatcgag ggcgacctca acccggacaa ctcggacgtg   540
gataagctct tcattcagct cgtgcagaca taccaaccagc tcttcgagga gaatcccatt   600
aacgcctcgg gggtcgacgc taaggctatt ctctcggctc ggctgtcgaa gtcgcgccgg   660
ctggaaatc tcattgccca gctcccaggc gagaagaaga acggcctctt cggcaacctg   720
attgccctgt cgctggggct cacaccgaat ttcaagtcga acttcgacct cgccgaggac   780
gctaagctcc agctcagcaa ggatacttac gatgatgacc tcgataacct gctcgcccag   840
attggggatc agtacgcgga tctgttcctc gcggccaaga atctcagcga tgctattctc   900
ctgtcggaca ttctccgcgt caacacagag attactaagg ccccactgtc ggcgagcatg   960
attaagaggt acgatgagca tcatcaggac ctgacactgc tcaaggcgct ggtccggcag  1020
cagctccccg agaagtacaa ggagattttc ttcgatcagt caaagaatgg gtacgcgggc  1080
tacattgatg gcgcgcgtc ccaggaggag ttctacaagt tcattaagcc catcctggaa  1140
aagtggacg ggaccaatga gctgctggtg aagctcaatc gggaggacct gctccggaag  1200
cagcgcacat tcgacaatgg ctcgattcct caccagattc acctgggcga gctgcacgcc  1260
atttctccgca ggcaggagga cttctacccg ttcctcaagg acaaccgcga gaagatcgag  1320
aagatcctga ccttccggat tccatactac gtggggccgc tcgcgcgggg gaactcccgg  1380
ttcgcgtgga tgactcgcaa gtccgaagaa acgattacac cgtggaattt cgaggaggtc  1440
gtcgacaagg gcgctagtgc gcagtcattc attgagagga tgaccaattt cgataagaac  1500
ctgcctaacg agaaggtgct gccgaagcat tcgctgctct acgagtactt caccgtttac  1560
aatgagctga ccaaggtgaa gtatgtgact gagggcatga ggaagccagc gttcctgagc  1620
ggcgagcaga agaaggctat cgtggacctg ctcttcaaga ctaaccggaa ggtgactgtg  1680
aagcagctca aggaggacta cttcaagaag attgagtgct tcgattccgt tgaggattagc  1740
gggggtggagg atcggttcaa tgcttcgctc gggacatacc acgatctcct gaagatcatt  1800
aaggataagg acttcctcga caacgaggag aacgaggaca ttctcgaaga tatttgtcctg  1860
accctcaccc tcttcgagga tcgggagatg atcgaggaga ggctcaagac atacgctcat  1920
ctgttcgatg ataaggtcat gaagcagctg aagcgcagctg ggtacaagga gtgggggcgg  1980
ctgagccgga agctgatcaa cgggattcgg gataagcagt ccgggaagac aatttctcgac  2040
ttcctcaagt ccgacgggtt cgctaaccgg aacttcatgc agctcattca tgatgactcg  2100
ctgacattca aggaggatat tcagaaggcg caggtttcgg ggcagggcga ctcgctccac  2160
gagcatattg cgaatctggc gggctccccc gcgattaaga agggcattct gcaaaccgtc  2220
aaggtggttg atgagctggt caaggtcatg gggcggcata agccagaaa tattgtcatc  2280
gagatggcgc gggagaatca gaccacacag aaggggcaga agaactcacg ggagcggatg  2340
aagcgcatcg aggagggcat caaggagctg ggtcgcaga tcctgaagga gcatcccgtg  2400
gagaacactc agctgcaaaa tgacctctact acctctact accctccaga cgggagggac  2460
atgtatgtgg atcaggagct ggatattaat aggctgagcg attacgatgt cgaccacatt  2520
gtcccacagt cgttcctgaa ggacgacagc attgacaaca aggtgctgac ccgctcggat  2580
aagaacaggg gcaagagcga taatgttcca agcgaggagg ttgtgaagaa gatgaagaac  2640
tactggcggc agctcctgaa cgcgaagctc atcacacagc ggaagttcga caacctcacc  2700
aaggctgagc gcggggggcct gagcgagctg gacaaggcgg ggttcattaa gaggcagtca  2760
gtcgagacac ggcagattac aaagcatgtt gcgcagattc tcgattcccg gatgaacacc  2820
aagtacgatg agaacgataa gctgattcgg gaggtcaagg taattaccct gaagtccaag  2880
ctggtgtccg acttcaggaa ggacttccag ttctacaagg ttcgggagat caacaactac  2940
caccacgcac atgatgccta cctcaacgcg tcgtggggaa ccgctctcat caagaagtac  3000
ccaaagctgg agtcagagtt cgtctacggg gattacaagg tttacgacgt gcggaagatg  3060
atcgctaaga gcgagcagga gattggcaag gctaccgcta agtacttctt ctactccaac  3120
atcatgaact tcttcaagac agagattacc ctcgcgaatg gcgagatccg gaagaggccc  3180
ctcatcgaga caaatgggga gacagggggag attgtctggg ataaggggcg ggatttcgcg  3240
accgtccgga aggtcctgtc gatgccccag gttaatattg tcaagaagac tgaggtccaa  3300
actggcggct tctcaaagga gtcgattctc ccaaagagga actccgataa gctcattgct  3360
cggaagaagg attgggaccc caagaagtac ggggggattcg actcccccac tgttgcttac  3420
tctgttctgt tgttgctaa ggtggagaag gggaagtcga gaagctgaa gagcgtgaag  3480
gagctgctcg ggattacaat tatggagagg tcatccttcg agaagaatcc catcgacttc  3540
ctggaagcca agggctacaa ggaggtgaag aaggacctca ttattaagct gcccaagtac  3600
tcgctccttc gagctcagaa tgggcggaag cggatgctgg cgtccgcggg ggagctgcaa  3660
aaggggaacg agctggcgct ccccttccaag tatgtgaact tcctctacct ggcgtcgcac  3720
tacgagaagc tgaaggggtc cccagaggat aatgagcaga agcagctctt cgtcgagcag  3780
cataagcact acctggacga gattatcgag cagattagcg agttctcgaa gcgggtcatc  3840
ctcgcggatg cgaacctgga taaggtgctc agcgcctaca ataagcaccg ggacaagccg  3900
```

```
attcgggagc aggcggagaa tattattcac ctcttcacac tcaccaacct cggggcacca   3960
gctgcgttca agtacttcga cactactatc gaccggaagc ggtacacctc gacgaaggag   4020
gtgctcgacg ccaccctcat tcaccagtcg atcacaggcc tgtacgagac acggattgac   4080
ctgtcccagc tcgggggcga c                                             4101

SEQ ID NO: 59          moltype = DNA   length = 4101
FEATURE                Location/Qualifiers
source                 1..4101
                       mol_type = other DNA
                       organism = synthetic construct
SEQUENCE: 59
gacaagaagt actccattgg cctggcgatt gggacaaact cggtggggtg ggccgtgatt    60
acggatgagt acaaggttcc aagcaagaag ttcaaggtcc tcgggaacac agatcggcat   120
tcgattaaga agaatctcat tggggcgctc ctcttcgact gggggagac agcggaggct   180
accaggctca agcggacagc caggcggcgg tacacaaggc ggaagaatcg catctgctac   240
ctccaggaga ttttctcgaa tgagatggcg aaggtggacg acagcttctt ccatcggctg   300
gaggagtcct tcctggtgga ggaggataag aagcacgaga ggcatccaat tttcgggaac   360
atcgtggacg aggttgcgta ccatgagaag taccctacaa tctaccatct gcggaagaag   420
ctggttgact ccacagacaa ggcggacctg aggctgatct acctcgctct ggcccacatg   480
attaagttcc gcgggcattt cctgatcgag ggggacctga atcccgacaa ttcggatgtg   540
gacaagctct tcatccagct ggtgcagacc tacaaccagc tgttcgagga gaatcccatc   600
aatgcgtcgg gcgttgacgc taaggccatt ctgtccgcta cgtgtcgaa gagcaggagg   660
ctggagaacc tgatcgccca gctgccaggc gagaagaaga atgggctctt cgggaatctg   720
attgcgctct ccctggggct gacaccgaac ttcaagagca atttcgatct ggctgaggac   780
gcgaagctcc agctctcgaa ggacacttac gacgatgacc tcgataacct cctcgcgcag   840
atcggggacg agtacgctga tctcttcctc gccgctaaaa acctctcgga tgctatcctg   900
ctctccgaca ttctccgggt taataccgag attacaaagg ccccactgtc ggcgtccatg   960
atcaagcggt acgatgagca tcatcaggat ctcaccctgc tcaaggccct cgtgcggcag  1020
cagctgcccg agaagtacaa ggagattttc ttcgaccaga gcaagaatgg gtacgctggc  1080
tacattgacg gcggggcctc acaggaggag ttctacaagt tcatcaagcc aatcctggag  1140
aagatggatg gacagagga gctgctggtg aagctcaacc gggaggatct gctcaggaag  1200
cagcggacgt cgacaacgg gtcgattccc catcagatcc acctggggga gctgcacgcg  1260
atcctgcgcc ggcaggagga tttctaccct ttcctgaagg ataatcggga agatcgag   1320
aagattctca ccttccggat tccctactac gtcgggccac tcgcgcgggg caatagcagg  1380
ttcgcctgga tgacacggaa gagcgaggag acaatcaccc cctggaactt cgaggaggtt  1440
gtcgacaagg gggcgtccgc ccagtcattc attgagcgga tgaccaattt cgacaagaat  1500
ctgccaaatg agaaggttct cccaaagcat agcctcctct acgagtactt cactgtttac  1560
aacgagctga ccaaggtgaa gtatgtgacc gagggcatgc ggaagcccgc gttcctgtcc  1620
ggcgagcaga agaaggccat tgtggacctc gtgttcaaga ccaatcgcaa ggtcacagtc  1680
aagcagctca aggaggatta cttcaagaag atcgagtgct tcgactcggt tgagattagc  1740
ggggtggagg atcggttcaa cgcgagcctc ggcacttacc acgaccctcc tgaagatcatc 1800
aaggataagg acttcctcga caacgaggag aacgaggata ttctggagga catcgtgctc  1860
accctgacgc tgttcgagga tcgggagatg atcgaggacg gcctgaaagac ctacgctcat  1920
ctcttcgatg ataaggtcat gaagcagctg aagaggaggc ggtacaccgg gtggggccgc  1980
ctgagcagga agctcattaa cgggatcagg gacaagcaga gcggcaagac catcctggac  2040
ttcctcaaga gcgatggctt cgccaaccgg aatttcatgc agctcatcca cgacgactcc  2100
ctcaccttca aggaggacat tcagaagctt caggtcaggc gccagggcga ctcgctgcat  2160
gagcacatcg ctaacctggc gggcagccca gccatcaaga agggcatcct ccagacagtg  2220
aaggtcgtgg atgagctggt gaaggtcatg ggccggcata agcccgagaa tattgtgatt  2280
gagatggcgc gggagaatca gaccactcag aagggccaga gaactcgcg ggagcgcatg  2340
aagaggatcg aggaggggat taaggagtcg ggcagcagga ttctcaagga gcaccccgtg  2400
gagaatcccc agctccagaa cgagaagctg tacctctact acctccagaa tgggcgggac  2460
atgtatgttg atcaggagct ggacatcaat cgcctctcgg attacgacgt ggaccacatc  2520
gtgccccaga gcttcctgaa ggatgatagc atcgacaata aggtcctgac ccgctccgac  2580
aagaatccgc gcaagagcga caacgtgccg agcgaggagg tcgtgaagaa gatgaagaac  2640
tactggcggc agctgctgaa cgcgaagctc attacacagc ggaagttcga taacctgacg  2700
aaggcggaga gggcggcct ctccgagctg acaaggcgg gcttcattaa gaggcagctc  2760
gtggagactc gccagatcac caagcacgtg gctcagatcc tcgatagccg gatgaatacg  2820
aagtacgatg agaatgacaa gctcatccgg gaggtgaagg taatcacccc gaagtcaaag  2880
ctcgttagcg atttccggaa ggacttccag ttctacaagg tgcgggagat taacaactac  2940
catcatgcgc acgatgcgta cctcaatgcg gtggtgggca cagcccctgat taagaagtac  3000
cccaagctgg agagcgagtt cgtctacggg gactacaagg tgtacgatgt cggaagatg   3060
atcgccaaga gcgagcagga gattgggaag gccaccgcta gtacttcttc ctactcgaat  3120
attatgaatt tcttcaagac cgagatcaca ctcgctaacg gggagattcg gaagcggccc  3180
ctcatcgaga ctaacgggga gactggcgag attgtgtggg acaaggggcg cgacttcgcg  3240
accgtgcgca aggtcctctc gatgcccag gttaatattg ttaagaagac agaggtgcag  3300
acgggcggt ctccaagga gtctatcctg ccgaagcgga actcggacaa gctgatcgcc  3360
cgcaagaagg attgggaccc caagaagtac gggggattcga atagcccaac cgtgcgcttac  3420
agcgtcctgg tggtcgccaa ggttgagaag gggaagtcaa gagcgttaag  3480
gagctgctgg gcatcaccat catggagcgg tccagcttcg agaagaatcc tatcgacttc  3540
ctggaggcta aggggtacaa ggaggtcaag aaggacctga tcattaagct gcccaagtac  3600
tctctgttcg agctgagaa cgggaggaag cggatgctgg cgtctgctgg cgagctacag  3660
aagggcaatg agctggcgct ccctcgaag tatgtcaact tcctctacct ggcttccat   3720
tacgagaagc tgaaggggctc gcccgaggat aatgagcaga agcagctct cgtggagtc   3780
cacaagcact acctcgacga gatcattgag cagatttcgg agttctcgaa gcgggtcatt  3840
ctcgcggacg cgaacctcga caaggtcctc tcggcgtaca acaagcaccg ggacaagccc  3900
atccgggagc aggccgagaa cattatccac ctcttcacac tgaccaacct cggcgctccc  3960
gccgcgttca agtacttcga caccaccatt gaccgcaaga gatacacatc caccaaggag  4020
gtgctggacg cgacccctcat ccaccagagc atcacaggcc tctacgagac acggatcgac  4080
```

```
ctctcgcagc tcggggcga t                                          4101

SEQ ID NO: 60           moltype = DNA  length = 4092
FEATURE                 Location/Qualifiers
source                  1..4092
                        mol_type = other DNA
                        organism = synthetic construct
SEQUENCE: 60
gacaagaagt actcgatcgg cctggcgatt ggcacaaaca gcgtgggtg ggctgtgatc     60
actgatgagt acaaggtgcc atcgaagaag ttcaaggtgc tggggaatac agaccggcat   120
tcgatcaaga agaatctcat tggcgctctc ctcttcgatt ccggcgagac tgctgaggcg   180
acccgcctga agcgcaccgc ccggcggcgc tacactcggc ggaagaatag gatttgctac   240
ctccaggaga ttttctcgaa tgagatggcc aaggtggatg acagcttctt ccaccgcctg   300
gaggagtcgt tcctggtcga ggaggacaag aagcatgagc ggcaccctat cttcgggaat   360
atcgttgatg aggtcgccta ccacgagaag taccccacta tctaccatct ccgcaagaag   420
ctcgtggaca gcacagataa ggccgacctc cgcctgatct acctcgccct cgcgcacatg   480
attaagttcc gggggcactt cctcattgag ggggatctga atcccgataa ctccgacgtg   540
gacaagctgt tcatccagct ggtgcagaca tacaaccagc tgttcgagga gaatcccatc   600
aacgcgagcg cgctggacgc taaggccatt ctgtcggcta ggctctcgaa gtcgaggcgg   660
ctggagaacc tgattgcgca gctccccggc gagaagaaga acgggctgtt cgggaatctc   720
atcgccctct ccctcggcct cacaccaaac ttcaagagca atttcgacct ggctgaggac   780
gctaagctgc aactctcaaa ggatacatac gatgacgaac tggacaattc ctggctcag    840
atcggcgacc agtacgctga cctgttcctc gcgccaagaa tctgtcgga cgcgattctc    900
ctcagcgaca tcctgcgcgt caataccgag attacgaagg ctccactgtc tgcgtcaatg   960
attaagcggt acgatgagca tcaccaggat ctgaccctcc tgaaggcgct cgtgcggcag  1020
cagctgcccg agaagtacaa ggagattttc ttcgatcaga gcaagaatgg ctacgccggc  1080
tacatcgacg ggggcgcgag ccaggaggag ttctacaagt tcatcaagcc catcctggaa  1140
aagatgacg gcaccgagga gctactcgtg aagctcaatc ggaggatct cctccggaag    1200
cagcggacat tcgataacgg gtctatccca caccagatcc acctcggcga gctgcatgcg  1260
attctgcggc ggcaggagga tttctaccct ttcctgaagg acaaccggga gaagatcgaa  1320
aagatcctca cattccggat tccatactac gtcggccccc tggcgagggg caatagccga  1380
ttcgcgtgga tgacaaggaa gtccgaggag actattaccc cgtggaattt cgaggaggtg  1440
gttgacaagg gcgcttccgc gcagagcttc attgagcgga tgacaaactt cgacaagaat  1500
ctcccaaacg agaaggtcct gccgaagcat agcctcctgt acgagtactt caccgtctac  1560
aatgagctaa ctaaggtcaa gtatgtgaca gagggcatgg ggaagccagc cttcctctca  1620
ggcgagcaga agaaggccat tgtgaccctc ctgttcaaga caaaccgcaa ggtgacagtg  1680
aagcagctga aggaggatta cttcaagaag attgagtgct tcgactcagt ggagatttca  1740
ggcgtggagg atcggttcaa cgcgagcctg gggacttacc acgacctgct gaagattatt  1800
aaggacaagg acttcctgga taacgaggag aatgaggaca tcctggagga tattgtgctc  1860
accctcaccc tgttcgagga cagggagatg attgaggagg ggctcaagac ctacgcgcac  1920
ctgttcgatg acaaggtcat gaagcagctg aagaggcggc gctacactgg gtggggccgc  1980
ctgtcgcgga agctgatcaa cggcattcgg gataagcagt ccgggaagac cattctggat  2040
ttcctgaagt cggacggctt cgccaacagg aatttcatgc agttgatcca cgacgactcc  2100
ctcaccttca aggaggacat tcagaaggcc caggttagcg gccaggggga ctcactccac  2160
gagcatattg ccaatctggc cggctctcca gctatcaaga agggcatcct gcaaacagtt  2220
aaggttgttg acgagctggt taaggtcatg gggcggcata agcccgagaa cattgtcatc  2280
gagatggctc gggagaacca gacaactcag aagggccaag agaactccag ggagcgcatg  2340
aagcggattg aggagggcat taaggagctg gggtcccaga tcctcaagga gcaccctgtc  2400
gagaacactc agctgcaaaa cgagaagctc tacctgtact acctccagaa cgggcgggat  2460
atgtatgtgg atcaggagct ggacatcaac aggctctccg actacgacgt ggatcacatt  2520
gtcccacagt cttttcctcaa ggatgattcc atcgacaaca aggtgctgac gcgcagcgac  2580
aagaataggg ggaagtcgga caacgttccg agcgaggagg tcgtgaagga gatgaagaat  2640
tactggaggc agctcctgaa tgcgaagctg atcactcaga ggaagttcga caatctgaca  2700
aaggcggaga ggggcgggct ctcggagctg gataagcggg gcttcatcaa gcggcagctc  2760
gttgaaaccc ggcagatcac caagcatgtc gcccagatcc tcgatagccg catgaacacc  2820
aagtacgatg agaacgacaa gctcattcgg gaggttaagg tcattacgct gaagtccaag  2880
ctcgtcagcg acttcaggaa ggatttccag ttctacaagg ttcgggagat taacaactac  2940
caccacgcgc atgatgcgta cctgaacgct gttgtcggca ctgctctcat caagaagtac  3000
ccaaagctgg agtccgagtt cgtctacggg gactacaagg tctacgatgt ccggaagatg  3060
atcgccaagt cggagcagga gatcgggaag gctactcgca agtacttctt ctacagcaac  3120
attatgaatt tcttcaagac ggagattacg ctggcgaacg gggagattag gaagaggccc  3180
ctcattgaga ctaatgggga gacaggcgag attgttggg acaagggccg cgacttcgcg  3240
actgtgcgga aggtcctgtc catgccacag gtgaatattg ttaagaagac agaggtgcag  3300
actggggct tctcgaagga gagcattctc ccaaagcgga acagcgataa gctcatcgcg  3360
cgcaagaagg attgggaccc taagaagtac ggcggcttcg attctcccac tgtggcctac  3420
tccgttctcg tggttgccaa ggttgagaag gggaagtcga agaagctgaa gtcggtcaag  3480
gagctgctcg ggattacaat catggagcgg agcagcttcg agaagaaccc tattgatttc  3540
ctggaggcca agggctacaa ggaggttaag aaggatctca ttatcaagct ccctaagtac  3600
tctctgttcg agctggagaa tggccggaag aggatgctga cctcggctgg cgagctacag  3660
aaggggaatg agctggccct cccgtcgaag tatgtgaatt tcctgtacct cgcgtcgcac  3720
tacgagaagc tcaagggcag cccggaggat aatgagcaga gcagctctt cgtggagcag  3780
cataagcact acctggacga gatcattgag cagatcagcg agttctcgaa gcgggttatt  3840
ctggctgatg ctaacctgga caaggttctg agcgcctaca ataagcatcg cgacaagccg  3900
attcggcaac aggcggaaa tattatccac ctgttcaccc tcactaacct gggagctcc   3960
gcggccttca agtacttcga taccacaata gataggaagc ggtacacctc gacgaaggag  4020
gtcctcgacg ccacactcat ccatcagtcg attacaggcc tgtacgagac acggattgac  4080
ctctcgcagc tg                                                      4092

SEQ ID NO: 61           moltype = DNA  length = 4101
```

| FEATURE | Location/Qualifiers |
|---|---|
| source | 1..4101 |
| | mol_type = other DNA |
| | organism = synthetic construct |

SEQUENCE: 61

```
gacaagaagt attccatagg cctggctatc ggcaccaaca gcgtgggctg ggccgtcatc   60
accgacgagt acaaagtgcc gagtaaaaag ttcaaagtgc tcggcaacac cgaccgccac  120
tccataaaga aaaacctgat cggggcgctc ctgttcgaca gcggcgagac ggcggaggcc  180
acccgcttga aacgcacggc ccgacggcgc tacacgcggc gcaagaaccg gatctgttac  240
ctacaggaga ttttctctaa cgagatggcg aaggtggacg actcgttctt tcaccgcctc  300
gaagagtcct tcctcgtgga ggaggacaag aaacacgagc gccacccgat cttcggcaac  360
atcgtggacg aggtggccta ccacgagaag tacccgacca tctaccacct ccggaagaaa  420
ctcgtggaca gcacggacaa ggccgacctg aggctcatct acctcgccct ggcgcacatg  480
attaagttcc ggggccactt cctgatcgag ggcgacctga acccggacaa cagcgacgtg  540
gacaagctgt tcatccagct agtccagacc tacaaccagc ttttcgagga aaaccccatc  600
aacgccagcg gggtggacgc gaaggcgatc ctgtccgccc ggctgagcaa gtcccggcgg  660
ctggagaacc tcatcgcgca gttgcccggc gagaagaaga cgggctgtt cgggaacctg  720
atcgccctct ccctggggct cacccccgaa ttcaagtcca acttcgacct cgccgaggac  780
gccaaactac agctgagcaa ggacacctac gacgacgacc tcgacaacct gctggccgag  840
atcgggacc agtacgcaga cctgttcctc gccgccaaga acctctccga cgccatcctg  900
ctgtcggaca tcctgcgggt gaacacggag atcacgaagg ccccgctctc ggcctcgatg  960
attaaacgct acgacgagca ccaccaggac ttgaccctcc tcaaggcgct ggtccgccag 1020
cagcttcccg agaagtacaa ggaaatcttt ttcgatcaga gcaagaacgg gtacgccggg 1080
tacatcgacg gcggggcgtc ccaggaggag ttctacaagt tcatcaagcc catcctggag 1140
aaaatggacg ggaccgagga gctgctcgtg aagctcaacc gcgaagattt gctccgcaag 1200
cagcgcacgt tcgacaacgg gtcgatcccg caccagatcc acctgggcga gctgcacgcg 1260
atcctcaggc gtcaggaaga cttctacccc ttcctcaagg acaaccgcga gaagatagag 1320
aagattctga ccttcagaat tccttattac gtgggcccgc tggctcgggg caactcgcgc 1380
ttcgcctgga tgacgcgcaa gtccgaggag accatcaccc cgtggaactt cgaggaggtg 1440
gtggataagg gtgcctcggc ccagtccttc atcgagcgga tgaccaactt cgacaagaac 1500
ctgccgaacg agaaggtgct ccccaagcac agcctgctct acgaatattt cacggtgtac 1560
aacgagctga cgaaggtcaa gtacgtgacc gagggaatga ggaaacctgc attcctctcc 1620
ggggagcaga agaaagccat agtcgacctc ctgttcaaga ccaaccggaa ggtcaccgtc 1680
aagcagctca aggaggacta cttcaagaag atcgagtgct tcgattcagt ggagatccag 1740
ggcgtcgagg accggttcaa cgccagcctg ggcacctacc acgacctgct caagatcatc 1800
aaggacaagg acttcctcga caacgaggag aacgaggaca tcctggagga catcgtgctg 1860
accctgacgc tcttcgagga ccgcgagatg atcgaggagc gcctcaagac ctacgcccac 1920
ctgttcgacg acaaggtgat gaagcagctc aagcggcgga gatatactgg gtggggccgc 1980
ctctcccgga agctcattaa cggtatcagg gataagcagt ccgggaaagc gatcctcgac 2040
ttcctcaagt cggacgggtt cgccaaccgc aacttcatgc agctcatcca cgacgactcc 2100
ctgacgttca aggaggacat ccagaaggcc aagtgtctg gtcaaggtga ctcgctccac 2160
gagcacatcg ccaacctcgc gggcagcccg gccatcaaga agggaatact ccagaccgtc 2220
aaggtggtgg acgagctggt gaaggtcatg ggccgccaca gccggagaa catcgtcatg 2280
gagatggcgc gggagaacca gaccacgcag aaggggcaga aaaatagccg tgagcgcatg 2340
aagcgcatcg aggagggggat taaggagttg ggcagccaga tcctcaagga gcaccctgtg 2400
gagaacacgc agttgcaaaa cgagaagctc tacctgtact acctccagaa cgggagggat 2460
atgtcgtgg accaagaact ggacatcaac cgcctgtccg actacgacgt ggaccacatc 2520
gtgccgcaga gcttcctcaa ggacgacagc atcgacaaca aggtgctcac ccggtccgac 2580
aagaatcggg gcaagtccga caacgtgccc agcgaggagg tcgtcaaaaa gatgaaaaac 2640
tactggcgac aactactgaa cgccaagctc atcccccagc gcaagttcga caacctcaca 2700
aaagccgagc gcggcgggtt gagcgagctg gacaaggccg ggttcatcaa gcggcagctc 2760
gtcgagacgc gccagatcac gaagcacgtc gcgcagatac tcgacagccg gatgaacacc 2820
aagtacgacg agaacgacaa gctcatccgg gaggtgaagg tcatcacccct caagtcgaag 2880
ctcgtgagcg acttccgcaa ggacttccag ttctacaagg tccgggagat caacaactac 2940
caccacgccc acgatgctta tcttaacgcc gtggtgggga cggccctcat taagaaatac 3000
ccgaagctgg agtcggagtt cgtgtacggc gactacaagg tgtacgacgt caggaagatg 3060
atcgccaagt ccgaacagga gatcgggaag gccacggcga aatacttctt ctacagcaac 3120
atcatgaact tcttcaagac cgagatcacc ctcgccaacg gcgagatccg caagcgcccg 3180
ctcatcgaga cgaacgggga gacccgcgag atcgtctggg acaagggggcg cgacttcgcg 3240
actgtgcgga aggtgctgtc gatgccccag gtcaacatcg tcaagaagac ggaggtccag 3300
acgggcgggt tcagcaagga gagcatcctc ccgaagcgca acagcgacaa gctgatcgcc 3360
cgcaaaaagg actgggatcc aaaaaagtac ggcggcttcg acagcccccac cgtcgcctac 3420
agcgtcctcg tcgtcgctaa agtcgagaag ggcaagtcca aaaagctcaa gagcgtcaag 3480
gagctgctcg ggatcaccat catggagcgg tccagcttcg agaagaaccc aattgatttc 3540
ctggaggcga agggctacaa ggaggtcaag aaagacctca tcataaagct gccgaagtac 3600
tcactcttcg agctggagaa cgggcgcaag cggatgctgg cgtcggcggg agagctccaa 3660
aagggcaacg agctggcgct gccgagcaag tacgtgaact tcctctacct ggcgtcccac 3720
tacgagaagc tcaagggcag tccagaggat aacgagcaga agcagctatt cgtggagcag 3780
cacaagcact acctggacga gatcatcgag cagatcagcg agttctccaa gcgcgtcatc 3840
ctggcggacg ccaacctgga caaggtgctg tccgcgtaca acaagcaccg cgacaagccg 3900
atccgcgagc aagccgagaa catcatccac ctgttcaccc tcacgaacct cggggcaccc 3960
gccgccttca aatatttcga cacgaccatc gaccgcaagc gctacaccag cacgaaggag 4020
gtgctcgacg ccaccctgat ccaccagagc atcaccgggc tgtacgagac ccgcatcgac 4080
ctctcgcagc tcggcgggga c                                           4101
```

| SEQ ID NO: 62 | moltype = DNA  length = 4101 |
|---|---|
| FEATURE | Location/Qualifiers |
| source | 1..4101 |
| | mol_type = other DNA |

```
                organism = synthetic construct
SEQUENCE: 62
gacaagaagt acagtattgg attggccatc gggacgaaca gcgtgggctg ggccgtcatc    60
accgacgagt acaaggtgcc atccaagaag tttaaggttc tggggaatac cgaccgccac   120
tcgatcaaga aaaatctcat cggggcgctg cttttcgaca gcggcgagac ggcggaagcg   180
acgcggctca agcggacggc tcgtcgccgt tacacccggc gtaagaaccg catctgttac   240
ctccaggaga tattcagcaa cgagatggcc aaggtggacg actccttttt ccaccgtctt   300
gaggagtcct tcctggtcga ggaggacaag aagcacgagc gccacccgat cttcgggaac   360
atcgtggacg aggtggccta ccacgagaag taccccacga tctaccacct ccgcaaaaaa   420
ctcgtggact caactgacaa ggccgatttg aggcttatct acctcgccct cgcccacatg   480
attaagttcc gtgggcactt cctaatcgag ggtgacctca accccgacaa ctctgacgtg   540
gacaagctgt tcatccagct tgtgcagacc tacaatcagc tctttgagga gaatccgatc   600
aacgcatctg tgtggacgc aaaggccatc ctcagcgcgc ggctgagcaa gtctaggcgg   660
ttggagaacc tgatcccca actgcccggc gagaagaaaa atggcctctt cggcaacctg   720
atcgccctgt cgctgggct cacgccgaac ttcaagagta actttgacct ggcggaggac   780
gctaagctcc agctatctaa ggacacatac gacgacgacc tggacaacct gctggcccag   840
atcggcgacc agtacgccga cctcttccta gccgccaaga acctgtccga cgccatcctc   900
ctcagcgaca tcctgcgcgt gaacacggag atccgaaagg ctccgctcag cgcctccatg   960
attaagcggt acgacgagca ccaccaagac ctaactttac tcaaagccct cgtgcgcag  1020
cagcttcccg agaagtacaa agagatattt tttgatcagt ccaagaacgg ttatgcgggc  1080
tacatcgacg gcggcgcgag ccaggaggag ttctacaagt tcatcaagcc catcctggag  1140
aagatggacg gcacggagga gctgctcgtg aagctcaacc gtgaagacct cctgcgaaag  1200
cagcgaacct tcgacaacgg ttcgatcccg caccagatcc acctcgggga gctgcacgcc  1260
atcctgaggc gacaggagga cttctaccct ttcctaaagg acaaccgcga gaagattgaa  1320
aaaatcctga cgtttcgcat accctactac gtcggcccgc tggcgcgcgg caactcccgg  1380
ttcgcctgga tgacccgtaa gagcgaggag acgatcacgc cgttggaact tcaggaggtc  1440
gtggacaagg gcgcgagcgc cagagcttc atcgagcgca tgaccaactt cgacaagaac  1500
ctcccgaacg agaaggtgct cccaaagcac tccctcctgt acgagtattt caccgtgtac  1560
aacgagttga caaaggtgaa gtacgtgacg gagggaatgc ggaagcctgc gttcctctcg  1620
ggcgagcaga gaaaggcaat cgtggacctg ctcttcaaga ccaaccggaa ggtgacggtg  1680
aagcagctca aggaggacta cttcaaaaaa atcgagtgct tcgactccgt ggagataagc  1740
ggcgtggagg accgattcaa cgcctccctc ggcacctacc acgacctcct taagatcatc  1800
aaggacaagg acttcctgga caacgaggag aacgaggaca tcctggagga catcgtgctc  1860
accctgaccc tcttcgagga ccgggagatg atcgaggagc gcctcaagac gtacgcccac  1920
ttgttcgacg acaaggtgat gaagcagctc aagcggcggc gatacaccgg gtggggccac  1980
ctatcccgca aacttatcaa cggcatccgc gacaagcagt ccggcaagac gatcctggat  2040
ttcctcaagt cggacgggtt cgccaaccgg aacttcatgc agctcatcca cgacgacagc  2100
ctcacgttca aggaggacat ccagaaggcc aagtgagcg gtcaagggga cagcctccac  2160
gagcacattg cgaaccttgc tgggacccct gcgatcaaga agggatatt gcaaaccgtg  2220
aaggtcgtgg acgagttggt gaaggtcatg gggcgacaca agcccgagaa catcgtgatc  2280
gagatggcca gggaaaatca gaccacgcag aagggcaaaa aaaacagccg cgagcggatg  2340
aagcggatcg aggagggcat caaggagctg gggtcgcaga tcctcaagga gcacccggtg  2400
gagaacgacg agctccagaa cgagaagctg tacctctatt acctacagaa cggcagggat  2460
atgtacgtgg accaggagct agacatcaac cgcctgtccg actacgacgt ggaccatatc  2520
gtcccgcagt cgttcttgaa ggacgacagc atcgacaaca aggtgctcac aagatcggat  2580
aagaatcgag gcaagtccga caacgtgccc tcggaggagg tggtcaagaa aatgaaaaac  2640
tactggcggc agttgctgaa cgccaagctc attacgcagc ggaagttcga caacctgacg  2700
aaggctgaac gtggtgggct cagcgagcta gacaaggcgg ggttcatcaa cggcagctc  2760
gtcgagaccc ggcagatcac caagcacgtg gcgcagatcc tggactcgcg catgaacacc  2820
aagtacgacg agaacgacaa gctcatccgt gaggtgaagg tcatcaccct taagtctaag  2880
ctggtcagtg acttccgcaa ggacttccag ttctacaagg tccgggagat caacaactac  2940
caccacgcgc acgacgccta cctcaacgcg gtgtgggga cggcgcttat taagaaatat  3000
cccaagctgg aaagcgagtt cgtttacggc gactacaagg tgtacgacgt ccgcaagatg  3060
atcgcaaagt cggaacagga aatcggaaag gcgacggcca atatttcctt ttactccaac  3120
atcatgaatt tttttaagac ggagatcacc ctggcgaacg gggagatccg caagcggcca  3180
ctcatcgaga ccaacgggga gacgggcgag atcgtctggg acaagggccg ggacttcgcc  3240
accgtgcgga aggtgctttc tatgcctcaa gtcaatatcg tcaaaaagac agaggtgcag  3300
accggcgggt tcagcaagga gtctatcctg ccgaagcgca actcggacaa gctcatcgcg  3360
cgcaagaaag actgggaccc caaaaaatat ggcgggttcg actgccgcac cgtcgcctac  3420
agcgtcctcg tggtggctaa ggtcgagaag gccaagagca aaaagctaaa gtcggtgaag  3480
gagctgctgg gcatcaccat catggagcgc tcgtctttcg agaagaatcc aatcgacttc  3540
ctagaggcga aggggtacaa ggaggtcaaa aaggatctta tcatcaaact gccgaagtac  3600
agtctgttcg agctggagaa cgggcggaag cggatgctga ctagtgcggg cgagttgcag  3660
aagggcaacg agttggcact gccctccaag tacgtgtacc tcctgtacct gcgcaaccgg  3720
tacgagaagc tcaagggggag ccccgaggac aacgagcaga agcagctatt cgtcgagcag  3780
cacaagcact acctggacga gatcatcgag cagatcagtg agttctccaa gcgggtcatc  3840
ctcgcggacg ccaacctgga caaggtgctg agcgcgtaca caagcacag ggacaagcca  3900
atcagggaac aggccgagaa catcatccac ctgttccacc tgaccaacct gggtgcaccg  3960
gctgccttca agtactttga cacgaccatc gaccggaagc gctacacctc cacgaaggag  4020
gtgctggacg ccacgctgat ccaccagagc atcaccgggc tctacgagac acggatcgac  4080
ctgagccagc ttggcgggga c                                            4101

SEQ ID NO: 63          moltype = DNA  length = 4092
FEATURE                Location/Qualifiers
source                 1..4092
                       mol_type = other DNA
                       organism = synthetic construct
SEQUENCE: 63
gacaaaaagt attccattgg actcgctatc ggcacgaaca gcgtcgggtg gcggtcatc    60
```

```
actgacgagt acaaggtgcc gagcaagaag tttaaggtgc tgggaaacac cgacaggcac   120
tcgatcaaga aaaatcttat cggggcccta ctcttcgact ccggagaaac cgccgaggcc   180
acccggttga agcgcacggc ccgccgtcgc tacaccaggc gcaagaaccg gatctgctac   240
ctccaggaga tattcagcaa tgagatggcg aaggtggacg actcgttttt tcacaggcta   300
gaggagtctt tcctcgtgga ggaggacaag aaacacggac gccacccat cttcggcaac    360
atcgtggatg aggtggcata tcacgagaag tacccaacca tctaccacct ccgcaaaaag   420
ctcgtggact ctaccgacaa ggccgacctc cgtctgatct acctcgcgct ggcccacatg   480
attaagttcc gaggacactt tctgatcgag ggcgacctga acccagacaa cagcgacgtg   540
gacaagctgt tcatccaact tgtccagacc tacaatcgac tcttcgagga aaccctatc    600
aacgcctcgg gcgtggacgc gaaggccatc ctgtccgccc gcctgagcaa gtcgcggcgg   660
ctggagaacc tgatcgccca gctccccggc gaaaaaaaga acggcctctt cggcaacctc   720
atcgcgttgt cgctggggct caccccgaac ttcaagtcca acttcgacct ggccgaggac   780
gctaaactcc agctctcgaa ggatacctac gacgacgacc tcgacaacct gctggcccag   840
atcggcgacc agtacgcgga ccttttcctg gcggccaaga acctgagcga cgcgatcctc   900
cttagcgaca tactccgtgt gaacaccgag atcacgaagg cccgctctc cgcgtccatg     960
attaagcgct acgacgagca ccaccaagac cttaccctgc ttaaggcgct ggtcaggcag  1020
cagttaccgg agaagtacaa ggagatcttt tttgatcaat ctaagaacgg ttacgccggg  1080
tacatcgacg gcggcgcgtc ccaggaggag ttctacaagt tcatcaagcc gatcttgag   1140
aaaatggacg gaccgaggag gctgctcgtg aagctcaacc gcgaagacct cctccgcaag  1200
cagcgcacct tcgacaacgg gagcatcccg caccagatcc acctgggaga gctgcacgcg  1260
atcctgcgga gacaagagga cttctacccc ttcctcaagg acaacgggga gaagattgaa  1320
aaaatactta cttttcgtat cccgtactac gtcgggcccc ttgcgaggg caactccaga   1380
ttcgcgtgga tgacccgcaa gtccgaggag accatcaccc cgtgaactt cgaggaggtg    1440
gtggacaagg gcgcgtcggc ccagtcgttc atcgagcgca tgaccaactt cgacaagaac  1500
cttccgaacg agaaggtgct cccgaagcac agcctgctct acgaatattt tactgtgtac  1560
aacgactga cgaaggtcaa gtacgttacg gaggggatga ggaagcccgc cttcctctcc   1620
ggcgagcaga agaaagccat tgtggatctc ctgttcaaga ccaaccgcaa ggtgacggtg  1680
aaacagctca agaggactac cttcaagaag atcgagtgct tcgactccgt agagatcagc  1740
ggggtcgagg accgcttcaa cgcctcgctg gcacgtacc acgacctgct aaagattatc   1800
aaggacaaag acttcctaga caatgaggaa aacgaggaca ttctggagga catcgtgctg  1860
actctgacgc tgttcgaaga ccgcgagatg atcgaggagc ggcttaagac gtacgcccac  1920
ctgttcgacg acaaggtgat gaagcagttg aacggcggc gctacaccgg gtggggccgc  1980
ctctcccgca agctcatcaa cggcatccgc gacaagcagt cggggaagac gatcctggac  2040
ttcctcaaga gcgacggctt cgccaaccga aacttcatgc agctaatcca cgacgacagc  2100
ctgacgttca aggaggacat ccagaaggcc caagtgacgc gccagggaga ctcgctctac  2160
gagcatatcg ccaacctggc tggcagcccg cgcgattaaga aaggaatcct ccaaaccgtc  2220
aaagtggtgg acgagctggt gaaggtgatg gccgccaca agcccgagaa cattgtgatc   2280
gagatggcgc gggagaacca gacgacgcag aagggcaaaa aaatagcag ggaaaaggatg  2340
aagcgaatag aggaggggat caaggagctg gggagccaga ttctcaaaga gcacccggtc   2400
gagaacacac agctccagaa cgagaagctg tacctctact acctccaaaa cggccgcgat  2460
atgtacgtgg accaggaact agacatcaac cggctgagcg actatgacgt ggaccacatc  2520
gtgccgcagt ccttcctcaa ggacgactcg attgacaaca agtgctcac tagatccgac   2580
aagaacagag gcaagagcga taacgtcccg tcggaggagg tcgtcaagaa aatgaaaaac  2640
tactggcggc agctcctaaa cgccaagctc atcacgcagc gtaagttcga caacctgacg  2700
aaggcggagc ggggcgggct gagcgagctg gacaaagcgg ggttcatcaa gcggcagctc  2760
gttgagacgc ggcagatcac aaagcacgtc gcgcaaatcc tcgactccg catgaacacc   2820
aagtacgacg agaacgacaa gctcatccgg gaggtgaaga tcattaccct taaatcgaag  2880
ctcgtcagcg actttcgtaa ggacttccaag ttctacaagg tcagagagat caacaactac  2940
caccacgccc acgacgccta tctgaacgcc gtggtgggca ccgcgcttat taagaagtac  3000
cccaagctgg agtccgagtt cgtgtacggc gactacaagg tttatgacgt caggaagatg  3060
atcgccaagg cggaacagga gatcggaaaa gctaccgcca aatatttctt ctatagcaac  3120
atcatgaact tcttcaaaac cgagatcacc ctcgccaacg gcgagatccg gaagcgcccc  3180
ctcatcgaga ccaacgggga gaccggggag atcgtctggg acaagggcg ggacttcgct   3240
actgtccgaa aggtgctctc catgccacaa gtgaatatcg tcaagaaaac agaggtgcag  3300
accggagggt tcagtaagga gtccatcctg cccaagcgga actccgacaa gctaattgct  3360
cgcaaaaagg attgggatcc taaaaaatat ggcggcttcg actcgcccac ggtcgcctac  3420
tctgtgctgg tcgtggcgaa ggtggagaag ggcaagtcca agaagctcaa gagcgtcaag  3480
gagctgctgg ggatcacgat catggagcgt agttcgtttg agaagaatcc catcgacttc  3540
ctggaggcta agggctacaa ggaggtcaaa aaggacctca tcattaagct gccgaagtac  3600
agcctcttcg agctggagaa cgggcggaag cgtatgctcg cctccgctgg ggagttacaa  3660
aaggggaacg agctggcgct gccgtctaag tacgtcaact tcctgtacct ggcctcccac  3720
tacgagaagc tcaaggggtc gccggaggac aacgagcaga agcagctctt cgtagagcag  3780
cacaagcact acctggacga gatcatcgag cagtttcag agttctcaaa gcgggtcatc   3840
ctcgccgacg ccaacctgga caaggtgctc tcggcctaca acaagcaccg ggacaagggtc  3900
atccgcgaac aggccgaaaa catcatccac ctgttcacgc tcaccaacct cggtgccccg  3960
gcggccttca gtactttgta cacgaccatc gaccggaagc gctatacctc gacgaaggag  4020
gtgctggacg ccacccctgat ccaccagtcc atcaccgggc tttacgagac ccggatcgac  4080
ctctcgcagc ta                                                       4092

SEQ ID NO: 64          moltype = DNA   length = 4101
FEATURE                Location/Qualifiers
source                 1..4101
                       mol_type = other DNA
                       organism = synthetic construct
SEQUENCE: 64
gacaagaagt atagtattgg actcgccatc ggaaccaact ctgtggggtg gctgttatt     60
acagatgaat ataaggtgcc atccaaaaag tttaaagttc tgggcaatac tgatagacac   120
tcaatcaaga agatctgat aggtgcactt ctgtttgata gtgagagac tgccgaggca    180
accagactta aaaggactgc aagaagaaga tataccagaa gaaagaatag gatttgctat   240
```

```
ttgcaggaaa tcttcagcaa cgaaatggcc aaggttgatg actcattttt ccataggttg  300
gaggagagtt ttcttgtgga ggaagataag aagcacgaaa gacacccaat tttcggggaat 360
atagtggacg aggtggctta tcatgagaag tatcccacta tctaccacct gagaaagaaa  420
cttgtggact caaccgataa ggctgatctt aggcttatat acttggccct tgcacatatg  480
atcaaattca ggggccattt tcttatcgaa ggcgatctta atcccgataa ctcagatgtg  540
gacaagctgt ttatacaact tgtgcaaacc tacaatcaac tcttcgagga gaatcccatt  600
aacgcctccg gcgtggatgc aaaagccata ctgtcagcca gactgagcaa aagtaggaga  660
ctggagaatc ttatagccca actgccggt gaaaagaaga atgggctctt cggaaatctg   720
atcgctcttt cattggggtt gacacccaac tttaagagta acttgactt ggcagaagat   780
gcaaagttgc agctcagtaa agacacatat gacgatgacc ttgacaatct cttggcacaa  840
ataggggatc aatacgctga ccttttcctc gctgccaaga acctcagcga cgctatactg  900
ttgtccgaca ttcttagggt taataccgaa attacaaagg cccctcttag tgcaagtatg  960
atcaaaaggt atgatgagca tcaccaagac cttcactgc tgaaggctct ggttagacag   1020
caactccctg aaaagtataa ggaaatattc ttcgaccaaa gtaagaacgg gtacgccggt  1080
tatattgatg ggggcgcaag tcaagaagaa ttttacaaat tcatcaagcc aattcttgaa  1140
aagatggacg ggactgagga attgctggtg aaactgaata gagggacct tcttagaaaa   1200
cagaggacat ttgacaatgg gtccatccca caccagattc atctggggga actccacgca  1260
atattgagga gacaagaaga cttttaccca ttccttaagg ataatagaga gaaaatcgaa  1320
aaaatcctga ctttcaggat tccttactat gttgggccac tggccagggg gaactcaaga  1380
ttcgcttgga tgacaaggaa gtcagaagaa accataaccc cttggaattt tgaagaggtg  1440
gttgataagg gggcatcagc ccagtctttc atagagagga tgaccaactt tgataaaaat  1500
cttccaaatg agaaggtttt gccaaaacat agtcttttgt acgagtactt tactgtttat  1560
aacgaattga ccaaggtgaa gtatgtgacc gagggaatga ggaagccagc atttttgtcc  1620
ggggagcaaa agaaagcaat cgttgatctt ctcttcaaga ccaacagaaa agtgaccgtg  1680
aaacaactga aggaagacta cttcaaaaag atagaatgtt tcgattcagt ggaaattagc  1740
ggtgttgaag acaggttcaa tgcttcattg ggtacttacc acgacctgtt gaagataatc  1800
aaagacaagg actttctcga taatgaggag aacgaagaca tcttggaaga cattgtgctt  1860
acactcactt tgtttgagga cagggaaatg attgaggaaa gactcaaaac ttacgctcat  1920
ttgtttgatg ataaggttat gaaacaacta aaaagaagaa ggtacaccgg ctggggaaga  1980
ttgagtagga aactgatcaa cggtattaga gataaacaat ccggaaaagc tatcctcgat  2040
ttccttaaga gtgatggctt tgcaaatagg aattttatgc agctgattca tgacgactca  2100
cttaccttca aagaagacat ccaaaaagct caggtgtctg ggcaaggcga cagtctgcat  2160
gaacatatag ctaacttggc tgggagtccc gccatcaaga aggggatact tcaaacagtt  2220
aaagttgtgg acgaattggt gaaggtaatg ggaaggcaca agcctgaaaa tatagtgata  2280
gaaatgccaa gggaaaatca aacaacccag aagggacaga agaacagtag ggaaaaggat  2340
aaaaggatag aagaggggat caaagagctt ggtagccaga tcctcaagga acatccagtg  2400
gagaataccc aacttcaaaa cgagaaactc tatttgtact acttgcagaa cggaagagat  2460
atgtatgtgg accaagagct tgatattaac aggctgagcg attatgacgt tgaccacata  2520
gtgccccaat cattcctcaa ggatgactct attgataata aggtgctgac aaggagtgac  2580
aagaatagag ggaaatccga caacgttcca tccgaggaag ttgtgaagaa gatgaagaac  2640
tactggaggc agttgctgaa cgctaagctc attacccaga ggaaattcga taacctgacc  2700
aaagcagaga gaggcgggct gagcgaactc gataaagcag gtttcatcaa gagacaactc  2760
gtggagacta ggcaaattac taagcacgtg ctcaaatac tcgacagcag gatgaacaca  2820
aagtacgacg agaacgacaa gctcattaga gaggttaagg ttattactct gaaaagtaaa  2880
ttggttagcg atttcagaaa ggatttccaa ttctataagg ttagagagat caacaattat  2940
catcatgcac atgatgccta tctgaatgct gtggttggta cagcccttat caagaagtac  3000
cctaagctag agagcgagtt tgtgtacgga gattataagg tgtatgatgt gaggaaaatg  3060
atcgctaaaa gtgagcaaga gattggaaag gctaccgcca aatacttctt ttattccaat  3120
attatgaatt tcttcaagac agaaatcacc ctggctaacg gcgagataag gaagaggccg  3180
cttatcgaaa ctaatgggga gacaggcgaa atagtgtggg acaaagggag ggatttcgca  3240
actgtgagga aggttttgag catgcctcag gtgaatatcg ttaagaaaac cgaagttcaa  3300
actggagggt tctctaagga aagcattctc cccaagagga actccgacaa gctgattgct  3360
agaaagaaag actgggaccc caagaagtat ggcggattcg actcacccac tgtggcatat  3420
agcgttctcg tggtggcaaa ggttgaaag ggtaaatcca aaaaactcaa atccgtgaag  3480
gaactcctg gcataactat tatggaaagg agtagctttg aaaagaatcc catcgacttt  3540
ctcgaagcta agggctataa ggaagttaag aaggaccta taatcaaact tccaaaatac  3600
tcccttttg agttggaaaa cggcagaaag agaatgttgg ccagtgccgg ggagcttcaa  3660
aagggcaacg aactggctct gcctagcaaa tatgtgaact ttttgtatct ggcatcacac  3720
tacgagaaac ttaaaggctc tcctgaggac aacgagcaaa aacagctctt tgttgaacag  3780
cataagcact accctcgacga gattattgag cagatcagcg agttctcaaa gagagttatt  3840
ctggctgacg ctaatcttga caaggttttt tccgcttaca caaacacag ggataagcca  3900
atcagggagc aggcagaaaa cataatccat ctctttaccc tgacaaacct cggtgccccc  3960
gctgctttca gtatttttga tactaccatt gacaggaaga gatatacttc cactaaggaa  4020
gtgctcgacg caacccctcat acaccaaagt atcacaggcc tctatgaaac taggatagat  4080
ttgtctcaac ttgggggcga t                                             4101

SEQ ID NO: 65         moltype = DNA  length = 4101
FEATURE               Location/Qualifiers
source                1..4101
                      mol_type = other DNA
                      organism = synthetic construct
SEQUENCE: 65
gacaaaaagt attccatcgg gcttgctatc ggaaccaact ctgtggggtg ggcagttatt   60
accgacgaat acaaggtgcc cagcaagaag tttaaggttc tggggaacac agatagacat  120
agcataaaga aaaacctgat aggcgcactg ttgttcgact ccggggaaac agccgaagct  180
accaggctga gagaactgc aagaagaagg tacaccagaa gaaaaacag aatatgttat  240
ctccaagaga ttttctctaa cgagatggcc aaggtggacg actcattctt tcacagactg  300
gaagaatctt tccttgtgga agaagataag aaacacgaga ggcaccctat ttttggcaat  360
atcgtggatg aggtggctta ccacgaaaaa taccctacaa tataccacct caggaaaaaa  420
```

```
ttggttgata gtacagacaa ggccgacctc aggctcatct atttggccct ggcccatatg    480
attaaattca gggggcactt tctcatcgag ggagatttga accccgacaa cagtgatgtt    540
gataagctct ttattcagct cgtgcagact tacaatcagt tgtttgagga aaaccccatt    600
aatgcttccg gggtggacgc caaggcaatc ctttctgcaa gactctcaaa gtcaaggaga    660
ctcgaaaatc tgatagcaca gcttccagga gagaagaaga acgggctctt tggaaacctg    720
atcgctctgt cactcggact cacacccaat ttcaaaagca attttgattt ggcagaggac    780
gctaagctgc aactcagtaa ggatacctac gacgatgact tggataatct gctcgcacaa    840
attggggacc agtatgcaga cctgtttctc gcagctaaga acttgagtga cgccatattg    900
ctcagtgaca tcctcagggt taataccgag attacaaaag ctccactctc tgcaagcatg    960
atcaagaggt atgacgagca ccatcaagac ctgacactcc ttaaggcgtt ggttaggcag   1020
caacttcctg aaaagtataa ggaaatcttc ttcgatcaaa gcaaaaacgg ctacgccggc   1080
tatatagacg ggggagcatc ccaagaagaa ttttataagt tcataaaacc tatattggag   1140
aagatggacg ggacagagga attgctcgtg aaactgaaca gggaggatct cctcaggaag   1200
caaaggacct tcgacaatgg ctccatccca catcagatte acctcggcga actgcacgca   1260
atactgagaa gacaagagga cttttatcct ttcctgaagg acaacaggga gaaaatcgag   1320
aaaatcttga cattcagaat cccatactac gttgggcctc tggccagagg taacagtagg   1380
ttcgcctgga tgactaggaa atcagaggag actattacac cctggaactt tgaagaagtt   1440
gttgataagg gagcttcagc acaatcattc atcgaaagaa tgacaactt tgacaaaaat   1500
ctgcctaatg agaaagtgct cccaaaacat tccctgctgt atgagtattt taccgtttat   1560
aacgagctta ccaaggtgaa atacgttact gaaggtatga gaaagccagc ttttctttca   1620
ggggagcaaa agaaggctat cgtggatctt ctcttttaaga ccaacagaaa ggttaccgtg   1680
aagcagctta aggaagacta cttaaaaaag atcgagtgtt ttgactcagt ggaaataagc   1740
ggtgttgaag atagattcaa cgcatccttg ggaacttatc atgatcttct taagataatc   1800
aaggataaag actttctcga caacgaggaa aacgaagata tactggagga catagttctg   1860
acacttactt tgttcgagga tagggagatg atcgaggaaa gactgaaaac atatgctcac   1920
cttttcgacg acaaagttat gaaacaactc aagagaagga gatatacagg tgtgggggaga   1980
ttgagcagga aactgattaa tggtatcaga gacaaacagt caggaaaaac aatactcgac   2040
tttttgaaat cagacgggtt cgcaaatagg aatttcatgc agcttataca cgacgattca   2100
cttactttta aagaggacat tcaaaaggct caagttagtg gacaaggtga ctccctccac   2160
gaacacatcg caaatctcgc tggcagccct gcaattaaga agggtatact ccagacagtt   2220
aaggttgttg acgagctggt taaagtgatg ggaagacaca aacccgagaa catagtgata   2280
gagatggcca gggaaaacca aaccactcaa aaagggcaga aaaattccag agagaggatg   2340
aaaaggatta agaaggtat caaggagctg ggtagccaaa ttctgaaaga acatcctgtg   2400
gaaaacactc aactccagaa tgagaaactc tatctgtact atctgcaaaa tgggagagat   2460
atgtatgtgg accaggaact ggacataaac aggctctcag attacgatgt ggatcatatc   2520
gtgccacagt cctttcttaa ggatgatagc atcgacaata aggtgcttac caggtccgac   2580
aagaacaggg gaaagtcaga taacgtgcct tctgaagaag ttgttaaaaa gatgaagaac   2640
tactggagac agctgcttaa cgctaagctc ataacacaga ggaagtttga caacttgacc   2700
aaggccgaga gaggcggact ctcagaattg gataaggcag ggttcataaa aaggcagctg   2760
gtggaaacaa ggcagataac taaacatgtg gctcagatcc tcgatagtag gatgaataca   2820
aaatacgatg agaacgacaa gctcataagg gaggttaaag tgataactct gaaatccaaa   2880
ctggttagcg attttaggaa ggatttccag ttttacaaag ttagggagat caacaattat   2940
catcacgccc acgatgccta cttgaacgca gttgtgggta ctgcacttat caaaaagtac   3000
cctaagctgg aatccgagtt tgtttatgga gactataagg tgtacgacgt tagaaaaatg   3060
attgcaaagt cagagcagga gatagggaaa gccactgcaa aatatttctt ttatagcaat   3120
atcatgaatt tcttaagac agaaatcaca ctggccaatg ggaaataag gaagaggccc   3180
ctgatcgaaa ctaatggcga gacagggga atttgtgggg ataaaggtag ggactttgca   3240
acagtgagga aagtgctgag catgcccaa gttaatatcg ttaaaaagac cgaggttcaa   3300
acaggggggct ttagtaagga aagcatttttg cccaagagga atagtgacaa attgattgct   3360
aggaaaaaag attgggaccc caaaaagtat ggcggatttg atagcccac tgttgcttac   3420
tccgtgctcg tggttgcaaa ggtggagaag ggaaagagca agaaactgaa gtcagttaag   3480
gaactccttg gtatcactat catggaaaga agctcctttg agaagaaccc tattgacttc   3540
ctggaggcta aagggtacaa agaggttaag aaagacctta tcattaaatt gcccaaatat   3600
agtcttttcg agcttgaaaa cggaagaaag aggatgcttg catccgctgg cgaattgcaa   3660
aagggcaatg agcttgctct ccccttccaag tatgtgaatt tccttatct tgcctcacac   3720
tatgaaaaac tcaaaggttc accccgaagac aacgaacaaa agcaactatt tgtggaacaa   3780
cacaagcact acctggacga aatcattgag caaatttctg agttttcaaa aagggtaatc   3840
ttggctgacg caaatctcga caaagtttttg tcagcttaca caaacatag agataagcca   3900
attagagagc aagctgagaa tatcatccat ctgtttaccc tgactaacct tggagcgcct   3960
gctgcttttta aatatttcga caccacaatc gacaggaaga ggtacactag cactaaggaa   4020
gttctcgacg ccaccctcat ccaccagagt attacaggcc tgtacgagac aagaattgat   4080
ctttctcaac ttggtggtga c                                            4101
```

SEQ ID NO: 66        moltype = DNA  length = 4101
FEATURE              Location/Qualifiers
source               1..4101
                      mol_type = other DNA
                      organism = synthetic construct
SEQUENCE: 66

```
gataagaagt actcaatcgg tctggcaatc ggaaccaact ctgtgggttg ggcagtgatt     60
acagatgagt ataaggtgcc aagcaaaaaa ttcaaggtgc tggtaatac cgacagacac    120
agcattaaga gaaatttgat tggagcactc ctctttgact caggggaaac agcagaggca    180
acaaggctga gaggacagc aaggcggagg tacacaaggc ggaaaaacag gatatgctac    240
ctccaggaaa tctttagcaa cgagatggct aaagtgagta atagctttttt ccatagactc    300
gaagaatcct tcttgttga agaggacaaa aagcatgaaa ggcatcccat cttcggcaat    360
atagttgatg aggttgcata ccatgagaag taccccacaa tctaccacct cagaaagaaa    420
cttgtggact ccacagataa agcagacctg aggctcatat acctcgcact cgcacacatg    480
atcaagttca gagggcactt tctcatcgaa ggtgacctga atcagataa ttcagatgtg    540
gataaactgt ttatacagct ggtgcaaaca tacaaccaac ttttcgagga aaacccaatc    600
```

```
aatgcctccg gtgttgatgc aaaggccatc ctgtcagcaa gactcagcaa aagcaggcgg    660
ctcgaaaacc tcatcgccca gcttccggt gaaaagaaga acgggctctt tggtaatctc     720
atcgcattga gccttggtct tactccaaac ttcaagagca attttgatct ggcagaggat    780
gctaaactgc aactctcaaa ggacacatat gacgatgacc ttgacaatct gttggcccag    840
atcgggacc aatatgcaga cctcttcctg gccgcaaaga atcgtcaga tgcaatcctc      900
ttgtccgaca tactgagagt taacactgag atcacaaagg cacctctgtc cgcctccatg    960
attaagagat acgatgagca tcaccaggat ctgactttgc tcaaagccct cgttagacag   1020
cagttgccag aaaagtacaa agaaatattc tttgatcaat caaaaacgg atatgcaggg    1080
tacatcgacg gtggggcaag ccaggaagag ttctacaaat tcatcaaacc tatcctggaa   1140
aagatggatg ggacagaaga gctgctggtt aagctgaata gggaagacct cctcagaaaag  1200
cagaggacat tgataacgg gagcatccct catcaaatcc acctcggtga actccatgct    1260
atcctgagaa ggcaggaaga cttttatcca tttttgaagg acaatagggga gaaatcgaa   1320
aaaatcctga cattcagaat cccatactac gttggtcctc tggcaagagg taacagtagg   1380
ttcgcatgga tgacaaggaa aagcgaggag acaatcacac cctggaattt tgagggaagt   1440
gttgacaagg gtgccagcgc acaatccttt atcgaaagaa tgacaaattt cgacaagaat   1500
ctgcctaacg aaaaggttct cccaaagcat tcactcctgt acgaatattt tacagtttat   1560
aacgaactga ctaaagttaa atacgttacc gagggtatga ggaagccagc attcctttcc   1620
ggggaacaga agaaagctat tgtggacctc ctgttcaaga caaatagaaa agtgacagtt   1680
aagcaactca aagaggatta cttcaaaaag atcgaatgtt ttgactctgt ggagatcagc   1740
ggggtggagg atagattcaa cgccagcctg ggtacatatc atgatctcct gaaaatcatt   1800
aaagacaagg acttccttga caacgaggag aacgaggaca ttctggaaga cattgttctg   1860
accctcacac tctttgagga tagggagatg attgaggaaa gactgaagac ctacgcccac   1920
ctctttgacg ataagtgat gaaacagctc aagagaagaa ggtatacagg ttgggggaga   1980
ctgagcagga agttgatcaa tgggattagg gacaaacagt ccgggaaaac aatcctcgat   2040
tttctgaagt cagacggttt cgcaaacaga aattttatgc agctcattca cgatgacagc   2100
ttgacattca aggaagacat ccaaaaggct caagtgacgg gccaagggga tagcctccac   2160
gagcatattg caaatctggc aggttcacca gccatcaaaa agggcatact tcagacagtt   2220
aaggttgtgg acgaattggt taagttatg ggcaggcata agccagagaa tatcgttatc   2280
gaaatggcaa gggagaacca aacaactcaa aagggcagaa aaatagcag agagaggatg   2340
aaaagaatcg aggaagggat caaggaactt gggtcccaaa tcctcaagga gcacccagtt   2400
gaaaatactc aactgcaaaa cgagaagctc tatctctact atctccaaaa cgggagggat   2460
atgtatgttg accaggagct ggatattaac agactgtcag attatgatgt tgatcatatc   2520
gtgccccagt cattcctgaa ggacgattcc atcgacaaca aagttctcac aaggtccgat   2580
aaaaacaggg gcaagtccga taacgttcca agcgaaagaa tggtgaaaaa gatgaaaaac   2640
tattggagac aacttctgaa tgcaaagttg attactcaga gaaagtttga caacctcaca   2700
aaagcagaaa gaggcgggct tagcgaactc gataagcag ggtttatcaa aagacagctg   2760
gttgagacaa ggcagatcac aaaacatgtg gcacagatcc ttgactcaag gatgaatacc   2820
aagtatgatg agaatgataa gttgatcagg gaggttaagg ttatcacact caaatccaaa   2880
ctggtgtcag acttcaggaa agactttcaa ttttataagg tgagggagat caataactac   2940
caccatgcac atgacgccta cctgaacgca gtggtgggta cagcattgat taaaaaatac   3000
cctaagctgg agtctgagtt tgtgtacggg gactacaagg tgtacgacgt gaggaaaatg   3060
atagccaagt ccgagcagga gatcgggaaa gcaacagcta gtatttcttt ttacagtaat   3120
atcatgaatt tctttaaac tgagattact ctggcaaacg gggagatcga gaaaagaccc   3180
ctcatcgaga ctaatggtga aacaggtgag atcgtttggg acaaggggag ggattttgct   3240
actgttagaa aagttctgag tatgccacaa gtgaatattg tgaaaaagac agaagttcag   3300
acaggtgggt tctccaaaga atccatcctg cccaagagaa attcagacaa gctcatcgca   3360
agaaagaagg actgggaccc taagaagtac ggaggatttg acagccccac cgtggcctat   3420
tccgtgcttg ttgtggcaaa ggtggagaaa gggaagagca aaaaactgaa atccgtgaaa   3480
gaactgctgg gaattaccat catggaaaga agctcctttg agaagaaccc aatcgacttc   3540
ctggaagcaa aaggatataa ggaagtgaaa aaggacctca ttatcaagct cccaaaatac   3600
tcacttttcg agttggagaa cggtagaaag aggatgctgg caagcgcagg ggaacttcag   3660
aaaggcaatg agctggcatt gccatcaaag tatgtgaact tcctctactt ggccagccat   3720
tacgagaaac ttaaaggtag cccagaagat aacgagcaaa aacagctctt tgtggaacag   3780
cataagcatt atctggatga gatcatagaa caaatctcag agttttccaa gagagttatc   3840
ctcgcagatg caaacctgga taaggttctc tcagcctata ataagcatag agacaagcca   3900
attagagagc aagcagagaa cattatccac ttgttcactc ttacaaacct ggggcacca    3960
gccgccttca aatatttcga tacaacaata gacagaaaga ggtataccag caccaaagaa   4020
gttctcgacg ccacactgat ccatcaatca atcacaggcc tttacgaaac taggatcgac   4080
ttgtcacaac tgggtgggga t                                             4101

SEQ ID NO: 67          moltype = DNA   length = 3307
FEATURE                Location/Qualifiers
source                 1..3307
                       mol_type = other DNA
                       organism = synthetic construct
SEQUENCE: 67
gagcaaggac acctacgacg acgacttgga caacctattg gcccagatag gtgaccagta     60
tgcagacctc ttccttgcgg ccaagaactt gagtgacgct atactgctca gtgacatcct    120
gagggtgaac actgagatca ctaaggcccc tctctctgco tcaatgatta agcgttacga    180
cgagcatcac caggatctca ccctgcttaa ggcccttgtt cggcagcagc tcctgagaa    240
gtacaaggag atattttttg accagtctaa gaacggctac gccggttaca ttgacggtgg    300
ggcaagccag gaggagttct acaagttcat caagccgatc cttgagaaga tggacggcac    360
cgaggagcta cttgtcaagt tgaaccggga agacctgctc cggaaacagc gtacattcga    420
caacggccag atccctcacc agatccacct cacgcccatc tccgacgtca    480
ggaggacttc tatccattct tgaaagataa caggaaaaaa atcgaaaaaa tacttacgtt    540
tcgaataccc tactacgtgg ggccccttgc tcggggaaaaa tccagattcg catggatgac    600
caggaagtca gaggagacca tcaccctg gaactttgag gaggtggttg acaaggtgtc    660
ttctgcccag tccttcattg agcggatgac taacttcgac aagaacctgc ccaacgaaa    720
ggtgctgcca aagcacagcc tgctctacga atactttact gtgtacaatg agctgacgaa    780
```

| | | | | |
|---|---|---|---|---|
| ggtgaagtac | gtgacagagg | ggatgcggaa | gcccgctttc | ctgagcggcg | agcaaaaaaa | 840 |
| agcaatcgtg | gacctactgt | tcaagaccaa | ccgaaaggtg | acagtgaagc | agctcaagga | 900 |
| ggactacttc | aaaaaaatcg | agtgcttcga | ctctgttgag | ataagcggcg | tggaggaccg | 960 |
| attcaacgcc | tcattgggaa | cctatcacga | cctgctcaag | atcattaagg | acaaggactt | 1020 |
| cctggataat | gaggagaatg | aggacatcct | ggaggatatt | gtgctgaccc | ttactctatt | 1080 |
| cgaggacagg | gagatgatcg | aggagcgact | caagacctac | gctcacctgt | tcgacgacaa | 1140 |
| ggttatgaag | caattgaagc | gtaggcgata | cacggggtgg | ggaagactct | cccgaaaact | 1200 |
| gataaacggc | atcagggaca | agcagtcagg | gaagacgatc | ttggacttcc | tgaaatccga | 1260 |
| cgggttcgcc | aaccgcaact | tcatgcagct | cattcacgac | gactcactaa | cgttcaaaga | 1320 |
| ggacattcag | aaggctcaag | tcagtgtgaca | aggcgactcc | ctgcacgagc | acattgcaaa | 1380 |
| ccttgcgggc | tccccggcga | ttaaaaaggg | cattctccaa | acggttaagg | tggtggacga | 1440 |
| gctggtgaag | gtgatgggcc | gacacaagcc | tgagaacatc | gtgatcgaga | tggccaggga | 1500 |
| gaaccagact | acccagaagg | gtcagaagaa | ctctcgggaa | cgtatgaagc | gtattgagga | 1560 |
| ggggattaag | gagttgggct | ctcaaatcct | caaggagcac | cctgtggaga | acactcagct | 1620 |
| ccaaaacgag | aagctgtacc | tgtactacct | gcaaaacggg | cgcgatatgt | acgtggatca | 1680 |
| ggagttggac | atcaacaggc | ttagcgatta | cgacgtggac | cacatcgtgc | acagtcatt | 1740 |
| cttaaaggac | gacagcatcg | acaacaaggt | tctgacgagg | agcgacaaga | atcgagggaa | 1800 |
| aagtgacaat | gttccatccg | aggagtggt | caagaaaatg | aagaactatt | ggcgtcagct | 1860 |
| tctgaacgcc | aagctcatca | cccagcggaa | attcgacaac | ctgactaagg | ctgagcgagg | 1920 |
| cggactctcc | gagcttgaca | aggctggctt | catcaagcgg | cagttggtcg | aaacccgaca | 1980 |
| gataacgaag | cacgttgccc | agatacttga | ctcccgtatg | aacaccaagt | acgacgagaa | 2040 |
| cgacaagctc | atcagggagg | tgaaggtcat | tacccttaag | tccaaactcg | tcagcgactt | 2100 |
| tcgtaaggac | ttccagttct | acaaggtgcg | cgagatcaat | aactaccacc | acgcacacga | 2160 |
| cgcctacctg | aacgcagtgg | ttggaaccgc | gttgattaaa | aagtaccca | agttggagtc | 2220 |
| ggagttcgtt | tacggggact | acaaggtgta | cgacgttcgg | aagatgatcg | ccaagtctga | 2280 |
| acaggagatc | gggaaagcaa | ccgccaagta | tttcttctat | agcaacatca | tgaacttctt | 2340 |
| taaaaccgag | atcacacttg | ccaatggcga | gatccgtaag | aggccgctga | tcgagacaaa | 2400 |
| tggggagact | ggcgagatcg | tgtgggacaa | gggccgcgac | ttcgcaaccg | ttcggaaagt | 2460 |
| cttgtccatg | cctcaagtca | acatcgtcaa | gaagactgag | gtgcaaacag | gcgggttctc | 2520 |
| gaaggagtcc | atactgccca | agaggaactc | agacaagctc | atagcacgca | aaaaagactg | 2580 |
| ggatccaaag | aaatacgcg | ggttcgactc | gccgacagtc | gcatactccg | tgttagtggt | 2640 |
| ggctaaagtg | gaaaaggga | agtccaagaa | gctcaagtcc | gtcaaggagt | tgctcgggat | 2700 |
| caccattatg | gaacggtcct | cattcgagaa | gaatcccatt | gacttcctag | aggcgaaggg | 2760 |
| ctacaaagag | gtcaaaaagg | acctaattat | taagctcccc | aagtattcac | tcttcgaact | 2820 |
| tgaaaatggt | cgtaagcgga | tgttggcaag | cgctggagag | cttcagaagg | ggaacgagct | 2880 |
| tgcactgcct | tccaagtacg | tgaacttcct | gtacctcgcc | tctcattacg | agaagttgaa | 2940 |
| gggctcaccg | gaggacaacg | agcagaagca | gttgttcgtg | gagcagcaca | agcactacct | 3000 |
| cgacgagatc | attgagcaga | taagtgagtt | cagcaaacgg | gtgatccttg | ccgacgctaa | 3060 |
| cctggacaag | gtgctgagcg | cctacaacaa | gcacagagac | aagccgatcc | gagagcaagc | 3120 |
| ggagaacatc | atacacctgt | tcaccctcac | gaacctcggg | gctcccgcag | ccttcaaata | 3180 |
| ttttgacacg | accatcgacc | gtaaacgcta | cactagcacg | aaggaggtgc | tggacgctac | 3240 |
| ccttatccac | cagtccatca | ccggcctgta | cgagacgaga | atcgacttgt | cgcagctcgg | 3300 |
| tggtgac | | | | | 3307 |

| | |
|---|---|
| SEQ ID NO: 68 | moltype = DNA   length = 4101 |
| FEATURE | Location/Qualifiers |
| source | 1..4101 |
| | mol_type = other DNA |
| | organism = synthetic construct |

SEQUENCE: 68

| | | | | | | |
|---|---|---|---|---|---|---|
| gacaaaaaat | actcaattgg | tctggcaatt | gggaccaaca | gtgtcggatg | ggccgtgatt | 60 |
| accgacgagt | acaaggtgcc | gtccaaaaaa | ttcaaggtgc | ttgggaacac | cgaccgccac | 120 |
| tcgatcaaga | aaaacctaat | cggtgcgttg | cttttcgaca | gtggggagac | cgccgaggca | 180 |
| acacgcttaa | aacgcacagc | taggaggaga | tatacacggc | gcaagaaccg | aatatgctac | 240 |
| ttacaggaga | tattctccaa | tgagatggcg | aaggtgacg | actctttctt | ccatcggctt | 300 |
| gaggaatcct | tcctggtcga | ggaggacaag | aagcacgagc | gacacccgat | attcgggaac | 360 |
| atcgttgatg | aggtggcgta | ccacgagaag | tacccaacga | tataccactt | acgcaagaag | 420 |
| ctcgtggact | ctacggacaa | ggccgacttg | cgccttatct | acttggcact | ggcccacatg | 480 |
| attaagttcc | gaggccactt | cctttatcga | ggtgacctga | accccgataa | ctccgacgtg | 540 |
| gacaagctct | tcatccaact | cgtccagaca | tacaaccagc | tattcgagga | gaatcctatc | 600 |
| aacgcctctg | gggtggacgc | taagcgtatc | ctctcagccc | gctgtcaaa | gtcgaggagg | 660 |
| ttggagaacc | taatcgccca | gcttccaggc | gagaagaaaa | atgggctgtt | cggaaacctt | 720 |
| atcgcactct | cactgggcct | aacccgaac | ttcagtcca | cttcgacct | ggcagaggac | 780 |
| gcgaaattgc | agttgtcgaa | agacacctat | gacgatgacc | tggacaacct | gttggcccag | 840 |
| ataggggacc | agtacgccga | cctgttccta | gcggccaaga | acctgtccga | cgccatcttg | 900 |
| ctgtcggata | tactgcgggt | gaacaccgag | atcactaaag | cacctctctc | cgccagcatg | 960 |
| attaagcgtt | acgacgagca | ccaccaagat | ttgaccctgc | taaaggcact | tgtacggcag | 1020 |
| cagcttcccg | agaagtacaa | ggagatcttt | ttcgaccaaa | gcaagaacgg | ctacgccggg | 1080 |
| tacatcgacg | gaggtgccag | ccaggaggaa | ttctacaagt | tcattaagcc | catcctgga | 1140 |
| aagatggacg | gactgaggaa | actacttgtg | aagctgaacc | gggaagactt | actacggaag | 1200 |
| cagcgtacct | tcgacaacgg | ttctatccca | catcagatcc | atcttgggga | gttgcacgcg | 1260 |
| atcctgcgac | gccaggagga | cttttacccc | ttcctgaaag | acaaccgcga | gaaaatcgag | 1320 |
| aagatactga | ccttcagaat | accttactac | gtcggacccc | ttgcgcgagg | caactcaaga | 1380 |
| ttcgcgtgga | tgaccaggaa | atcagaggag | accatcgac | cctggaattt | cgaggaggtg | 1440 |
| gttgacaagg | gtgcctccgc | ccagtccttt | atcgaacgaa | tgaccaactt | cgacaagaac | 1500 |
| ttgcccaacg | agaaggtgct | ccccaaacac | agctcctct | acgaatattt | cacagtgtac | 1560 |
| aacgagctta | ctaaagttaa | gtatgttact | gagggcatga | ggaaacccgc | cttcctgtca | 1620 |
| ggcgagcaga | agaaagctat | tgtggacctc | ttttcaaga | ccaaccggaa | ggtgacagtg | 1680 |
| aagcagctca | aggaggacta | cttcaagaag | atagagtgct | tcgacagcgt | ggagatcagc | 1740 |

```
gggg tggagg  acagattcaa  tgcctctctc  ggaacatacc  acgacttgct  taagatcatc  1800
aaggacaagg  acttcctcga  caacgaggaa  aacgaggata  ttctggagga  tattgttctg  1860
actcttaccc  tgttcgagga  ccgggagatg  atcgaggagc  gtctcaagac  ctacgcccac  1920
ctgttcgacg  acaaagttat  gaagcagctc  aagcgtcgga  gatataccgg  atggggccgt  1980
ctgtctcgga  agctcatcaa  cgggatcagg  gacaagcagt  cagggaagac  gatcttagac  2040
ttccttaagt  ctgacggctt  cgccaacagg  aacttcatgc  agttgatcca  cgacgacagc  2100
cttaccttca  aggaggacat  ccagaaggcc  caagtgagtg  gccagggtga  cagcctccac  2160
gagcatattg  ctaatcttgc  gggttcccca  gcgattaaaa  agggcatact  tcaaaccgtt  2220
aaggtggtgg  acgagcttgt  caaggtgatg  gggcgacaca  agcccgagaa  catcgtgatc  2280
gagatggcca  gggagaacca  gaccacccag  aaggggcaga  agaatagccg  agaacgcatg  2340
aagcgcatcg  aggaggggat  taaggagcta  gggagccaga  tcctcaagga  acatcccgtc  2400
gagaacaccc  agctccagaa  cgagaagcta  tacctctact  acttgcaaaa  cgggagggat  2460
atgtacgtgg  atcaggagtt  ggacattaac  cgcctaagcg  actacgacgt  agatcacatc  2520
gtgcctcagt  cattcctcaa  agacgacagc  attgacaaca  aagtcttgac  ccgatccgac  2580
aagaaccgag  gaaaatccga  caatgtgccc  tcagaggagg  tcgtcaagaa  aatgaagaac  2640
tattggaggc  agctacttaa  cgccaaactc  ataacccagc  ggaagttcga  caaccctgaca  2700
aaggctgagc  ggggtgggct  cagcgagctt  gacaaggctg  gcttcatcaa  gcggcagttg  2760
gtggagacaa  gacagataac  gaagcacgtg  gctcagatcc  tggactctcg  catgaacacg  2820
aagtacgacg  agaacgacaa  attgatccgc  gaggtcaagg  ttattacgct  caagagcaaa  2880
cttgtcagcg  atttccgcaa  ggacttccag  ttctacaagg  tgagggagat  taacaactac  2940
caccatgcac  atgatgccta  cttgaacgca  gtggtgggga  ccgcgcttat  taaaaagtac  3000
cctaagttgg  agtcagagtt  cgtttatggg  gactacaagg  tgtacgacgt  ccggaagatg  3060
attgcaaagt  ctgaacagga  aatcgggaag  gccaccgcca  aatatttctt  ctacagtaac  3120
attatgaatt  ttttaagac  tgaaattact  ctcgcaaacg  gcgagatcag  gaagcgtccc  3180
ctcatcgaga  caaacgggga  gaccggggag  atagtctggg  acaaggggcg  ggacttcgct  3240
acggtgagga  aggtgctctc  gatgccacaa  gtgaacatcg  tcaaaaagac  agaggtgcag  3300
accggtggct  tctcaaagga  gtcaatcctg  ccaaaacgta  acagcgacaa  gctcatcgcg  3360
cgcaagaaag  actgggaccc  taagaagtat  ggtgggttcg  actcaccgac  ggtcgcatac  3420
tccgttctgg  tcgtggcaaa  ggtggaaaag  ggcaagtcca  aaaaactgaa  atccgtgaag  3480
gagttgcttg  gcattaccat  catggaacgc  agcacgttgc  agaagaaccc  cattgacttc  3540
ctggaggcta  aagggtacaa  ggaggtcaag  aaagatttaa  ttattaagct  acctaagtac  3600
agcttgttcg  agctggagaa  cggccgaaaa  cgaatgctcg  catccgccgg  ggaacttcaa  3660
aagggcaacg  agcttgcgct  gccctccaag  tacgtgaact  tcctgtactt  ggcatcccac  3720
tacgagaaac  tcaagggtag  cccagaggac  aacgagcaga  agcagctatt  cgtggagcgg  3780
cacaagcact  acctcgacga  gataatcgag  cagatcagtg  agttcagtaa  gcgggtgata  3840
ctcgcggacg  ccaacttgga  caaggtgctt  agtgcctaca  acaagcaccg  tgacaagccc  3900
atccgagaac  aggctgagaa  catcatccac  cttttcactc  tgacaaacct  cggtgctccc  3960
gccgccttca  aatacttcga  cactaccatc  gacaggaagc  gctacacatc  tacgaaggaa  4020
gttcttgacg  ctacgcttat  tcatcagtct  atcacagggc  tgtacgagac  aaggatcgac  4080
cttagccaac  tcggcgggga  t                                                4101
```

| SEQ ID NO: 69 | moltype = DNA  length = 4022 |
|---|---|
| FEATURE | Location/Qualifiers |
| source | 1..4022 |
|  | mol_type = genomic DNA |
|  | organism = Zea mays |

SEQUENCE: 69

```
aggcagcgat  tcgcgatgag  ggcgagcagt  cgagggcagg  gggcacatgc  catgtgacgt   60
gaccccacca  ccactctctc  ccgcccttcc  ctcacctaca  gctgttaatt  tgcttcccgt  120
ctcctgcgct  ccccctctct  ctctgtcttt  acactgttgc  ttctttcttc  ctgctcctct  180
ctctaggtat  agcagcccat  tcctccacac  tcccacctcc  gctcatccac  tctccctctc  240
ctaccatctc  gtcggctcct  ccccccgtcg  ccgacccgct  tctttaatgg  ttttaaggta  300
gcgcgctagt  tcatggaatc  tccggggctg  ttcgctgtag  tggcactctt  cgtcgtcgtc  360
gtggcggcg  cggccgccga  cgatgcccag  ctgctggagc  agttcaagga  ggccgtgccg  420
agccaggcca  cggacctccg  cgggtggagc  gccagcgatg  gcctgcag  gttcccaggc  480
gccggctgca  gggcgggcg  gctcacgtcg  ctgtcgctcg  ccgccgtccc  gctcaatgcc  540
gacttccggg  ccgtcgcggc  caccctgctg  cagctggcca  gcctcgagac  gctcagcctg  600
cgcggcgcca  acgtcagcgg  cacgctggcc  gcggtgccga  ggtgcgggc  caagctgcag  660
tcgctcgacc  tgtcagcgaa  tgccggcctg  cggggctccg  tctccgacgt  cgaggcgctt  720
gtcgctgcct  gcgcgggct  tagcgcgctg  aacctctccg  gcggttcgat  tggtgggccg  780
aggtctgccg  gcgttgtcgc  ctccggattt  gccgctag  acgctctcga  cttgtccggc  840
aacaagatct  ccggcgatgg  cgacctccgg  tggatggtgg  gcgccggcgt  cggagcagtc  900
cgccaactgg  acctctccgg  gaacaagatc  tctagcctgc  cggagttcac  caactgctct  960
gggctggagt  acctcgacct  ctccggcaac  ctcatcgcg  cgaggtggc  cggcaggact 1020
ctcgctgact  gccgtggtct  gagaacgctc  aacctctcag  gcaaccacct  ggtcggccg  1080
ttccgccgg  acgtcgccgc  cctcacctcg  ctcgccggac  tcaacctctc  aaacaacaac 1140
ttctccagcg  acctccccgc  cgacgctttc  accgagctac  agcagctcaa  ggtggtcgcc  1200
ctctccttca  accacttcaa  cggcagtatt  ccggactcct  tggcagcgct  gccggagctc  1260
gacgtgctgg  acctcagctc  caacaccttc  tccggcacca  tcccttcgtc  catctgccaa  1320
ggccccaact  ccagcctccg  catgctgtac  ctccagaaca  actacctctc  cggcgccatc  1380
cctgagtcaa  tctccaactg  caccaggctc  gaatctctcg  atctcagcct  caacaacatc  1440
aacggcaccc  tccggcatc  cctcgggaag  ctcggggagc  tccgggacct  cattctttgg  1500
cagaacttct  tggagggcga  gattccgcg  tccctggaaa  atttggataa  gctcgagcat  1560
ctcatcctga  actacaacgg  gctcaccggc  agcaaccgc  cggaactctc  caagtgcaag  1620
gagctgaact  ggatatcctt  ggcaagcaac  cagctgtctg  gtccgatccc  ggcttggctt  1680
gggcagctca  gtaacttggc  catcttgaag  ctgagcaaca  attccttctc  cggaccaata  1740
ccggctgagc  tcggcaactg  ccagagtttg  gtctggctgg  acctgaacag  caaccagctt  1800
aacgggtcaa  taccggcgga  actggcaaag  cagtctggga  gatgaacat  cggtcttgtc  1860
attgggcggc  cgtatgtgta  tcttcgcaat  gacgagctga  gcagcgagtg  ccatggcaag  1920
```

```
gggagcttgc tagagttcac cagtatccga cctgaagagc tcagtcggat gccgagcaag 1980
gagctgtgca acttcactcg ggtgtacatg gggagcaccg agtatacctt caataagaat 2040
ggctccatga tatttctgga tttgtcattt aatcagcttg actcagagat cccaaaggag 2100
cttgggaaca tgtactacct catgatcctg aatcttggcc acaacttgct gtctggcgtc 2160
atcccaccag aactagctgg tgccaagaag cttgctgtac tcgacctgtc acacaaccag 2220
ttggaagggc ctattcccaa ctctttctcg acgttgtcct tgtcggagat caacctttca 2280
aataatcagt tgaatggttc aattccagag ctcggttcgc tgttcacatt cccgaagatt 2340
tcatatgaga ataactctgg tctttgtggc ttcccactgt tgccatgcgg gcacaatgct 2400
ggctcaagtt cttccgatgg ccaccgatcc caccggaacc aggcttcact cgcgggtagt 2460
gttgctatgg gactcttgtt ctcgctgttc tgtatagttg gaattgtcat catagttgtt 2520
gagtgcaaga agcggaagca gatcaatgaa gaggcaagta cctctcgtga catatacatt 2580
gatagccggt ctcattctgg gactatgaat tccaattgga gactctctgg tactaacgcc 2640
ctcagcgtca accttgctgc atttgagaag cgactgcaga aactcacctt taatgatctt 2700
attgtggcca ccaatggctt ccacaatgat agcctagttg ggtctggtgg ttttggtgat 2760
gtctataagg cccagctcaa ggatggaaag gttgttgcaa tcaagaagct tatacatgtg 2820
agtggccagg gtgaccggga gtttactgca gaaatggaga ccattggtag gatcaaacac 2880
cgcaatcttg ttccgctcct cggctactgc aagtgtggtg aggagcggct gctggtttat 2940
gattacatga ggtttggcag cttggaagat gtgttgcatg accggaaaaa gaccgggatt 3000
aagctaaatt gggcagcaag gaaaaagatc gccattgggg ctgcaagggg attggcatac 3060
ctccaccaca actgtattcc acacatcatc caccgagaca tgaagtcaag caatgtgctt 3120
atcgatgagc aattagaggc aagggtatct gatttggaa tggcaagaat gatgagcgtg 3180
gtggacaccc acttgagtgt gtccactctc gccggcactc caggttacgt ggccaccggag 3240
tattaccaga gcttcagatg cactaccaag ggcgatgtgt atagctacgg tgttgtattg 3300
ctcgagctgc tcactgggaa accgcctaca gattcaactg acttcggtga cgacaacaat 3360
cttgtaggat gggtcaaaca acactcgaag tcgaggctca cggatctgtt tgatcctgaa 3420
ctcgtgaagg aagatccagc cctgagctc gagctactgg agcacctaaa agttgcttgt 3480
gcatgcttgg acgacagacc gtcgaagcgt ccgacaatgc tgaaggtcat ggcaatgttc 3540
aaggagatgc aggccagttc gacagtggac tcaaagactt cggcgtgcac agacgatgca 3600
tgttttgccg atgtggagat gacgaccctg aagaagaca aggaggagaa ggactaacaa 3660
ggccaccgac acgcgagaaa ctgctcctgg tgcacctgca caggggtga gtggcagcag 3720
ctacacggcg agtcagaggc aaaatgcccg taggaggaat cagttggtga ggataccatt 3780
tgaagtctct tgttgagctt agcattccct tcttgatggt agaagacaga agttttccct 3840
catagcttcg ccagttgaat atgctgtgta cctatgggag taggttgatt ttcttttctt 3900
ctttcttttt aagctttctt catctcttct tgtcacacgt cagtaagatc tgtgtatgta 3960
catatataaa tggtgatttt tttcttcggt gccaaatcca cttcgttcta tttcttattg 4020
tc                                                                  4022
SEQ ID NO: 70       moltype = DNA  length = 3345
FEATURE             Location/Qualifiers
source              1..3345
                    mol_type = other DNA
                    organism = Zea mays
SEQUENCE: 70
atggaatctc cggggctgtt cgctgtagtg gcactcttcg tcgtcgtcgt ggcggcggcg 60
gccgccgacg atgcccagct gctggagcag ttcaaggagg ccgtgccgag ccaggccacg 120
gacctccgcg ggtggagcgc cagcgatggc gcctgcaggt tccaggcgc cggctgcagg 180
ggcggcggc tcacgtcgct gtcgctcgcc gccgtccgtg tcaatgccga cttccgggcc 240
gtcgcggcca ccctgctgca gctgccagc ctcgagacgc tcagcctgcg cggcgccaac 300
gtcagcggca cgctggccgc ggtgccgagg tgcgggcca agctgcagtc gctcgacctg 360
tcagcgaatg ccggcctgcg gggctccgtc tccgacgtcg aggcgcttgt cgctgcctgc 420
gccgggctta gcgcgctgaa cctctccggg ttcgattg gtgggccgag gtctgccgtg 480
gttgtcgcct ccggatttgc ccggctagac gctctcgact tgtccggcaa caagatctcc 540
ggcgatggcg acctccggtg gatggtgggc ccggcgtcg agcagtccg ccaactggac 600
ctctccggga acaagatctc tagcctgccg gagttcacca actgctctgg gctggagtac 660
ctcgacctct ccggcaacct catcgccggc gaggtgccg gcaggactct cgctgactgc 720
cgtggtctga aacgctcaa cctctcaggc aaccacctgg tcggcccgtt cccgccggac 780
gtcgccgccc tcacctcgct cgccggactc aacctctcaa caacaacttt ctccagcgac 840
ctccccgccg acgctttcac cgagctacag cagctcaagg tggtcgccct ctccttcaac 900
cacttcaacg gcagtattcc ggactccttg gcagcgctgc cggagctcga cgтtgctggac 960
ctcagctcca acaccttctc cggcaccatc cttcgtccga tctgccaagg ccccaactgc 1020
agcctccgca tgctgtacct ccagaacaac tacctctccg cgccatccc tgagtcaatc 1080
tccaactgca ccaggctcga atctctcgat tcagcctca caacatcaa cggcaccctc 1140
ccggcatccc tcgggaagct cggggagctc cgggacctca ttctttggca gaacttcttg 1200
gagggcgaca ttccggcgtc cctggaaaat tggataagc tcgagcatct catcctcgac 1260
tacaacgggc tcaccggcag catcccgccg gaactctcca agtgcaagga gctgaactgg 1320
atatccttgg caagcaacca gctgtctggt ccgatcccgg cttggcttgg gcagctcagt 1380
aacttggcca tcttgaagct gagcaacaat tccttctccg gaccaatacc ggctgagctc 1440
ggcaactgcc agagtttggt ctggctggac ctgaacagca accagcttaa cgggtcaata 1500
ccggcggaac tggcaaagca gtctggcaag atgaacatcg atcttgtcat caggcggccg 1560
tatgtgtatc ttcgcaatga cgagctgagc agcgagtgcc atggcaaggg gagcttgcta 1620
gagttcacca gtatccgacc tgaagagctc agtcggatgc cgagcaagga gctgtgcaac 1680
ttcactcggg tgtacatggg gagcaccgag tataccttca ataagaatgg ctccatgata 1740
tttctggatt tgtcatttaa tcagcttgac tcagagatcc caaggagct tgggaacatg 1800
tactacctca tgatcctgt tcttggccac aacttgctgt ctggcgtcat cccaccagaa 1860
ctagctggtt ccaagaagct tgctgtactc gacctgtcac acaaccagtt ggaagggcct 1920
atcccaact cttctcgac gttgtccttg tcggagatca acctttcaaa taatcagttg 1980
aatggttcaa ttccagagct cggttcgctg ttcacattcc cgaagatttc aatgagaat 2040
aactctggtc tttgtggctt cccactgttg ccatgcgggc acaatgctgg ctcaagttct 2100
tccgatggcc accgatccca ccggaaccag gcttcactcg cgggtagtgt tgctatggga 2160
```

-continued

```
ctcttgttct cgctgttctg tatagttgga attgtcatca tagttgttga gtgcaagaag    2220
cggaagcaga tcaatgaaga ggcaagtacc tctcgtgaca tatacattga tagccggtct    2280
cattctggga ctatgaattc caattggaga ctctctggta ctaacgccct cagcgtcaac    2340
cttgctgcat ttgagaagcg actgcagaaa ctcacctttta atgatcttat tgtggccacc    2400
aatgccttcc acaatgatag cctagttggg tctggtggtt ttggtgatgt ctataaggcc    2460
cagctcaagg atggaaaggt tgttgcaatc aagaagctta tacatgtgag tggccagggt    2520
gaccgggagt ttactgcaga aatggagacc attggtagga tcaaacaccg caatcttgtt    2580
ccgctcctcg gctactgcaa gtgtggtgag gagcggctgc tggtttatga ttacatgagg    2640
tttggcagct tggaagatgt gttgcatgac cggaaaaaga ccgggattaa gctaaattgg    2700
gcagcaagga aaaagatcgc cattggggct gcaagggat tggcatacct ccaccacaac    2760
tgtattccac acatcatcca ccgagacatg aagtcaagca atgtgcttat cgatgagcaa    2820
ttagaggcaa gggtatctga ttttggaatg caagaatga tgagcgtggt ggacacccac    2880
ttgagtgtgt ccactctcgc cggcactcca ggttacgtgc caccggagta ttaccagagc    2940
ttcagatgca ctaccaaggg cgatgtgtat agctacggtg ttgtattgct cgagctgctc    3000
actgggaaac cgcctacaga ttcaactgac ttcggtgacg acaacaatct tgtaggatgg    3060
gtcaaacaac actcgaagtc gaggctcacg gatctgtttg atcctgaact cgtgaaggaa    3120
gatccagccc tggagctcga gctactggag caccttaaaaag ttgcttgtgc atgcttggac    3180
gacagaccgt cgaagcgtcc gacaatgctg aaggtcactg caatgttcaa ggagatgcag    3240
gccagttcga cagtggactc aaagacttcg gcgtgcacag acgatgcatg ttttgccgat    3300
gtggagatga cgaccctgaa agaagacaag gaggagaagg actaa                    3345

SEQ ID NO: 71           moltype = AA   length = 1114
FEATURE                 Location/Qualifiers
source                  1..1114
                        mol_type = protein
                        organism = Zea mays
SEQUENCE: 71
MESPGLFAVV ALFVVVAAA AADDAQLLEQ FKEAVPSQAT DLRGWSASDG ACRFPGAGCR    60
GGRLTSLSLA AVPLNADFRA VAATLLQLAS LETLSLRGAN VSGTLAAVPR CGAKLQSLDL   120
SANAGLRGSV SDVEALVAAC AGLSALNLSG GSIGGPRSAG VVASGFARLD ALDLSGNKIS   180
GDGDLRWMVG AGVGAVRQLD LSGNKISSLP EFTNCSGLEY LDLSGNLIAG EVAGRTLADC   240
RGLRTLNLSG NHLVGPFPPD VAALTSLAGL NLSNNNFSSD LPADAFTELQ QLKVVALSFN   300
HFNGSIPDSL AALPELDVLD LSSNTFSGTI PSSICQGPNS SLRMLYLQNN YLSGAIPESI   360
SNCTRLESLD LSLNNINGTL PASLGKLGEL RDLILWQNFL EGEIPASLEN LDKLEHLILD   420
YNGLTGSIPP ELSKCKELNW ISLASNQLSG PIPAWLGQLS NLAILKLSNN SFSGPIPAEL   480
GNCQSLVWLD LNSNQLNGSI PAELAKQSGK MNIGLVIGRP YVYLRNDELS SECHGKGSLL   540
EFTSIRPEEL SRMPSKELCN FTRVYMGSTE YTFNKNGSMI FLDLSFNQLD SEIPKELGNM   600
YYLMILNLGH NLLSGVIPPE LAGAKKLAVL DLSHNQLEGP IPNSFSTLSL SEINLSNNQL   660
NGSIPELGSL FTFPKISYEN NSGLCGFPLL PCGHNAGSSS SDGHRSHRNQ ASLAGSVAMG   720
LLFSLFCIVG IVIIVVECKK RKQINEEAST SRDIYIDSRS HSGTMNSNWR LSGTNALSVN   780
LAAFEKRLQK LTFNDLIVAT NGFHNDSLVG SGGFGDVYKA QLKDGKVVAI KKLIHVSGQG   840
DREFTAEMET IGRIKHRNLV PLLGYCKCGE ERLLVYDYMR FGSLEDVLHD RKKTGIKLNW   900
AARKKIAIGA ARGLAYLHHN CIPHIIHRDM KSSNVLIDEQ LEARVSDFGM ARMMSVVDTH   960
LSVSTLAGTP GYVPPEYYQS FRCTTKGDVY SYGVVLLELL TGKPPTDSTD FGDDNNLVGW  1020
VKQHSKSRLT DLFDPELVKE DPALELELLE HLKVACACLD DRPSKRPTML KVMAMFKEMQ  1080
ASSTVDSKTS ACTDDACFAD VEMTTLKEDK EEKD                              1114

SEQ ID NO: 72           moltype = DNA   length = 240
FEATURE                 Location/Qualifiers
source                  1..240
                        mol_type = other DNA
                        organism = Zea mays
SEQUENCE: 72
agacatgaag tcaagcaatg tgcttatcga tgagcaatta gaggcaaggg tatctgattt    60
tggaatggca agaatgatga gcgtggtgga cacccacttg agtgtgtcca ctctcgccgg   120
cactccaggt tacgtgccac cggagtatta ccagagcttc agatgcacta ccaagggcga   180
tgtgtatagc tacggtgttg tattgctcga gctgctcact gggaaaccgc ctacagattc   240

SEQ ID NO: 73           moltype = DNA   length = 160
FEATURE                 Location/Qualifiers
source                  1..160
                        mol_type = other DNA
                        organism = Zea mays
SEQUENCE: 73
gaggcaaggg tatctgattt tggaatggca agaatgatga gcgtggtgga cacccacttg    60
agtgtgtcca ctctcgccgg cactccaggt tacgtgccac cggagtatta ccagagcttc   120
agatgcacta ccaagggcga tgtgtatagc tacggtgttg                         160

SEQ ID NO: 74           moltype = DNA   length = 120
FEATURE                 Location/Qualifiers
source                  1..120
                        mol_type = other DNA
                        organism = Zea mays
SEQUENCE: 74
tggaatggca agaatgatga gcgtggtgga cacccacttg agtgtgtcca ctctcgccgg    60
cactccaggt tacgtgccac cggagtatta ccagagcttc agatgcacta ccaagggcga   120

SEQ ID NO: 75           moltype = DNA   length = 62
FEATURE                 Location/Qualifiers
```

```
source                   1..62
                         mol_type = other DNA
                         organism = Zea mays
SEQUENCE: 75
gcgtggtgga cacccacttg agtgtgtcca ctctcgccgg cactccaggt tacgtgccac    60
cg                                                                  62

SEQ ID NO: 76            moltype = DNA  length = 35
FEATURE                  Location/Qualifiers
source                   1..35
                         mol_type = other DNA
                         organism = Zea mays
SEQUENCE: 76
cccacttgag tgtgtccact ctcgccggca ctcca                              35

SEQ ID NO: 77            moltype = AA  length = 74
FEATURE                  Location/Qualifiers
source                   1..74
                         mol_type = protein
                         organism = Zea mays
SEQUENCE: 77
DMKSSNVLID EQLEARVSDF GMARMMSVVD THLSVSTLAG TPGYVPPEYY QSFRCTTKGD    60
VYSYGVVLLE LLTG                                                     74

SEQ ID NO: 78            moltype = AA  length = 53
FEATURE                  Location/Qualifiers
source                   1..53
                         mol_type = protein
                         organism = Zea mays
SEQUENCE: 78
EARVSDFGMA RMMSVVDTHL SVSTLAGTPG YVPPEYYQSF RCTTKGDVYS YGV          53

SEQ ID NO: 79            moltype = AA  length = 39
FEATURE                  Location/Qualifiers
source                   1..39
                         mol_type = protein
                         organism = Zea mays
SEQUENCE: 79
GMARMMSVVD THLSVSTLAG TPGYVPPEYY QSFRCTTKG                          39

SEQ ID NO: 80            moltype = AA  length = 20
FEATURE                  Location/Qualifiers
source                   1..20
                         mol_type = protein
                         organism = Zea mays
SEQUENCE: 80
VVDTHLSVST LAGTPGYVPP                                               20

SEQ ID NO: 81            moltype = AA  length = 11
FEATURE                  Location/Qualifiers
source                   1..11
                         mol_type = protein
                         organism = Zea mays
SEQUENCE: 81
HLSVSTLAGT P                                                        11

SEQ ID NO: 82            moltype = DNA  length = 23
FEATURE                  Location/Qualifiers
source                   1..23
                         mol_type = other DNA
                         organism = synthetic construct
SEQUENCE: 82
agtgtgtcca ctctcgccgg cac                                           23

SEQ ID NO: 83            moltype = DNA  length = 23
FEATURE                  Location/Qualifiers
source                   1..23
                         mol_type = other DNA
                         organism = synthetic construct
SEQUENCE: 83
gtgtccactc tcgccggcac tcc                                           23

SEQ ID NO: 84            moltype = DNA  length = 23
FEATURE                  Location/Qualifiers
source                   1..23
                         mol_type = other DNA
                         organism = synthetic construct
SEQUENCE: 84
gtggcacgta acctggagtg ccg                                           23
```

SEQ ID NO: 85         moltype = DNA  length = 4401
FEATURE               Location/Qualifiers
source                1..4401
                      mol_type = genomic DNA
                      organism = Glycine max
SEQUENCE: 85
gacttttgac tctctctctc tctctctcta cagtagtagt agtagtattc attcatattc   60
atactttgata tcatgtcaca cacacactat ctctctctct ctctctctaa tggcagagct  120
agctcagacc cttaacacag accacagcct ctgagagaaa ccactctcac tctcactctc  180
cttaacctttt caccttccat atctggcgaa aatgaaagct ctgtacagaa gctctctctt  240
gctcctcttc ttcctctccg tctgttctgc atcttcttct tcggttccca ctctgcaact  300
cctaagcttc aaaaactctc tcccgaaccc aaccctgctc ccgaactggc tcccgaacca  360
aagcccatgc tcattcaccg gcatcacctg caacgacgtc cagcaccctca cttccataga  420
cctctccggc gtccctctca ccacaaacct caccgtcatc gccaccttcc tcctcaccct  480
cgacaacctc cagtcactct ccttaaaatc caccaacctc tccggccccg ccgccatgcc  540
tcctcctctc tcccactcca agtgcgcctc cacattaacc tccctagatc tatcacaaaa  600
cgccctctcc ggttccctca acgacatgtc gtttctctcc tcctgctcca acctccaatc  660
cctcaatctc tccagcaacc ttcttgaatt cgactcctct cactggaagc tccacctcct  720
cgtcgccgac ttttcctaca acaagatttc cggcccggt atcctcccct ggcttctcaa  780
ccctgaaatc gaacacctcg ctctgaaagg caacaaagtc accggcgaaa ccgacttctc  840
cggttccaat tctctccagt ttttagacct ttcttccaac aactttttctg ttacgcttcc  900
tactttcggc gagtgttctt cgcttgagta tttggacctc tccgccaaca agtacttcgg  960
cgacattgct cgcactctct cgccttgcaa gaacctcgtt tacttaaaact tctccagcaa 1020
ccagttctcc ggtccggttc cttcccttcc ctccggttcg ctacagttcg tgtacccttgc 1080
ttcaaaccac ttccacggcc agattcctct cccctcgcc gacctctgct ccactctcct 1140
ccagctcgat ctctcctcca caacctctc aggcgctctc ccgaagcctt cggcgcttgc 1200
acttctcttc agtccttcga catctccagc aacctcttcg ccggtgcgct gcctatggac 1260
gttctcacgc aaatgaaaag cctcaaagag ctcgcggtgg cgttcaacgc gttccttggt 1320
cccttccgg agtctctgac gaagctctcc actttagagt cgctggatct tagctccaac 1380
aacttcagcg gctcaatccc gacaacgctg tgcggtggtg acgctgggaa taataatatt 1440
ctgaaggaac tttacctgca gaacaaccgg ttcacggggtt ttattccacc cacgctcagc 1500
aactgttcaa acctcgttgc tttggacttg agtttcaact tcctcacggg aactattcct 1560
ccaagctag ggtctcttttc caagcttaaa gacttgatca tctggctcaa ccagctccat 1620
ggagaaatac cgcaggagct catgtatctg aaaagcctcg agatttgat cctggatttc 1680
aacgacttga ctgggaacat tcctctgggg cttgttaact gcaccaagct gaactggatc 1740
tccctctcca acaacaggct cagcggcgag attccgcgt ggattgggaa gctttctaat 1800
ctcgccatac ttaagctcag taataactct ttctccggcc ggattccgcc ggagctcggc 1860
gattgtacta gttttaatatg gttggatctg aatactacta tgctcaccgg gcccattccg 1920
ccggagctgt tcaagcagtc ggggaagatc gcggtgaatt tcatcagtgg gaagacgtat 1980
gtgtatataa agaacgatgg gagcaaagag tgtcatggtg cggggaactt gctggagttt 2040
gccgggatca gtcagcagca gttgaacagg atttcgacga ggaacccgtg caatttcact 2100
aggttttatg gaggtaagtt gcagccaacg tttaaccata atggttctat gatattttg 2160
gatatctcgc acaacatgtt gtcagggagt attcccaagg agattgggc catgtactat 2220
ttgtacattc tcaatttggg tcataataat gtgtctggga gcattcctca agagcttggg 2280
aagatgaaga atctcaacat ccttgatctc tcaagtaata gactggaggg gcaaattcct 2340
cagagtctca cggggcttttc cttgctcact gagattgacc tgtcgaataa cttgcttacg 2400
gggacgattc ctgagtcggg tcaatttgat actttccctg cggcgagatt tcagaacaac 2460
tctggtctct gtggagttcc tctcggccca tgtggttcgg acccggcgaa taacgggaat 2520
gcgcaacata tgaagtctca caggaggcag gcttctctgg tggggagtgt ggccatgggt 2580
ttgttgtttt ccctctctg cgtctttggt ttgatcatta ttgccattga gaccaggaag 2640
aggaggaaga agaaggaggc tgctcttgaa gcctatgctg atggtaattt gcattcgggt 2700
cctgccaacg tgagctggaa gcacaccagt acccgggaag cgcttagcat aaaccttgca 2760
acgtttaaga ggccgctcag gaggcttact tttgcggacc ttcttgacgc taccaatggc 2820
tttcacaatg atagtctcat tggctctggt gggtttgggg atgtttacaa ggctcagttg 2880
aaggatggaa gtgttgtggc tatcaagaag ctgattcatg tcagcggcca aggggacagg 2940
gaattcactg ctgaaatgga gaccattggg aagatcaagc acaggaacct tgttcctctg 3000
ttgggatact gcaaggttgg ggaagagagg ctcttggttt atgagtacat gaaatatgga 3060
agcttagagg atgttcttca tgatccgaag aaagctgggga tcaagttgaa ttggtcgatt 3120
aggaggaaaa ttgctattgg agctgctagg ggattgtctt ttcttcacca caattgtagc 3180
ccccacatca ttcatagaga catgaagtca agcaatgtgt tacttgatga aacctggaa 3240
gctagagtct ctgattttgg aatggctagg catatgagtg ctatggatac acatttgagt 3300
gtgagcacac tggcaggcac accagggtat gttcctccgg agtactatga gagcttcaga 3360
tgctctacca aaggtgatgt ctacagttat ggtgtgcttt tgttggagct gctaactggg 3420
aaaaggccaa cagattcggc tgatttggt gataataatc ttgttggatg ggttaaacaa 3480
catgccaagc tgaaaataag tgatattttt gacccagagc tcatgaagga agaccccaat 3540
ttggagatgt agcttttgca gcacctgaag attgcagttt cctgtttgga tgatcggcat 3600
tggagacgtc caacgatgat tcaagtgttg acaatgttca aggagattca ggcaggatct 3660
gggattgatt ctcagtcaac catgccaat gaagatgaca gtttcaatgc agttgaaatg 3720
gtggagatga gcattaaaga aaccctgaa ttgagcaagc attaggcaac aaattccgga 3780
agtgtcatgt ggattcttttg ggaaacagac aagaagagag aaaaggagga gatgacggat 3840
tcagctcccc tcaaagtttt ttccttcctc tttgccgctt caaattattt cagacacaag 3900
ggggaaacgg ttaagggggg aatgaatgcc tttgatgtat gtagtcttgt tattttatac 3960
aaaaaaaaa agttgtttaa cttgtatata aacagcttca gttgttacca tctgtgtttt 4020
cctagaattt tcaaaagtac ttttctcatt cagatataat cctgaaaagg atctctgttc 4080
aatctggcga ccccagtgat ggcgactaag tggaggatct tttggccatt tctttaggcc 4140
tcttgatttt tttcccccat tgatcaact gcaacttttg ctccgatttg cgatataatt 4200
tgtcaaaaca tgcttcttct aaaatcactc ataacataaa ttttcttgaa ttacaatttt 4260
ataccctccc ctcccccaact tgttctgcgc cttctgaccc ttcttgtttt gtttgctagt 4320

```
ttaccctgta ggaaaaagta tcactctact caaatagtat tttcacctct tctggccata   4380
aataattttg gcctaattca g                                             4401

SEQ ID NO: 86           moltype = DNA   length = 2511
FEATURE                 Location/Qualifiers
source                  1..2511
                        mol_type = other DNA
                        organism = Glycine max
SEQUENCE: 86
atggacgttc tcacgcaaat gaaaagcctc aaagagctcg cggtggcgtt caacgcgttc     60
cttggtcccc ttccggagtc tctgacgaag ctctccactt tagagtcgct ggatcttagc    120
tccaacaact tcagcggctc aatcccgaca acgctgtgcg gtggtgacgc tgggaataat    180
aatattctga aggaacttta cctgcagaac aaccggttca cgggttttat tccacccacg    240
ctcagcaact gttcaaacct cgttgctttg gacttgagtt tcaacttcct cacgggaact    300
attcctccaa gcctagggtc tcttttccaag cttaaagact tgatcatctg gctcaaccag    360
ctccatggag aaataccgca ggagctcatg tatctgaaaa gcctcgagaa tttgatcctg    420
gatttcaacg acttgactgg gaacattccc tctgggcttg ttaactgcac aagctgaac    480
tggatctccc tctccaacaa caggctcagc ggcgagatcc cgcggtggat tgggaagctt    540
tctaatctcg ccatacttaa gctcagtaat aactctttct ccggccggat tccgccggaa    600
ctcggcgatt gtactagttt aatatggttg gatctgaata ctaatatgct caccgggccc    660
attccgccgg agctgttcaa gcagtcgggg aagatcgcgg tgaatttcat cagtgggaag    720
acgtatgtgt atataaagaa cgatgggagc aaagagtgct tggtgcggg gaacttgctg    780
gagtttgccg ggatcagtca gcagcagttg aacaggattt cgacgaggaa cccgtgcaat    840
ttcactaggg tttatggagg taagttcag ccaacgttta accataatgg ttctatgata    900
tttttggata tctcgcacaa catgttgtca ggagtattcc caaggagat ggggccatg    960
tactatttgt acattctcaa tttgggtcat aataatgtgt cggggagcat tcctcaagag   1020
cttgggaaga tgaagaatct caacatcctt gatctctcaa gtaatagact ggaggggcaa   1080
attcctcaga gtctcacggg gctttccttg ctcactgaga ttgacctgtc gaataacttg   1140
cttacgggga cgattcctga gtcgggtcaa tttgatactt ccctgcggc gagatttcag   1200
aacaactctg gtctcgtgtg agttcctctc ggccatgtg gttcggaccc ggcgaataac   1260
gggaatgcgc aacatatgaa gtctcacagg aggcaggctc tctggtggg gagtgtggcc   1320
atgggttttgt tgttttccct cttcgcgtc tttggtttga tcattattgc cattgagacc   1380
aggaagagga ggaagaagaa ggaggctgct cttgaagcct atgctgatgg taatttgcat   1440
tcgggtcctg ccaacgtgag ctggaagcac accagtaccc gggaagcgct tagcataaac   1500
cttgcaacgt ttaagaggcc gctcaggagg cttacttttg cggaccttct tgacgctacc   1560
aatggctttc acaatgatag tctcattggc tctggtgggt ttgggggatgt ttacaaggct   1620
cagttgaagg atgaagtgt tgtggctatc aagaagctga ttcatgtcag cggccaaggg   1680
gacagggaat tcactgctga atggagacc attgggaaga tcaagcacag gaaccttgtt   1740
cctctgttgg gatactgcaa ggttgggaa gagaggctct tggttatga gtacatgaaa   1800
tatgaagct tagaggatgt tcttcatgat ccgaagaaag ctgggatcaa gttgaattgg   1860
tcgattagga ggaaaattgc tattggagct gctaggggat tgtctttct tcaccacaat   1920
tgtagccccc acatcattca tagagacatg aagtcaagca atgtgttact tgatgaaaac   1980
ctggaagcta gagtctctga ttttggaatg ctaggcata tgagtgctat ggatacactt   2040
ttgagtgtga gcacactggc aggcacacca gggtatgttc ctccggagta ctatgagagc   2100
ttcagatgct ctaccaaagg tgatgtctac agttatggtg tggttttgtt ggagctgcta   2160
actgggaaaa ggccaacaga ttcggctgat tttggtgata taatcttgt tggatgggtt   2220
aaacaacatg ccaagctgaa aatagtgat attttgacc gaaggaagac                 2280
cccaatttgg agatggagct tttgcagcac ctgaagattg cagttcctg tttggatgat   2340
cggcattgga gacgtccaac gatgattcaa gtgttgacaa tgttcaagga gattcaggca   2400
ggatctggaa ttgattctca gtcaaccata gccaatgaag atgacagttt caatgcagtt   2460
gaaatggtgg agatgagcat taagaaaacc cctgaattga gcaagcatta g             2511

SEQ ID NO: 87           moltype = AA   length = 1184
FEATURE                 Location/Qualifiers
source                  1..1184
                        mol_type = protein
                        organism = Glycine max
SEQUENCE: 87
MKALYRSSLL LLFFLSVCSA SSSSVPTLQL LSFKNSLPNP TLLPNWLPNQ SPCSFTGITC     60
NDTQHLTSID LSGVPLTTNL TVIATFLLTL DNLQSLSLKS TNLSGPAAMP PPLSHSKCAS    120
TLTSLDLSQN ALSGSLNDMS FLSSCSNLQS LNLSSNLLEF DSSHWKLHLL VADFSYNKIS    180
GPGILPWLLN PEIEHLALKG NKVTGETDFS GSNSLQFLDL SSNNFSVTLP TFGECSSLEY    240
LDLSANKYFG DIARTLSPCK NLVYLNFSSN QFSGPVPSLP SGSLQFVYLA SNHFHGQIPL    300
PLADLCSTLL QLDLSSNNLS GALPEAFGAC TSLQSFDISS NLFAGALPMD VLTQMKSLKE    360
LAVAFNAFLG PLPESLTKLS TLESLDLSSN NFSGSIPTTL CGGDAGNNNI LKELYLQNNR    420
FTGFIPPTLS NCSNLVALDL SFNFLTGTIP PSLGSLSKLK DLIIWLNQLH GEIPQELMYL    480
KSLENLILDF NDLTGNIPSG LVNCTKLNWI SLSNNRLSGE IPRWIGKLSN LAILKLSNNS    540
FSGRIPPELG DCTSLIWLDL NTNMLTGPIP PELFKQSGLI AVNFISGKTY VYIKNDGSKE    600
CHGAGNLLEF AGISQQQLNR ISTRNPCNFT RVYGGKLQPT FNHNGSMIFL DISHNMLSGS    660
IPKEIGAMYY LYILNLGHNN VSGSIPQELG KMKNLNILDL SSNRLEGQIP QSLTGLSLLT    720
EIDLSNNLLT GTIPESGQFD TFPAARFQNN SGLCGVPLGP CGSDPANNGN AQHMKSHRRQ    780
ASLVGSVAMG LLFSLFCVFG LIIIAIETRK RRKKEAALE AYADGNLHSG PANVSWKHTS    840
TREALSINLA TFKRPLRRLT FADLLDATNG FHNDSLIGSG GFGDVYKAQL KDGSVVAIKK    900
LIHVSGQGDR EFTAEMETIG KIKHRNVLPL LGYCKVGEER LLVYEYMKYG SLEDVLHDPK    960
KAGIKLNWSI RRKIAIGAAR GLSFLHHNCS PHIIHRDMKS SNVLLDENLE ARVSDFGMAR   1020
HMSAMDTHLS VSTLAGTPGY VPPEYYESFR CSTKGDVYSY GVVLLELLTG KRPTDSADFG   1080
DNNLVGWVKQ HAKLKISDIF DPELMKEDPN LEMELLQHLK IAVSCLDDRH WRRPTMIQVL   1140
TMFKEIQAGS GIDSQSTIAN EDDSFNAVEM VEMSIKETPE LSKH                    1184
```

| SEQ ID NO: 88 | moltype = AA length = 1184 |
| --- | --- |
| FEATURE | Location/Qualifiers |
| source | 1..1184 |
| | mol_type = protein |
| | organism = Glycine max |

SEQUENCE: 88

| MKALYRSSLL | LLFFLSVCSA | SSSSVPTLQL | LSFKNSLPNP | TLLPNWLPNQ | SPCSFTGITC | 60 |
| --- | --- | --- | --- | --- | --- | --- |
| NDTQHLTSID | LSGVPLTTNL | TVIATFLLTL | DNLQSLSLKS | TNLSGPAAMP | PPLSHSKCAS | 120 |
| TLTSLDLSQN | ALSGSLNDMS | FLSSCSNLQS | LNLSSNLLEF | DSSHWKLHLL | VADFSYNKIS | 180 |
| GPGILPWLLN | PEIEHLALKG | NKVTGETDFS | GSNSLQFLDL | SSNNFSVTLP | TFGECSSLEY | 240 |
| LDLSANKYFG | DIARTLSPCK | SLVYLNFSSN | QFSGPVPSLP | SGSLQFVYLA | SNHFHGQIPL | 300 |
| PLANLCSTLL | QLDLSSNNLS | GALPEAFGAC | TSLQSFDISS | NLFAGALPMD | VLTQMKSLKE | 360 |
| LAVAFNAFLG | PLPESLTKLS | TLESLDLSSN | NFSGSIPTTL | CGGDAGNNNI | LKELYLQNNR | 420 |
| FTGFIPPTLS | NCSNLVADLL | SFNLTGTIP | PSLGSLSKLK | DLIIWLNQLH | GEIPQELMYL | 480 |
| KSLENLILDF | NDLTGNIPSG | LVNCTKLNWI | SLSNNRLSGE | IPRWIGKLSN | LAILKLSNNS | 540 |
| FSGRIPPELG | DCTSLIWLDL | NTNMLTGPIP | PELFKQSGKI | AVNFISGKTY | VYIKNDGSKE | 600 |
| CHGAGNLLEF | AGISQQQLNR | ISTRNPCNFT | RVYGGKLQPT | FNHNGSMIFL | DISHNMLSGS | 660 |
| IPKEIGAMYY | LYILNLGHNN | VSGSIPQELG | KMKNLNILDL | SSNRLEGQIP | QSLTGLSLLT | 720 |
| EIDLSNNLLT | GTIPESGQFD | TFPAARFQNN | SGLCGVPLGP | CGSDPANNGN | AQHMKSHRRQ | 780 |
| ASLVGSVAMG | LLFSLFCVFG | LIIIAIETRK | RRKKKEAALE | AYADGNLHSG | PANVSWKHTS | 840 |
| TREALSINLA | TFKRPLRRLT | FADLLDATNG | FHNDSLIGSG | GFGDVYKAQL | KDGSVVAIKK | 900 |
| LIHVSGQGDR | EFTAEMETIG | KIKHRNLVPL | LGYCKVGEER | LLVYEYMKYG | SLEDVLHDPK | 960 |
| KAGIKLNWSI | RRKIAIGAAR | GLSFLHHNCS | PHIIHRDMKS | SNVLLDENLE | ARVSDFGMAR | 1020 |
| HMSAMDTHLS | VSTLAGTPGY | VPPEYYESFR | CSTKGDVYSY | GVVLLELLTG | KRPTDSADFG | 1080 |
| DNNLVGWVKQ | HAKLKISDIF | DPELMKEDPN | LEMELLQHLK | IAVSCLDDRH | WRRPTMIQVL | 1140 |
| TMFKEIQAGS | GIDSQSTIAN | EDDSFNAVEM | VEMSIKETPE | LSKH | | 1184 |

| SEQ ID NO: 89 | moltype = DNA length = 223 |
| --- | --- |
| FEATURE | Location/Qualifiers |
| source | 1..223 |
| | mol_type = other DNA |
| | organism = Glycine max |

SEQUENCE: 89

| agacatgaag | tcaagcaatg | tgttacttga | tgaaaacctg | gaagctagag | tctctgattt | 60 |
| --- | --- | --- | --- | --- | --- | --- |
| tggaatggct | aggcatatga | gtgctatgga | tacacatttg | agtgtgagca | cactggcagg | 120 |
| cacaccaggg | tatgttcctc | cggagtacta | tgagagcttc | agatgctcta | ccaaaggtga | 180 |
| tgtctacagt | tatggtgtgg | ttttgttgga | gctgctaact | ggg | | 223 |

| SEQ ID NO: 90 | moltype = DNA length = 160 |
| --- | --- |
| FEATURE | Location/Qualifiers |
| source | 1..160 |
| | mol_type = other DNA |
| | organism = Glycine max |

SEQUENCE: 90

| aaacctggaa | gctagagtct | ctgattttgg | aatggctagg | catatgagtg | ctatggatac | 60 |
| --- | --- | --- | --- | --- | --- | --- |
| acatttgagt | gtgagcacac | tggcaggcac | accagggtat | gttcctccgg | agtactatga | 120 |
| gagcttcaga | tgctctacca | aaggtgatgt | ctacagttat | | | 160 |

| SEQ ID NO: 91 | moltype = DNA length = 143 |
| --- | --- |
| FEATURE | Location/Qualifiers |
| source | 1..143 |
| | mol_type = other DNA |
| | organism = Glycine max |

SEQUENCE: 91

| gaagctagag | tctctgattt | tggaatggct | aggcatatga | gtgctatgga | tacacatttg | 60 |
| --- | --- | --- | --- | --- | --- | --- |
| agtgtgagca | cactggcagg | cacaccaggg | tatgttcctc | cggagtacta | tgagagcttc | 120 |
| agatgctcta | ccaaaggtga | tgt | | | | 143 |

| SEQ ID NO: 92 | moltype = DNA length = 95 |
| --- | --- |
| FEATURE | Location/Qualifiers |
| source | 1..95 |
| | mol_type = other DNA |
| | organism = Glycine max |

SEQUENCE: 92

| aatggctagg | catatgagtg | ctatggatac | acatttgagt | gtgagcacac | tggcaggcac | 60 |
| --- | --- | --- | --- | --- | --- | --- |
| accagggtat | gttcctccgg | agtactatga | gagct | | | 95 |

| SEQ ID NO: 93 | moltype = DNA length = 63 |
| --- | --- |
| FEATURE | Location/Qualifiers |
| source | 1..63 |
| | mol_type = other DNA |
| | organism = Glycine max |

SEQUENCE: 93

| gtgctatgga | tacacatttg | agtgtgagca | cactggcagg | cacaccaggg | tatgttcctc | 60 |
| --- | --- | --- | --- | --- | --- | --- |
| cgg | | | | | | 63 |

| SEQ ID NO: 94 | moltype = DNA length = 37 |
| --- | --- |
| FEATURE | Location/Qualifiers |
| source | 1..37 |

```
                        mol_type = other DNA
                        organism = Glycine max
SEQUENCE: 94
acatttgagt gtgagcacac tggcaggcac accaggg                                   37

SEQ ID NO: 95           moltype = AA  length = 74
FEATURE                 Location/Qualifiers
source                  1..74
                        mol_type = protein
                        organism = Glycine max
SEQUENCE: 95
DMKSSNVLLD ENLEARVSDF GMARHMSAMD THLSVSTLAG TPGYVPPEYY ESFRCSTKGD           60
VYSYGVVLLE LLTG                                                            74

SEQ ID NO: 96           moltype = AA  length = 52
FEATURE                 Location/Qualifiers
source                  1..52
                        mol_type = protein
                        organism = Glycine max
SEQUENCE: 96
NLEARVSDFG MARHMSAMDT HLSVSTLAGT PGYVPPEYYE SFRCSTKGDV YS                   52

SEQ ID NO: 97           moltype = AA  length = 31
FEATURE                 Location/Qualifiers
source                  1..31
                        mol_type = protein
                        organism = Glycine max
SEQUENCE: 97
MARHMSAMDT HLSVSTLAGT PGYVPPEYYE S                                         31

SEQ ID NO: 98           moltype = AA  length = 12
FEATURE                 Location/Qualifiers
source                  1..12
                        mol_type = protein
                        organism = Glycine max
SEQUENCE: 98
HLSVSTLAGT PG                                                              12

SEQ ID NO: 99           moltype = DNA  length = 3915
FEATURE                 Location/Qualifiers
source                  1..3915
                        mol_type = genomic DNA
                        organism = Glycine max
SEQUENCE: 99
atgccatggt caccaagaag agaagcaccg atagtagtga ggttcgttgt gattgcctta          60
ttcatcatga taacagtacc aacaccacca acagcagcag atgcagaagc agaagcagca         120
acaacaactt ctgatgcagt tttattgata cagttcaagc atttacacgt ttcctctgat         180
ccctacagct tcctctccga ctgggaccca cacgcgccat cccgtgcgc gtggcgaggt          240
atcacctgct cctcctccgg cggcgtcagc gccatcgacc tcagcggcgc tgccctctcc         300
ggcacactgc acctccccac actcacgtca ctttcatcgc tccaaaacct aatcctacgt         360
ggcaactcct tctcctcttt caacctcacc gtttcgccac tttgtacgct cgaaacactc         420
gacctctctc acaacaactt ctccggcaag tttcctttcg caaacctcgc tccatgtatc         480
cgccttagct atctcaacct ctcaataat ctcatcaccg ctgggcctgg gcctggccc           540
gagctggccc aacttgattt gtctagaaac cgtgtctccg acgtggacct tctcgtttcc         600
gctctcggaa gctcaactct cgttttttctt aacttctcgg acaataaact cgcgggtcaa        660
ctcagcgaaa cgctcgtttc gaagagcctg aatctctcca ctttggacct ctcttataat         720
cttttctccg gaaaggttcc gccgaggctt ctaaacgacg ccgttcaggt cctggatttc         780
tcgttcaaca atttctcgga atttgacttc ggtttcggtt cgtgtgagaa tctagttcgg         840
ttgagtttct cgcacaatgc aatctcttca aacgagtttc cgcgcgggtt gggtaactcg         900
aacaatcttg aggttctaga tcttttctcac aatgagctca tgatcgagat tccgtcggaa        960
attcttctga atttgaagag tttgaagtct ctgtttctcg cacacaacaa atttccggc         1020
gaaatcccga gtgagcttgg aagcctttgc aaaactctag ttgaacttga tctctcggag        1080
aacaatcttt ctggttcgtt gcctttgagt ttcactcaat gttcttctct gcagagtctg        1140
aatctcgcga gaaactttt ttctgggaac ttccttgttt ccgtggtgaa caagcttcgg         1200
agtctaaagt atctaaacgc agcgtttaac aacataacgg gaccggttcc ggtgtcgctt        1260
gtgagcttga aagagcttcg ggttcttgac ctgagctcga accggttcag cggcaatgtt        1320
ccgtcgtctt tatgtcctc cggggttgag aatttgatcc tcgctggcaa ttacctttca        1380
gggacggtac cgtcacagct cggtgagtgt aggaacttga aaactattga tttcagcttt       1440
aacagtttga acggttccat accgtggaag gtgtgggctt tgcctaattt aactgatttg       1500
attatgtggg ctaataaact cactggagaa atccccgagg gaatttgtgt taagggaggg       1560
aacttggaga cgttgatttt gaacaacaat ttaatttctg gtccattcc gaagtcaatt        1620
gcgaattgca ccaacatgat atgggtgtcg ttggcgagca accggttaac cggggagata       1680
acggctggga ttgggaattt gaatgcattg gcgattcttc agctggggaa taactcgctc       1740
agtggaggga ttccgccgga gataggcgag tgcaagaggt tgatatggtt ggatttgaat       1800
agcaataacc taaccgggga tatccctttc cagcttgctg atcaggcagg ttggttatc        1860
ccaggtaggg tttcggggaa gcagtttgcg tttgtgagga atgagggtgg gactagttgc       1920
agggtgctg gtgggttggt tgagtttgag gatatcagga cagagaggct tgaaggtttt       1980
ccaatggtga attcatgccc gttgacacg atttactccg gttggactgt gtatactttt       2040
gcttccaatg ggagtatgat ctaccttgac ctttcctaca acttgttgtc tggtagcatc       2100
```

```
cctgagaatt tgggtgagat ggcctatttg caggtgctga atttgggca  caataggttg  2160
agtgggaaca ttcctgatag gcttggtggt ttgaaagcaa tagggtgct  tgatctgtct  2220
cataatagtc ttaatgggtc catccctggg gcattggagg gtcttctttt tctcagtgac  2280
cttgatgtgt ctaataataa tctcactggg tccattcctt ctggaggtca gttaactact  2340
tttccagctg ccagatatga gaacaactct ggcctttgtg gggtgccttt gtcagcgtgt  2400
ggggcttcaa agaatcactc cgttgctgtt gggggttgga agaagaagca gcctgctgca  2460
gctggggttg tcattggttt gctttgcttc ctcgtgtttg cacttgggct tgtgttggct  2520
ttgtaccgag tgaggaagac acagaggaag gaggagatga gggaaaagta tatagagagt  2580
cttccaactt ctgggggcag tagttggaag ctatccagct ttcctgagcc tttgagcatc  2640
aatgttgcca cctttgagaa gcctctgcgg aagctgacgt ttgcacatct tcttgaggct  2700
actaatggtt tcagtgccga gagtttgata ggttctgggg ggtttggtga ggtgtacaaa  2760
gctaagctaa aagatggttg tgttgttgct atcaagaagc tcattcacgt gacgggtcag  2820
ggagatagg  agttcatggc tgagatggaa actattggga agattaagta taggaacctg  2880
gttcagctgc tgggttactg taaagttgga gaggagagc  tgcttgtgta tgagtacatg  2940
agatggggaa gtctcgaggc tgtttttacat gagagagcaa aaggaggagg ttcaaagctt  3000
gattgggcag caaggaagaa gattgccata gggtcagcaa gaggtctcgc atttcttcac  3060
catagttgca ttcctcacat tatacacagg gacatgaagt ccagcaatat tcttcttgat  3120
gaaaatttg  aggccagagt ttctgatttt ggcatggcga gattggttaa tgccctcgac  3180
actcatctca ctgttagcct tgccggaaca cctggttatg tacccctga  gtactaccag  3240
agttttagat gtacagcaaa aggggatgtc tatagctatg tgtcatact  gctagagctt  3300
ctatcaggga agagaccaat tgactcttct gagtttggtg atgatagcaa tcttgttgga  3360
tggtcaaaga tgctttacaa agagaaaaga attaatgaaa tacttgatcc tctgatttaatt 3420
gtgcaaacat ctagtgaaag tgaactatta caatatttga gaattgcttt tgaatgtctg  3480
gatgagagac cataccggcg gccaaccatg atacaagtga tggctatgtt taaagagctt  3540
caggttgaca catttaatga tatgcttgat agcttctctc tgagagacaa tgttattgat  3600
gaagcatgag aagacgatct ttactataag actcaaagcc ctttgacagt taaggaaata  3660
aaaaggttct caacatttgg catgttgctg gactaagttg acaatttggt gacactggtc  3720
tatcctatct gaaattggag gacggttctt tcaccttttt ctgttgtata taagacactt  3780
aatgagacca agagatcaaa ggcaatcatg aattgaatgg aaggttgaga cttgaggtta  3840
tagacagagt tttgtatgct tcttttgtgc tgatctagtg tttgatcact tgaaatcggt  3900
agatatattt ttttt                                                    3915

SEQ ID NO: 100          moltype = DNA  length = 3606
FEATURE                 Location/Qualifiers
source                  1..3606
                        mol_type = other DNA
                        organism = Glycine max
SEQUENCE: 100
atgccatggt caccaagaag agaagcaccg atagtagtga ggttcgttgt gattgcctta  60
ttcatcatga taacagtacc aacaccacca acagcagcag atgcagaagc agaagcagca  120
acaacaactg ctgatgcagt tttattgata cagttcaagc atttacacgt ttcctctgat  180
ccctacagct tcctctccga ctgggaccca cacgcgccat ccccgtgcgc gtggcgaggt  240
atcacctgct cctcctccgg cggcgtcagc gccatcgact cagcggcgc  tgccctctcc  300
ggcacactgc acctccccac actcacgtca cttttcatcgc tccaaaacct aatcctacgt  360
ggcaactcct tctcctcttt caacctcacc gtttcgccac tttgtacgct cgaaacactc  420
gacctctctc acaacaactt ctccggcaag tttccttttcg caaacctcgc tccatgtatc  480
cgccttagct atctcaacct ctctaataat ctcatcaccg ctgggcctgg gccctggccc  540
gagctggccc aacttgattt gtctagaaac cgtgtctccg acgtggacct tctcgtttcc  600
gctctcggaa gctcaactct cgttttctct aacttctcgg acaataaact cgcgggtcaa  660
ctcagcgaaa cgctcgtttc gaagagcctg aatctctcca ctttgacct  ctcttataat  720
cttttctccg gaaaggttcc gccgaggctt ctaaacgacg tcgttcaggt cctggatttc  780
tcgttcaaca attttctcgga atttgacttc ggtttcggtt cgtgtgagaa tctagttcgg  840
ttgagtttct cgcacaatgc aatctcttca aacgagtttc cgcgcgggtt gggtaactgc  900
aacaatcttg aggttctaga tcttttctcac aatgagctca tgatggagat tccgtcggaa  960
attcttctga atttgaagag tttgaagtct ctgtttctcg cacacaacaa attttccggc  1020
gaaatcccga gtgagcttgg aagcctttgc aaaactctag ttgaacttga tctctcggag  1080
aacaatcttc tggttcgtt  gcctttgagt ttcactcaat gttcttctct gcagagtctg  1140
aatctcgcga gaaactattt ttctgggaac ttccttgttt ccgtggtgaa caagcttcgg  1200
agtctaaagt atctaaacgc agcgtttaac aacataacgg gaccggttcc ggtgtcgctt  1260
gtgagcttga aagagcttcg ggttcttgac ctgagctcga accggttcag cggcaatgtt  1320
ccgtcgtctt tatgtccttc cgggttggag aatttgatcc tcgctggcaa ttaccttttca  1380
gggacggtac cgtcacagct cggtgagtgt aggaacttga aaactattga tttcagcttt  1440
aacagtttga acggttccat accgtggaag gtgtgggctt tgcctaattt aactgatttg  1500
attatgtggg ctaataaact cactggagaa atccccgagg gaatttgtgt taagggaggg  1560
aacttggaga cgttgatttt gaacaacaat ttaatttctg ggtccattcc gaagtcaatt  1620
gcgaattgca ccaacatgat atgggtgtcg tggcgagca  accggttaac cggggagata  1680
acggctggga ttgggaattt gaatgcattg gcgattcttc agctgggaa  taactcgctc  1740
agtgggagga ttccgccgga gataggcgag tgcaagaggt tgatatggtt ggatttgaat  1800
agcaataacc taaccgggga tatcccttc  cagcttgcgg atcaggcagg gttggttatc  1860
ccaggtaggg tttcggggaa gcagtttgcg tttgtgagga atgagggtgg gactagttgc  1920
aggggtgctg tgggttggtt tgagtttgag gatatcagga cagagaggct tgaaggtttt  1980
ccaatggtgc attcatgccc gttgacacgg atttactccg gttggactgt gtatactttt  2040
gcttccaatg ggagtatgat ctaccttgac ctttcctaca acttgttgtc tggtagcatc  2100
cctgagaatt tgggtgagat ggcctatttg caggtgctga atttgggca  caataggttg  2160
agtgggaaca ttcctgatag gcttggtggt ttgaaagcaa tagggtgct  tgatctgtct  2220
cataatagtc ttaatgggtc catccctggg gcattggagg gtcttctttt tctcagtgac  2280
cttgatgtgt ctaataataa tctcactggg tccattcctt ctggaggtca gttaactact  2340
tttccagctg ccagatatga gaacaactct ggcctttgtg gggtgccttt gtcagcgtgt  2400
ggggcttcaa agaatcactc cgttgctgtt gggggttgga agaagaagca gcctgctgca  2460
```

```
gctggggttg tcattggttt gctttgcttc ctcgtgtttg cacttgggct tgtgttggct  2520
ttgtaccgag tgaggaagac acagaggaag gaggagatga gggaaaagta tatagagagt  2580
cttccaactt ctgggggcag tagttggaag ctatccagct ttcctgagcc tttgagcatc  2640
aatgttgcca cctttgagaa gcctctgcgg aagctgacgt tgcacatct tcttgaggct   2700
actaatggtt tcagtgccga gagtttgata ggttctgggg ggtttggtga ggtgtacaaa  2760
gctaagctaa aagatggttg tgttgttgct atcaagaagc tcattcacgt gacgggtcag  2820
ggagataggg agttcatggc tgagatgaaa actattggga agattaagca taggaacctg  2880
gttcagctgc tgggttactg taaagttgga gaggagaggc tgcttgtgta tgagtacatg  2940
agatgggcaa gtctcgaggc tgttttacat gagagagcaa aaggaggagg ttcaaagctt  3000
gattgggcag caaggaagaa gattgccata gggtcagcaa gaggtctcgc atttcttcac  3060
catagttgca ttcctcacat tatacacagg gacatgaagt ccagcaatat tcttcttgat  3120
gaaaattttg aggccagagt ttctgatttt ggcatggcga gattggttaa tgccctcgac  3180
actcatctca ctgttagcct tgccggaaca cctggttatg taccccctga gtactaccag  3240
agttttagat gtacagcaaa aggggatgtc tatagctatg gtgtcatact gctagagctt  3300
ctatcaggga agagaccaat tgactcttct gagtttggtg atgatagcaa tcttgttgga  3360
tggtcaaaga tgcttacaa agagaaaaga attaatgaaa tacttgatcc tgatttaatt  3420
gtgcaaacat ctagtgaaag tgaactatta caatatttga gaattgcttt tgaatgtctg  3480
gatgagagac cataccggcg gccaaccatg atacaagtga tggctatgtt taaagagctt  3540
caggttgaca catttaatga tatgcttgat agcttctctc tgagagacaa tgttattgat  3600
gaagca                                                            3606

SEQ ID NO: 101         moltype = AA   length = 1227
FEATURE                Location/Qualifiers
source                 1..1227
                       mol_type = protein
                       organism = Glycine max
SEQUENCE: 101
MKHESEKPQK GEKMKREKPY LMKKMPWSPR REAPIVVRFV VIALFIMITV PTPPTAADAE   60
AEAATTTSDA VLLIQFKHLH VSSDPYSFLS DWDPHAPSPC AWRGITCSSS GGVSAIDLSG  120
AALSGTLHLP TLTSLSSLQN LILRGNSFSS FNLTVSPICT LETLDLSHNN FSGKFPPANL  180
APCIRLSYLN LSNNLITAGP GPWPELAQLD LSRNRVSDVD LLVSALGSST LVFLNFSDNK  240
LAGQLSETLV SKSLNLSTLD LSYNLFSGKV PPRLLNDAVQ VLDFSFNNFS EPDFGFGSCE  300
NLVRLSFSHN AISSNEFPRG LGNCNNLEVL DLSHNELMME IPSEILLNLK SLKSLFLAHN  360
KFSGEIPSEL GSLCKTLVEL DLSENNLSGS LPLSFTQCSS LQSLNLARNY FSGNFLVSVV  420
NKLRSLKYLN AAFNNITGPV PVSLVSLKEL RVLDLSSNRF SGNVPSSLCP SGLENLILAG  480
NYLSGTVPSQ LGECRNLKTI DFSFNSLNGS IPWKVWALPN LTDLIMWANK LTGEIPEGIC  540
VKGGNLETLI LNNNLISGSI PKSIANCTNM IWVSLASNRL TGEITAGIGN LNALAILQLG  600
NNSLSGRIPP EIGECKRLIW LDLNSNNLTG DIPFQLADQA GLVIPGRVSG KQFAFVRNEG  660
GTSCRGAGGL VEFEDIRTER LEGFPMVHSC PLTRIYSGWT VYTFASNGSM IYLDLSYNLL  720
SGSIPENLGE MAYLQVLNLG HNRLSGNIPD RLGGLKAIGV LDLSHNSLNG SIPGALEGLS  780
FLSDLDVSNN NLTGSIPSGG QLTTFPAARY ENNSGLCGVP LSACGASKNH SVAVGGWKKK  840
QPAAAGVVIG LLCFLVFALG LVLALYRVRK TQRKEEMREK YIESLPTSGG SSWKLSSFPE  900
PLSINVATFE KPLRKLTFAH LLEATNGFSA ESLIGSGGFG EVYKAKLKDG CVVAIKKLIH  960
VTGQGDREFM AEMETIGKIK HRNLVQLLGY CKVGEERLLV YEYMRWGSLE AVLHERAKGG 1020
GSKLDWAARK KIAIGSARGL AFLHHSCIPH IIHRDMKSSN ILLDENFEAR VSDFGMARLV 1080
NALDTHLTVS TLAGTPGYVP PEYYQSFRCT AKGDVYSYGV ILLELLSGKR PIDSSEFGDD 1140
SNLVGWSKML YKEKRINEIL DPDLIVQTSS ESELLQYLRI AFECLDERPY RRPTMIQVMA 1200
MFKELQVDTF NDMLDSFSLR DNVIDEA                                    1227

SEQ ID NO: 102         moltype = DNA   length = 223
FEATURE                Location/Qualifiers
source                 1..223
                       mol_type = other DNA
                       organism = Glycine max
SEQUENCE: 102
attcctcaca ttatacacag ggacatgaag tccagcaata ttcttcttga tgaaaattt   60
gaggccagag tttctgattt tggcatggcg agattggtta atgccctcga cactcatctc  120
actgttagcc ttgccggaac acctggttat gtaccccctg agtactacca gagttttaga  180
tgtacagcaa aaggggatgt ctatagctat ggtgtcatac tgc                    223

SEQ ID NO: 103         moltype = DNA   length = 143
FEATURE                Location/Qualifiers
source                 1..143
                       mol_type = other DNA
                       organism = Glycine max
SEQUENCE: 103
ttcttcttga tgaaaattt gaggccagag tttctgattt tggcatggcg agattggtta   60
atgccctcga cactcatctc actgttagcc ttgccggaac acctggttat gtaccccctg  120
agtactacca gagttttaga tgt                                          143

SEQ ID NO: 104         moltype = DNA   length = 103
FEATURE                Location/Qualifiers
source                 1..103
                       mol_type = other DNA
                       organism = Glycine max
SEQUENCE: 104
gaggccagag tttctgattt tggcatggcg agattggtta atgccctcga cactcatctc   60
actgttagcc ttgccggaac acctggttat gtaccccctg agt                    103
```

```
SEQ ID NO: 105            moltype = DNA   length = 63
FEATURE                   Location/Qualifiers
source                    1..63
                          mol_type = other DNA
                          organism = Glycine max
SEQUENCE: 105
tggcatggcg agattggtta atgccctcga cactcatctc actgttagcc ttgccggaac    60
acc                                                                  63

SEQ ID NO: 106            moltype = DNA   length = 48
FEATURE                   Location/Qualifiers
source                    1..48
                          mol_type = other DNA
                          organism = Glycine max
SEQUENCE: 106
actcatctca ctgttagcct tgccggaaca cctggttatg tacccct                  48

SEQ ID NO: 107            moltype = AA    length = 75
FEATURE                   Location/Qualifiers
source                    1..75
                          mol_type = protein
                          organism = Glycine max
SEQUENCE: 107
IPHIIHRDMK SSNILLDENF EARVSDFGMA RLVNALDTHL TVSTLAGTPG YVPPEYYQSF    60
RCTAKGDVYS YGVIL                                                    75

SEQ ID NO: 108            moltype = AA    length = 48
FEATURE                   Location/Qualifiers
source                    1..48
                          mol_type = protein
                          organism = Glycine max
SEQUENCE: 108
LLDENFEARV SDFGMARLVN ALDTHLTVST LAGTPGYVPP EYYQSFRC                 48

SEQ ID NO: 109            moltype = AA    length = 35
FEATURE                   Location/Qualifiers
source                    1..35
                          mol_type = protein
                          organism = Glycine max
SEQUENCE: 109
EARVSDFGMA RLVNALDTHL TVSTLAGTPG YVPPE                              35

SEQ ID NO: 110            moltype = AA    length = 21
FEATURE                   Location/Qualifiers
source                    1..21
                          mol_type = protein
                          organism = Glycine max
SEQUENCE: 110
GMARLVNALD THLTVSTLAG T                                             21

SEQ ID NO: 111            moltype = AA    length = 17
FEATURE                   Location/Qualifiers
source                    1..17
                          mol_type = protein
                          organism = Glycine max
SEQUENCE: 111
THLTVSTLAG TPGYVPP                                                  17

SEQ ID NO: 112            moltype = DNA   length = 4088
FEATURE                   Location/Qualifiers
source                    1..4088
                          mol_type = genomic DNA
                          organism = Glycine max
SEQUENCE: 112
atgagagtga aaaaggtga aaaatgaaa agagagaaag catacctag gaggaagatg       60
tcatggtcag caagaagagt agtgaggttc cttgtgactg ccttattcat cataaccgca   120
gcagaagcaa caaactctga tgcgcttcta ttgatacact tcaagcactt acacgtttcc   180
tccgatccct tcaactttct ctccgactgg gacccgcacg cgccatctcc atgcgcgtgg   240
cgtgctatca cctgctcctc cctcctccgg cgacgtcacct ccatcgacct cggcggcgcc   300
tccctctccg gcaccctctt cctcccatt ctcacgtccc ttccctctct tcaaaaccta   360
atcctccgtg gcaactcctt ctcctctttc aacctcaccg tttctccact ttgcactctc   420
caaacactcg acctctctca caacaacttc tccggcaagt ttcccttcgc agactttgct   480
ccctgtaacc gcctcagcta cctcaacctc tctaataacc tcatcaccgc tgggcttgtg   540
cctgggcctg ggccctggcc cgagctggcc caacttgact tgtccagaaa ccgcgtctcc   600
gacgtggaac ttctcgtctc cgctctcgga agctcaactc tcgtttact taacttctcc   660
gacaacaaac taacgggtca actcagcgaa acgtcgtttt cgaagagtgc gaacctctca   720
tatttggacc tctcttataa cgttctctcc gggaaggttc gtcgaggct tctaaacgac   780
gccgttcggg tcctcgattt ctcgttcaac aatttctcgg aatttgactt cggtttcggt   840
tcgtgcaaga atctagttcg gttgagtttc tcgcacaatg caatctcttc gaacgagttt   900
```

-continued

```
ccgcgcgggt tgagcaactg caacaatctt gaagttctag atctttctca caatgagttc    960
gccatggaga ttccatcaga aattcttgtc agtttgaaga gtttgaagtc tctgtttctc   1020
gcacacaaca agttttccgg cgaaattccg agtgagcttg gaggcctttg tgaaactctt   1080
gttgaacttg atctctccga gaacaagctt tctggttcgt tgccttttgag tttcactcag  1140
tgttcttctc tgcagagtct taacctcgcg aggaattttc tctctgggaa cttgcttgtt   1200
tccgtggtga gcaagcttgg gagtctaaag tatctaaacg cagcgtttaa taacatgacg   1260
ggaccggttc cgttgtcgtc gcttgttaac ttgaaagaac ttcgggttct tgacctaagc   1320
tcgaaccggt tcagcggcaa tgttccatcg ttattttgtc cttcggagtt ggagaagttg   1380
atcctcgctg gcaattacct ttcagggact gtaccgtcgc agctcggtga gtgtaagac    1440
ttgaaaacta ttgatttcag ctttaacagt ttgaacggtt cgataccgtg ggaggtgtgg   1500
tctttgccta atttaactga tttgattatg tgggctaata aactcaacgg agaaatcccc   1560
gaggggattt gtgttgaggg agggaacttg gagactttga ttttgaacaa taatctaatt   1620
tcggggtcca ttccgaagtc gattgcgaat tgcaccaaca tgatatgggt gtcgttggcg   1680
agcaaccggt taactgggca gataccggct gggattgggt atttgaacgc attggcgatt   1740
cttcagctgg gcaataactc gttgagtggg agggttccac cggagatagg cgagtgcagg   1800
agattgatat ggttggattt gaatagtaat aacctaactg gggatatccc tttccagctt   1860
gctgatcagg ccgggtttgt tatccccgggg agggtttcgg ggaagcagtt tgcgtttgtg   1920
aggaatgagg gtgggactag ttgcagggt gctggtgggt tgttgagtt tgaggatatt   1980
aggacagaga ggcttgaagg ttttcccatg gtgcattcct gcccgttgac gcggatttac   2040
tccggtagga ccgtgtatac ttttgcttcc aatgggagca tgatctacct tgacctttcc   2100
tacaacttgt tgtctgggag cattcctgag aatttgggtg agatgcctta tttgcaggtg   2160
ttgaatttgg ggcacaatag gtgattgggg aacattccaa ataggtttgg tggtttgaaa   2220
gcaataggg tgcttgatct gtctcataat agtcttaatg ggtccatccc tgggggcgttg   2280
gagggtcttt cttttctcag tgaccttgat gtgtctaata ataatctcaa tgggtccatt   2340
ccttctggtg gtcagttaac tacttttcca gcttccagat atgagaacaa ctctggcctt   2400
tgtgggtgc ctttgccggc gtgtgggct tcaaagaatc actcggttgc tgttggggat    2460
tggaagaagc agcagcctgt tgtagctggg gtcgtcattg gtttgctttg cttcctcgtg   2520
tttgcacttg ggcttgtgtt ggctttgtac cgagtgagga aggcgcagag aaggaggag    2580
atgagggaaa agtatataga gagtcttcca acttctggga gcagtagttg gaagcttcc    2640
agctttcctg agccttttgag tatcaatgtt gccaccttg agaagcctct gcggaagctg   2700
acttttgcgc atcttcttga ggctactaac ggtttcagtg ctgagagttt gataggttct   2760
ggggggtttg gtgaggtgta caaagctaag ctgaaagatg gttgtgttgt tgctatcaag   2820
aagctcattc atgtgacggg tcaggagat agggagttca tggctgagat ggaaacaatt   2880
gggaagatta agcataggaa cctggttcag ctgctgggtt actgtaaaat tggagaggag   2940
aggctgcttg tgtatgagta catgaaatgg gaagtcttg aggctgtttt acatgagagg   3000
gcaaaagcag gagtttcaaa gcttgattgg gcagcaagga agaagattgc cataggggtca   3060
gcaagaggtc ttgcatttct tcaccatagt tgcattcctc acattataca ccgggacatg   3120
aagtccagca atattcttct tgatgaaaat tttgaggcca gagtttctga ttttggcatg   3180
gcgagattgg ttaatgccct tgacactcat ctcacagtca gcacgcttgc cggaaccgtg   3240
ggctatgtac ccccagagta ctaccagagt tttagatgta cagcaaaagg ggatgtctat   3300
agctatggtg tcatattgct agagcttcta tcaggaaaga gaccaattga ctcttctgag   3360
tttggtgatg acagcaatct tgttggatgg tctaagaagc tttacaaaga gaacgaatt    3420
aacgaaataa ttgatcctga tttaattgtg cagacatcta gtgaaagtga actattacaa   3480
tattttgagaa ttgcttttga atgtctggat gagagaccat accggcggcc aactatgata   3540
caagtgatgg ctatgtttaa agagcttcag gttgacacag ataatgatat gcttgatagc   3600
ttctctctca gagacaatgt tattgatgaa gcttgagaag aggatctttt ctacaagact   3660
caaagccctt tgacagttga gaaggaaata aagaggttct caaaatttgg agtgttgctg   3720
actaagttga caattctggt gacactgatc tatatctatc ctatctgaaa ttggaggagg   3780
gttcttcac ctttttttga tgtatataag acacttaatg agaccaagag atcaaaggca   3840
atcatggatt gaattgaagg ttgagactta aggttataga cagttttgta tgcttctttt   3900
ttgccgatct agtgttcagc cacttgaaat tggtagatat atatgtattt ttcctatga   3960
cttcacacac tccatcatca atgccacttt tgctgatcac ttcaatattt tgtttgccat   4020
ttccattggg ttctgatact accacagttt tgctcatttg gtgttttggt tcatatttca   4080
actgtcaa                                                           4088
```

SEQ ID NO: 113        moltype = DNA   length = 3636
FEATURE                Location/Qualifiers
source                 1..3636
                        mol_type = other DNA
                        organism = Glycine max
SEQUENCE: 113

```
atgagagtga aaaaggtga aaaatgaaa agagagaaag catacctttag gaggaagatg     60
tcatggtcag caagaagagt agtgaggttc cttgtgactg ccttattcat cataaccgca   120
gcagaagcaa caaactctga tgcgcttcta ttgatacact tcaagcactt acacgtttcc   180
tccgatccct tcaactttct ctccgactgg gacccgcacg cgccatctcc atgcgcgtgg   240
cgtgctatca cctgctcctc ctcctccggc gacgtcacct ccatcgacct cggcggcgcc   300
tccctctccg gcaccctctt cctccccatt ctcacgtccc ttccctctct tcaaaaccta   360
atcctccgtg gcaactcctt ctcctctttc aacctcacgc tttctccact ttgcactctt   420
caaacactcg acctctctca caacaacttc tccggcaagt ttcccttcgc agactttgct   480
ccctgtaacc gctcagcta cctcaactc tctaataacc tcatcaccgc tgggcttgtg   540
cctgggcctg ggccctggcc cgagctggcc caacttgact tgtccagaaa ccgcgtctcc   600
gacgtggaac ttctcgtctc cgctctcgga agctcaactc tcgttttact taacttctcc   660
gacaacaaac taacgggtca actcagcgaa acgtcgttt cgaagagtgc gaacctctca   720
tatttgacac tctcttataa cgttctctcc gggaaggttc cgtcgaggct tctaaacgac   780
gccgttcggg tcctcgattt ctcgttcaac aatttctcgg aatttgactt cggttttcggt   840
tcgtgcaaga atcagttcg gttgagtttc tcgcacaatg caatctcttc gaacgagttt   900
ccgcgcgggt tgagcaactg caacaatctt gaagttctag atctttctca caatgagttc   960
gccatggaga ttccatcaga aattcttgtc agtttgaaga gtttgaagtc tctgtttctc  1020
gcacacaaca agttttccgg cgaaattccg agtgagcttg gaggcctttg tgaaactctt  1080
```

```
gttgaacttg atctctccga gaacaagctt tctggttcgt tgcctttgag tttcactcag   1140
tgttcttctc tgcagagtct taacctcgcg aggaattttc tctctgggaa cttgcttgtt   1200
tccgtggtga gcaagcttgg gagtctaaag tatctaaacg cagcgtttaa taacatgacg   1260
ggaccggttc cgttgtcgtc gcttgttaac ttgaaagaac ttcgggttct tgacctaagc   1320
tcgaaccggt tcagcggcaa tgttccatcg ttatttgtc cttcggagtt ggagaagttg   1380
atcctcgctg gcaattacct ttcagggact gtaccgtcgc agctcggtga gtgtaagaac   1440
ttgaaaacta ttgatttcag cttaacagt tgaacggtt cgataccgtg ggaggtgtgg   1500
tctttgccta atttaactga tttgattatg tgggctaata aactcaacgg agaaatcccc   1560
gaggggattt gtgttgaggg agggaacttg gagacttga ttttgaacaa taatctaatt   1620
tcggggtcca ttccgaagtc gattgcgaat tgcaccaaca tgatatgggt gtcgttggcg   1680
agcaaccggt taactgggca gataccggct gggattggga atttgaacgc attggcgatt   1740
cttcagctgg gcaataactc gttgagtggg agggttccac cggagatagg cgagtgcagg   1800
agattgatat ggttggattt gaatagtaat aaccaactg gggatatccc tttccagctt   1860
gctgatcagg ccgggtttgt tatcccgggg agggttcgg ggaagcagtt tgcgtttgtg   1920
aggaatgagg gtgggactag ttgcagggg gctggtggg tggttgagtt tgaggatatt   1980
aggacagaga ggcttgaagg tttttcccat gtgcattcct gcccgttgac gcggatttac   2040
tccggtagga ccgtgtatac ttttgcttcc aatgggagca tgatctacct tgaccttcc   2100
tacaacttgt tgtctgggag cattcctgag aatttgggtg aggtgccta tttgcaggtg   2160
ttgaatttgg ggcacaatag gttgagtggg aacattccag ataggtttgg tggtttgaaa   2220
gcaatagggg tgcttgatct gtctcataat agtcttaatg ggtccatccc tggggcgttg   2280
gagggtcttt cttttctcag tgaccttgat gtgtctaata ataatctcaa tgggtccatt   2340
ccttcggtg gtcagttaac tacttttcca gcttccagat atgagaacaa ctctcggcct   2400
tgtggggtgc ctttgccggc gtgtgggct tcaaagaatc actcggttgc tgttggggat   2460
tggaagaagc agcagcctgt tgtagctggg gtcgtcattg gttgctttg cttcctcgtg   2520
tttgcacttg gcttgtgtt ggctttgtac cgagtgagga aggcgcagag gaaggaggag   2580
atgagggaaa agtatataga gagtcttcca acttctgggg actagttg gaagctttcc   2640
agctttcctg agcctttgag tatcaatgtt gccacctttg agaagcctct gcggaagctg   2700
acttttgcgc atcttcttga ggctactaac ggtttcagtg ctgagagttt gatagttct   2760
gggggggtttg tgaggtgta caaagctaag ctgaaagatg gttgtgttgt tgctatcaag   2820
aagtcattc atgtgacggg tcagggagat agggaagttca gctctgagat ggaaacaatt   2880
gggaagatta agcataggaa cctggttcag ctgctgggtt actgtaaaat tggagaggag   2940
aggctgcttg tgtatgagta catgaaatgg ggaagtcttg aggctgtttt acatgagagg   3000
gcaaaagcag gagtttcaaa gcttgattgg gcagcaagga agaagattgc catagggtca   3060
gcaagaggtc ttgcatttct tcaccatagt tgcattcctc acattataca ccgggcaggg   3120
aagtccagca atattcttct tgatgaaaat tttgaggcca gagtttctga ttttggcatg   3180
gcgagattgg ttaatgccct tgacactcat ctcacagtca gcacgcttgc cggaacaccg   3240
ggctatgtac ccccagagta ctaccagagt tttagatgta cagcaaaagg ggatgtctat   3300
agctatggtg tcatattgct agagcttcta tcaggaaaga gaccaattga ctcttctgag   3360
tttggtgatg acaacaatct tgttggatgg tctaagaagc tttacaaaga gaaacgaatt   3420
aacgaaataa ttgatcctga tttaattgtg cagacatcta gtgaaagtga actattacaa   3480
tatttgaaga ttgcttttga atgtctggat gagagaccat accggcggcc aactatgata   3540
caagtgatgg ctatgtttaa agagcttcag gttgacacag ataatgatat gcttgatagc   3600
ttctctctca gagacaatgt tattgatgaa gcttga                             3636

SEQ ID NO: 114         moltype = AA  length = 1211
FEATURE                Location/Qualifiers
source                 1..1211
                       mol_type = protein
                       organism = Glycine max
SEQUENCE: 114
MRVKKGEKMK REKAYLRRKM SWSARRVVRF LVTALFIITA AEATNSDALL LIHFKHLHVS     60
SDPFNFLSDW DPHAPSPCAW RAITCSSSSG DVTSIDLGGA SLSGTLFLPI LTSLPSLQNL    120
ILRGNSFSSF NLTVSPLCTL QTLDLSHNNF SGKFPFADFA PCNRLSYLNL SNNLITAGLV    180
PGPGPWPELA QLDLSRNRVS DVELLVSALG SSTLVLLNFS DNKLTGQLSE TLVSKSANLS    240
YLDLSYNVLS GKVPSRLLND AVRVLDFSFN NFSEFDFGPG NVCNLVRLSF SHNAISSNEF    300
PRGLSNCNNL EVLDLSHNEF AMEIPSEILV SLKSLKSLFL AHNKFSGEIP SELGGLCETL    360
VELDLSENKL SGSLPLSFTQ CSSLQSLNLA RNFLSGNLLV SVVSKLGSLK YLNAAFNNMT    420
GPVPLSSLVN LKELRVLDLS SNRFSGNVPS LFCPSELEKL ILAGNYLSGT VPSQLGECKN    480
LKTIDFSFNS LNGSIPWEVW SLPNLTDLIM WANKLNGEIP EGICVEGGNL ETLILNNNLI    540
SGSIPKSIAN CTNMIWVSLA SNRLTGQIPA GIGNLNALAI LQLGNNSLSG RVPPEIGECR    600
RLIWLDLNSN NLTGDIPFQL ADQAGFVIPG RVSGKQFAFV RNEGGTSCRG AGGLVEFEDI    660
RTERLEGFPM VHSCPLTRIY SGRTVYTFAS NGSMIYLDLS YNLLSGSIPE NLGEMAYLQV    720
LNLGHNRLSG NIPDRFGGLK AIGVLDLSHN SLNGSIPGAL EGLSFLSDLD VSNNNLNGSI    780
PSGGQLTTFP ASRYENNSGL CGVPLPACGA SKNHSVAVGD WKKQQPVVAG VVIGLLCFLV    840
FALGLVLALY RVRKAQRKEE MREKYIESLP TSGSSSWKLS SFPEPLSINV ATFEKPLRKL    900
TFAHLLEATN GFSAESLIGS GGFGEVYKAK LKDGCVVAIK KLIHVTGQGD REFMAEMETI    960
GKIKHRNLVQ LLGYCKIGEE RLLVYEYMKW GSLEAVLHER AKAGVSKLDW AARKKIAIGS   1020
ARGLAFLHHS CIPHIIHRDM KSSNILLDEN FEARVSDFGM ARLVNALDTH LTVSTLAGTP   1080
GYVPPEYYQS FRCTAKGDVY SYGVILLELL SGKRPIDSSE FGDDSNLVGW SKKLYKEKRI   1140
NEIIDPDLIV QTSSESELLQ YLRIAFECLD ERPYRRPTMI QVMAMFKELQ VDTDNDMLDS   1200
FSLRDNVIDE A                                                       1211

SEQ ID NO: 115         moltype = DNA  length = 144
FEATURE                Location/Qualifiers
source                 1..144
                       mol_type = other DNA
                       organism = Glycine max
SEQUENCE: 115
aattttgagg ccagagtttc tgattttggc atggcgagat tggttaatgc ccttgacact     60
```

```
catctcacag tcagcacgct tgccggaaca ccgggctatg taccccccaga gtactaccag    120
agttttagat gtacagcaaa aggg                                            144

SEQ ID NO: 116           moltype = DNA  length = 103
FEATURE                  Location/Qualifiers
source                   1..103
                         mol_type = other DNA
                         organism = Glycine max
SEQUENCE: 116
gattttggca tggcgagatt ggttaatgcc cttgacactc atctcacagt cagcacgctt     60
gccggaacac cgggctatgt accccccagag tactaccaga gtt                     103

SEQ ID NO: 117           moltype = DNA  length = 63
FEATURE                  Location/Qualifiers
source                   1..63
                         mol_type = other DNA
                         organism = Glycine max
SEQUENCE: 117
ggttaatgcc cttgacactc atctcacagt cagcacgctt gccggaacac cgggctatgt     60
acc                                                                   63

SEQ ID NO: 118           moltype = DNA  length = 42
FEATURE                  Location/Qualifiers
source                   1..42
                         mol_type = other DNA
                         organism = Glycine max
SEQUENCE: 118
cactcatctc acagtcagca cgcttgccgg aacaccgggc ta                        42

SEQ ID NO: 119           moltype = AA  length = 47
FEATURE                  Location/Qualifiers
source                   1..47
                         mol_type = protein
                         organism = Glycine max
SEQUENCE: 119
FEARVSDFGM ARLVNALDTH LTVSTLAGTP GYVPPEYYQS FRCTAKG                   47

SEQ ID NO: 120           moltype = AA  length = 34
FEATURE                  Location/Qualifiers
source                   1..34
                         mol_type = protein
                         organism = Glycine max
SEQUENCE: 120
DFGMARLVNA LDTHLTVSTL AGTPGYVPPE YYQS                                 34

SEQ ID NO: 121           moltype = AA  length = 20
FEATURE                  Location/Qualifiers
source                   1..20
                         mol_type = protein
                         organism = Glycine max
SEQUENCE: 121
VNALDTHLTV STLAGTPGYV                                                 20

SEQ ID NO: 122           moltype = AA  length = 13
FEATURE                  Location/Qualifiers
source                   1..13
                         mol_type = protein
                         organism = Glycine max
SEQUENCE: 122
THLTVSTLAG TPG                                                        13

SEQ ID NO: 123           moltype = DNA  length = 4244
FEATURE                  Location/Qualifiers
source                   1..4244
                         mol_type = genomic DNA
                         organism = Glycine max
SEQUENCE: 123
gtagatacaa gtatggagga gagtggaaat aggaaaaaat agcttagaga gatttattta     60
cgaacaggaa gagtcacatg gcatgtgtcc agtcttccac atgataaata cccttcttac    120
cttccttact aggactttttg actctctctc tctctatcta tggtagtagt agtagtagta   180
ttcattcatt ctctctaatg gcagagctca caccctaaac acaaaccaga gcctctgaga   240
gaaacaacca caaactctcc cttaatcttg tcggttccca tatctgctga aaatgaaagc   300
tctgtacaga agctctctct tgctcttgct cttgctcttc atctccgtgt gttttgcatc   360
ttcttcttct ccggtcactc agcaactcct aagcttcaaa aactctctcc cgaacccatc   420
cctgctcccc aactggctcc ctaaccaaag cccgtgcaca ttcagcggca tcagctgcaa   480
cgacacagag ctcacatcca tagacctcag ctccgtccct ctcagcacta acctaaccgt   540
catcgccagc ttcctcctta gcctggacca cctccagtca ctcctccttaa aatccaccaa   600
cctctccggt ccgccgccaa tgcctcctct ctcccactcc cagtgctcct cctcattaac   660
ctccctagat ctctccccaaa actccctctc tgcctcccctc aacgacatgt cgtttctcgc   720
```

```
ctcctgctcc aacctccaat ccctcaacct ctcctccaac ctcctccaat tcggcccccc   780
gccccactgg aagctccacc acctccgctt cgccgacttc tcttacaaca agatttccgg   840
ccccggcgtc gtttcttggc ttctcaaccc cgtcatcgaa ctcctctctc tcaaaggcaa   900
caaagtcacc ggcgaaaccg acttctccgg ctcaatttct ctccagtatt tagaccttc   960
ttccaacaac ttttctgtta cgcttcctac tttcggcgag tgttcttcgc ttgagtattt  1020
ggacctctcc gctaacaagt acttgggcga cattgcacgc actctctccc cttgcaagag  1080
cctcgtttac cttaacgtct ccagcaacca gttctccggt ccggttcctt cccttccctc  1140
cggttcgcta cagtttgtgt accttgctgc aaaccacttc cacggccaga ttcctctctc  1200
cctcgccgac ctctgctcca ctctcctcca gctcgatctc tcctccaaca atctcaccgg  1260
cgctcttccc ggcgcgttcg gcgcgtgcac ttctcttcaa tcccttgaca tctccagcca  1320
cctcttcgcc ggcgcgttgc cgatgtcggt tctcacgcaa atgaccagcc tgaaagagct  1380
cgcggttgcg ttcaacggct tcctcggtgc tctcccggag tctctgtcga agctctccgc  1440
tctggagttg ctggatctga gctccaacaa ctttagcggc tcaatcccg cctcgctgtg  1500
cggcggcggt gacgctggga ttaataataa tctgaaggaa ctttatctgc agaataaccg  1560
gttcacgggt tttattccgc ccacgctcag caactgttca aacctcgttg ctttggattt  1620
gagtttcaac ttcctcacgg ggactattcc tccgagccta gggtctcttt cgaatctcaa  1680
agacttcatc atctggctca accagctcca cggggagata ccgcaggagc tcatgtatct  1740
taaaagcctc gagaatttga tcctgggattt caacgacttg actgggaaca ttccctctgg  1800
cctcgttaac tgcaccaagt tgaactggat ctccctctcc aacaacaggc tcagcggcga  1860
gattccgccg tggattggga agctttctaa tctcgccata ctcaagctca gcaataactc  1920
tttctccggc cggattccgc cggagctcgg cgactgtact agtttaatat ggttggatct  1980
gaatacaaat atgctcaccg ggcccattcc gccggagctg ttcaagcagt cggggaagat  2040
cgccgtgaat ttcatcagtg ggaagacgta tgtgtatata aagaacgatg ggagcaagga  2100
gtgccatggt gcgggaact tgcttgagtt tgcgggatc agtcagcagc agctgaacag  2160
gatttcgacg aggaacccct gcaatttcac taggggttat ggaggtaagt tgcagccaac  2220
gtttaaccat aatggttcta tgatattttt ggatatctca cacacagtct gtcagggag  2280
tattcccaag gagattgggg ccatgtacta tttgtacatt ctcaatttgg gtcacaataa  2340
tgtgtctggg agcattcctc aagagcttgg gaagatgaag aatctcaaca ttcttgatct  2400
gtcgaataat agactggagg gccaaattcc gcagagcctc acgggctttt ctttgctcac  2460
tgagattgac ttgtccaaca acttgcttac cgggacgatt cctgagtcgg gtcaatttga  2520
tactttccct gcggcgaagt ttcagaacaa ctctggtcta tgtggagttc ctctgggtcc  2580
gtgtggttcg gagccggcaa acaatggaaa tgcgcaacat atgaagtctc acaggaggca  2640
ggcttctctg gcgggagtg tggccatggg gttgttgttt tccctctttt gcgtctttgg  2700
tttgatcatt attgccattg agaccaggaa gaggaggaag gagaaggagg ctgctcttga  2760
agcctatggt gatggtaatt cccattcggg tccggccaat gtgagctgga agcacaccgg  2820
tactcgggaa gctcttagca taaaccttgc aacatttgag aagccgctcc ggaagcttac  2880
ttttgcggac cttcttgacg ctaccaatgg ttttcacaac gacagtctca ttggctctgg  2940
cgggtttggg gatgtgtaca aggctcagtt gaaggatgga agtgttgtgg ctatcaagaa  3000
gctgattcat gttagcggac aaggggacag ggaattcacc gctgaaatgg agactattgg  3060
gaaaatcaag cacaggaacc ttgttcccct gttgggatac tgcaaggtag gggaagagag  3120
gctcttggtt tatgagtaca tgaaatatgg aagtttagag gatgttctac atgatcagaa  3180
gaaagctggg atcaagctga actgggccat taggcggaaa attgctattg gagctgctag  3240
gggattggct tttcttcacc acaattgtat ccccacatc attcataga atatgaagtc  3300
gagcaatgtg ttacttgatg aaaacctgga agccagagtc tctgattttg gaatggctag  3360
gcttatgagt gctatggata cacatttgag tgtgagcaca ttggctggca caccggggta  3420
tgttcctccc gagtactatc agagcttcag atgctccaca aaaggtgatg tctacagtta  3480
tggtgtggtt ttgttggagc tgctaactgg gaaaaggcca acggactcgg ctgatttttgg  3540
agataataat cttgttggat gggttaaaca acatgccaag ctgaaaatca gtgatattt  3600
tgacccggag ctcatgaagg aagacccaa tctggagatg gagctttttgc agcacttgaa  3660
gattgcggtt tcctgtttgg atgatcgacc gtggaggcgt ccgacgatga ttcaagtgat  3720
ggcaatgttc aaggagattc aggcgggatc cgggattgat tctcagtcaa ccatagccaa  3780
tgacgaggaa ggtttcaatg cagttgaaat ggtggagatg agcattaaag aagcccctga  3840
attgagcaag cattaggcat taaagtgtcg tgtggattct ttgggaaaca gacaagaaga  3900
gaggaggaga tgacggattc agctcccctc agtttttttcc ttctttgccg cttcaaatta  3960
tttcagacat aagggaaaac ggttaaaagg ggaatgaatg cttttgatgt atgtattctt  4020
gttatttttat acataaaaaa aagttgttta acttgtatat aaacagcttc agttgttacc  4080
atctgtgttt tcctagaatt ttcaaagtac ttttctcatt caaatataat cctgaaaagg  4140
ttctctgttc aatctgcgac cccagtgatg gcaactaagt ggatcaacag caacttttgc  4200
tccgatttgc gatataattt gtcaaaacat gcctctaaaa tcac                   4244

SEQ ID NO: 124       moltype = DNA   length = 3564
FEATURE              Location/Qualifiers
source               1..3564
                     mol_type = other DNA
                     organism = Glycine max
SEQUENCE: 124
atgaaagctc tgtacagaag ctctctcttg tccttgctct tgctcttcat ctccgtgtgt    60
tttgcatctt cttcttctcc ggtcactcag caactcctaa gcttcaaaaa ctctctcccg   120
aacccatccc tgctccccaa ctggctccct aaccaaagcc cgtcacatt cagcggcatc   180
agctgcaacg acacagagct cacatcccata gacctcagct ccgtccctct cagcactaac   240
ctaaccgtca tcgccagctt cctccttagc ctggaccacc tccagtcact ctccttaaaa   300
tccaccaacc tctccggtcc cgccgccatg cctcctctct cccactccca gtgctcctcc   360
tcattaacct ccctagatct ctcccaaaac tccctctctg cctccctcaa cgacatgtcg   420
tttctcgcct cctgctcaa cctccaatcc ctcaacctc tcaaccct cctccaattc   480
ggccccccgc cccactggaa gctccaccac ctccgcttcg ccgacttctc ttacaacaag   540
atttccggcc ccggcgtcgt ttcttggctt ctcaacccg tcatcgaact cctctctctc   600
aaaggcaaca aagtcaccgg cgaaaccgac ttctccggct caatttctct ccagtattta   660
gaccttcttt ccaacaactt ttctgttacg cttcctactt cggcgagtg ttcttcgctt   720
gagtatttgg acctctccgc taacaagtac ttgggcgaca ttgcacgcac tctctcccct   780
```

```
tgcaagagcc tcgtttacct taacgtctcc agcaaccagt tctccggtcc ggttccttcc    840
cttccctccg gttcgctaca gtttgtgtac cttgctgcaa accacttcca cggccagatt    900
cctctctccc tcgccgacct ctgctccact ctcctccagc tcgatctctc ctccaacaat    960
ctcaccggcc tcttcccgg cgcgttcggc gcgtgcactt ctcttcaatc ccttgacatc    1020
tccagcaacc tcttcgcgg cgcgttgccg atgtcggttc tcacgcaaat gaccagcctg    1080
aaagagctcg cggttgcgtt caacggcttc tccggtgctc tcccggagtc tctgtcgaag    1140
ctctccgctc tggagttgct ggatctgagc tccaacaact ttagcggctc aatccccgcc    1200
tcgctgtgcg gcggcggtga cgctgggatt aataataatc tgaaggaact ttatctgcag    1260
aataaccggt tcacgggttt tattccgccc acgctcagca actgttcaaa cctcgttgct    1320
ttggatttga gtttcaactt cctcacgggg actattcctc cgagcctagg gtctcttttcg    1380
aatctcaaag acttcatcat ctggctcaac cagctccacg gggagatacc gcaggagctc    1440
atgtatctta aaagcctcga gaatttgatc ctggattttca acgacttgac tgggaacatt    1500
ccctctggcc tcgttaactg caccaagttg aactggatct ccctctccaa caacaggctg    1560
agcggcgaga ttccgccgtg gattgggaag ttttctaatc tcgccatact caagctcagc    1620
aataactctt tctccggccg gattccgccg gagctcggcg actgtactag tttaatatgg    1680
ttggatctga atacaaatat gctcaccggg cccattccgc cggagctgtt caagcagtcg    1740
gggaagatcg ccgtgaattt catcagtggg aagacgtatg tgtatataaa gaacgatggg    1800
agcaaggagt gccatggtgc ggggaacttg cttgagtttg cgggggatcag tcagcagcag    1860
ctgaacagga tttcgacgag gaaccccttg aatttcacta gggtttatgg aggtaagttg    1920
cagccaacgt ttaaccataa tggttctatg atatttttgg atatctcgca caacatgttg    1980
tcagggagta ttcccaagga gattgggccc atgtactatt tgtacattct caatttgggt    2040
cacaataatg tgtctgggga cattcctcaa gagcttggga agatgaagaa tctcaacatt    2100
cttgatctgt cgaataatag actggagggc caaattccgc agagcctcac ggggcttttct    2160
ttgctcactg agattgactt gtccaacaac ttgcttaccg ggacgattcc tgagtcgggt    2220
caatttgata ctttccctgc ggcgaagttt cagaacaact ctggtctatg tggagttcct    2280
ctgggtccgt gtggttcgga gccgccaaac aatggaaatg cgcaacatat gaagtctcac    2340
aggaggcagg cttctctggc ggggagtgtg gccatgggga tgttgttttc cctcttttgc    2400
gtctttggtt tgatcattat tgccattgag accaggaaga ggaggaagaa gaaggaggct    2460
gctcttgaag cctatggtga tggtaattcc cattcgggtc cggccaatgt gagctggaag    2520
cacaccagta ctcgggaagc tcttagcata aaccttgcaa catttgagaa gccgctccgg    2580
aagcttactt ttgcggacct tcttgacgct accaatggtt tcacaacga cagtctcatt    2640
ggctctggcg ggtttgggga tgtgtacaag gctcagttga aggatggaag tgttgtggct    2700
atcaagaagc tgattcatgt tagcggacaa ggggacaggg aattcaccgc tgaaatggag    2760
actattggga aaatcaagca caggaaccttc gttccctgt tggggatactg caaggtaggg    2820
gaagagtgc tcttggttta tgagtacatg aaatatggaa gtttagagga tgttctacat    2880
gatcagaaga agctgggat caagctgaac tgggccatta gcggaaaat tgctattgga    2940
gctgctaggg gattggcttt tcttcaccac aattgtatcc cccacatcat tcatagagat    3000
atgaagtcga gcaatgtgtt acttgatgaa aacctggaag ccagagtctc tgattttgga    3060
atggctaggc ttatgagtgc tatggataca catttgagttg tgagcacatt ggctggcaca    3120
ccgggggtatg ttcctcccga gtactatcag agcttcagat gctccacaaa aggtgatgtc    3180
tacagttatg gtgtggtttt gttggagctg ctaactggga aaaggccaac ggactcggct    3240
gattttggag ataataatct tgttggatgg gttaaacaac atgccaagct gaaaatcagt    3300
gatattttg acccggaatc catgaaggaa gaccccaatc ttgagatgga gcttttgcag    3360
cacttgaaga ttgcggtttc ctgtttggat gatcgaccgt ggaggcgtcc gacgatgatt    3420
caagtgatgg caatgttcaa ggagattcag gcgggatccg ggattgattc tcagtcaacc    3480
atagccaatg acgaggaagg tttcaatgca gttgaaatgg tggagatgag cattaaagaa    3540
gccccctgaat tgagcaagca ttag                                         3564

SEQ ID NO: 125        moltype = AA   length = 1187
FEATURE               Location/Qualifiers
source                1..1187
                      mol_type = protein
                      organism = Glycine max
SEQUENCE: 125
MKALYRSSLL LLLLLFISVC FASSSSPVTQ QLLSFKNSLP NPSLLPNWLP NQSPCTFSGI     60
SCNDTELTSI DLSSVPLSTN LTVIASFLLS LDHLQSLSLK STNLSGPAAM PPLSHSQCSS    120
SLTSLDLSQN SLSASLNDMS FLASCSNLQS LNLSSNLLQF GPPPHWKLHH LRFADFSYNK    180
ISGPGVVSWL LNPVIELLSL KGNKVTGETD FSGSISLQYL DLSSNNFSVT LPTFGECSSL    240
EYLDLSANKY LGDIARTLSP CKSLVYLNVS SNQFSGPVPS LPSGSLQFVY LAANHPHGQI    300
PLSLADLCST LLQLDLSSNN LTGALPGAFG ACTSLQSLDI SSNLFAGALP MSVLTQMTSL    360
KELAVAFNGF LGALPESLSK LSALELLDLS SNNFSGSIPA SLCGGGDAGI NNNLKELYLQ    420
NNRFTGFIPP TLSNCSNLVA LDLSFNFLTG TIPPSLGSLS NLKDFIIWLN QLHGEIPQEL    480
MYLKSLENLI LDFNDLTGNI PSGLVNCTKL NWISLSNNRL SGEIPPWIGK LSNLAILKLS    540
NNSFSGRIPP ELGDCTSLIW LDLNTNMLTG PIPPELFKQS GKIAVNFISG KTYVYIKNDG    600
SKECHGAGNL LEFAGISQQQ LNRISTRNPC NFTRVYGGKL QPTFNHNGSM IFLDISHNML    660
SGSIPKEIGA MYYLYILNLG HNNVSGSIPQ ELGKMKNLNI LDLSNNRLEG QIPQSLTGLS    720
LLTEIDLSNN LLTGTIPESG QFDTFPAAKF QNNSGLCGVP LGPCGSEPAN NGNAQHMKSH    780
RRQASLAGSV AMGLLFSLFC VFGLIIIAIE TRKRRKKEA ALEAYGDGNS HSGPANVSWK    840
HTSTREALSI NLATFEKPLR KLTFADLLDA TNGFHNDSLI GSGGFGDVYK AQLKDGSVVA    900
IKKLIHVSGQ GDREFTAEME TIGKIKHRNL VPLLGYCKVG EERLLVYEYM KYGSLEDVLH    960
DQKKAGIKLN WAIRRKIAIG AARGLAFLHH NCIPHIIHRD MKSSNVLLDE NLEARVSDFG   1020
MARLMSAMDT HLSVSTLAGT PGYVPPEYYQ SFRCSTKGDV YSYGVVLLEL LTGKRPTDSA   1080
DFGDNNLVGW VKQHAKLKIS DIFDPELMKE DPNLEMELLQ HLKIAVSCLD DRPWRRPTMI   1140
QVMAMFKEIQ AGSGIDSQST IANDEEGFNA VEMVEMSIKE APELSKH                 1187

SEQ ID NO: 126        moltype = DNA   length = 223
FEATURE               Location/Qualifiers
source                1..223
                      mol_type = other DNA
```

```
                                organism = Glycine max
SEQUENCE: 126
agatatgaag tcgagcaatg tgttacttga tgaaaacctg gaagccagag tctctgattt    60
tggaatggct aggcttatga gtgctatgga tacacatttg agtgtgagca cattggctgg   120
cacaccgggg tatgttcctc ccgagtacta tcagagcttc agatgctcca caaaaggtga   180
tgtctacagt tatggtgtgg ttttgttgga gctgctaact ggg                     223

SEQ ID NO: 127          moltype = DNA   length = 143
FEATURE                 Location/Qualifiers
source                  1..143
                        mol_type = other DNA
                        organism = Glycine max
SEQUENCE: 127
gaagccagag tctctgattt tggaatggct aggcttatga gtgctatgga tacacatttg    60
agtgtgagca cattggctgg cacaccgggg tatgttcctc ccgagtacta tcagagcttc   120
agatgctcca caaaaggtga tgt                                           143

SEQ ID NO: 128          moltype = DNA   length = 103
FEATURE                 Location/Qualifiers
source                  1..103
                        mol_type = other DNA
                        organism = Glycine max
SEQUENCE: 128
tggaatggct aggcttatga gtgctatgga tacacatttg agtgtgagca cattggctgg    60
cacaccgggg tatgttcctc ccgagtacta tcagagcttc aga                     103

SEQ ID NO: 129          moltype = DNA   length = 63
FEATURE                 Location/Qualifiers
source                  1..63
                        mol_type = other DNA
                        organism = Glycine max
SEQUENCE: 129
gtgctatgga tacacatttg agtgtgagca cattggctgg cacaccgggg tatgttcctc    60
ccg                                                                  63

SEQ ID NO: 130          moltype = DNA   length = 39
FEATURE                 Location/Qualifiers
source                  1..39
                        mol_type = other DNA
                        organism = Glycine max
SEQUENCE: 130
cacatttgag tgtgagcaca ttggctggca caccggggt                           39

SEQ ID NO: 131          moltype = AA   length = 74
FEATURE                 Location/Qualifiers
source                  1..74
                        mol_type = protein
                        organism = Glycine max
SEQUENCE: 131
DMKSSNVLLD ENLEARVSDF GMARLMSAMD THLSVSTLAG TPGYVPPEYY QSFRCSTKGD    60
VYSYGVVLLE LLTG                                                      74

SEQ ID NO: 132          moltype = AA   length = 47
FEATURE                 Location/Qualifiers
source                  1..47
                        mol_type = protein
                        organism = Glycine max
SEQUENCE: 132
EARVSDFGMA RLMSAMDTHL SVSTLAGTPG YVPPEYYQSF RCSTKGD                  47

SEQ ID NO: 133          moltype = AA   length = 34
FEATURE                 Location/Qualifiers
source                  1..34
                        mol_type = protein
                        organism = Glycine max
SEQUENCE: 133
GMARLMSAMD THLSVSTLAG TPGYVPPEYY QSFR                                34

SEQ ID NO: 134          moltype = AA   length = 20
FEATURE                 Location/Qualifiers
source                  1..20
                        mol_type = protein
                        organism = Glycine max
SEQUENCE: 134
AMDTHLSVST LAGTPGYVPP                                                20

SEQ ID NO: 135          moltype = AA   length = 12
FEATURE                 Location/Qualifiers
source                  1..12
```

```
                         mol_type = protein
                         organism = Glycine max
SEQUENCE: 135
HLSVSTLAGT PG                                                          12

SEQ ID NO: 136           moltype = DNA   length = 23
FEATURE                  Location/Qualifiers
source                   1..23
                         mol_type = other DNA
                         organism = synthetic construct
SEQUENCE: 136
atgccctcga cactcatctc act                                              23

SEQ ID NO: 137           moltype = DNA   length = 23
FEATURE                  Location/Qualifiers
source                   1..23
                         mol_type = other DNA
                         organism = synthetic construct
SEQUENCE: 137
ggcaagcgtg ctgactgtga gat                                              23

SEQ ID NO: 138           moltype = DNA   length = 23
FEATURE                  Location/Qualifiers
source                   1..23
                         mol_type = other DNA
                         organism = synthetic construct
SEQUENCE: 138
agtgtgagca cactggcagg cac                                              23

SEQ ID NO: 139           moltype = DNA   length = 23
FEATURE                  Location/Qualifiers
source                   1..23
                         mol_type = other DNA
                         organism = synthetic construct
SEQUENCE: 139
agtgtgagca cattggctgg cac                                              23

SEQ ID NO: 140           moltype = DNA   length = 4395
FEATURE                  Location/Qualifiers
source                   1..4395
                         mol_type = other DNA
                         organism = synthetic construct
SEQUENCE: 140
gactttgac  tctctctctc tctctctcta cagtagtagt agtagtattc attcatattc      60
atacttgata tcatgtcaca cacacactat ctctctctct ctctctctaa tggcagagct     120
agctcagacc cttaacacag accacagcct ctgagagaaa ccactctcac tctcactctc     180
cttaaccttt caccttccat atctggcgaa aatgaaagct ctgtacagaa gctctctctt     240
gctcctcttc ttcctctccg tctgttctgc atcttcttct tcggttccca ctctgcaact     300
cctaagcttc aaaaactctc tcccgaaccc aaccctgctc ccgaactggc tcccgaacca     360
aagcccatgc tcattcaccg gcatcacctg caacgacacc cagcacctca cttccataga     420
cctctccggc gtccctctca ccacaaacct caccgtcatc gccaccttcc tcctcaccct     480
cgacaacctc cagtcactct ccttaaaaatc caccaacctc tccggccccg ccgccatgcc     540
tcctcctctc tcccactcca agtgcgcctc cacattaacc tccctagatc tatcacaaaa     600
cgccctctcc ggttccctca cgacatgtc gtttctctcc tcctgctcca acctccaatc     660
cctcaatctc tccagcaacc ttcttgaatt cgactcctct cactggaagc tccacctcct     720
cgtcgccgac ttttcctaca caagatttc cggcccggt atcctcccct ggcttctcaa     780
ccctgaaatc gaacacctcg ctctgaaagg caacaaagtc accggcgaaa ccgacttctc     840
cggttccaat tctctccagt ttttagacct tcttccaac aactttttctg ttacgcttcc     900
tactctcggc gagtgttctt cgcttgagta tttggacctc tccgccaaca agtacttcgg     960
cgacattgct cgcactctct cgccttgcaa gaacctcgtt tacttaaact tctccagcaa    1020
ccagttctcc ggtccggttc cttcccttcc ctccggttcg ctacagtcg tgtaccttgc    1080
ttcaaaccac ttccacggcc agattcctct ccccctcgcc gacctctgct ccactctcct    1140
ccagctcgat ctctcctcca caacctctc aggcgctctc ccgaagcctt cggcgcttgc    1200
acttctcttc agtccttcga catctccagc aacctcttcc ccggtcgcgt gcctatggac    1260
gttctcacgc aaatgaaaag cctcaaagag ctcgcggtgg cgttcaacgc gttccttggt    1320
ccccttccgg agtctctgac gaagctctcc actttagagt cgctggatct tagctccaac    1380
aacttcagcg gctcaatccc gacaacgctg tgcggtggtg acgctgggaa taataatatt    1440
ctgaaggaac tttacctgca gaacaaccgg ttcacgggtt ttattccacc cacgctcagc    1500
aactgttcaa accctcgttgc tttggacttg agtttcaact tcctcacggg aactattcct    1560
ccaagcctag ggtctctttc caagcttaaa gacttgatca tctggctcaa ccagctccat    1620
ggagaaatac cgcaggagct catgtatctg aaaagcctcg agaatttgat cctgatttc     1680
aacgacttga ctgggaacat tccctctggg cttgttaact gcaccaagct gaactggatc    1740
tccctctcca caacaggct cagcggcgag attccgcgt ggattgggaa gctttctaat     1800
ctcgccatac ttaagctcag taataactct ttctccggcc ggattccgcc ggagctggcc    1860
gattgtacta gttaatatg gttggatctg aatactaata tgctcaccgg gccattccg     1920
ccggagctgt tcaagcagtc ggggaagatc gcggtgaatt tcatcagtgg gaagacgtat    1980
gtgtatataa agaacgatgg gagcaaagag tgtcatggtg cggggaactt gctggagttt    2040
gccgggatca gtcagcagca gttgaacagg atttcgacga ggaacccgtg caatttcact    2100
agggtttatg gaggtaagtt gcagccaacg tttaaccata atggttctat gatattttg    2160
```

```
gatatctcgc acaacatgtt gtcagggagt attcccaagg agattggggc catgtactat  2220
ttgtacattc tcaatttggg tcataataat gtgtctggga gcattcctca agagcttggg  2280
aagatgaaga atctcaacat ccttgatctc tcaagtaata gactggaggg gcaaattcct  2340
cagagtctca cggggctttc cttgctcact gagattgacc tgtcgaataa cttgcttacg  2400
gggacgattc ctgagtcggg tcaatttgat actttccctg cggcgagatt tcagaacaac  2460
tctggtctct gtggagttcc tctcggccca tgtggttcgg acccggcgaa taacgggaat  2520
gcgcaacata tgaagtctca caggaggcag gcttctctgg tggggagtgt ggccatgggt  2580
ttgttgtttt ccctcttctg cgtctttggt ttgatcatta ttgccattga gaccaggaag  2640
aggaggaaaa agaaggaggc tgctcttgaa gcctatgctg atggtaattt gcattcgggt  2700
cctgccaacg tgagctggaa gcacaccagt acccggaag cgcttagcat aaaccttgca  2760
acgtttaaga ggccgctcag gaggcttact tttgcggacc ttcttgacgc taccaatggc  2820
tttcacaatg atagtctcat tggctctggt gggtttgggg atgtttacaa ggctcagttg  2880
aaggatggaa gtgttgtggc tatcaagaag ctgattcatg tcagcggcca aggggacagg  2940
gaattcactg ctgaaatgga gaccattggg aagatcaagc acaggaacct tgttcctctg  3000
ttgggatact gcaaggttgg ggaagagagg ctcttggttt atgagtacat gaaatatgga  3060
agcttagagg atgttcttca tgatccgaag aaagctggga tcaagttgaa ttggtcgatt  3120
aggaggaaaa ttgctattgg agctgctagg ggattgtctt ttcttcacca caattgtagc  3180
ccccacatca ttcatagaga catgaagtca agcaatgtgt tacttgatga aaacctggaa  3240
gctagagtct ctgattttgg aatggctagg catatgagtg ctatggatac acatttgagt  3300
gcactggcag gcacaccagg gtatgttcct ccggagtact atgagagctt cagatgctct  3360
accaaaggtg atgtctacag ttatggtgtg gttttgttgg agctgctaac tgggaaaagg  3420
ccaacagatt cggctgattt tggtgataat aatcttgttg gatgggttaa acaacatgcc  3480
aagctgaaaa taagtgatat ttttgaccca gagctcatga aggaagaccc caatttggag  3540
atggagcttt tgcagcacct gaagattgca gtttcctgtt tggatgatcg gcattggaga  3600
cgtccaacga tgattcaagt gttgacaatg ttcaaggaga ttcaggcagg atctgggatt  3660
gattctcagt caaccatagc caatgaagat gacagttcga atgcagttga aatggtggag  3720
atgagcatta agaaacccc tgaattgagc aagcattagg caacaaattc cggaagtgtc  3780
atgtggattc tttgggaaac agacaagaag agagaaagg aggagatgac ggattcagct  3840
cccctcaaag tttttttcctt cctctttgcc gcttcaaatt atttcagaca caggggggaa  3900
acggttaaag ggggaatgaa tgcctttgat gtatgtagtc ttgttatttt atacaaaaaa  3960
aaaaagttgt ttaacttgta tataaacagc ttcagttgtt accatctgtg ttttcctaga  4020
attttcaaaa gtactttcct cattcagata taatcctgaa aaggatctct gttcaatctg  4080
gcgaccccac tgatgcgac taagtggagg atctttggc catttcttta ggcctcttga  4140
tttgtttccc ccatttgatc aactgcaact tttgctccga tttgctgatat aatttgtcaa  4200
aacatgcttc ttctaaaatc actcataaca taaattttct tgaattacaa ttttataccc  4260
tccctcccc aacttgttct gcgcttctg acccttcttg ttttgtttgc tagtttaccc  4320
tgtaggaaaa agtatcactc tactcaaata gtattttcac ctcttctggc cataaataat  4380
tttggcctaa ttcag                                                   4395

SEQ ID NO: 141           moltype = DNA   length = 4392
FEATURE                  Location/Qualifiers
source                   1..4392
                         mol_type = other DNA
                         organism = synthetic construct
SEQUENCE: 141
gacttttgac tctctctctc tctctctcta cagtagtagt agtagtattc attcatattc    60
atacttgata tcatgtcaca cacacactat ctctctctct ctctctctaa tggcagagct   120
agctcagacc cttaacacag accacagcct ctgagagaaa ccactctcac tctcactctc   180
cttaaccttt caccttccat atctggcgaa aatgaaagct ctgtacagaa gctctctctt   240
gctcctcttc ttcctctccg tctgttctgc atcttcttct tcggttccca ctctgcaact   300
cctaagctcc aaaaactctc tcccgaaccc aaccctgcc ccgaactggc tcccgaacca   360
aagcccatgc tcattcaccg gcatcacctg caacgacacc cagcacctca cttccctaga   420
cctctccggc gtccctctca ccacaaacct caccgtcatc gccaccttcc tcctcacccct   480
cgacaacctc cagtcactct ccttaaaatc caccaacctc tccggccccg ccgccatgcc   540
tcctcctctc tcccactcca agtgcgcctc cacattaactc ccctagatc tatcacaaaa   600
cgccctctcc ggttccctca acgacatgtc gtttctctcc tctgctccaa acctccaatc   660
cctcaatctc tccagcaacc ttcttgaatt cgactcctct cactggaagc tccacctcct   720
cgtcgccgac ttttcctaca acaagatttc cggccccgt atcctcccct ggcttctcaa   780
ccctgaaatc gaacacctcg ctctgaaagg caacaaagtc acggcgaaa ccgacttctc   840
cggttccaat tctctccagt ttttagacct ttcttccaac aacttttctg ttacgcttcc   900
tacttcggc gagtgttctt cgcttgagta tttggacctc tccgccaaca agtacttcgg   960
cgacattgct cgcactctct cgccttgcaa gaacctcgtt tacttaaaact ctccagcaa   1020
ccagttctcc ggtccggttc cttcccttcc ctccggttcg ctacagttcg tgtaccttgc  1080
ttcaaaccac ttccacggcc agattcctct ccccctcgcc gacctctgct ccactcctca  1140
ccagctcgat ctctcctcca caacctctc aggcgctctc ccgaagcctt cggcgcttgc  1200
acttctcttc agtccttcga catctccagc aacctcttcg ccggtgcgct gcctatggac  1260
gttctcacgc aaatgaaaag cctcaaagag ctcgcggtgg cgttcaacgc gttccttggt  1320
ccccttccgg agtctctgac gaagctctcc actttagagt cgctcggatct tagctccaac  1380
aacttcagcg gctcaatccc tgcggtggtg acgctgggaa taataattt  1440
ctgaaggaac tttacctgca gaacaaccgg ttcacgggtt ttattccacc acgctcagc   1500
aactgttcaa acctcgttgc tttggacttg agtttcaact tcctcacggg aactattcct   1560
ccaagcctag ggtctctttc caagcttaaa gacttgatca tctggctcaa ccagctccat  1620
ggagaaatac cgcaggagct catgtatctg aaaagcctcg agaattgat cctggatttc  1680
aacgacttga ctgggaacat tccctctggg cttgttaact gcaccaagct gaactggatc  1740
tccctcteca acaacaggct cagcggcgag attccgcggt ggattgggaa gctttctaat  1800
ctcgccatac ttaagctcag taataactct ttctccggcc ggattccgcc ggagctcggc  1860
gattgtacta gttaatatg gttggatctg aatactaata tgctcaccgg gcccattccg  1920
ccggagctgt tcaagcagtc ggggaagatc gcggtgaatt tcatcagtgg gaagacgtat  1980
gtgtatataa agaacgatgg gagcaaagag tgtcatggtg cggggaactt gctggagttt  2040
```

```
gccgggatca gtcagcagca gttgaacagg atttcgacga ggaacccgtg caatttcact   2100
agggtttatg gaggtaagtt gcagccaacg tttaaccata atggttctat gatattttg   2160
gatatctcgc acaacatgtt gtcagggagt attcccaagg agattggggc catgtactat   2220
ttgtacattc tcaatttggg tcataataat gtgtctggga gcattcctca agagcttggg   2280
aagatgaaga atctcaacat ccttgatctc tcaagtaata gactggaggg gcaaattcct   2340
cagagtctca cggggctttc cttgctcact gagattgacc tgtcgaataa cttgcttacg   2400
gggacgattc ctgagtcggg tcaatttgat actttccctg cggcgagatt tcagaacaac   2460
tctggtctct gtgagttcc tctcggccca tgtggttcgg acccggcgaa taacgggaat   2520
gcgcaacata tgaagtctca caggaggcag gcttctctgg tggggagtgt ggccatgggt   2580
ttgttgtttt ccctcttctg cgtcttggt ttgatcatta ttgccattga gaccaggaag   2640
aggaggaaga agaaggaggc tgctcttgaa gccatgctg atggtaattt gcattcgggt   2700
cctgccaacg tgagctggaa gcacaccagt acccgggaag cgcttagcat aaaccttgca   2760
acgtttaaga ggccgctcag gaggcttact tttgcggacc ttcttgacgc taccaatggc   2820
tttcacaatg atagtctcat tggctctggt gggtttgggg atgtttacaa ggctcagttg   2880
aaggatggaa gtgttgtggc tatcaagaag ctgattcatg tcagcggcca aggggacagg   2940
gaattcactg ctgaaatgga gaccattggg aagatcaagc acaggaacct tgttcctctg   3000
ttgggatact gcaaggttgg ggaagagagg ctccttggttt atgagtacat gaaatatgga   3060
agcttagagg atgttcttca tgatccgaag aaagctgaag tcaagttgaa ttggtcgtat   3120
aggaggaaaa ttgctattgg agctgctagg ggattgtctt ttcttcacca caattgtagc   3180
ccccacatca ttcatagaga catgaagtca agcaatgtgt tacttgatga aaacctggaa   3240
gctagagtct ctgattttgg aatggctagg catatgagtg ctatggatac acatttgagt   3300
ctggcaggca caccagggta tgttcctccg gagtactatg agagcttcag atgctctacc   3360
aaaggtgatg tctacagtta tggtgtggtt ttgttggagc tgctaactgg gaaaaggcca   3420
acagattcgg ctgattttgg tgataataat cttgttggat gggttaaaca acatgccaag   3480
ctgaaaataa gtgatatttt tgacccagag ctcatgaagg aagacccaa tttggagatg   3540
gagcttttgc agcacctgaa gattgcagtt tcctgttttg atgatcggca ttggagacgt   3600
ccaacgatga ttcaagtgtt gacaatgttc aaggagattc aggcaggatc tgggattgat   3660
tctcagtcaa ccatagccaa tgaagatgac agtttcaatg cagttgaaat ggtggagatg   3720
agcattaaag aaaccctga attgagcaag cattaggcaa caaattccgg aagtgtcatg   3780
tggattcttt gggaaacaga caagaagaga gaaaaggagg agatgacgga ttcagctccc   3840
ctcaaagttt tttccttcct ctttgccgct tcaaattatt tcagacacaa ggggggaaacg   3900
gttaaagggg gaatgaatgc ctttgatgta tgtagtcttg ttattttata caaaaaaaaa   3960
aagttgttta acttgtatat aaacagcttc agttgttacc atctgtgttt tcctagaatt   4020
ttcaaaagta cttttctcat tcagatataa tcctgaaaag gatctctgtt caatctggcg   4080
accccagtga tggcgactaa gtggaggatc ttttggccat ttctttaggc ctctcttgattt   4140
gtttccccca tttgatcaac tgcaacttt gctccgattt gcgatataat ttgtcaaaac   4200
atgcttcttc taaaatcact cataacataa attttcttga attacaattt tatacccctcc   4260
cctccccaac ttgttctgcg ccttctgacc cttcttgttt tgtttgctag tttacccgt   4320
aggaaaaagt atcactctac tcaaatagta ttttcacctc ttctgccat aaataatttt   4380
ggcctaattc ag                                                       4392

SEQ ID NO: 142          moltype = DNA  length = 4238
FEATURE                 Location/Qualifiers
source                  1..4238
                        mol_type = other DNA
                        organism = synthetic construct
SEQUENCE: 142
gtagatacaa gtatggagga gagtggaaat aggaaaaaat agcttagaga gatttattta    60
cgaacaggaa gagtcacatg gcatgtgtcc agtcttccac atgataaata ccccttcttac   120
cttccttact aggactttttg actctctctc tctctatcta tggtagtagt agtagtagta   180
ttcattcatt ctctctaatg gcagagctca caccctaaca acaaaccaga gcctctgaca   240
gaaacaacca caaactctcc cttaatcttg tcggtttcca tatctgctga aaatgaaagc   300
tctgtacaga agctctctct tgctcttgct cttgctcttc atctccgtgt gttttgcatc   360
ttcttcttct ccggtcactc agcaactcct aagcttcaaa aactctctcc cgaacccatc   420
cctgctcccc aactggctcc ctaaccaaag cccgtgcaca ttcagcggca tcagctgcaa   480
cgacacagag ctcacatcca tagacctcag ctccgtccct ctcagcacta acctaaccgt   540
catcgccagc ttcctcctta gcctggacca cctccagtca ctctccttaa aatccaccaa   600
cctctccggt cccgccgcca tgcctcctct ctcccactcc cagtgctcct cctcattaac   660
ctccctagat ctctcccaaa actccctctc tgcctccctc aacgacatgt cgtttctcgc   720
ctcctgctcc aacctccaat ccctcaacct ctcctccaac ctcctccaat tcggcccccc   780
gccccactgg aagctccacc acctccgctt cgccgacttc tcttacaaca agatttccgg   840
ccccggcgtc gtttcttggc ttctcaaccc cgtcatcgaa ctcctctctc tcaaaggcaa   900
caaagtcacc ggcgaaaccg acttctccgg ctcaattttct ctccagtatt tagaccccttc   960
ttccaacaac ttttctgtta cgcttcctac tttcggcagg tgttcttcgc ttgagtattt   1020
ggacctctcc gctaacaagt acttgggcga cattgcacgg actctctccc cttgcaagag   1080
cctcgtttac cttaacgtct ccagcaacca gttctccggt ccggttcctt cccttccctc   1140
cggttcgcta cagtttgtgt accttgctgc aaaccacttc cacggccaga ttcctctctc   1200
cctcgccgac ctctgctcca ctctcctcca gctcgatctc tcctccaaca atctccaccg   1260
cgctcttccc ggccgcgttc g gcgcgtcac ttctcttcaa tcccttgaca tctccagcaa   1320
cctcttcgcc ggcgcgttgc cgatgtcggt tctcacgcaa atgaccagcc tgaaagagct   1380
cgcggttgcg ttcaacggct tcctcggtgc tccccggag tctctgtcga gctctccgc   1440
tctggagttg ctggatctga gctccaacaa ctttagcggc tcaatccccg cctcgctgtg   1500
cggcggcggt gacgctggga ttaataataa tctgaaggaa ctttatctgc agaataaccg   1560
gttcacgggt tttattccgc ccacgctcag aacctcgttg ctttggattt   1620
gagtttcaac ttcctcacgg ggactattcc tccgagccta gggtctcttt cgaatctcaa   1680
agacttcatc atctgctcca accagctcca cggggagata ccgcaggagc tcatgtatct   1740
taaaagcctc gagaatttga tcctggattt caacgacttg actgggaaca ttccctctgg   1800
cctcgttaac tgcaccaagt tgaactggat ctccctctcc aacaacaggc tcagcggcga   1860
gattccgccg tggattggga agctttctaa tctcgccata ctcaagctca gcaataactc   1920
```

```
tttctccggc cggattccgc cggagctcgg cgactgtact agtttaatat ggttggatct  1980
gaatacaaat atgctcaccg ggcccattcc gccggagctg ttcaagcagt cggggaagat  2040
cgccgtgaat tcatcagtg ggaagacgta tgtgtatata aagaacgatg ggagcaagga  2100
gtgccatggt gcggggaact tgcttgagtt tgcgggatc agtcagcagc agctgaacag  2160
gatttcgacg aggaacccct gcaatttcac tagggtttat ggaggtaagt tgcagccaac  2220
gtttaaccat aatggttcta tgatattttt ggatatctcg cacaacatgt tgtcagggag  2280
tattcccaag gagattgggg ccatgtacta ttttgtacatt ctcaatttgg gtcacaataa  2340
tgtgtctggg agcattcctc aagagcttgg gaagatgaag aatctcaaca ttcttgatct  2400
gtcgaataat agactggagg gccaaattcc gcagagcctc acggggcttt ctttgctcac  2460
tgagattgac ttgtccaaca acttgcttac cgggacgatt cctgagtcgg gtcaatttga  2520
tactttccct gcggcgaagt ttcagaacaa ctctggtcta tgtggagttc ctctgggtcc  2580
gtgtggttcg gagccggcaa acaatggaaa tgcgcaacat atgaagtctc acaggaggca  2640
ggcttctctg gcggggagtg tggccatggg gttgttgttt tccctctttt gcgtcttggg  2700
tttgatcatt attgccattg agaccaggaa gaggaggaaa agaaggagg ctgctcttga  2760
agcctatggt gatggtaatt cccattcggg tccggccaat gtgagctgga agcacaccgg  2820
tactcgggaa gctcttagca taaaccttgc aacatttgag aagccgctcc ggaagcttac  2880
ttttgcggac cttcttgacg ctaccaatgg ttttcacaa gacagtctca ttggctctgg  2940
cggggtttggg gatgtgtaca aggctcagtt gaaggatgga agtgttgtgg tcatcaagaa  3000
gctgattcat gttagcggac aaggggacag ggaattcacc gctgaaatgg agactattgg  3060
gaaaatcaag cacaggaacc ttgttcccct gttgggatac tgcaaggtag gggaagagag  3120
gctcttggtt tatgagtaca tgaaatatgg aagtttagag gatgttctac atgatcagaa  3180
gaaagctggg atcaagctga actggccat taggcggaaa atgctattg gagctgctag  3240
gggattgtct tttcttcacc acaattgtat cccccacatc attcatagag atatgaagtc  3300
gagcaatgtg ttacttgatg aaaacctgga agccagagtc tctgattttg gaatggctag  3360
gcttatgagt gctatggata cacatttgag tgtgttggct ggcacaccgg ggtatgttcc  3420
tcccgagtac tatcagagct tcagatgctc cacaaaaggt gatgtctaca gttatggtgt  3480
ggttttgttg gagctgctaa ctgggaaaag gccaacggac tcggctgatt ttggagataa  3540
taatcttgtt ggatgggtta acaacatgc caagctgaaa atcagtgata ttttgtgaccc  3600
ggagctcatg aaggaagacc ccaatctgga gatggagctt ttgcagcact tgaagattgc  3660
ggttttcctgt ttgggatgatc gaccgtggag gcgtccgacg atgattcaag tgatggcaat  3720
gttcaaggag attcaggcgg gatccgggat tgattctcag tcaaccatag ccaatgacga  3780
ggaaggttc aatgcagttg aaatggtgga gatgagcatt aaagaagccc ctgaattgag  3840
caagcattag gcattaaagt gtcgtgtgga ttcttgggga aacagacaag aagagaggag  3900
gagatgacgg attcagctcc cctcagttt ttccttcttt gccgcttcaa attatttcag  3960
acataaggga aaacggttaa aagggggaatg aatgcttttg atgtatgtat tcttgttatt  4020
ttatacataa aaaaaagttg tttaacttgt atataaacag cttcagttgt taccatctgt  4080
gttttcctag aattttcaaa gtactttct cattcaaata taatcctgaa aaggttctct  4140
gttcaatctg cgaccccagt gatggcaact aagtggatca acagcaactt ttgctccgat  4200
ttgcgatata atttgtcaaa acatgcctct aaaatcac                          4238

SEQ ID NO: 143         moltype = DNA   length = 4015
FEATURE                Location/Qualifiers
source                 1..4015
                       mol_type = other DNA
                       organism = synthetic construct
SEQUENCE: 143
aggcagcgat tcgcgatgag ggcgagcagt cgagggcagg gggcacatgc catgtgacgt  60
gaccccacca ccactctctc ccgcccttcc ctcacctaca gctgttaatt tgcttcccgt  120
ctcctgcgct cccctctct ctctgtcttt acactgttgc ttctttcttc ctgctcctct  180
ctctaggtat agcagcccat tcctccacac tcccacctcc gctcatcacc tctccctctc  240
ctaccatctc gtcggctcct ccccgtcgg cgacccgct tctttaatgg ttttaaggta  300
gcgcgctagt tcatggaatc tccgggctg ttcgctgtag tggcactctt cgtcgtcgtc  360
gtggcggcgg cggccgccga cgatgcccag ctgctggagc agttcaagga ggccgtgccg  420
agccaggcca cggacctccg cgggtggagc gccagcgatg gcgcctgcag gttcccaggc  480
gccggctgca ggggcggcg gctcacgtcg tgtcgctcg ccgccgtccc gctcaatgcc  540
gacttccggg ccgtcgcgg caccctgctg cagctggcca gcctcgagac gctcagcctg  600
cgcggcgcca acgtcgcgg cacgctggcg gcggtgccga ggtgcgggc caagctgcag  660
tcgctcgacc tgtcagcgaa tgccggcctg cggggtccg tctccgacgt cgaggcgctt  720
gtcgctgcct gcgccgggct tagcgcgctg aacctctccg gcggttcgat tggtgggccg  780
aggtctgccg gcgttgtcgc ctccggattt gcccgctag acgctctcga cttgtccggc  840
aacaagatct ccggcgatgg cgacctccgg tggatggtgg gcgccggcgt cggagcagtc  900
cgccaactgg acctctccgg gaacaagatc tctagcctgc cggagttcac caactgctct  960
gggctggagt acctcgacct ctccggcaac ctcatcgccg gcgaggtggc cggcaggact  1020
ctcgctgact ccgtggtct gagaacgctc aacctctcag gcaaccacct ggtcgtcgcc  1080
ttcccgccgg acgtcgccgc cctcacctcg ctcgccggac tcaacctctc aaacaacaac  1140
ttctccagcg acctccccgc cgacgctttc accgagctac agcagctcaa ggtggtcgcc  1200
ctctccttca accacttcaa cggcagtatt ccggactcct ggcagcgct gccggagctc  1260
gacgtgctgg acctcagctc caacaccttc tccggcacca tcccttcgtc catctgccaa  1320
ggcccaaact ccagcctccg catgctgtac ctccagaaca actacctctc cggccgcatc  1380
cctgagtcaa tctccaactg caccaggctc gaatctctcg atctcagcct caacaacatc  1440
aacggcaccc tccccggcatc cctcgggaag ctcggggagc tccgggacct cattctttgg  1500
cagaacttct tggagggcga gattccggcg tccctgaaa atttggataa gctcgagcat  1560
ctcatccctcg actacaacgg gctcaccggc agcatcccgc cggaactctc caagtgcaag  1620
gagctgaact ggatatcctt ggcaagcaac cagctgtctg gtcgatccc ggcttggctt  1680
gggcagctca gtaacttggc catcttgaag ctgagcaaca attccttctc cggaccaata  1740
ccggctgagc tcggcaactg ccagagtttg gtctggctgg acctgaacag caaccagctt  1800
aacgggtcaa taccggcgga actggcaaag cagtctggga gatgaacat cggtcttgtc  1860
attgggcggc cgtatgtgta tcttcgcaat gacgagctga gcagcgagtg ccatggcaag  1920
gggagcttgc tagagttcac cagtatccga cctgaagagc tcagtcggat gccgagcaag  1980
```

```
gagctgtgca acttcactcg ggtgtacatg gggagcaccg agtataccttt caataagaat   2040
ggctccatga tatttctgga tttgtcattt aatcagcttg actcagagat cccaaaggag   2100
cttgggaaca tgtactacct catgatcctg aatcttggcc acaacttgct gtctggcgtc   2160
atcccaccag aactagctgg tgccaagaag cttgctgtac tcgacctgtc acacaaccag   2220
ttggaagggc ctattcccaa ctctttctcg acgttgtcct tgtcggagat caacctttca   2280
aataatcagt tgaatggttc aattccagag ctcggttcgc tgttcacatt cccgaagatt   2340
tcatatgaga ataactctgg tctttgtggc ttcccactgt tgccatgcgg gcacaatgct   2400
ggctcaagtt cttccgatgg ccaccgatcc caccggaacc aggcttcact cgcgggtagt   2460
gttgctatgg gactcttgtt ctcgctgttc tgtatagttg gaattgtcat catagttgtt   2520
gagtgcaaga agcggaagca gatcaatgaa gaggcaagta cctctcgtga catatacatt   2580
gatagccggt ctcattctgg gactatgaat tccaattgga gactctctgg tactaacgcc   2640
ctcagcgtca accttgctgc atttgagaag cgactgcaga aactcacctt taatgatctt   2700
attgtggcca ccaatggctt ccacaatgat agcctagttg ggtctggtgg ttttggtgat   2760
gtctataagg cccagctcaa ggatgaaaag gttgttgaa tcaagaagct tatacatgtg   2820
agtggccagg gtgaccggga gtttactgca gaaatggaga ccattggtag gatcaaacac   2880
cgcaatcttg ttccgctcct cggctactgc aagtgtggtg aggagcggct gctggtttat   2940
gattacatga ggtttggcag cttggaagat gtgttgcatg accggaaaaa gacccgggatt   3000
aagctaaatt gggcagcaag gaaaaagatc gccattgggg ctgcaagggg attggcatac   3060
ctccaccaca actgtattcc acacatcatc caccgagaca tgaagtcaag caatgtgctt   3120
atcgatgagc aattagaggc aagggtatct gattttggaa tggcaagaat gatgagcgtg   3180
gtggacaccc acttgagtgt gtccactctc gcccaggtta cgtgccaccg gagtattacc   3240
agagcttcag atgcactacc aagggcgatg tgtatagcta cggtgttgta ttgctcgagc   3300
tgctcactgg gaaaccgcct acagattcaa ctgacttcgg tgacgacaac aatcttgtag   3360
gatgggtcaa acaacactcg aagtcgaggc tcacggatct gtttgatcct gaactcgtga   3420
aggaagatcc agccctggag ctcgagctac tggagcacct aaaagttgct tgtgcatgct   3480
tggacgacag accgtcgaag cgtccgacaa tgctgaaggt catggcaatg ttcaaggaga   3540
tgcaggccag ttcgacagtg gactcaaaga cttcggcgtg cacagacgat gcatgttttg   3600
ccgatgtgga gatgacgacc ctgaaagaag acaaggagga gaaggactaa caaggccacc   3660
gacacgcgag aaactgctcc tggtgcacct gcccaggggg tgagtggcag cagctacacg   3720
gcgagtcaga ggcaaaatgc ccgtaggagg aatcagttgg tgaggatcc atttgaagtc   3780
tcttgttgag cttagcattc ccttcttgat ggtagaagac agaagttttc cctcatagct   3840
tcgccagttg aatatgctgt gtacctatgg gagtaggttg atttctttt cttctttctt   3900
tttaagcttt cttcatctct tcttgtcaca cgtcagtaag atctgtgtat gtacatatat   3960
aaatggtgat ttttttcttc ggtgccaaat ccacttcgtt ctatttctta ttgtc         4015

SEQ ID NO: 144        moltype = DNA   length = 4016
FEATURE               Location/Qualifiers
source                1..4016
                      mol_type = other DNA
                      organism = synthetic construct
SEQUENCE: 144
aggcagcgat tcgcgatgag ggcgagcagt cgagggcagg gggcacatgc catgtgacgt   60
gaccccacca ccactctctc ccgcccttcc ctcacctaca gctgttaatt tgcttcccgt   120
ctcctgcgct cccctctct ctctgtcttt acactgttgc ttctttcttc ctgctcctct   180
ctctaggtat agcagcccat tcctccacac tcccacctcc gctcatcacc tctccctctc   240
ctaccatctc gtcggctcct ccccgtcgg ccgacccgct tctttaatgg ttttaaggta   300
gcgcgctagt tcatggaatc tccggggctg ttcgctgtag tggcactctt cgtcgtcgtc   360
gtggcggcgg cggccgccga cgatgcccag ctgctggagc agttcaagga ggccgtgccg   420
agccaggcca cggacctccg cgggtggagc gccagcgatg gcgcctgcag gttcccaggc   480
gccggctgca ggggcgggcg gctcacgtcg ctgtcgctcg ccgccgtccc gctcaatgcc   540
gacttccggg ccgtcgcggc caccctgctg cagctgagcg gcctcgagac gctcagcctg   600
cgcggcgcca acgtcagcgg cacgctggcc gcggtgccga ggtgcgggc caagctgcag   660
tcgctcgacc tgtcagcgaa tgccggcctg cggggctccg tctccgacgt cgaggcgctt   720
gtcgctgcct gcgccgggct tagcgcgctg aacctctccg gcggttcgat tggtgggccg   780
aggtctgccg gcgttgtcgc ctcccggattt gcccggctag acgctctcga cttgtccggc   840
aacaagatct ccggcgatgt cgacctccgg tggatggtgg gcgccggcgt cggagcagtc   900
cgccaactgg acctctccgg gaacaagatc tctagcctgc cggagttcac caactgctct   960
gggctggagt acctcgacct ctccggcaac ctcatcgccg gcgaggtggc cggcaggact   1020
ctcgctgact gccgtggtct gagaacgctc aacctctcag gcaacacctc ggtcggcccg   1080
ttcccgccgg acgtcgcgc cctcacctcg ctcgccggac tcaacctctc aaacaacaac   1140
ttctccagcg acctccccgc cgacgctttc accgagctac agcagctcaa ggtggtcgcc   1200
ctctccttca accacttcaa cggcagtatt ccggactcct ggcagcgct gccggagctc   1260
gacgtgctgg acctcagctc caacaccttc tccggcacca tccttcgtc catctgccaa   1320
ggcccaact ccagcctccg catgctgtac ctccagaaca actacctctc cggcgccaag   1380
cctgagtcaa tctccaactg caccaggctc gaatctctcg atctcagcct caacaacatc   1440
aacggcaccc tccggcatc cctcgggaag ctcggggagc tccggaacct cattctttgg   1500
cagaacttct tggagggcga gattccgcg tccctgaaaa atttggataa gctcgagcat   1560
ctcatcctcg actacaacgg gctcaccggc agcatcccgc cggaactctc caagtgcaag   1620
gagctgaact ggatatcctt ggcaagcaac cagctgtctg gtccgatccc ggcttggctt   1680
gggcagctca gtaacttggc catcttgaag ctgagcaaca attccttctc cggaccaata   1740
ccggctgagc tcggcaactg ccagagtttg gtctggctgg acctgaacag caaccagctt   1800
aacgggtcaa taccggcgga actggcaaag cagtctggga agatgaacat cggtcttgtc   1860
attgggcggc cgtatgtgta tcttcgcaat gacgagctga gcagcgagtg ccatggcaag   1920
gggagcttgc tagagttcac cagtatccga cctgaagagc tcagtcggat gccgagcaag   1980
gagctgtgca acttcactcg ggtgtacatg gggagcaccg agtataccttt caataagaat   2040
ggctccatga tatttctgga tttgtcattt aatcagcttg actcagagat cccaaaggag   2100
cttgggaaca tgtactacct catgatcctg aatcttggcc acaacttgct gtctggcgtc   2160
atcccaccag aactagctgg tgccaagaag cttgctgtac tcgacctgtc acacaaccag   2220
ttggaagggc ctattcccaa ctctttctcg acgttgtcct tgtcggagat caacctttca   2280
```

```
aataatcagt tgaatggttc aattccagag ctcggttcgc tgttcacatt cccgaagatt   2340
tcatatgaga ataactctgg tctttgtggc ttcccactgt tgccatgcgg gcacaatgct   2400
ggctcaagtt cttccgatgg ccaccgatcc caccggaacc aggcttcact cgcgggtagt   2460
gttgctatgg gactcttgtt ctcgctgttc tgtatagttg gaattgtcat catagttgtt   2520
gagtgcaaga agcggaagca gatcaatgaa gaggcaagta cctctcgtga catatacatt   2580
gatagccggt ctcattctgg gactatgaat tccaattgga gactctctgg tactaacgcc   2640
ctcagcgtca accttgctgc atttgagaag cgactgcaga aactcacctt taatgatctt   2700
attgtggcca ccaatggctt ccacaatgat agcctagttg ggtctggtgg ttttggtgat   2760
gtctataagg cccagctcaa ggatgaaaag gttgttgcaa tcaagaagct tatacatgtg   2820
agtggccagg gtgaccggga gtttactgca gaaatggaga ccattggtag gatcaaacac   2880
cgcaatcttg ttccgctcct cggctactgc aagtgtggtg aggagcggct gctggtttat   2940
gattacatga ggtttggcag cttggaagat gtgttgcatg accggaaaaa gacccgggatt   3000
aagctaaatt gggcagcaag gaaaaagatc gccattgggg ctgcaagggg attggctac   3060
ctccaccaca actgtattcc acacatcatc caccgagaca tgaagtcaag caatgtgcct   3120
atcgatgagc aattagaggc aagggtatct gattttggaa tggcaagaat gatgagcgtg   3180
gtggacaccc acttgagtgt gtccactctc gccccaggtt acgtgccacc ggagtattac   3240
cagagcttca gatgcactac caagggcgat gtgtatagct acggtgttgt attgctcgag   3300
ctgctcactg ggaaaccgcc tacagattca actgacttcg gtgacgacaa caatcttgta   3360
ggatgggtca acaacactc gaagtcgagg ctcacggatc tgtttgatcc tgaactcgtg   3420
aaggaagatc cagccctgga gctcgagcta ctggagcacc taaaagttgc ttgtgcatgc   3480
ttggacgaca gaccgtcgaa gcgtccgaca atgctgaagg tcatggcaat gttcaaggag   3540
atgcaggcca gttcgacagt ggactcaaag acttcggcgt gacagacga tgcatgtttt   3600
gccgatgtgg agatgacgac cctgaaagaa gacaaggagg agaaggacta acaaggccac   3660
cgacacgcga gaaactgctc ctggtgcacc tgcccagggg gtgagtggca gcagctacac   3720
ggcgagtcag aggcaaaatg cccgtaggag gaatcagttg gtgaggatac catttgaagt   3780
ctcttgttga gcttagcatt cccttccttga tggtagaaga cagaagtttt ccctcatagc   3840
ttcgccagtt gaatatgctg tgtacctatg ggagtaggtt gattttcttt tcttcttcct   3900
ttttaagctt tcttcatctc ttcttgtcac acgtcagtaa gatctgtgta tgtacatata   3960
taaatggtga tttttttctt cggtgccaaa tccacttcgt tctatttctt attgtc      4016

SEQ ID NO: 145         moltype = DNA   length = 4015
FEATURE                Location/Qualifiers
source                 1..4015
                       mol_type = other DNA
                       organism = synthetic construct
SEQUENCE: 145
aggcagcgat tcgcgatgag ggcgagcagt cgagggcagg gggcacatgc catgtgacgt   60
gaccccacca ccactctctc ccgccccttcc tcacctaca gctgttaatt tgcttcccgt   120
ctcctgcgct cccctctct ctctgtcttt acactgttgc ttctttcttc ctgctcctct   180
ctctaggtat agcagcccat tcctccacac tcccacctcc gctcatcacc tctccctctc   240
ctaccatctc gtcggctcct ccccgtcgg ccgaccgct tctttaatgg ttttaaggta     300
gcgcgctagt tcatggaatc tccggggctg ttcgctgtag tggcactctt cgtcgtcgtc   360
gtggcgggcc cggccgccga cgatgcccag ctgctggaga agttcaagga ggccgtgcag   420
agccaggcca cggacctccg cgggtggagc gccagcgatg cgcctgcag gttcccaggc   480
gccggctgca ggggcgggcg gctcacgtcg ctgtcgctcg ccgccgtccc gctcaatgcc   540
gacttccggg ccgtcgcggc caccctgctg cagctggcca gcctcgagac gctcagcctg   600
cgcggccgca acgtcagcgg cacgctggcc gcggtgcagg ggtgcggggc caagctgcag   660
tcgctcgacc tgtcagcgaa tgccggcctg cggggctccg tctccgacgt cgaggcgctt   720
gtcgctgcct cgcgccgggct tagcgcgctg aacctctccg gcggttcgat tggtgggccg   780
aggtctgccg gcgttgtcgc ctccggattt gcccggctag acgctctcga cttgtccggc   840
aacaagatct ccggcgatgg cgacctccgg tggatgtcgg gccggcgt ggagcagctc     900
cgccaactgg acctctccgg gaacaagatc tctagcctgc cggagttcac caactgctct   960
gggctggagt acctcgacct ctccggcaac ctcatcgccg gcgaggtggc cggcaggact  1020
ctcgctgact gccgtggtct gagaacgctc aacctctcag gcaaccacct ggtcggcccg  1080
ttcccgccgg acgtcgccgc cctcacctcg ctcgccgaac tcaacctctc aaacaacaac  1140
ttctccagcg acctccccgc cgacgctttc accgagctac agcagctcaa ggtggtcgcc  1200
ctctccttca accacttcaa cggcagtatt ccggactcct tggcagcgct gccggagctc  1260
gacgtgctgg acctcagctc caacaccttc tccggcacca tcccttcgtc catctgccaa  1320
ggcccaact ccagcctccg cctgctgtac ctccagaaca actacctctc cggcgccatc    1380
cctgagtcaa tctccaactg caccaggctc gaatctctcg atctcagcct caacaacatc  1440
aacggcaccc tcccggcatc cctcgggaag ctcggggagc tccggggacct cattctttgg  1500
cagaacttct tggagggcga gattccgcg tccctggaaa atttggataa gctcgagcat    1560
ctcatcctcg actacaacgg gctcaccggc agcatcccgc cggaactctc caagtgcaag  1620
gagctgaacct ggatatcctt ggcaagcaac cagctgtgtc gtccgatccg ggcttggctt  1680
gggcagctca gtaacttggc catcttgaag ctgagcaaca attccttctc cggaccaata  1740
ccggctgagc tcggcaactg ccagagtttg gtctggctgg acctgaacag caaccagctt  1800
aacgggtcaa taccggcgga actggcaaag cagtctggga gatgaacat cggtcttgtc    1860
attgggcggc cgtatgtgta tcttcgcaat gacgagctga gcagcgagtg ccatggcaag  1920
gggagcttgc tagagttcac cagtatccga cctgaagagc tcagtcggat gccgagcaag  1980
gagctgtgca acttcactcg ggtgtacatg gggagcaccg agtataccttt caataagaat  2040
ggctccatga tatttctgga tttgtcattt aatcagcttg actcagagat cccaaaggag  2100
cttgggaaca tgtactacct catgatcctg aatcttggcc acaacttgct gtctggcgtc  2160
atcccaccag aactagctgg tgccaagaag cttgctgtac tcgacctgtc acacaaccag  2220
ttggaaggc ctattcccaa ctctttctcg acgttgcgat tgtcggagat caaccttta     2280
aataatcagt tgaatggttc aattccagag ctcggttcgc tgttcacatt cccgaagatt  2340
tcatatgaga ataactctgg tctttgtggc ttcccactgt tgccatgcgg gcacaatgct  2400
ggctcaagtt cttccgatgg ccaccgatcc caccggaacc aggcttcact cgcgggtagt  2460
gttgctatgg gactcttgtt ctcgctgttc tgtatagttg gaattgtcat catagttgtt  2520
gagtgcaaga agcggaagca gatcaatgaa gaggcaagta cctctcgtga catatacatt  2580
```

-continued

```
gatagccggt ctcattctgg gactatgaat tccaattgga gactctctgg tactaacgcc    2640
ctcagcgtca accttgctgc atttgagaag cgactgcaga aactcaccttt taatgatctt   2700
attgtggcca ccaatggctt ccacaatgat agcctagttg ggtctggtgg ttttggtgat    2760
gtctataagg cccagctcaa ggatggaaag gttgttgcaa tcaagaagct tatacatgtg    2820
agtggccagg gtgaccggga gtttactgca gaaatggaga ccattggtag gatcaaacac    2880
cgcaatcttg ttccgctcct cggctactgc aagtgtggtg aggagcggct gctggtttat    2940
gattacatga ggtttggcag cttggaagat gtgttgcatg accggaaaaa gaccgggatt    3000
aagctaaatt gggcagcaag gaaaaagatc gccattgggg ctgcaagggg attggcatac    3060
ctccaccaca actgtattcc acacatcatc caccgagaca tgaagtcaag caatgtgctt    3120
atcgatgagc aattagaggc aagggtatct gattttggaa tggcaagaat gatgagcgtg    3180
gtggacaccc acttgagtgt gtccactctc gccggggtta cgtgccaccg gagtattacc    3240
agagcttcag atgcactacc aagggcgatg tgtatagcta cggtgttgta ttgctcgagc    3300
tgctcactgg gaaaccgcct acagattcaa ctgacttcgg tgacgacaac aatcttgtag    3360
gatgggtcaa acaacactcg aagtcgaggc tcacggatct gtttgatcct gaactcgtga    3420
aggaagatcc agccctggag ctcgagctac tggagcacct aaaagttgct tgtgcatgct    3480
tggacgacag accgtcgaag cgtccgacaa tgctgaaggt catggcaatg ttcaaggaga    3540
tgcaggccag ttcgacagtg gactcaaaga cttcggcgtg cacagacgat gcatgttttg    3600
ccgatgtgga gatgacgacc ctgaaagaag acaaggagga gaaggactaa caaggccacc    3660
gacacgcgag aaactgctcc tggtgcacct gcccagggg tgagtggcag cagctacacg     3720
gcgagtcaga ggcaaaatgc ccgtaggagg aatcagttgg tgaggatacc atttgaagtc    3780
tcttgttgag cttagcattc ccttcttgat ggtagaagac agaagttttc cctcatagct    3840
tcgccagttg aatatgctgt gtacctatgg gagtaggttg attttctttt cttctttctt    3900
tttaagcttt cttcatctct tcttgtcaca cgtcagtaag atctgtgtat gtacatatat    3960
aaatggtgat ttttttcttc ggtgccaaat ccacttcgtt ctatttctta ttgtc         4015
```

UNITED STATES PATENT AND TRADEMARK OFFICE
CERTIFICATE OF CORRECTION

PATENT NO. : 12,365,911 B2  
APPLICATION NO. : 17/819023  
DATED : July 22, 2025  
INVENTOR(S) : Bate et al.

Page 1 of 2

It is certified that error appears in the above-identified patent and that said Letters Patent is hereby corrected as shown below:

In the Specification

Column 5, Line 36: Please correct "BM" to read --BRI1--

Column 37, Line 64: Please correct "BM" to read --BRI1--

Column 37, Line 67: Please correct "BM/gene" to read --BRI1 gene--

Column 41, Line 2: Please correct "BM" to read --BRI1--

Column 45, Line 66: Please insert a paragraph break between "cassette." and "In some"

Column 54, Line 10: Please correct "MZDTO9Y" to read --MZDT09Y--

Column 56, Line 9: Please correct "(0" to read --(f)--

Column 59, Line 6: Please correct "CRiSPR-Cas" to read --CRISPR-Cas--

Column 62, Line 25: Please correct "(Cast2a)" to read --(Cas12a)--

Column 69, Line 63: Please insert a paragraph break between "length." and "As"

In the Claims

Column 177, Line 53, Claim 6: Please correct "BRI1gene" to read --BRI1 gene--

Signed and Sealed this  
Thirteenth Day of January, 2026

John A. Squires  
*Director of the United States Patent and Trademark Office*

CERTIFICATE OF CORRECTION (continued)
U.S. Pat. No. 12,365,911 B2

Column 178, Line 26, Claim 7: Please correct "BRI1gene" to read --BRI1 gene--

Column 179, Line 12, Claim 12: Please correct "BRI1gene" to read --BRI1 gene--